US008249814B2

(12) United States Patent
Liew et al.

(10) Patent No.: US 8,249,814 B2
(45) Date of Patent: Aug. 21, 2012

(54) METHOD, COMPUTER READABLE MEDIUM, AND SYSTEM FOR DETERMINING A PROBABILITY OF COLORECTAL CANCER IN A TEST SUBJECT

(75) Inventors: Choong-Chin Liew, Toronto (CA); Mark Han, North York (CA); Thomas Yager, Mississauga (CA); Samuel Chao, Concord (CA); Run Zheng, Richmond Hill (CA); Hongwei Zhang, Toronto (CA)

(73) Assignee: GeneNews Inc., Richmond Hill, Ontario (CA)

( * ) Notice: Subject to any disclaimer, the term of this patent is extended or adjusted under 35 U.S.C. 154(b) by 1033 days.

(21) Appl. No.: 12/091,049

(22) PCT Filed: Oct. 23, 2006

(86) PCT No.: PCT/US2006/041600

§ 371 (c)(1), (2), (4) Date: Apr. 21, 2008

(87) PCT Pub. No.: WO2007/048074

PCT Pub. Date: Apr. 26, 2007

(65) Prior Publication Data

US 2009/0208942 A1 Aug. 20, 2009

Related U.S. Application Data

(60) Provisional application No. 60/729,055, filed on Oct. 21, 2005, provisional application No. 60/758,418, filed on Jan. 12, 2006.

(51) Int. Cl.
*G01N 33/48* (2006.01)

(52) U.S. Cl. ................ 702/19; 702/20; 702/189; 703/2; 703/11; 435/6.1; 435/6.14; 436/63; 436/64

(58) Field of Classification Search ........................ None
See application file for complete search history.

(56) References Cited

U.S. PATENT DOCUMENTS

2007/0213939 A1 9/2007 Liew et al.

FOREIGN PATENT DOCUMENTS

| | | |
|---|---|---|
| WO | WO 02/44403 | 6/2002 |
| WO | WO 2004/079368 | 9/2004 |
| WO | WO 2005/024054 | 3/2005 |
| WO | WO 2005/077065 | 8/2005 |

OTHER PUBLICATIONS

S. Frank, "Identification of Genes Involved in Human Mesothelial Cancer Progression Using a Modified Differential Display Technique," *Cancer Letters 123* (1998), pp. 7-14.

W. Shin-Ichi, et al., "Expression of Cytidine Deaminase in Human Solid Tumors and Its Regulation by 1 alpha, 25-dihydroxyvitamin D-3," *Biochimica et Biophysica Acta*) 1312:99-104 (1996) (Abstract).

K. Yokoyama, et al., "BANK regulates BCR-induced calcium mobilization by promoting tyrosine phosphorylation of $IP_3$ Receptor," *The EMBO Journal*, 21:83-92 (2002).

PCT International Search Report for PCT/US2006/041600 dated Mar. 9, 2007, 3 pages.

Restriction Requirement in U.S. Appl. No. 11/585,666, mailed Mar. 16, 2010 (9 pages).

Fish and Richardson P.C., Amendment and Response to Restriction Requirement in U.S. Appl. No. 11/585,666, dated Mar. 16, 2010, filed Sep. 15, 2010 (17 pages).

USPTO Non-Final Office Action in U.S. Appl. No. 11/585,666, mailed Nov. 26, 2010 (9 pages).

Fish and Richardson P.C., Amendment in Reply to Office Action in U.S. Appl. No. 11/585,666, dated Nov. 26, 2010, filed Sep. 15, 2010 (18 pages).

Non-final Office Action in U.S. Appl. No. 11/585,666, mailed Aug. 16, 2011, 13 pages.

Fish & Richardson P.C., Amendment in Reply to Office Action in U.S. Appl. No. 11/585,666, mailed Aug. 16, 2011, filed Feb. 15, 2012 (9 pages).

Notice of Allowance in U.S. Appl. No. 11/585,666, mailed Apr. 3, 2012 (10 pages).

*Primary Examiner* — Carolyn L. Smith
(74) *Attorney, Agent, or Firm* — Fish & Richardson P.C.

(57) ABSTRACT

Disclosed is a method of testing for colorectal cancer in a test individual by providing data corresponding to a level of products of selected biomarkers and applying the data to a formula to provide an indication of whether the test individual has colorectal cancer. Also disclosed are kits for measuring data corresponding to the products of selected biomarkers, and kits and methods of monitoring therapeutic efficacy of treatments for colorectal cancer.

16 Claims, 6 Drawing Sheets

SEQUENCE LISTING

```
<160> NUMBER OF SEQ ID NOS: 351

<210> SEQ ID NO 1
<211> LENGTH: 3878
<212> TYPE: DNA
<213> ORGANISM: Homo sapiens
<300> PUBLICATION INFORMATION:
<308> DATABASE ACCESSION NUMBER: NM_001005386
<309> DATABASE ENTRY DATE: 2006-09-24
<313> RELEVANT RESIDUES IN SEQ ID NO: (1)..(3878)

<400> SEQUENCE: 1

ggagcccggc ggcggcttcc ggtcggggga aaaaagttgg gccgaaggag gggccgggaa     60

gacgcaagag gaagaagaga aaacggccgg gcggcggtgg ctgtaggttg tgcggctgca    120

gcggctcttc cctgggcgga cgatggacag ccagggcagg aaggtggtgg tgtgcgacaa    180
```

```
cggcaccggg tttgtgaagt gtggatatgc aggctctaac tttccagaac acatcttccc    240
agctttggtt ggaagaccta ttatcagatc aaccaccaaa gtgggaaaca ttgaaatcaa    300
gaataacaaa aagatggatc ttatggttgg tgatgaggca agtgaattac gatcaatgtt    360
agaagttaac taccctatgg aaaatggcat agtacgaaat tgggatgaca tgaaacacct    420
gtgggactac acatttggac cagagaaact taatatagat accagaaatt gtaaaatctt    480
actcacagaa cctcctatga acccaaccaa aaacagagag aagattgtag aggtaatgtt    540
tgaaacttac cagttttccg gtgtatatgt agccatccag gcagttctga ctttgtacgc    600
tcaaggttta ttgactggtg tagtggtaga ctctggagat ggtgtgactc acatttgccc    660
agtatatgaa ggcttttctc tccctcatct taccaggaga ctggatattg ctgggaggga    720
tataactaga tatcttatca agctacttct gttgcgagga tacgccttca accactctgc    780
tgattttgaa acggttcgca tgattaaaga aaaactgtgt tacgtgggat ataatattga    840
gcaagagcag aaactggcct tagaaaccac agtattagtt gaatcttata cactcccaga    900
tggacgtatc atcaaagttg gggagagag atttgaagca ccagaagctt tatttcagcc    960
tcacttgatc aatgttgaag gagttggtgt tgctgaattg ctttttaaca caattcaggc   1020
agctgacatt gataccagat ctgaattcta caaacacatt gtgctttctg gagggtctac   1080
tatgtatcct ggcctgccat cacggttgga acgagaactt aaacagcttt acttagaacg   1140
agttttgaag ggtgatgtgg aaaaactttc taaatttaag atccgcattg aagacccacc   1200
ccgcagaaag cacatggtat tcctgggtgg tgcagttcta gcggatatca tgaaagacaa   1260
agacaacttt tggatgaccc gacaagagta ccaagaaaag ggtgtccgtg tgctagagaa   1320
acttggtgtg actgttcgat aaactccaaa gcttgttccc gtcatacccg taatgctttc   1380
ttttttcctt tattgccaat ctttgaactc attcaactcc aggacatgga agaggcctct   1440
ctctgccctt tgactggaaa ggtcaagttt tattctggtg tcttggggaa gctttgttaa   1500
atttttgtta atgtgggtaa atctgagttt aattcaactg cttccctaca tagactagag   1560
ggctaaggat tctgtctgct gctttgtttc ttctaagtag gcatttagat cattcctgta   1620
ggcttcctat tttcacttta ctgctctaat gctgctagtc gtagtcttta gcacactagg   1680
tggtatgcct ttattagcat aaaacaaaaa aaactttaac aggagctttt acatattact   1740
gggatggggg gtggttcggg atgggtgggc agctgctgaa ccctttaggg catttcctct   1800
gtaatgtggc gctttcaact gtactgctgc agctttaagt accttaaagc ttctcctgtg   1860
aacttcttag ggaaatgtta ggttcagaac taaagtgttt tgggtgggtt ttgttgcggg   1920
ggggagggta acaatgggtg gtcttctgat ttttattttt gaggttttgt caactggagt   1980
acgtagagga actttattta cagtactttg atttggcagg ttttcttcta cttgtgctct   2040
gcctggagct gtttccatat gatataaaaa gcaagtgtag tattccatta ctatgtggct   2100
tagggattta tttgtttttt aaaatcaacc atgttagctg ggattagact ccctacagtc   2160
cttcaatgga aaagtaacat ttaaaaatcc tttgggtaat tcgaattaca gatttaaaag   2220
agcttaagat ctggtgtttt gttaatgctt ctgtttattc cagaagcatt aaggtaaccc   2280
attgccaagt atcattcttg caaattattc ttttatataa ctgaccagtg cttaataaaa   2340
caagcaggta cttacaaata attactggca gtaggttata attggtggtt taaaaataac   2400
attggaatac aggacttgtt gccaattggg taattttcat tagttgtttt gtttgttttg   2460
atttgaaacc tggaaataca gtaaaatttg actgtttaaa atgttggcca aaaaaatcaa   2520
gatttaattt ttttatttgt actgaaaaac taatcataac tgttaattct cagccatctt   2580
```

```
tgaagcttga aagaagagtc tttggtattt tgtaaacgtt agcagacttt cctgccagtg   2640

tcagaaaatc ctatttatga atcctgtcgg tattccttgg tatctgaaaa aaataccaaa   2700

tagtaccata catgagttat ttctaagttt gaaaaataaa aagaaattgc atcacactaa   2760

ttacaaaata caagttctgg aaaaaatatt tttcttcatt ttaaaacttt tttttaacta   2820

ataatggctt tgaaagaaga ggcttaattt gggggtggta actaaaatca aaagaaatga   2880

ttgacttgag ggtctctgtt tggtaagaat acatcattag cttaaataag cagcagaagg   2940

ttagttttaa ttatgtagct tctgttaata ttaagtgttt tttgtctgtt ttacctcaat   3000

ttgaacagat aagtttgcct gcatgctgga catgcctcag aaccatgaat agcccgtact   3060

agatcttggg aacatggatc ttagagtcac tttggaataa gttcttatat aaataccccc   3120

agccttttga gaacggggct tgttaaagga cgcgtatgta gggcccgtac ctactggcag   3180

ttgggttcag ggaaatggga ttgacttggc cttcaggctc ctttggtcat aattttaaaa   3240

tatgggagta gaaaacaaca aagaatggaa tggactctta aaacaatgaa agagcattta   3300

tcgtttgtcc cttgaatgta gaatttgttt ttgatttcat aattctgctg gtaaatgtga   3360

cagttaaaat ggtgcattat gtatatatat tataatttag aaataccatt ttataatttt   3420

actattccag ggtgacataa tgcatttaaa tttgggattt gggtggagta ttatgtttaa   3480

ctggagttgt caagtatgag tccctcagga aaaaaaaaaa ttctgtttta aaaagcaatc   3540

tgattcttag ctcttgaaac tattgctact taaatttcca ataattaaaa atttaaaatt   3600

tttaaattag aattgccaat acttctacat ttgagaaggg ttttttttaga aatacattta   3660

gtaaagtccc caagacatta gtcttacatt taaacttttt tctttaaaac atggttttgg   3720

tggttaactt ttacacagtt ctgagtactg ttaatatctg gaaagtatct tgagatatca   3780

gtggaaagct aaacagtcta aattaacatg aaatacttca ttttgattga gaaaataaaa   3840

tcagattttt tcaaagtcaa aaaaaaaaaa aaaaaaaa                          3878
```

<210> SEQ ID NO 2
<211> LENGTH: 3863
<212> TYPE: DNA
<213> ORGANISM: Homo sapiens
<300> PUBLICATION INFORMATION:
<308> DATABASE ACCESSION NUMBER: NM_005722
<309> DATABASE ENTRY DATE: 2006-09-24
<313> RELEVANT RESIDUES IN SEQ ID NO: (1)..(3863)

<400> SEQUENCE: 2

```
ggagcccggc ggcggcttcc ggtcggggga aaaaagttgg gccgaaggag gggccgggaa     60

gacgcaagag gaagaagaga aaacggccgg gcggcggtgg ctgtaggttg tgcggctgca    120

gcggctcttc cctgggcgga cgatggacag ccagggcagg aaggtggtgg tgtgcgacaa    180

cggcaccggg tttgtgaagt gtggatatgc aggctctaac tttccagaac acatcttccc    240

agctttggtt ggaagaccta ttatcagatc aaccaccaaa gtgggaaaca ttgaaatcaa    300

ggatcttatg gttggtgatg aggcaagtga attacgatca atgttagaag ttaactaccc    360

tatggaaaat ggcatagtac gaaattggga tgacatgaaa cacctgtggg actacacatt    420

tggaccagag aaacttaata tagataccag aaattgtaaa atcttactca cagaacctcc    480

tatgaaccca accaaaaaca gagagaagat tgtagaggta atgtttgaaa cttaccagtt    540

ttccggtgta tatgtagcca tccaggcagt tctgactttg tacgctcaag gtttattgac    600

tggtgtagtg gtagactctg gagatggtgt gactcacatt tgcccagtat atgaaggctt    660

ttctctccct catcttacca ggagactgga tattgctggg agggatataa ctagatatct    720
```

```
tatcaagcta cttctgttgc gaggatacgc cttcaaccac tctgctgatt ttgaaacggt    780
tcgcatgatt aaagaaaaac tgtgttacgt gggatataat attgagcaag agcagaaact    840
ggccttagaa accacagtat tagttgaatc ttatacactc ccagatggac gtatcatcaa    900
agttgggggga gagagatttg aagcaccaga agctttattt cagcctcact tgatcaatgt    960
tgaaggagtt ggtgttgctg aattgctttt taacacaatt caggcagctg acattgatac   1020
cagatctgaa ttctacaaac acattgtgct ttctggaggg tctactatgt atcctggcct   1080
gccatcacgg ttggaacgag aacttaaaca gctttactta gaacgagttt tgaagggtga   1140
tgtggaaaaa ctttctaaat ttaagatccg cattgaagac ccaccccgca gaaagcacat   1200
ggtattcctg ggtggtgcag ttctagcgga tatcatgaaa gacaaagaca acttttggat   1260
gacccgacaa gagtaccaag aaaagggtgt ccgtgtgcta gagaaacttg gtgtgactgt   1320
tcgataaact ccaaagcttg ttcccgtcat acccgtaatg ctttcttttt tcctttattg   1380
ccaatctttg aactcattca actccaggac atggaagagg cctctctctg ccctttgact   1440
ggaaaggtca agttttattc tggtgtcttg ggaagcttt gttaaatttt tgttaatgtg   1500
ggtaaatctg agtttaattc aactgcttcc ctacatagac tagagggcta aggattctgt   1560
ctgctgcttt gtttcttcta agtaggcatt tagatcattc ctgtaggctt cctattttca   1620
ctttactgct ctaatgctgc tagtcgtagt ctttagcaca ctaggtggta tgcctttatt   1680
agcataaaac aaaaaaaact ttaacaggag cttttacata ttactgggat ggggggtggt   1740
tcgggatggg tgggcagctg ctgaaccctt tagggcattt cctctgtaat gtggcgcttt   1800
caactgtact gctgcagctt taagtacctt aaagcttctc ctgtgaactt cttagggaaa   1860
tgttaggttc agaactaaag tgttttgggt gggttttgtt gcgggggggga gggtaacaat   1920
gggtggtctt ctgattttta tttttgaggt tttgtcaact ggagtacgta gaggaacttt   1980
atttacagta ctttgatttg gcaggttttc ttctacttgt gctctgcctg gagctgtttc   2040
catatgatat aaaaagcaag tgtagtattc cattactatg tggcttaggg atttatttgt   2100
tttttaaaat caaccatgtt agctgggatt agactcccta cagtccttca atggaaaagt   2160
aacatttaaa aatcctttgg gtaattcgaa ttacagattt aaaagagctt aagatctggt   2220
gttttgttaa tgcttctgtt tattccagaa gcattaaggt aacccattgc caagtatcat   2280
tcttgcaaat tattctttta tataactgac cagtgcttaa taaaacaagc aggtacttac   2340
aaataattac tggcagtagg ttataattgg tggtttaaaa ataacattgg aatacaggac   2400
ttgttgccaa ttgggtaatt ttcattagtt gttttgtttg ttttgatttg aaacctggaa   2460
atacagtaaa atttgactgt ttaaaatgtt ggccaaaaaa atcaagattt aatttttttta   2520
tttgtactga aaaactaatc ataactgtta attctcagcc atctttgaag cttgaaagaa   2580
gagtctttgg tattttgtaa acgttagcag actttcctgc cagtgtcaga aaatcctatt   2640
tatgaatcct gtcggtattc cttggtatct gaaaaaaata ccaaatagta ccatacatga   2700
gttatttcta agtttgaaaa ataaaaagaa attgcatcac actaattaca aaatacaagt   2760
tctggaaaaa atatttttct tcattttaaa acttttttttt aactaataat ggctttgaaa   2820
gaagaggctt aatttggggg tggtaactaa aatcaaaaga aatgattgac ttgagggtct   2880
ctgtttggta agaatacatc attagcttaa ataagcagca gaaggttagt tttaattatg   2940
tagcttctgt taatattaag tgttttttgt ctgttttacc tcaatttgaa cagataagtt   3000
tgcctgcatg ctggacatgc ctcagaacca tgaatagccc gtactagatc ttgggaacat   3060
ggatcttaga gtcactttgg aataagttct tatataaata cccccagcct tttgagaacg   3120
```

```
gggcttgtta aaggacgcgt atgtagggcc cgtacctact ggcagttggg ttcagggaaa   3180

tgggattgac ttggccttca ggctcctttg gtcataattt taaaatatgg gagtagaaaa   3240

caacaaagaa tggaatggac tcttaaaaca atgaaagagc atttatcgtt tgtcccttga   3300

atgtagaatt tgtttttgat ttcataattc tgctggtaaa tgtgacagtt aaaatggtgc   3360

attatgtata tatattataa tttagaaata ccattttata attttactat tccagggtga   3420

cataatgcat ttaaatttgg gatttgggtg gagtattatg tttaactgga gttgtcaagt   3480

atgagtccct caggaaaaaa aaaaattctg ttttaaaaag caatctgatt cttagctctt   3540

gaaactattg ctacttaaat ttccaataat taaaaattta aaatttttaa attagaattg   3600

ccaatacttc tacatttgag aagggttttt ttagaaatac atttagtaaa gtccccaaga   3660

cattagtctt acatttaaac tttttctttt aaaacatggt tttggtggtt aacttttaca   3720

cagttctgag tactgttaat atctggaaag tatcttgaga tatcagtgga aagctaaaca   3780

gtctaaatta acatgaaata cttcattttg attgagaaaa taaaatcaga ttttttcaaa   3840

gtcaaaaaaa aaaaaaaaaa aaa                                           3863
```

```
<210> SEQ ID NO 3
<211> LENGTH: 1200
<212> TYPE: DNA
<213> ORGANISM: Homo sapiens
<300> PUBLICATION INFORMATION:
<308> DATABASE ACCESSION NUMBER: NM_020350
<309> DATABASE ENTRY DATE: 2006-05-07
<313> RELEVANT RESIDUES IN SEQ ID NO: (1)..(1200)

<400> SEQUENCE: 3

ctgcgctggg gttggagtgg ccgcaacggg cggggcgggg cggggccggg caagtttgtt     60

ccccgagttc ggagcctagg agccccccgc ggctgcggcg caggtgccct cggcctgagt    120

cgggatggag ctgcctgctg tgaacctgaa ggtgattctc ctaggtcact ggctgctgac    180

aacctggggc tgcattgtat tctcaggctc ctatgcctgg gccaacttca ccatcctggc    240

cttgggcgtg tgggctgtgg ctcagcggga ctccatcgac gccataagca tgtttctggg    300

tggcttgctg gccaccatct tcctggacat cgtgcacatc agcatcttct acccgcgggt    360

cagcctcacg gacacgggcc gctttggcgt gggcatggcc atcctcagct tgctgctcaa    420

gccgctctcc tgctgcttcg tctaccacat gtaccgggag cgcgggggtg agctcctggt    480

ccacactggt ttccttgggt cttctcagga ccgtagtgcc taccagacga ttgactcagc    540

agaggcgccc gcagatccct ttgcagtccc agagggcagg agtcaagatg cccgagggta    600

ctgaagccag ccacgctgcg cccggccctg ccccgggcct tcctcgtgcc tgggaggtcg    660

ttctagggat gctcctgacc tccgtctctt ggacctaaga tggaatgtgt ccccagctca    720

gggattgcct gaaccaagag gccaggagcc cccatgggcc gcccagtacc atgcacactc    780

ctgtcccgaa ctccctgagg cctcccctcc cttcagggca cccactggtt cccaggctgg    840

aaccagggtc tctctttacc tcctacccca tggtggcacc acagaggccc tcagccgagt    900

cctgcctgag tgttgcaagc tcaggccttt aaggactgct gatgcccccct caggcctccc    960

ccaagtttgc tgggctttgg tggaagccct gagagcttca ggtcctgctc agcccgagga   1020

gcagtctggc atgggagtga ggccccgtcc ttctcactgc ctggtcacat ggtgcctagg   1080

gatgcagggc tggaggccag aggtgtcagc aacactgtgt cccaccacaa cctccagcct   1140

ccctttttcag agcacagcat taaagtttgg ggaattctgt agaaaaaaaa aaaaaaaaaa   1200
```

<210> SEQ ID NO 4
<211> LENGTH: 1802
<212> TYPE: DNA
<213> ORGANISM: Homo sapiens
<300> PUBLICATION INFORMATION:
<308> DATABASE ACCESSION NUMBER: NM_138441
<309> DATABASE ENTRY DATE: 2006-10-04
<313> RELEVANT RESIDUES IN SEQ ID NO: (1)..(1802)

<400> SEQUENCE: 4

```
agcctggggt tccccttcgg gtcgcagact cttgtgtgcc cgccagtagt gcttggtttc      60

caacagctgc tgctggctct tcctcttgcg gccttttcct gaaacggatt cttctttcgg     120

ggaacagaaa gcgccagcca tgcagccttg gcacggaaag gccatgcaga gagcttccga     180

ggccggagcc actgccccca aggcttccgc acggaatgcc aggggcgccc cgatggatcc     240

caccgagtct ccggctgccc ccgaggccgc cctgcctaag gcgggaaagt tcggccccgc     300

caggaagtcg ggatcccggc agaaaaagag cgccccggac acccaggaga ggccgcccgt     360

ccgcgcaact ggggcccgcg ccaaaaaggc ccctcagcgc gcccaggaca cgcagccgtc     420

tgacgccacc agcgcccctg ggcagagggg gctggagcct cctgcggctc gggagccggc     480

tctttccagg gctggttctt gccgccagag gggcgcgcgc tgctccacga agccaagacc     540

tccgcccggg ccctgggacg tgcccagccc cggcctgccg gtctcggccc ccattctcgt     600

acggagggat gcggcgcctg ggcctcgaa gctccgggcg gttttggaga agttgaagct     660

cagccgcgat gatatctcca cggcggcggg gatggtgaaa ggggttgtgg accacctgct     720

gctcagactg aagtgcgact ccgcgttcag aggcgtcggg ctgctgaaca ccgggagcta     780

ctatgagcac gtgaagattt ctgcacctaa tgaatttgat gtcatgttta aactggaagt     840

ccccagaatt caactagaag aatattccaa cactcgtgca tattactttg tgaaatttaa     900

aagaaatccg aaagaaaatc ctctgagtca gtttttagaa ggtgaaatat tatcagcttc     960

taagatgctg tcaaagttta ggaaaatcat taaggaagaa attaacgaca ttaaagatac    1020

agatgtcatc atgaagagga aagaggaggg gagccctgct gtaacacttc ttattagtga    1080

aaaaatatct gtggatataa ccctggcttt ggaatcaaaa agtagctggc ctgctagcac    1140

ccaagaaggc ctgcgcattc aaaactggct ttcagcaaaa gttaggaagc aactacgact    1200

aaagccattt taccttgtac ccaagcatgc aaaggaagga aatggtttcc aagaagaaac    1260

atggcggcta tccttctctc acatcgaaaa ggaaattttg aacaatcatg gaaaatctaa    1320

aacgtgctgt gaaaacaaag aagagaaatg ttgcaggaaa gattgtttaa aactaatgaa    1380

ataccttttta gaacagctga aagaaaggtt taaagacaaa aaacatctgg ataaattctc    1440

ttcttatcat gtgaaaactg ccttctttca cgtatgtacc cagaaccctc aagacagtca    1500

gtgggaccgc aaagacctgg gcctctgctt tgataactgc gtgacatact ttcttcagtg    1560

cctcaggaca gaaaaacttg agaattattt tattcctgaa ttcaatctat tctctagcaa    1620

cttaattgac aaaagaagta aggaatttct gacaaagcaa attgaatatg aaagaaacaa    1680

tgagtttcca gtttttgatg aattttgaga ttgtattttt agaaagatct aagaactaga    1740

gtcaccctaa atcctggaga atacaagaaa aatttgaaaa ggggccagac gctgtggctc    1800

ac                                                                   1802
```

<210> SEQ ID NO 5
<211> LENGTH: 2573
<212> TYPE: DNA
<213> ORGANISM: Homo sapiens
<300> PUBLICATION INFORMATION:
<308> DATABASE ACCESSION NUMBER: NM_030764

<309> DATABASE ENTRY DATE: 2006-04-09
<313> RELEVANT RESIDUES IN SEQ ID NO: (1)..(2573)

<400> SEQUENCE: 5

```
ggtgaccaag agtacatctc ttttcaaata gctggattag gtcctcatgc tgctgtggtc      60
attgctggtc atctttgatg cagtcactga acaggcagat tcgctgaccc ttgtggcgcc     120
ctcttctgtc ttcgaaggag acagcatcgt tctgaaatgc cagggagaac agaactggaa     180
aattcagaag atggcttacc ataaggataa caaagagtta tctgttttca aaaaattctc     240
agatttcctt atccaaagtg cagttttaag tgacagtggt aactatttct gtagtaccaa     300
aggacaactc tttctctggg ataaaacttc aaatatagta aagataaaag tccaagagct     360
ctttcaacgt cctgtgctga ctgccagctc cttccagccc atcgaagggg gtccagtgag     420
cctgaaatgt gagacccggc tctctccaca gaggttggat gttcaactcc agttctgctt     480
cttcagagaa aaccaggtcc tggggtcagg ctggagcagc tctccggagc tccagatttc     540
tgccgtgtgg agtgaagaca cagggtctta ctggtgcaag gcagaaacgg tgactcacag     600
gatcagaaaa cagagcctcc aatcccagat tcacgtgcag agaatcccca tctctaatgt     660
aagcttggag atccgggccc ccgggggaca ggtgactgaa ggacaaaaac tgatcctgct     720
ctgctcagtg gctgggggta caggaaatgt cacattctcc tggtacagag aggccacagg     780
aaccagtatg ggaaagaaaa cccagcgttc cctgtcagca gagctggaga tcccagctgt     840
gaaagagagt gatgccggca aatattactg tagagctgac aacggccatg tgcctatcca     900
gagcaaggtg gtgaatatcc ctgtgagaat tccagtgtct cgccctgtcc tcaccctcag     960
gtctcctggg gcccaggctg cagtggggga cctgctggag cttcactgtg aggccctgag    1020
aggctctccc ccaatcttgt accaatttta tcatgaggat gtcacccttg ggaacagctc    1080
ggccccctct ggaggagggg cctccttcaa cctctctttg actgcagaac attctggaaa    1140
ctactcctgt gaggccaaca acggcctggg ggcccagtgc agtgaggcag tgccagtctc    1200
catctcagga cctgatggct atagaagaga cctcatgaca gctggagttc tctggggact    1260
gtttggtgtc cttggtttca ctggtgttgc tttgctgttg tatgccttgt tccacaagat    1320
atcaggagaa agttctgcca ctaatgaacc cagaggggct tccaggccaa atcctcaaga    1380
gttcacctat tcaagcccaa ccccagacat ggaggagctg cagccagtgt atgtcaatgt    1440
gggctctgta gatgtggatg tggtttattc tcaggtctgg agcatgcagc agccagaaag    1500
ctcagcaaac atcaggacac ttctggagaa caaggactcc caagtcatct actcttctgt    1560
gaagaaatca taacacttgg aggaatcaga agggaagatc aacagcaagg atggggcatc    1620
attaagactt gctataaaac cttatgaaaa tgcttgaggc ttatcacctg ccacagccag    1680
aacgtgcctc aggaggcacc tcctgtcatt tttgtcctga tgatgtttct tctccaatat    1740
cttcttttac ctatcaatat tcattgaact gctgctacat ccagacactg tgcaaataaa    1800
ttatttctgc taccttctct taagcaatca gtgtgtaaag atttgaggga agaatgaata    1860
agagatacaa ggtctcacct tcatctactg tgaagtgatg agaacaggac ttgatagtgg    1920
tgtattaact tatttatgtg ctgctggata cagtttgcta atattttgtt gagaattttt    1980
gcaaatatgt tcattgggaa tattggcctg aaattttctt ttccactgtg tctctgccag    2040
aatgtttgta tcaggctgat gctggcttca tagaatgagt taggcaggag cccttcctcc    2100
ttgatttttt ggcatagttt cagcaggatt ggtaccagtt attctttctg catcttgtag    2160
aattcagcta tgaatccatc tggtctaggg cttttgtgtt ggttggtaag tttttttatta    2220
ctaattcaac ttcagcgctt gatattggtc taggaggggt ttctgtctct tcctggttca    2280
```

```
atcttgggag attgtgtgtt tccaggaatt tagccgtttc ctccagattt tcttctttat   2340

gtgcatcgac ttgagtgtaa acataactta tatgcactgg gaaaccaaaa aatctgtgtg   2400

acttgcttta ttgcagcatt tgttttattt tggtagtctg gaactgaacc tgcaatatca   2460

ccaaagtatg catatagttg caaaaatgtg atttttgaca tagtaaatat gagtatttgc   2520

aataaactat gatattactt ttgtaagtat atagaataaa atgtaaataa tct          2573


<210> SEQ ID NO 6
<211> LENGTH: 1815
<212> TYPE: DNA
<213> ORGANISM: Homo sapiens
<300> PUBLICATION INFORMATION:
<308> DATABASE ACCESSION NUMBER: NM_000308
<309> DATABASE ENTRY DATE: 2006-08-20
<313> RELEVANT RESIDUES IN SEQ ID NO: (1)..(1815)

<400> SEQUENCE: 6

ggggagatga tccgagccgc gccgccgccg ctgttcctgc tgctgctgct gctgctgctg     60

ctagtgtcct gggcgtcccg aggcgaggca gcccccgacc aggacgagat ccagcgcctc    120

cccgggctgg ccaagcagcc gtctttccgc cagtactccg gctacctcaa aagctccggc    180

tccaagcacc tccactactg gtttgtggag tcccagaagg atcccgagaa cagccctgtg    240

gtgctttggc tcaatggggg tcccggctgc agctcactag atgggctcct cacagagcat    300

ggccccttcc tggtccagcc agatggtgtc accctggagt acaaccccta ttcttggaat    360

ctgattgcca atgtgttata cctggagtcc ccagctgggg tgggcttctc ctactccgat    420

gacaagtttt atgcaactaa tgacactgag gtcgcccaga gcaattttga ggcccttcaa    480

gatttcttcc gcctctttcc ggagtacaag aacaacaaac ttttcctgac cggggagagc    540

tatgctggca tctacatccc caccctggcc gtgctggtca tgcaggatcc cagcatgaac    600

cttcaggggc tggctgtggg caatggactc tcctcctatg agcagaatga caactccctg    660

gtctactttg cctactacca tggccttctg ggaacaggc tttggtcttc tctccagacc     720

cactgctgct ctcaaaacaa gtgtaacttc tatgacaaca aagacctgga atgcgtgacc    780

aatcttcagg aagtggcccg catcgtgggc aactctggcc tcaacatcta caatctctat    840

gccccgtgtg ctggaggggt gcccagccat tttaggtatg agaaggacac tgttgtggtc    900

caggatttgg gcaacatctt cactcgcctg ccactcaagc ggatgtggca tcaggcactg    960

ctgcgctcag gggataaagt gcgcatggac cccccctgca ccaacacaac agctgcttcc   1020

acctacctca acaacccgta cgtgcggaag gccctcaaca tcccggagca gctgccacaa   1080

tgggacatgt gcaactttct ggtaaactta cagtaccgcc gtctctaccg aagcatgaac   1140

tcccagtatc tgaagctgct tagctcacag aaataccaga tcctattata taatggagat   1200

gtagacatgg cctgcaattt catgggggat gagtggtttg tggattccct caaccagaag   1260

atggaggtgc agcgccggcc ctggttagtg aagtacgggg acagcgggga gcagattgcc   1320

ggcttcgtga aggagttctc ccacatcgcc tttctcacga tcaagggcgc cggccacatg   1380

gttcccaccg acaagcccct cgctgccttc accatgttct cccgcttcct gaacaagcag   1440

ccatactgat gaccacagca accagctcca cggcctgatg cagcccctcc cagcctctcc   1500

cgctaggaga gtcctcttct aagcaaagtg cccctgcagg cgggttctgc cgccaggact   1560

gcccccttcc cagagccctg tacatcccag actgggccca gggtctccca tagacagcct   1620

gggggcaagt tagcacttta ttcccgcagc agttcctgaa tggggtggcc tggccccttc   1680

tctgcttaaa gaatgccctt tatgatgcac tgattccatc ccaggaaccc aacagagctc   1740
```

aggacagccc acagggaggt ggtggacgga ctgtaattga tagattgatt atggaattaa 1800
attgggtaca gcttc 1815

<210> SEQ ID NO 7
<211> LENGTH: 4827
<212> TYPE: DNA
<213> ORGANISM: Homo sapiens
<300> PUBLICATION INFORMATION:
<308> DATABASE ACCESSION NUMBER: NM_003633
<309> DATABASE ENTRY DATE: 2006-08-20
<313> RELEVANT RESIDUES IN SEQ ID NO: (1)..(4827)

<400> SEQUENCE: 7
gcggtggcgc tgcggagacc cggtccagac gcctggcggc cgccggcaca caaggcgctt 60
tctagctccc tcccccgagc gcacagcccg cctccttccg cggcgcctgc agtggcaggc 120
ttgctctgcc ctaccgtgac gcgctccgga gacgctctgc gggtcctgga caccgggtcc 180
gcggcgtggg gacgacagac ggaggcgaac gccatcggta gccggtccgc gagccatcgt 240
tcggggcgca gtcctctccc cggctggccc tcctttctcc ggggcattcg ccaccgcttc 300
cctgggctga gacgaccggt tcgtcgcctc cttgcccgtg accgtcgcta gaactcagtt 360
gtgcgttgcg gccagtcgcc actgctgagt ggaagcaaaa tgtcagtcag tgtgcatgag 420
aaccgcaagt ccagggccag cagcggctcc attaacatct atctgtttca caagtcctcc 480
tacgctgaca gcgtcctcac tcacctgaat cttttacgcc agcagcgtct cttcactgac 540
gtccttctcc atgccggaaa taggaccttc ccttgccacc gggcagtgct ggctgcatgc 600
agtcgctact ttgaggccat gttcagtggt ggcctgaaag agagccagga cagtgaggtc 660
aactttgaca attccatcca cccagaagtc ttggagctgc tgcttgacta tgcgtactcc 720
tcccgggtca tcatcaatga agaaaatgca gaatcgctcc tggaagctgg tgacatgctg 780
gagtttcaag acatccggga tgcatgtgca gagttcctgg aaaagaacct gcatcccacc 840
aactgcctgg gcatgctgct gctgtctgat gcacaccagt gcaccaagct gtacgaacta 900
tcttggagaa tgtgtctcag caacttccaa accatcagga agaatgaaga tttcctccag 960
ctgccccagg acatggtagt gcaactcttg tccagtgaag agctggagac agaggatgaa 1020
aggcttgtgt acgagtctgc aattaactgg atcagctatg acctgaagaa gcgctattgc 1080
tacctcccag aactgttgca gacagtaagg ctggcacttc tgccagccat ctatctcatg 1140
gagaatgtgg ccatggagga actcatcacc aagcagagaa agagtaagga aattgtggaa 1200
gaggccatca ggtgcaaact gaaaatcctg cagaatgacg gtgtggtaac cagcctctgt 1260
gcccgacctc ggaaaactgg ccatgccctc ttccttctgg gaggacagac tttcatgtgt 1320
gacaagttgt atctggtaga ccagaaggcc aaagaaatca ttcccaaggc tgacattccc 1380
agcccaagaa aagagtttag tgcatgtgcg attggctgca aagtgtacat tactgggggg 1440
cgggggtctg aaaatggggt ctcgaaagat gtctgggttt atgataccct gcacgaggag 1500
tggtccaagg ctgcccccat gctggtggcc aggtttggcc atggctctgc tgaactgaag 1560
cactgcctgt atgtggttgg ggggcacacg gccgcaactg gctgcctccc ggcctccccc 1620
tcagtctctc taaagcaggt agaacattat gaccccacaa tcaacaaatg gaccatggtg 1680
gccccactcc gagaaggcgt tagcaacgcc gcagtagtga gtgccaaact taagttattt 1740
gctttcggag gtaccagtgt cagtcatgac aagctcccca aagttcagtg ttacgatcag 1800
tgtgaaaaca ggtggactgt accggccacc tgtccccagc cctggcgtta cacagcagca 1860
gctgtgctgg ggaaccagat tttttattatg gggggtgata cagaattctc tgcctgctct 1920
gcttataaat tcaacagtga gacttaccag tggaccaaag tgggagatgt gacagcaaag 1980
cgcatgagct gccatgctgt ggcctctgga aacaaactct acgtggttgg aggatacttt 2040
ggcattcagc gatgcaagac tttggactgc tacgatccaa cattagacgt gtggaacagc 2100
atcaccactg tcccgtactc gctgattcct actgcatttg tcagcacctg gaaacatctg 2160
ccttcttaaa tgcagtacat tctaaagaga gtgagcatga gctcactcca tcactcgatg 2220
agataatatg agatttctac ttcggagagg ccaagtctaa tgaagagaaa aaaaggaaaa 2280
gaagttgcaa gactcgaata aaatctgctg caccttgtaa atgctctaac tggacatgaa 2340
ggaaaggggc gagggagggg ggtgggattt ttggtgcaag tagcacatgg tttaaatatg 2400
aatgaacaaa cctgtgatct agtccttgtc ttgtaattgt ggattaatgt caatgttaat 2460
cagcccctca aagggagaga aaagctggac cttttccctt gctgtaccat attcagcatt 2520
tgatttccat gggccccacc atttatgtgt agaatttgaa atggttgtca cctctctctg 2580
aggacagagc ttgaagcctc cacaccagct gctgctggag attcaaagcc caactgtggg 2640
tccgagaggg aagctggctg ggctggctga agaatgaaga ccactggact ctccgttaat 2700
ctctaagggg tctgctcccc aggaacgttt ctgaacaatg gggactttgt tggtagccat 2760
ttggtagatg ttcttttcta tttataagtg actttaaact ttcccttggc tgttaagaag 2820
tttgttatag atttagctat ttattgttcg atgcctgcat gctgaaacaa tgcctacagc 2880
tgtcttcaca tgtatggacg tgtgtgaatg gttgtacgtt ttgcacattt tgtggctgtt 2940
gagatgtgct ttgctgcaca aacatgaaaa tttttgagtt acaatttgga gcataactgg 3000
agggtgggct ggggaggggt ggatttttaa aatgtcaaga cagggaagga tgacaaaatg 3060
gaaatttaaa tgacatccta gaggtagaga aaccgtggag atcgcttttc tcagactcac 3120
caacttttaa tgggatttca tggggtttgg ttgtgctgat agggtaaggg gaggctgctt 3180
tctgcccttc tccccactcc catctgattt acttaattca gtctcagctg ctgaaatttg 3240
gaaaggacca aattgcttta cagttttttt ctttgtgtag tatcttgaaa tcctggaaaa 3300
ttctatggaa tagttctgta tatagggcac aagtaaaggc attgtccaaa gtttatttat 3360
ttatttatta ccctaagaat gctttgccat aaccacattt aatgggaaaa acggcatgta 3420
tcacagatgt aaattaactc accagattta ctgggcctga actcattctc ttcttgctat 3480
atgatttagc aagttctaga aggtctccaa gacaataatt acattggcac aatgtatact 3540
tcagtgctca cccgtagcaa atctcttttt aaaaaactct ttggtgcaca agtaacacat 3600
ttggccacaa aacaccaaag aattgtaggc agtggcccct attgagaagt tttccggtag 3660
agttggaaat cagttgtgaa tacattcttt gctagttgga gtgcttgttt actaagcatg 3720
tgccgtcgta ggtattagtg ctagtctcaa ataggtgctt cccctgaggt gcaggggaag 3780
accaaagttt gcaactcgaa ctgctttcgt ccatgtttct cacattgctg tattttagaa 3840
aataggggtt aagactgata acaacctttt acattgtgac tgtgtttgca ttgtctaatg 3900
acagataaat ccttaacatt tctctccacc ttagtacttt agactaattg tgtttgtccg 3960
tccatgccat gaatgagtgg gctgtagttg ggcctaaata aatgagctgt tggaagaaaa 4020
gaatcacagt actttccagc agtcagtccc tggttcctag atgtgttcta agcaatgcaa 4080
atgtctaatt gtcccccagt gggcatagtc agtgtcgttt atattgtagc agttacagct 4140
ctgtagttta tgatgcaaat ctgccaagag agatgtatgt gtcactgcat ggcttctgaa 4200
agcaggatga attttctgca gctgtttcaa agttggggtc tgttcttgaa tcctctatta 4260
attactgtgt gtgagccaga gggagctgtg gtaagggttg ggcccccagc ctgtagggaa 4320

```
ctttctggac tcccactctt tgaatcgata taggcatttg gtctcactac ttgaccattc   4380

tcaccctgtg aaacgtccca cactttgaag caaatacaat tcacagcaca gtacacacaa   4440

aaaccttggc ataagacaga gaaggttctt cttattttgt gggctggttg ctgtagaaac   4500

atataacaaa gggcagccct ccacttctgg tataattgtg tagccccttt tctttgggct   4560

tgacacctgt cttgaataag agtgattaga gctgcataat gtccctctct tggctattga   4620

ccatgtggtt cacgtacaaa actctgtata agttgaagga aaatgttcat gttcatatgt   4680

acttgtttgc tatgactaca ttttgaggtt ttgtaaaact gttatttttt ttttttttcac   4740

aatgtgaaac tgaaggtcaa taaattatta gagattttct cttcaaaaaa aaaaaaaaaa   4800

aaaaaaaaaa aaaaaaaaaa aaaaaaa                                         4827


<210> SEQ ID NO 8
<211> LENGTH: 1807
<212> TYPE: DNA
<213> ORGANISM: Homo sapiens
<300> PUBLICATION INFORMATION:
<308> DATABASE ACCESSION NUMBER: NM_004130
<309> DATABASE ENTRY DATE: 2006-09-17
<313> RELEVANT RESIDUES IN SEQ ID NO: (1)..(1807)

<400> SEQUENCE: 8

ctctgagtca ccaacctgag gctgccccgg ccgcctgcgc acccggcagc accatgacag     60

atcaggcctt tgtgacacta accacaaacg atgcctacgc caaaggtgcc ctggtcctgg    120

gatcatctct gaaacagcac aggaccacca ggaggctggt cgtgctcgcc acccctcagg    180

tctcagactc catgagaaaa gttttagaga cagtctttga tgaagtcatc atggtagatg    240

tcttggacag tggcgattct gctcatctaa ccttaatgaa gaggccagag ttgggtgtca    300

cgctgacaaa gctccactgc tggtcgctta cacagtattc aaaatgtgta ttcatggatg    360

cagatactct ggtcctagca aatattgatg atcttttttga cagagaagaa ttgtcagcag    420

caccagaccc agggtggcct gactgcttca attccggagt cttcgtttat cagccttcag    480

ttgaaacata caatcagctg ttgcatcttg cttctgagca aggtagtttt gatggtgggg    540

accaaggcat actgaacaca ttttttagca gctgggcaac aacagatatc agaaaacacc    600

tgccgtttat ttataaccta agcagcatct ctatatactc ctacctcccg gcatttaaag    660

tgtttggtgc aagtgccaaa gttgtgcatt tcctgggacg agtcaaacca tggaattata    720

cttatgatcc caaaacaaaa agtgtcaaaa gtgaggccca tgatcccaac atgactcatc    780

cagagtttct catcctgtgg tggaacatct ttaccaccaa cgttttacct ctgcttcaac    840

aatttggcct tgtcaaagac acctgctcat atgtaaatgt gctttcagac ttggtctata    900

cactggcttt ctcttgtggc ttctgtagaa aggaagatgt ctcaggagcc atatcacatc    960

tgtcccttgg ggagatccca gctatggcac agccgtttgt atcctcggaa gaacggaagg   1020

aacgatggga acagggccag gctgattata tgggagcaga ttcctttgac aacatcaaga   1080

ggaaacttga cacttacctc cagtagaaac actgcatttt tctgtgaaca catccacttc   1140

acaagccttg tttctgatac ttagtatcta gagctgggtt gagaaaagtc tgttacagtt   1200

gctagaggtt ttcattaaaa cttatcagat gagaggcttt tttaggataa gaggtgagaa   1260

ctgggcaaaa gttgtgaagc agcaattctg ttatatggac agtgttctgc tttttaatcc   1320

tatttagctt gtttcagaaa ttctcacttt tgttgactgc caacatacaa agtaagggaa   1380

actcaagata ttaagatggc tgtatcagtt cttaaaatct gcagagcctg gttcaaaatc   1440

agtcactccc ttcagaagca gacatggcat ctgttccttg cttgcttgtt ggttgtgtac   1500
```

```
ctttcacgag acctgaattt tagaattgcc cagtgctgcc agagtgagtg agtgtaattc   1560

tcctttcagg taaagatagg ctatctcaac actgctgagt gattcataaa catatcaacc   1620

aatagcatta acccatttta tttcctgtcc ttagtgtctg aagatgctca ccagttttct   1680

gtgtacagta aggcagcatg ctaaaatgct tttgttcagt tctggatatt tgaaaatagc   1740

agtgtgttct ctgatggtta cctgcagtgg caccctgtac aaaaaataaa agacttattg   1800

gtgtaaa                                                             1807
```

<210> SEQ ID NO 9
<211> LENGTH: 4923
<212> TYPE: DNA
<213> ORGANISM: Homo sapiens
<300> PUBLICATION INFORMATION:
<308> DATABASE ACCESSION NUMBER: NM_014900
<309> DATABASE ENTRY DATE: 2006-10-15
<313> RELEVANT RESIDUES IN SEQ ID NO: (1)..(4923)

<400> SEQUENCE: 9

```
cggcggcggc gcccgcgggc tgggagccgg ggcccgcagg tggaagcgca cccgggaggc     60

gggccggccg gggctggagc ggctcgggcg ggctcttgac gctcagccag cttcgctccg    120

gcctcgggaa ggcgcgcgtc ccgccctgac ccgccggcct ctcccacccc agcagtgacg    180

cgccgcctgg gagctggagc ccgcgcagcg ccccgcaggg cgatggacgg ccgaaccccg    240

cgcccgcagg acgccccagc caggagaaaa ccaaaagcca aggcaccact tcctccagct    300

gagaccaaat atactgatgt ctcttcagct gctgattctg tagaatccac tgctttcatc    360

atggaacaga aagaaaacat gatagataaa gacgttgaac tctcagtggt cctacctggg    420

gatattatca aatctactac tgttcatggc agtaaaccta tgatggactt gttgatattc    480

ctttgtgcac agtatcactt aaatccatca agttacacaa tcgatctgtt gtcagctgaa    540

cagaaccaca ttaaatttaa gccaaacaca ccaataggaa tgttggaggt agagaaggta    600

attttaaagc caaaaatgtt ggataagaaa aaacctacac ctataatacc agagaaaact    660

gtgagagtag tgattaattt taagaaaaca cagaagacca tagtgagagt gagtccacat    720

gcatcgcttc aagagcttgc ccctattata tgtagcaaat gtgagtttga tccgttgcat    780

acactattgt tgaaagatta tcaatcgcag gagcctcttg acttgacaaa atctcttaat    840

gacctgggac taagagaatt atatgcgatg gatgtcaaca gagagtcctg ccaaatatca    900

caaaacctag atattatgaa ggagaaagaa aataaagggt ttttcagttt ttttcaacgc    960

agtaagaaaa agcgagacca aactgcaagt gcccctgcaa cccctctagt aaataagcac   1020

cgcccaactt ttacaaggtc caataccatt tccaaaccat atatttccaa caccctgccg   1080

tcggatgcac ccaagaagag gcgggctcca ctgcccccga tgccagcatc tcagagtgtc   1140

ccccaagacc ttgcacacat ccaggagagg cctgcttctt gtatagtgaa atccatgagc   1200

gtggatgaga cagataagag tccctgtgaa gcaggaagag tgagggcagg ttcactgcag   1260

ctcagcagca tgtctgcagg gaattcatct ttgagaagga caaagcgaaa agcaccttcc   1320

ccaccctcca aaataccccc gcatcaaagt gatgaaaata gtcgtgtgac tgccttacag   1380

ccagtagatg gagttcctcc agacagtgct tcagaagcaa actctcctga ggagctatcc   1440

agcccagaaa cctttcaccc tgggctttcc agtcaggagc agtgcactgc gcccaaactg   1500

atggaggaaa cctctgtctt tgagtgccct gggacacctg aggcagccat aacatcattg   1560

acatctggaa taagctctga ttatagcctt gaagagatag atgaaaagga agaactgagt   1620

gaagtgccta aagttgaagc tgaaaatatt tctccgaagt cacaagatat tccttttgta   1680
```

```
tctactgata taataaatac actgaaaaat gatcctgact cagcccttgg caatggtagt   1740
ggagagttct cacaaaactc catggaagaa aaacaagaaa ctaaaagcac agatggacaa   1800
gaaccacaca gtgtagtata tgatacaagc aatggaaaga aggtagttga cagtataaga   1860
aacttgaagt cgttgggccc aaaccaagag aatgttcaaa atgaaataat tgtctatcca   1920
gagaacacag aagacaatat gaaaaatgga gtgaagaaaa cagaaatcaa tgtagaaggt   1980
gttgccaaaa ataacaacat tgatatggaa gttgagagac catcaaactc tgaggcacat   2040
gaaactgata ctgctataag ttacaaggaa aaccatctag cagcttcatc agtaccagat   2100
caaaaactga atcaacccag tgcagaaaag acaaaagatg cagcaattca gacaacccct   2160
tcttgtaaca gttttgatgg gaaacaccaa gatcataatt tatctgactc caaagttgaa   2220
gaatgtgtgc aaacttcaaa taacaacata tcaactcaac actcatgctt aagttcacaa   2280
gattctgtaa atacctcaag ggaattcagg agtcaaggca ccctaattat acattcagaa   2340
gatccgctta ccgtaaaaga tccaatttgt gcacatggta atgatgatct tttgcctcct   2400
gtagatagga ttgacaaaaa ttccactgct tcttacctaa agaattaccc actttataga   2460
caggactaca atcccaagcc aaaaccttca aatgaaatta cacgagagta tatacccaaa   2520
attggcatga ctacttataa aatagtgcct cccaaatcct tggaaatatc gaaagactgg   2580
caatcagaaa ccatagagta taaagatgat caggacatgc atgctttagg gaaaaagcac   2640
actcatgaga atgtgaaaga aactgccatc caaacagaag attctgctat ttctgaaagc   2700
ccagaagagc cactgccaaa ccttaaaccg aagcctaacc tgagaacaga gcatcaagtg   2760
cccagttctg tgagctcacc tgatgatgcc atggttagtc ctctgaaacc tgctcccaaa   2820
atgacaagag acactggcac agctcctttt gcaccaaatt tggaagaaat aaacaatatt   2880
ttggaatcaa aatttaaatc tcgggcttca aatgcccagg ccaaacccag ctcttttttt   2940
ttgcagatgc agaagagagt atcgggtcac tatgtgacat ctgcagctgc caagagtgtc   3000
catgctgccc ctaatcctgc tccaaaagaa ctgacaaata aagaggcaga aagggatatg   3060
ctgccttctc cggagcagac tctttctccc ttaagtaaaa tgcctcactc tgttccacaa   3120
ccccttgttg aaaaaactga tgatgatgtc atcggtcagg ctcctgctga agcctcccct   3180
cctcccatag ctccaaaacc tgtgacaatt cctgctagtc aggtatccac acaaaatctg   3240
aagactttga aaacttttgg tgccccacga ccatactcaa gttctggtcc ttcaccgttt   3300
gctcttgctg tagtgaaaag gtcacagtct ttcagtaaag agcgcaccga gtcacctagt   3360
gccagtgcat tggtccaacc tccagccaac acagaggaag ggaagactca ttctgtaaat   3420
aaatttgtgg acatcccaca gcttggtgtg tctgataagg aaaataactc tgcacataat   3480
gaacagaatt cccaaatacc aactccaact gatggcccat cattcactgt tatgagacaa   3540
agttctttaa cattccaaag ctctgaccca gaacagatgc gacagagttt gctgactgca   3600
atccgttcgg gagaggctgc tgccaaattg aaaagggtta ccattccatc aaatacaata   3660
tctgtgaatg gaaggtcaag actcagccat tccatgtccc ctgatgccca ggacggccat   3720
taaatgttac cctgccacac cactgcactt cacttccact tcagaccaac ttcatactaa   3780
tggaacattt tggcaaatgt atattcagat gtacactaat atattatcta ttaaaatatt   3840
agaatttgtg ttgtggcttt taatgccaga agaaaagtta ccagaattta taatttatag   3900
taattttttg atcttttttt tgccttaaga gttgaatatg ctgctttaga actttaaaac   3960
aaggtgtaaa tgattttcat tttttacaaa tgaaaaataa ttcctttgta ttgatttcac   4020
ttaccagcac attctctaca atggtgactt agacaaaagt ataagattca tagactttat   4080
```

```
atttgtatga catacaacta ggacaaacat agatatgaca tttgctgcct cagtgtagca   4140

attggaaata tttataagtt atatgaaagc ctgttttggg ctgaaagaat gatttagaaa   4200

actagtgata ccaaataagt atattcagtt caataattat tttcaatgat gaatcactta   4260

gtgtgaaaga cttgccttgt gtattcttta tgtaattaca aatcactgtc aattttatgg   4320

gaagctcata gtattttaat attttattaa catggaactc ttgttttttt aatctttaga   4380

acttaaattc tacaagaatt ttaaatattt tctgtatata attatgacat tgtcacacag   4440

aaattacaca ttttatgtgc cagaagcctt aaacatcttt ctgtgaaaat gctgatatat   4500

tgtgacagtt atttcacatt tgatatgtag agaggaatag ggttagttt atgtttatat    4560

tgaaaaactt taaagactat ttggaagttc cagaaattct ggttttaatt caagtaaaat   4620

gataaaatag tcattatata gttcagatgc taatattcta agtaataata tatatttaca   4680

ttgaagctaa aactgttaag caaaacaatg cccatttgtc ggcttacagc tcttccggag   4740

tctagagcct gttggtgttc tgtccctact ttaagaattt aattgctcac ttattctgaa   4800

agctttgttc aaacaagatg atattaaatt tgttttcact aaaactactg ggatatctgc   4860

ctcttgggga tttttttttc aatttaataa aagcaagttg tatatttggg gtgcttttta   4920

aaa                                                                 4923
```

<210> SEQ ID NO 10
<211> LENGTH: 3806
<212> TYPE: DNA
<213> ORGANISM: Homo sapiens
<300> PUBLICATION INFORMATION:
<308> DATABASE ACCESSION NUMBER: NM_004244
<309> DATABASE ENTRY DATE: 2006-10-15
<313> RELEVANT RESIDUES IN SEQ ID NO: (1)..(3806)

<400> SEQUENCE: 10

```
gaattcttag ttgttttctt tagaagaaca tttctaggga ataatacaag aagatttagg     60

aatcattgaa gttataaatc tttggaatga gcaaactcag aatggtgcta cttgaagact    120

ctggatctgc tgacttcaga agacattttg tcaacttgag tcccttcacc attactgtgg    180

tcttacttct cagtgcctgt tttgtcacca gttctcttgg aggaacagac aaggagctga    240

ggctagtgga tggtgaaaac aagtgtagcg ggagagtgga agtgaaagtc caggaggagt    300

ggggaacggt gtgtaataat ggctggagca tggaagcggt ctctgtgatt tgtaaccagc    360

tgggatgtcc aactgctatc aaagcccctg gatgggctaa ttccagtgca ggttctggac    420

gcatttggat ggatcatgtt tcttgtcgtg ggaatgagtc agctctttgg gattgcaaac    480

atgatggatg gggaaagcat agtaactgta ctcaccaaca agatgctgga gtgacctgct    540

cagatggatc caatttggaa atgaggctga cgcgtggagg gaatatgtgt tctggaagaa    600

tagagatcaa attccaagga cggtggggaa cagtgtgtga tgataacttc aacatagatc    660

atgcatctgt catttgtaga caacttgaat gtggaagtgc tgtcagtttc tctggttcat    720

ctaattttgg agaaggctct ggaccaatct ggtttgatga tcttatatgc aacggaaatg    780

agtcagctct ctggaactgc aaacatcaag gatggggaaa gcataactgt gatcatgctg    840

aggatgctgg agtgatttgc tcaaagggag cagatctgag cctgagactg gtagatggag    900

tcactgaatg ttcaggaaga ttagaagtga gattccaagg agaatggggg acaatatgtg    960

atgacggctg ggacagttac gatgctgctg tggcatgcaa gcaactggga tgtccaactg   1020

ccgtcacagc cattggtcga gttaacgcca gtaagggatt tggacacatc tggcttgaca   1080

gcgtttcttg ccagggacat gaacctgctg tctggcaatg taaacaccat gaatggggaa   1140
```

```
agcattattg caatcacaat gaagatgctg gcgtgacatg ttctgatgga tcagatctgg   1200
agctaagact tagaggtgga ggcagccgct gtgctgggac agttgaggtg gagattcaga   1260
gactgttagg gaaggtgtgt gacagaggct ggggactgaa agaagctgat gtggtttgca   1320
ggcagctggg atgtggatct gcactcaaaa catcttatca agtgtactcc aaaatccagg   1380
caacaaacac atggctgttt ctaagtagct gtaacggaaa tgaaacttct ctttgggact   1440
gcaagaactg gcaatggggt ggacttacct gtgatcacta tgaagaagcc aaaattacct   1500
gctcagccca cagggaaccc agactggttg gaggggacat tccctgttct ggacgtgttg   1560
aagtgaagca tggtgacacg tggggctcca tctgtgattc ggacttctct ctggaagctg   1620
ccagcgttct atgcagggaa ttacagtgtg gcacagttgt ctctatcctg gggggagctc   1680
actttggaga gggaaatgga cagatctggg ctgaagaatt ccagtgtgag ggacatgagt   1740
cccatctttc actctgccca gtagcacccc gcccagaagg aacttgtagc cacagcaggg   1800
atgttggagt agtctgctca agatacacag aaattcgctt ggtgaatggc aagaccccgt   1860
gtgagggcag agtggagctc aaaacgcttg gtgcctgggg atccctctgt aactctcact   1920
gggacataga agatgcccat gttctttgcc agcagcttaa atgtggagtt gccctttcta   1980
ccccaggagg agcacgtttt ggaaaaggaa atggtcagat ctggaggcat atgtttcact   2040
gcactgggac tgagcagcac atgggagatt gtcctgtaac tgctctaggt gcttcattat   2100
gtccttcaga gcaagtggcc tctgtaatct gctcaggaaa ccagtcccaa acactgtcct   2160
cgtgcaattc atcgtctttg ggcccaacaa ggcctaccat tccagaagaa agtgctgtgg   2220
cctgcataga gagtggtcaa cttcgcctgg taaatggagg aggtcgctgt gctgggagag   2280
tagagatcta tcatgagggc tcctggggca ccatctgtga tgacagctgg gacctgagtg   2340
atgcccacgt ggtttgcaga cagctgggct gtggagaggc cattaatgcc actggttctg   2400
ctcattttgg ggaaggaaca gggcccatct ggctggatga gatgaaatgc aatggaaaag   2460
aatcccgcat ttggcagtgc cattcacacg gctgggggca gcaaaattgc aggcacaagg   2520
aggatgcggg agttatctgc tcagaattca tgtctctgag actgaccagt gaagccagca   2580
gagaggcctg tgcagggcgt ctggaagttt tttacaatgg agcttggggc actgttggca   2640
agagtagcat gtctgaaacc actgtgggtg tggtgtgcag gcagctgggc tgtgcagaca   2700
aagggaaaat caaccctgca tctttagaca aggccatgtc cattcccatg tgggtggaca   2760
atgttcagtg tccaaaagga cctgacacgc tgtggcagtg cccatcatct ccatgggaga   2820
agagactggc cagcccctcg gaggagacct ggatcacatg tgacaacaag ataagacttc   2880
aggaaggacc cacttcctgt tctggacgtg tggagatctg gcatggaggt tcctggggga   2940
cagtgtgtga tgactcttgg gacttggacg atgctcaggt ggtgtgtcaa caacttggct   3000
gtggtccagc tttgaaagca ttcaaagaag cagagtttgg tcaggggact ggaccgatat   3060
ggctcaatga agtgaagtgc aaagggaatg agtcttcctt gtgggattgt cctgccagac   3120
gctggggcca tagtgagtgt gggcacaagg aagacgctgc agtgaattgc acagatattt   3180
cagtgcagaa aaccccacaa aaagccacaa caggtcgctc atcccgtcag tcatcccttta   3240
ttgcagtcgg gatccttggg gttgttctgt tggccatttt cgtcgcatta ttcttcttga   3300
ctaaaaagcg aagacagaga cagcggcttg cagtttcctc aagaggagag aacttagtcc   3360
accaaattca ataccgggag atgaattctt gcctgaatgc agatgatctg gacctaatga   3420
attcctcaga aaattcccat gagtcagctg atttcagtgc tgctgaacta atttctgtgt   3480
ctaaatttct tcctatttct ggaatggaaa aggaggccat tctgagccac actgaaaagg   3540
```

```
aaaatgggaa tttataaccc agtgagttca gcctttaaga taccttgatg aagacctgga   3600

ctattgaatg gagcagaaat tcacctctct cactgactat tacagttgca tttttatgga   3660

gttcttcttc tcctaggatt cctaagactg ctgctgaatt tataaaaatt aagtttgtga   3720

atgtgactac ttagtggtgt atatgagact ttcaagggaa ttaaataaat aaataagaat   3780

gttattgatt tgagtttgct ttaatt                                        3806
```

```
<210> SEQ ID NO 11
<211> LENGTH: 3728
<212> TYPE: DNA
<213> ORGANISM: Homo sapiens
<300> PUBLICATION INFORMATION:
<308> DATABASE ACCESSION NUMBER: NM_203416
<309> DATABASE ENTRY DATE: 2006-10-15
<313> RELEVANT RESIDUES IN SEQ ID NO: (1)..(3728)

<400> SEQUENCE: 11

gaattcttag ttgttttctt tagaagaaca tttctaggga ataatacaag aagatttagg     60

aatcattgaa gttataaatc tttggaatga gcaaactcag aatggtgcta cttgaagact    120

ctggatctgc tgacttcaga agacattttg tcaacttgag tcccttcacc attactgtgg    180

tcttacttct cagtgcctgt tttgtcacca gttctcttgg aggaacagac aaggagctga    240

ggctagtgga tggtgaaaac aagtgtagcg ggagagtgga agtgaaagtc caggaggagt    300

ggggaacggt gtgtaataat ggctggagca tggaagcggt ctctgtgatt tgtaaccagc    360

tgggatgtcc aactgctatc aaagcccctg gatgggctaa ttccagtgca ggttctggac    420

gcatttggat ggatcatgtt tcttgtcgtg ggaatgagtc agctctttgg gattgcaaac    480

atgatggatg gggaaagcat agtaactgta ctcaccaaca agatgctgga gtgacctgct    540

cagatggatc caatttggaa atgaggctga cgcgtggagg gaatatgtgt tctggaagaa    600

tagagatcaa attccaagga cggtggggaa cagtgtgtga tgataacttc aacatagatc    660

atgcatctgt catttgtaga caacttgaat gtggaagtgc tgtcagtttc tctggttcat    720

ctaattttgg agaaggctct ggaccaatct ggtttgatga tcttatatgc aacggaaatg    780

agtcagctct ctggaactgc aaacatcaag gatggggaaa gcataactgt gatcatgctg    840

aggatgctgg agtgatttgc tcaaagggag cagatctgag cctgagactg gtagatggag    900

tcactgaatg ttcaggaaga ttagaagtga gattccaagg agaatggggg acaatatgtg    960

atgacggctg ggacagttac gatgctgctg tggcatgcaa gcaactggga tgtccaactg   1020

ccgtcacagc cattggtcga gttaacgcca gtaagggatt tggacacatc tggcttgaca   1080

gcgtttcttg ccagggacat gaacctgctg tctggcaatg taaacaccat gaatggggaa   1140

agcattattg caatcacaat gaagatgctg gcgtgacatg ttctgatgga tcagatctgg   1200

agctaagact tagaggtgga ggcagccgct gtgctgggac agttgaggtg gagattcaga   1260

gactgttagg gaaggtgtgt gacagaggct ggggactgaa agaagctgat gtggtttgca   1320

ggcagctggg atgtggatct gcactcaaaa catcttatca agtgtactcc aaaatccagg   1380

caacaaacac atggctgttt ctaagtagct gtaacggaaa tgaaacttct ctttgggact   1440

gcaagaactg gcaatggggt ggacttacct gtgatcacta tgaagaagcc aaaattacct   1500

gctcagccca cagggaaccc agactggttg gaggggacat tccctgttct ggacgtgttg   1560

aagtgaagca tggtgacacg tggggctcca tctgtgattc ggacttctct ctggaagctg   1620

ccagcgttct atgcagggaa ttacagtgtg gcacagttgt ctctatcctg gggggagctc   1680

actttggaga gggaaatgga cagatctggg ctgaagaatt ccagtgtgag ggacatgagt   1740
```

```
cccatctttc actctgccca gtagcacccc gcccagaagg aacttgtagc cacagcaggg   1800

atgttggagt agtctgctca agatacacag aaattcgctt ggtgaatggc aagaccccgt   1860

gtgagggcag agtggagctc aaaacgcttg gtgcctgggg atccctctgt aactctcact   1920

gggacataga agatgcccat gttctttgcc agcagcttaa atgtggagtt gccctttcta   1980

ccccaggagg agcacgtttt ggaaaaggaa atggtcagat ctggaggcat atgtttcact   2040

gcactgggac tgagcagcac atgggagatt gtcctgtaac tgctctaggt gcttcattat   2100

gtccttcaga gcaagtggcc tctgtaatct gctcaggaaa ccagtcccaa acactgtcct   2160

cgtgcaattc atcgtctttg ggcccaacaa ggcctaccat tccagaagaa agtgctgtgg   2220

cctgcataga gagtggtcaa cttcgcctgg taaatggagg aggtcgctgt gctgggagag   2280

tagagatcta tcatgagggc tcctggggca ccatctgtga tgacagctgg gacctgagtg   2340

atgcccacgt ggtttgcaga cagctgggct gtggagaggc cattaatgcc actggttctg   2400

ctcattttgg ggaaggaaca gggcccatct ggctggatga gatgaaatgc aatggaaaag   2460

aatcccgcat ttggcagtgc cattcacacg gctgggggca gcaaaattgc aggcacaagg   2520

aggatgcggg agttatctgc tcagaattca tgtctctgag actgaccagt gaagccagca   2580

gagaggcctg tgcagggcgt ctggaagttt tttacaatgg agcttggggc actgttggca   2640

agagtagcat gtctgaaacc actgtgggtg tggtgtgcag gcagctgggc tgtgcagaca   2700

aagggaaaat caaccctgca tctttagaca aggccatgtc cattcccatg tgggtggaca   2760

atgttcagtg tccaaaagga cctgacacgc tgtggcagtg cccatcatct ccatgggaga   2820

agagactggc cagcccctcg gaggagacct ggatcacatg tgacaacaag ataagacttc   2880

aggaaggacc cacttcctgt tctggacgtg tggagatctg gcatggaggt tcctggggga   2940

cagtgtgtga tgactcttgg gacttggacg atgctcaggt ggtgtgtcaa caacttggct   3000

gtggtccagc tttgaaagca ttcaaagaag cagagtttgg tcaggggact ggaccgatat   3060

ggctcaatga agtgaagtgc aaagggaatg agtcttcctt gtgggattgt cctgccagac   3120

gctggggcca tagtgagtgt gggcacaagg aagacgctgc agtgaattgc acagatattt   3180

cagtgcagaa aaccccacaa aaagccacaa caggtcgctc atcccgtcag tcatccttta   3240

ttgcagtcgg gatccttggg gttgttctgt tggccatttt cgtcgcatta ttcttcttga   3300

ctaaaaagcg aagacagaga cagcggcttg cagtttcctc aagaggagag aacttagtcc   3360

accaaattca ataccgggag atgaattctt gcctgaatgc agatgatctg gacctaatga   3420

attcctcagg aggccattct gagccacact gaaaaggaaa atgggaattt ataacccagt   3480

gagttcagcc tttaagatac cttgatgaag acctggacta ttgaatggag cagaaattca   3540

cctctctcac tgactattac agttgcattt ttatggagtt cttcttctcc taggattcct   3600

aagactgctg ctgaatttat aaaaattaag tttgtgaatg tgactactta gtggtgtata   3660

tgagactttc aagggaatta aataaataaa taagaatgtt attgatttga gtttgcttta   3720

attacttg                                                            3728
```

```
<210> SEQ ID NO 12
<211> LENGTH: 836
<212> TYPE: DNA
<213> ORGANISM: Homo sapiens
<300> PUBLICATION INFORMATION:
<308> DATABASE ACCESSION NUMBER: NM_002038
<309> DATABASE ENTRY DATE: 2006-08-20
<313> RELEVANT RESIDUES IN SEQ ID NO: (1)..(836)

<400> SEQUENCE: 12
```

```
ccagccttca gccggagaac cgtttactcg ctgctgtgcc catctatcag caggctccgg      60

gctgaagatt gcttctcttc tctcctccaa ggtctagtga cggagcccgc gcgcggcgcc     120

accatgcggc agaaggcggt atcgcttttc ttgtgctacc tgctgctctt cacttgcagt     180

ggggtggagg caggtaagaa aaagtgctcg gagagctcgg acagcggctc cgggttctgg     240

aaggccctga ccttcatggc cgtcggagga ggactcgcag tcgccgggct gcccgcgctg     300

ggcttcaccg gcgccggcat cgcggccaac tcggtggctg cctcgctgat gagctggtct     360

gcgatcctga atgggggcgg cgtgcccgcc ggggggctag tggccacgct gcagagcctc     420

ggggctggtg gcagcagcgt cgtcataggt aatattggtg ccctgatggg ctacgccacc     480

cacaagtatc tcgatagtga ggaggatgag gagtagccag cagctcccag aacctcttct     540

tccttcttgg cctaactctt ccagttagga tctagaactt tgcctttttt tttttttttt     600

tttttttgag atgggttctc actatattgt ccaggctaga gtgcagtggc tattcacaga     660

tgcgaacata gtacactgca gcctccaact cctagcctca agtgatcctc ctgtctcaac     720

ctcccaagta ggattacaag catgcgccga cgatgcccag aatccagaac tttgtctatc     780

actctcccca acaacctaga tgtgaaaaca gaataaactt cacccagaaa acactt         836
```

<210> SEQ ID NO 13
<211> LENGTH: 848
<212> TYPE: DNA
<213> ORGANISM: Homo sapiens
<300> PUBLICATION INFORMATION:
<308> DATABASE ACCESSION NUMBER: NM_022872
<309> DATABASE ENTRY DATE: 2006-08-20
<313> RELEVANT RESIDUES IN SEQ ID NO: (1)..(848)

<400> SEQUENCE: 13

```
ccagccttca gccggagaac cgtttactcg ctgctgtgcc catctatcag caggctccgg      60

gctgaagatt gcttctcttc tctcctccaa ggtctagtga cggagcccgc gcgcggcgcc     120

accatgcggc agaaggcggt atcgcttttc ttgtgctacc tgctgctctt cacttgcagt     180

ggggtggagg caggtgagaa tgcgggtaag aaaaagtgct cggagagctc ggacagcggc     240

tccgggttct ggaaggccct gaccttcatg gccgtcggag gaggactcgc agtcgccggg     300

ctgcccgcgc tgggcttcac cggcgccggc atcgcggcca actcggtggc tgcctcgctg     360

atgagctggt ctgcgatcct gaatgggggc ggcgtgcccg ccggggggct agtggccacg     420

ctgcagagcc tcggggctgg tggcagcagc gtcgtcatag gtaatattgg tgccctgatg     480

ggctacgcca cccacaagta tctcgatagt gaggaggatg aggagtagcc agcagctccc     540

agaacctctt cttccttctt ggcctaactc ttccagttag gatctagaac tttgcctttt     600

tttttttttt tttttttttg agatgggttc tcactatatt gtccaggcta gagtgcagtg     660

gctattcaca gatgcgaaca tagtacactg cagcctccaa ctcctagcct caagtgatcc     720

tcctgtctca acctcccaag taggattaca agcatgcgcc gacgatgccc agaatccaga     780

actttgtcta tcactctccc caacaaccta gatgtgaaaa cagaataaac ttcacccaga     840

aaacactt                                                              848
```

<210> SEQ ID NO 14
<211> LENGTH: 860
<212> TYPE: DNA
<213> ORGANISM: Homo sapiens
<300> PUBLICATION INFORMATION:
<308> DATABASE ACCESSION NUMBER: NM_022873
<309> DATABASE ENTRY DATE: 2006-08-20
<313> RELEVANT RESIDUES IN SEQ ID NO: (1)..(860)

<400> SEQUENCE: 14

```
ccagccttca gccggagaac cgtttactcg ctgctgtgcc catctatcag caggctccgg     60
gctgaagatt gcttctcttc tctcctccaa ggtctagtga cggagcccgc gcgcggcgcc    120
accatgcggc agaaggcggt atcgcttttc ttgtgctacc tgctgctctt cacttgcagt    180
ggggtggagg caggtgagaa tgcgggtaag gatgcaggta agaaaaagtg ctcggagagc    240
tcggacagcg gctccgggtt ctggaaggcc ctgaccttca tggccgtcgg aggaggactc    300
gcagtcgccg ggctgcccgc gctgggcttc accggcgccg gcatcgcggc caactcggtg    360
gctgcctcgc tgatgagctg gtctgcgatc ctgaatgggg gcggcgtgcc cgccgggggg    420
ctagtggcca cgctgcagag cctcggggct ggtggcagca gcgtcgtcat aggtaatatt    480
ggtgccctga tgggctacgc cacccacaag tatctcgata gtgaggagga tgaggagtag    540
ccagcagctc ccagaacctc ttcttccttc ttggcctaac tcttccagtt aggatctaga    600
actttgcctt tttttttttt tttttttttt tgagatgggt tctcactata ttgtccaggc    660
tagagtgcag tggctattca cagatgcgaa catagtacac tgcagcctcc aactcctagc    720
ctcaagtgat cctcctgtct caacctccca agtaggatta caagcatgcg ccgacgatgc    780
ccagaatcca gaactttgtc tatcactctc cccaacaacc tagatgtgaa aacagaataa    840
acttcaccca gaaaacactt                                                860
```

<210> SEQ ID NO 15
<211> LENGTH: 4894
<212> TYPE: DNA
<213> ORGANISM: Homo sapiens
<300> PUBLICATION INFORMATION:
<308> DATABASE ACCESSION NUMBER: NM_000212
<309> DATABASE ENTRY DATE: 2006-10-08
<313> RELEVANT RESIDUES IN SEQ ID NO: (1)..(4894)

<400> SEQUENCE: 15

```
cgccgcggga ggcggacgag atgcgagcgc ggccgcggcc ccggccgctc tgggcgactg     60
tgctggcgct gggggcgctg gcgggcgttg gcgtaggagg gcccaacatc tgtaccacgc    120
gaggtgtgag ctcctgccag cagtgcctgg ctgtgagccc catgtgtgcc tggtgctctg    180
atgaggccct gcctctgggc tcacctcgct gtgacctgaa ggagaatctg ctgaaggata    240
actgtgcccc agaatccatc gagttcccag tgagtgaggc ccgagtacta gaggacaggc    300
ccctcagcga caagggctct ggagacagct cccaggtcac tcaagtcagt ccccagagga    360
ttgcactccg gctccggcca gatgattcga agaatttctc catccaagtg cggcaggtgg    420
aggattaccc tgtggacatc tactacttga tggacctgtc ttactccatg aaggatgatc    480
tgtggagcat ccagaacctg ggtaccaagc tggccaccca gatgcgaaag ctcaccagta    540
acctgcggat tggcttcggg gcatttgtgg acaagcctgt gtcaccatac atgtatatct    600
ccccaccaga ggccctcgaa aacccctgct atgatatgaa gaccacctgc ttgcccatgt    660
ttggctacaa acacgtgctg acgctaactg accaggtgac ccgcttcaat gaggaagtga    720
agaagcagag tgtgtcacgg aaccgagatg ccccagaggg tggctttgat gccatcatgc    780
aggctacagt ctgtgatgaa aagattggct ggaggaatga tgcatcccac ttgctggtgt    840
ttaccactga tgccaagact catatagcat tggacggaag gctggcaggc attgtccagc    900
ctaatgacgg gcagtgtcat gttggtagtg acaatcatta ctctgcctcc actaccatgg    960
attatccctc tttggggctg atgactgaga agctatccca gaaaaacatc aatttgatct   1020
ttgcagtgac tgaaaatgta gtcaatctct atcagaacta tagtgagctc atcccaggga   1080
```

```
ccacagttgg ggttctgtcc atggattcca gcaatgtcct ccagctcatt gttgatgctt   1140

atgggaaaat ccgttctaaa gtagagctgg aagtgcgtga cctccctgaa gagttgtctc   1200

tatccttcaa tgccacctgc ctcaacaatg aggtcatccc tggcctcaag tcttgtatgg   1260

gactcaagat tggagacacg gtgagcttca gcattgaggc caaggtgcga ggctgtcccc   1320

aggagaagga gaagtccttt accataaagc ccgtgggctt caaggacagc ctgatcgtcc   1380

aggtcacctt tgattgtgac tgtgcctgcc aggcccaagc tgaacctaat agccatcgct   1440

gcaacaatgg caatgggacc tttgagtgtg ggtatgccg ttgtgggcct ggctggctgg   1500

gatcccagtg tgagtgctca gaggaggact atcgcccttc ccagcaggac gaatgcagcc   1560

cccgggaggg tcagcccgtc tgcagccagc ggggcgagtg cctctgtggt caatgtgtct   1620

gccacagcag tgactttggc aagatcacgg gcaagtactg cgagtgtgac gacttctcct   1680

gtgtccgcta caagggggag atgtgctcag gccatggcca gtgcagctgt ggggactgcc   1740

tgtgtgactc cgactggacc ggctactact gcaactgtac cacgcgtact gacacctgca   1800

tgtccagcaa tgggctgctg tgcagcggcc gcggcaagtg tgaatgtggc agctgtgtct   1860

gtatccagcc gggctcctat ggggacacct gtgagaagtg ccccacctgc ccagatgcct   1920

gcacctttaa gaaagaatgt gtggagtgta agaagtttga ccggggagcc ctacatgacg   1980

aaaatacctg caaccgttac tgccgtgacg agattgagtc agtgaaagag cttaaggaca   2040

ctggcaagga tgcagtgaat tgtacctata agaatgagga tgactgtgtc gtcagattcc   2100

agtactatga agattctagt ggaaagtcca tcctgtatgt ggtagaagag ccagagtgtc   2160

ccaagggccc tgacatcctg gtggtcctgc tctcagtgat gggggccatt ctgctcattg   2220

gccttgccgc cctgctcatc tggaaactcc tcatcaccat ccacgaccga aaagaattcg   2280

ctaaatttga ggaagaacgc gccagagcaa aatgggacac agccaacaac ccactgtata   2340

aagaggccac gtctaccttc accaatatca cgtaccgggg cacttaatga taagcagtca   2400

tcctcagatc attatcagcc tgtgccacga ttgcaggagt ccctgccatc atgtttacag   2460

aggacagtat ttgtggggag ggatttgggg ctcagagtgg ggtaggttgg gagaatgtca   2520

gtatgtggaa gtgtgggtct gtgtgtgtgt atgtgggggt ctgtgtgttt atgtgtgtgt   2580

gttgtgtgtg ggagtgtgta atttaaaatt gtgatgtgtc ctgataagct gagctcctta   2640

gcctttgtcc cagaatgcct cctgcaggga ttcttcctgc ttagcttgag ggtgactatg   2700

gagctgagca ggtgttcttc attacctcag tgagaagcca gctttcctca tcaggccatt   2760

gtccctgaag agaagggcag ggctgaggcc tctcattcca gaggaaggga caccaagcct   2820

tggctctacc ctgagttcat aaatttatgg ttctcaggcc tgactctcag cagctatggt   2880

aggaactgct gggcttggca gcccgggtca tctgtacctc tgcctccttt cccctccctc   2940

aggccgaagg aggagtcagg gagagctgaa ctattagagc tgcctgtgcc ttttgccatc   3000

ccctcaaccc agctatggtt ctctcgcaag ggaagtcctt gcaagctaat tctttgacct   3060

gttgggagtg aggatgtctg ggccactcag gggtcattca tggcctgggg gatgtaccag   3120

catctcccag ttcataatca caacccttca gatttgcctt attggcagct ctactctgga   3180

ggtttgttta gaagaagtgt gtcaccctta ggccagcacc atctctttac ctcctaattc   3240

cacaccctca ctgctgtaga catttgctat gagctgggga tgtctctcat gaccaaatgc   3300

ttttcctcaa agggagagag tgctattgta gagccagagg tctggcccta tgcttccggc   3360

ctcctgtccc tcatccatag cacctccaca tacctggccc tgtgccttgg tgtgctgtat   3420

ccatccatgg ggctgattgt atttaccttc tacctcttgg ctgccttgtg aaggaattat   3480
```

```
tcccatgagt tggctgggaa taagtgccag gatggaatga tgggtcagtt gtatcagcac   3540
gtgtggcctg ttcttctatg ggttggacaa cctcatttta actcagtctt taatctgaga   3600
ggccacagtg caattttatt ttattttttct catgatgagg ttttcttaac ttaaaagaac   3660
atgtatataa acatgcttgc attatatttg taaatttatg tgatggcaaa gaaggagagc   3720
ataggaaacc acacagactt gggcagggta cagacactcc cacttggcat cattcacagc   3780
aagtcactgg ccagtggctg gatctgtgag gggctctctc atgatagaag gctatgggga   3840
tagatgtgtg gacacattgg acctttcctg aggaagaggg actgttcttt tgtcccagaa   3900
aagcagtggc tccattggtg ttgacataca tccaacatta aaagccaccc ccaaatgccc   3960
aagaaaaaaa gaaagactta tcaacatttg ttccatgagc agaaaactgg agctctggcc   4020
tcagtgttac agctaaataa tctttaatta aggcaagtca ctttcttctt cttaaagctg   4080
ttttctagtt tgagaaatga tgggatttta gcagccagtc ttgaaggtct ctttcagtat   4140
caacattcta agatgctggg acttactgtg tcatcaaatg tgcggttaag attctctggg   4200
atattgatac tgtttgtgtt tttagttggg agatctgaga gacctggctt tggcaagagc   4260
agatgtcatt ccatatcacc tttctcaatg aaagtctcat tctatcctct ctccaaaccc   4320
gttttccaac atttgttaat agttacgtct ctcctgatgt agcacttaag cttcatttag   4380
ttattatttc tttcttcact ttgcacacat ttgcatccac atattaggga agaggaatcc   4440
ataagtagct gaaatatcta ttctgtatta ttgtgttaac attgagaata agccttggaa   4500
ttagatatgg ggcaatgact gagccctgtc tcacccatgg attactcctt actgtaggga   4560
atggcagtat ggtagaggga taaatagggg gcggggaggg atagtcatgg atccaagaag   4620
tccttagaaa tagtggcagg gaacaggtgt ggaagctcat gcctgtaatt ataaccttca   4680
gctactaaga caggtgtggt ggctcacgcc tgtgattata atcttcagtt actaagacag   4740
agtccatgag agtgttaatg ggacattttc tttagataag atgttttata tgaagaaact   4800
gtatcaaagg gggaagaaaa tgtatttaac aggtgaatca aatcaggaat cttgtctgag   4860
ctactggaat gaagttcaca ggtcttgaag acca                              4894
```

<210> SEQ ID NO 16
<211> LENGTH: 1574
<212> TYPE: DNA
<213> ORGANISM: Homo sapiens
<300> PUBLICATION INFORMATION:
<308> DATABASE ACCESSION NUMBER: NM_001001522
<309> DATABASE ENTRY DATE: 2006-10-15
<313> RELEVANT RESIDUES IN SEQ ID NO: (1)..(1574)

<400> SEQUENCE: 16

```
tcaccacggc ggcagccctt taaacccctc acccagccag cgccccatcc tgtctgtccg     60
aacccagaca caagtcttca ctccttcctg cgagccctga ggaagccttg tgagtgcatt    120
ggctggggct tggagggaag ttgggctgga gctggacagg agcagtgggt gcatttcagg    180
caggctctcc tgaggtccca ggcgccagct ccagctccct ggctagggaa acccaccctc    240
tcagtcagca tgggggccca agctccaggc agggtgggct ggatcactag cgtcctggat    300
ctctctcaga ctgggcagcc ccgggctcat tgaaatgccc cggatgactt ggctagtgca    360
gaggaattga tggaaaccac cggggtgaga gggaggctcc ccatctcagc cagccacatc    420
cacaaggtgt gtgtaagggt gcaggcgccg gccggttagg ccaaggctct actgtctgtt    480
gcccctccag gagaacttcc aaggagcttt ccccagacat ggccaacaag ggtccttcct    540
atggcatgag ccgcgaagtg cagtccaaaa tcgagaagaa gtatgacgag gagctggagg    600
```

```
agcggctggt ggagtggatc atagtgcagt gtggccctga tgtgggccgc ccagaccgtg    660

ggcgcttggg cttccaggtc tggctgaaga atggcgtgat tctgagcaag ctggtgaaca    720

gcctgtaccc tgatggctcc aagccggtga aggtgcccga gaacccaccc tccatggtct    780

tcaagcagat ggagcaggtg gctcagttcc tgaaggcggc tgaggactat ggggtcatca    840

agactgacat gttccagact gttgacctct ttgaaggcaa agacatggca gcagtgcaga    900

ggaccctgat ggctttgggc agcttggcag tgaccaagaa tgatgggcac taccgtggag    960

atcccaactg gtttatgaag aaagcgcagg agcataagag ggaattcaca gagagccagc   1020

tgcaggaggg aaagcatgtc attggccttc agatgggcag caacagaggg gcctcccagg   1080

ccggcatgac aggctacgga cgacctcggc agatcatcag ttagagcgga gagggctagc   1140

cctgagcccg gccctccccc agctccttgg ctgcagccat cccgcttagc ctgcctcacc   1200

cacacccgtg tggtaccttc agccctggcc aagctttgag gctctgtcac tgagcaatgg   1260

taactgcacc tgggcagctc ctccctgtgc cccagcctc agcccaactt cttacccgaa    1320

agcatcactg ccttggcccc tccctcccgg ctgcccccat cacctctact gtctcctccc   1380

tgggctaagc aggggagaag cgggctgggg gtagcctgga tgtgggccaa gtccactgtc   1440

ctccttggcg gcaaaagccc attgaagaag aaccagccca gcctgccccc tatcttgtcc   1500

tggaatattt ttggggttgg aactcaaaaa aaaaaaaaaa aaatcaatct tttctcaaaa   1560

aaaaaaaaaa aaaa                                                     1574


<210> SEQ ID NO 17
<211> LENGTH: 1177
<212> TYPE: DNA
<213> ORGANISM: Homo sapiens
<300> PUBLICATION INFORMATION:
<308> DATABASE ACCESSION NUMBER: NM_003186
<309> DATABASE ENTRY DATE: 2006-10-15
<313> RELEVANT RESIDUES IN SEQ ID NO: (1)..(1177)

<400> SEQUENCE: 17

tcaccacggc ggcagccctt taaacccctc acccagccag cgccccatcc tgtctgtccg     60

aacccagaca caagtcttca ctccttcctg cgagccctga ggaagccttc tttccccaga    120

catggccaac aagggtcctt cctatggcat gagccgcgaa gtgcagtcca aaatcgagaa    180

gaagtatgac gaggagctgg aggagcggct ggtggagtgg atcatagtgc agtgtggccc    240

tgatgtgggc cgcccagacc gtgggcgctt gggcttccag gtctggctga agaatggcgt    300

gattctgagc aagctggtga acagcctgta ccctgatggc tccaagccgg tgaaggtgcc    360

cgagaaccca ccctccatgg tcttcaagca gatggagcag gtggctcagt tcctgaaggc    420

ggctgaggac tatggggtca tcaagactga catgttccag actgttgacc tctttgaagg    480

caaagacatg gcagcagtgc agaggaccct gatggctttg ggcagcttgg cagtgaccaa    540

gaatgatggg cactaccgtg gagatcccaa ctggtttatg aagaaagcgc aggagcataa    600

gagggaattc acagagagcc agctgcagga gggaaagcat gtcattggcc ttcagatggg    660

cagcaacaga ggggcctccc aggccggcat gacaggctac ggacgacctc ggcagatcat    720

cagttagagc ggagagggct agccctgagc ccggccctcc cccagctcct tggctgcagc    780

catcccgctt agcctgcctc acccacaccc gtgtggtacc ttcagccctg gccaagcttt    840

gaggctctgt cactgagcaa tggtaactgc acctgggcag ctcctccctg tgcccccagc    900

ctcagcccaa cttcttaccc gaaagcatca ctgccttggc cctccctcc cggctgcccc     960

catcacctct actgtctcct ccctgggcta agcaggggag aagcgggctg gggtagcct    1020
```

ggatgtgggc caagtccact gtcctccttg gcggcaaaag cccattgaag aagaaccagc 1080
ccagcctgcc ccctatcttg tcctggaata tttttggggt tggaactcaa aaaaaaaaaa 1140
aaaaaatcaa tcttttctca aaaaaaaaaa aaaaaaa 1177

<210> SEQ ID NO 18
<211> LENGTH: 985
<212> TYPE: DNA
<213> ORGANISM: Homo sapiens
<300> PUBLICATION INFORMATION:
<308> DATABASE ACCESSION NUMBER: NM_001785
<309> DATABASE ENTRY DATE: 2006-08-20
<313> RELEVANT RESIDUES IN SEQ ID NO: (1)..(985)

<400> SEQUENCE: 18
caaaccatgg gaggctcctc tcctagaccc tgcatcctga aagctgcgta cctgagagcc 60
tgcggtctgg ctgcagggac acacccaagg ggaggagctg caatcgtgtc tggggcccca 120
gcccaggctg gccggagctc ctgtttcccg ctgctctgct gcctgcccgg ggtaccaaca 180
tggcccagaa gcgtcctgcc tgcaccctga agcctgagtg tgtccagcag ctgctggttt 240
gctcccagga ggccaagaag tcagcctact gcccctacag tcactttcct gtgggggctg 300
ccctgctcac ccaggagggg agaatcttca aagggtgcaa catagaaaat gcctgctacc 360
cgctgggcat ctgtgctgaa cggaccgcta tccagaaggc cgtctcagaa gggtacaagg 420
atttcagggc aattgctatc gccagtgaca tgcaagatga ttttatctct ccatgtgggg 480
cctgcaggca agtcatgaga gagtttggca ccaactggcc cgtgtacatg accaagccgg 540
atggtacgta tattgtcatg acggtccagg agctgctgcc ctcctccttt gggcctgagg 600
acctgcagaa gacccagtga cagccagaga atgcccactg cctgtaacag ccacctggag 660
aacttcataa agatgtctca cagccctggg gacacctgcc cagtgggccc cagccctaca 720
gggactgggc aaagatgatg tttccagatt acactccagc ctgagtcagc acccctccta 780
gcaacctgcc ttgggactta gaacaccgcc gccccctgcc ccacctttcc tttccttcct 840
gtgggccctc tttcaaagtc cagcctagtc tggactgctt ccccatcagc cttcccaagg 900
ttctatcctg ttccgagcaa cttttctaat tataaacatc acagaacatc ctggatcaaa 960
aaaaaaaaaa aaaaaaaaaa aaaaa 985

<210> SEQ ID NO 19
<211> LENGTH: 1828
<212> TYPE: DNA
<213> ORGANISM: Homo sapiens
<300> PUBLICATION INFORMATION:
<308> DATABASE ACCESSION NUMBER: NM_013314
<309> DATABASE ENTRY DATE: 2006-10-15
<313> RELEVANT RESIDUES IN SEQ ID NO: (1)..(1828)

<400> SEQUENCE: 19
acttctccct agagcagggg tgtttgccag cagcctgcac tctcagaaat cagacttgag 60
tggccggaac ccttgagacc agaggcttac catgctgctc cctaggaggg ccaggaactg 120
ctgacgtgac cactggacag ttattcgtgt ctcttacaat taccaaacag aatggacaag 180
cttaataaaa taaccgtccc cgccagtcag aagttgaggc agcttcaaaa gatggtccat 240
gatattaaaa acaatgaagg tggaataatg aataaaatca aaaagctaaa agtcaaagca 300
cctccaagtg ttcctcgaag ggactacgct tcagagagcc ctgctgacga agaggagcag 360
tggtccgatg actttgacag cgactatgaa aatccagatg agcactcgga ctcagagatg 420
tacgtgatgc ccgccgagga gaacgctgat gacagctacg agccgcctcc agtagagcag 480

```
gaaaccaggc cggttcaccc agccctgccc ttcgccagag gcgagtatat agacaatcga    540

tcaagccaga ggcattcccc acccttcagc aagacacttc ccagtaagcc cagctggcct    600

tcagagaaag caaggctcac ctccaccctg ccggccctga ctgctttgca gaaacctcaa    660

gtcccaccca aacccaaagg cctccttgag gatgaggctg attatgtggt ccccgtggaa    720

gataatgatg aaaactatat tcatcccaca gaaagcagtt cacctccacc tgaaaaagct    780

cccatggtga atagatcaac caagccaaat tcctcaacgc ccgcctctcc tccaggaaca    840

gcttcaggtc gaaacagtgg ggcctgggaa accaagtcac ctccaccagc tgcaccatcc    900

ccgttgccac gggccgggaa aaaaccaacg acaccactga agacaactcc agttgcctct    960

caacagaatg cttcaagtgt ttgtgaagaa aaacctatac ctgctgaacg ccaccgaggg   1020

tcaagtcaca gacaagaagc tgtgcagtca ccagtgtttc ctcctgccca gaaacaaatc   1080

caccaaaaac ccatacctct gccaagattt acagaagggg gaaacccaac tgtggatggg   1140

cccctaccca gcttttcatc taattccact atttcagaac aggaagctgg cgttctctgc   1200

aagccatggt atgctggagc ctgtgatcga aagtctgctg aagaggcatt gcacagatca   1260

aacaaggatg gatcatttct tattcggaaa agctctggcc atgattccaa acaaccatat   1320

acactagttg tattctttaa taagcgagta tataatattc ctgtgcgatt tattgaagca   1380

acaaaacaat atgccttggg cagaaagaaa aatggtgaag agtactttgg aagtgttgct   1440

gaaatcatca ggaatcatca acatagtcct ttggttctta ttgacagtca gaataacaca   1500

aaagattcca ccagactgaa gtatgcagtt aaagtttcat aaagggggaa aaaaaagatc   1560

aataccattg cttcagacac tttcccaaag tttctccttt tgagaaaaag tcccaaaact   1620

tcatattttg gattatgaat catccagtaa taaaatggaa gatggagtca gctattgaag   1680

tggtcatcca tttcttttta agaagctcat gtggacttgt tctattgcct gacctgatga   1740

actgttaata tctggtgagg ttgagttatc atgctactaa tattttccaa ataaatattt   1800

ttatttttaa aaataaaaaa aaaaaaaa                                      1828
```

```
<210> SEQ ID NO 20
<211> LENGTH: 1364
<212> TYPE: DNA
<213> ORGANISM: Homo sapiens
<300> PUBLICATION INFORMATION:
<308> DATABASE ACCESSION NUMBER: NM_002262
<309> DATABASE ENTRY DATE: 2006-08-20
<313> RELEVANT RESIDUES IN SEQ ID NO: (1)..(1364)

<400> SEQUENCE: 20

ctgtattgtg gttcctggaa cactttagag gcttgtgatt ctactgcttc ttattcacac     60

tataatacat gtctcaccaa tagatgattc aagaacatca tttaaataca caatttttca    120

ttctctattt ttgctaaatt tcttcatact caactttcag attctttaat ctccagctca    180

gcttcaacaa ttcaacgctg ttctttctga aaaagtacac atcgtgcctt ctctacttcg    240

ctcttggaac ataatttctc atggcagtgt ttaagaccac tctgtggagg ttaatttctg    300

ggaccttagg gataaatatgc ctttcgttga tggctacgtt gggaattttg ttgaaaaatt    360

cttttactaa actgagtatt gagccagcat ttactccagg acccaacata gaactccaga    420

aagactctga ctgctgttct tgccaagaaa aatgggttgg gtaccggtgc aactgttact    480

tcatttccag tgaacagaaa acttggaacg aaagtcggca tctctgtgct tctcagaaat    540

ccagcctgct tcagcttcaa aacacagatg aactggattt tatgagctcc agtcaacaat    600

tttactggat tggactctct tacagtgagg agcacaccgc ctggttgtgg gagaatggct    660
```

```
ctgcactctc ccagtatcta tttccatcat ttgaaacttt taatacaaag aactgcatag    720

cgtataatcc aaatggaaat gctttagatg aatcctgtga agataaaaat cgttatatct    780

gtaagcaaca gctcatttaa atgtttcttg gggcagagaa ggtggagagt aaagacccaa    840

cattactaac aatgatacag ttgcatgtta tattattact aattgtctac ttctggagtc    900

tataaaatgt ttttaaacag tgtcatatac aattgtcatg tatgtgaaac aatgtgtttt    960

aaaattgatg aaattcgttc acctacattt gagaattata aaattaacat aaagaatttt   1020

gtattttcat ttaatgtata taatgttaaa ttcaatgtag ttttattaca catttatgta   1080

attttattta cattcttgct aattctcagc agaaatttaa ataagattta attcacatca   1140

aataaaattt agaaaataaa atttaactca cactgcccag gctggagcat agtggcaaga   1200

tcatagctca ttgcaagctc aagtgatcct cctgactcag cctcccaagt agctaggact   1260

gcaggcacca tgtcactatg cccgactaat ttttaatttt taattttttg tcaagacaag   1320

gtcttgctat gttgcccagg ctggtcttga actcctggcc tcaa                    1364
```

```
<210> SEQ ID NO 21
<211> LENGTH: 1271
<212> TYPE: DNA
<213> ORGANISM: Homo sapiens
<300> PUBLICATION INFORMATION:
<308> DATABASE ACCESSION NUMBER: NM_007334
<309> DATABASE ENTRY DATE: 2006-08-20
<313> RELEVANT RESIDUES IN SEQ ID NO: (1)..(1271)

<400> SEQUENCE: 21

ctgtattgtg gttcctggaa cactttagag gcttgtgatt ctactgcttc ttattcacac     60

tataatacat gtctcaccaa tagatgattc aagaacatca tttaaataca caatttttca    120

ttctctattt ttgctaaatt tcttcatact caactttcag attctttaat ctccagctca    180

gcttcaacaa ttcaacgctg ttctttctga aaaagtacac atcgtgcctt ctctacttcg    240

ctcttggaac ataatttctc atggcagctt ttactaaact gagtattgag ccagcattta    300

ctccaggacc caacatagaa ctccagaaag actctgactg ctgttcttgc caagaaaaat    360

gggttgggta ccggtgcaac tgttacttca tttccagtga acagaaaact tggaacgaaa    420

gtcggcatct ctgtgcttct cagaaatcca gcctgcttca gcttcaaaac acagatgaac    480

tggattttat gagctccagt caacaatttt actggattgg actctcttac agtgaggagc    540

acaccgcctg gttgtgggag aatggctctg cactctccca gtatctattt ccatcatttg    600

aaacttttaa tacaaagaac tgcatagcgt ataatccaaa tggaaatgct ttagatgaat    660

cctgtgaaga taaaaatcgt tatatctgta agcaacagct catttaaatg tttcttgggg    720

cagagaaggt ggagagtaaa gacccaacat tactaacaat gatacagttg catgttatat    780

tattactaat tgtctacttc tggagtctat aaaatgtttt taaacagtgt catatacaat    840

tgtcatgtat gtgaaacaat gtgttttaaa attgatgaaa ttcgttcacc tacatttgag    900

aattataaaa ttaacataaa gaattttgta ttttcattta atgtatataa tgttaaattc    960

aatgtagttt tattacacat ttatgtaatt ttatttacat tcttgctaat tctcagcaga   1020

aatttaaata agatttaatt cacatcaaat aaaatttaga aaataaaatt taactcacac   1080

tgcccaggct ggagcatagt ggcaagatca tagctcattg caagctcaag tgatcctcct   1140

gactcagcct cccaagtagc taggactgca ggcaccatgt cactatgccc gactaatttt   1200

taatttttaa tttttgtca agacaaggtc ttgctatgtt gcccaggctg gtcttgaact   1260

cctggcctca a                                                        1271
```

<210> SEQ ID NO 22
<211> LENGTH: 374
<212> TYPE: DNA
<213> ORGANISM: Homo sapiens
<300> PUBLICATION INFORMATION:
<308> DATABASE ACCESSION NUMBER: NM_003543
<309> DATABASE ENTRY DATE: 2006-10-18
<313> RELEVANT RESIDUES IN SEQ ID NO: (1)..(374)

<400> SEQUENCE: 22

```
atgtctggcc gtggtaaagg tggaaaaggt ttgggtaagg gaggagctaa gcgtcatcgc     60

aaggttttgc gcgataacat ccagggcatc actaagccag ctatccggcg ccttgctcgt    120

cgcggcggtg tcaagcgaat ttctggcctt atctatgagg agactcgtgg tgttctgaag    180

gtgttcctgg agaacgtgat tcgtgacgct gtcacttaca cagagcacgc caaacgcaag    240

accgtgacag caatggatgt ggtctacgcg ctgaagcgac agggacgcac tctttacggc    300

ttcggtggct aaggctcctg cttgctgcac tcttattttc attttcaacc aaaggccctt    360

ttcagggccg ccca                                                      374
```

<210> SEQ ID NO 23
<211> LENGTH: 13302
<212> TYPE: DNA
<213> ORGANISM: Homo sapiens
<300> PUBLICATION INFORMATION:
<308> DATABASE ACCESSION NUMBER: NM_006738
<309> DATABASE ENTRY DATE: 2006-08-20
<313> RELEVANT RESIDUES IN SEQ ID NO: (1)..(13302)

<400> SEQUENCE: 23

```
gaagcgcctg tgctctgccg agactgccgt gcccattgct cgcctcggtc gccgccgctt     60

tagccgcctc cgggggagcg gccgcctatt gtctttctcc gcggcgaagg tgaagagttg    120

tcccagctcg gcccgcgggg gagccccggg agccgcacgt gtcctgggtc atgaaactta    180

atccacagca agctccctta tatggtgatt gtgttgttac agtgctgctt gctgaagagg    240

acaaagctga agatgatgta gtgttttact tggtattttt gggttccacc ctccgtcact    300

gtacaagtac tcggaaggtc agttctgata cattggagac cattgctcct ggtcatgatt    360

gttgtgaaac agtgaaggtg cagctctgtg cttccaaaga gggccttccc gtgtttgtgg    420

tggctgaaga agactttcat ttcgtccagg atgaagcgta tgatgcagct caattcctag    480

caaccagtgc tggaaatcag caggctttga actttacccg ttttcttgac cagtcaggac    540

ccccatctgg ggatgtgaat tcccttgata agaagttggt gctggcattc aggcacctga    600

agctgcccac ggagtggaat gtattgggga cagatcagag tttgcatgat gctggcccgc    660

gagagacatt gatgcatttt gctgtgcggc tgggactgct gaggttgacg tggttcctgt    720

tgcagaagcc aggtggccgc ggagctctca gtatccacaa ccaggaaggg gcgacgcctg    780

tgagcttggc cttggagcga ggctatcaca agctgcacca gcttctaacc gaggagaatg    840

ctggagaacc agactcctgg agcagtttat cctatgaaat accgtatgga gactgttctg    900

tgaggcatca tcgagagttg gacatctata cattaacctc tgagtctgat tcacatcatg    960

aacacccatt tcctggagac ggttgcactg gaccaatttt taaacttatg aacatccaac   1020

agcaactaat gaaaacaaac ctcaagcaga tggacagtct tatgccctta atgatgacag   1080

cacaggatcc ttccagtgcc ccagagacag atggccagtt tcttccctgt gcaccggagc   1140

ccacggaccc tcagcgactt tcttcttctg aagagactga gagcactcag tgctgcccag   1200

ggagccctgt tgcacagact gaaagtccct gtgatttgtc aagcatagtt gaggaggaga   1260
```

-continued

```
atacagaccg ttcctgtagg aagaaaaata aaggcgtgga aagaaaaggg gaagaggtgg   1320
agccagcacc tattgtggac tctggaactg tatctgatca agacagctgc cttcagagct   1380
tgcctgattg tggagtaaag ggcacggaag gcctttcgtc ctgtggaaac agaaatgaag   1440
aaactggaac aaaatcttct ggaatgccca cagaccagga gtccctgagc agtggagatg   1500
ctgtgcttca gagagacttg gtcatggagc caggcacagc ccagtattcc tctggaggtg   1560
aactgggagg catttcaaca acaaatgtca gtaccccaga cactgcaggg gaaatggaac   1620
atgggctcat gaacccagat gccactgttt ggaagaatgt gcttcaggga ggggaaagta   1680
caaaggaaag atttgagaac tctaatattg gcacagctgg agcctctgac gtgcacgtca   1740
caagtaagcc tgtggataaa atcagtgttc caaactgtgc ccctgctgcc agttccctgg   1800
atggtaacaa acctgctgag tcttcacttg catttagtaa tgaagaaacc tccactgaaa   1860
aaacagcaga aacggaaact tcacgaagtc gtgaggagag tgctgatgct ccagtagatc   1920
agaattctgt ggtgattcca gctgctgcaa aagacaagat ttcagatgga ttagaacctt   1980
atactctctt agcagcaggc ataggtgagg caatgtcacc ctcagattta gcccttcttg   2040
ggctggaaga agatgtaatg ccacaccaga actcagaaac aaattcatct catgctcaaa   2100
gccaaaaggg caaatcctca cccatttgtt ctacaactgg agacgataaa ctttgtgcag   2160
actctgcatg tcaacagaac acagtgactt ctagtggcga tttggttgca aaactgtgtg   2220
ataacatagt tagcgagtcc gaaagcacca cagcaaggca acccagctca caagatccac   2280
ccgatgcctc ccactgtgaa gacccacagg ctcatacagt cacctctgac cctgtaaggg   2340
atacccagga acgtgcggat ttttgtcctt tcaaagtggt ggataacaaa ggccaacgaa   2400
aagatgtgaa actagataaa cctttaacaa atatgcttga ggtggtttca catccacatc   2460
cagttgtccc taaaatggag aaagaactgg tgccagacca ggcagtaata tcagacagta   2520
ctttctctct ggcaaacagt ccaggcagtg aatcagtaac caaggatgac gcactttctt   2580
ttgtcccctc ccagaaagaa aagggaacag caactcctga actacataca gctacagatt   2640
atagagatgg cccagatgga aattcgaatg agcctgatac gcggccacta gaagacaggg   2700
cagtaggcct gtccacatcc tccactgctg cagagcttca gcacgggatg gggaatacca   2760
gtctcacagg acttggtgga gagcatgagg gtcccgcccc tccagcaatc ccagaagctc   2820
tgaatatcaa ggggaacact gactcttccc tgcaaagtgt gggtaaggcc actttggctt   2880
tagattcagt tttgactgaa gaaggaaaac ttctggtggt ttcagaaagc tctgcagctc   2940
aggaacaaga taaggataaa gcggtgacct gttcctctat taaggaaaat gctctctctt   3000
caggaacttt gcaggaagag cagagaacac cacctcctgg acaagatact caacaatttc   3060
atgaaaaatc aatctcagct gactgtgcca aggacaaagc acttcagcta agtaattcac   3120
cgggtgcatc ctctgccttt cttaaggcag aaactgaaca taacaaggaa gtggccccac   3180
aagtctcact gctgactcaa ggtggggctg cccagagcct ggtgccacca ggagcaagtc   3240
tggccacaga gtcaaggcag gaagccttgg gggcagagca caacagctcc gctctgttgc   3300
catgtctgtt gccagatggg tctgatgggt ccgatgctct taactgcagt cagccttctc   3360
ctctggatgt tggagtgaag aacactcaat cccagggaaa aactagtgcc tgtgaggtga   3420
gtggagatgt gacggtggat gttacagggg ttaatgctct acaaggtatg gctgagccca   3480
gaagagagaa tatatcacac aacacccaag acatcctgat tccaaacgtc ttgttgagcc   3540
aagagaagaa tgccgttcta ggtttgccag tggctctaca ggacaaagct gtgactgacc   3600
cacagggagt tggaacccca gagatgatac ctcttgattg ggagaaaggg aagctggagg   3660
```

```
gagcagacca cagctgtacc atgggtgacg ctgaggaagc ccaaatagac gatgaagcac   3720
atcctgtcct actgcagcct gttgccaagg agctccccac agacatggag ctctcagccc   3780
atgatgatgg ggccccagct ggtgtgaggg aagtcatgcg agccccgcct tcaggcaggg   3840
aaaggagcac tccctctcta ccttgcatgg tctctgccca ggacgcacct ctgcctaagg   3900
gggcagactt gatagaggag gctgccagcc gtatagtgga tgctgtcatc gaacaagtca   3960
aggccgctgg agcactgctt actgaggggg aggcctgtca catgtcactg tccagccctg   4020
agttgggtcc tctcactaaa ggactagaga gtgcttttac agaaaaagtg agtactttcc   4080
cacctgggga gagcctacca atgggcagta ctcctgagga agccacgggg agccttgcag   4140
gatgttttgc tggaagggag gagccagaga agatcatttt acctgtccag gggcctgagc   4200
cagcagcaga aatgccagac gtgaaagctg aagatgaagt ggattttaga gcaagttcaa   4260
tttctgaaga agtggctgta gggagcatag ctgctacact gaagatgaag caaggcccaa   4320
tgacccaggc gataaaccga gaaaactggt gtacaataga gccatgccct gatgcagcat   4380
ctcttctggc ttccaagcag agcccagaat gtgagaactt cctggatgtt ggactgggca   4440
gagagtgtac ctcaaaacaa ggtgtactta aaagagaatc tgggagtgat tctgacctct   4500
ttcactcacc cagtgatgac atggacagca tcatcttccc aaagccagag gaagagcatt   4560
tggcctgtga tatcaccgga tccagttcat ccaccgatga cacggcttca ctggaccgac   4620
attcttctca tggcagtgat gtgtctctct cccagatttt aaagccaaac aggtcaagag   4680
atcggcaaag ccttgatgga ttctacagcc atgggatggg agctgagggt cgagaaagtg   4740
agagtgagcc tgctgaccca ggcgacgtgg aggaggagga gatggacagt atcactgaag   4800
tgcctgcaaa ctgctctgtc ctaaggagct ccatgcgctc tctttctccc ttccggaggc   4860
acagctgggg gcctgggaaa aatgcagcca gcgatgcaga aatgaaccac cggagtatga   4920
gctggtgccc ctctggtgtg cagtactctg ctggcctgag tgctgacttt aattacagaa   4980
gtttcagtct agaaggcttg acaggaggag ctggtgtcgg aaacaagcca tcctcatctc   5040
tagaagtaag ctctgcaaat gccgaagagc tcagacaccc attcagtggt gaggaacggg   5100
ttgactcttt ggtgtcactt tcagaagagg atctggagtc agaccagaga gaacatagga   5160
tgtttgatca gcagatatgt cacagatcta agcagcaggg atttaattac tgtacatcag   5220
ccatttcctc tccattgaca aaatccatct cattaatgac aatcagccat cctggattgg   5280
acaattcacg gcccttccac agtaccttcc acaataccag tgctaatctg actgagagta   5340
taacagaaga gaactataat ttcctgccac atagcccctc caagaaagat tctgaatgga   5400
agagtggaac aaaagtcagt cgtacattca gctacatcaa gaataaaatg tctagcagca   5460
agaagagcaa agaaaaggaa aaagaaaaag ataagattaa ggagaaggag aaagattcta   5520
aagacaagga gaaagataag aagactgtca acgggcacac tttcagttcc attcctgttg   5580
tgggtcccat cagctgtagc cagtgtatga agcccttcac caacaaagat gcctatactt   5640
gtgcaaattg cagtgctttt gtccacaaag gctgccgaga aagtctagcc tcctgtgcaa   5700
aggtcaaaat gaagcagccc aaagggagcc ttcaggcaca tgacacatca tcactgccca   5760
cggtcattat gagaaacaag ccctcacagc ccaaggagcg tcctcggtcc gcagtcctcc   5820
tggtggatga aaccgctacc accccaatat ttgccaatag acgatcccag cagagtgtct   5880
cgctctccaa aagtgtctcc atacagaaca ttactggagt tggcaatgat gagaacatgt   5940
caaacacctg gaaattcctg tctcattcaa cagactcact aaataaaatc agcaaggtca   6000
atgagtcaac agaatcactt actgatgagg gagtaggtac agacatgaat gaaggacaac   6060
```

```
tactgggaga ctttgagatt gagtccaaac agctggaagc agagtcttgg agtcggataa   6120

tagacagcaa gtttctaaaa cagcaaaaga aagatgtggt caaacggcaa gaagtaatat   6180

atgagttgat gcagacagag tttcatcatg tccgcactct caagatcatg agtggtgtgt   6240

acagccaggg gatgatggcg gatctgcttt ttgagcagca gatggtagaa aagctgttcc   6300

cctgtttgga tgagctgatc agtatccata gccaattctt ccagaggatt ctggagcgga   6360

agaaggagtc tctggtggat aaaagtgaaa agaactttct catcaagagg ataggggatg   6420

tgcttgtaaa tcagttttca ggtgagaatg cagaacgttt aaagaagaca tatggcaagt   6480

tttgtgggca acataaccag tctgtaaact acttcaaaga cctttatgcc aaggataagc   6540

gttttcaagc ctttgtaaag aagaagatga gcagttcagt tgttagaagg cttggaattc   6600

cagagtgcat attgcttgta actcagcgga ttaccaagta cccagtttta ttccaaagaa   6660

tattgcagtg taccaaagac aatgaagtgg agcaggaaga tctagcacag tccttgagcc   6720

tggtgaagga tgtgattgga gctgtagaca gcaaagtggc aagttatgaa aagaaagtgc   6780

gtctcaatga gatttataca aagacagata gcaagtcaat catgaggatg aagagtggtc   6840

agatgtttgc caaggaagat ttgaaacgga agaagcttgt acgtgatggg agtgtgtttc   6900

tgaagaatgc agcaggaagg ttgaaagagg ttcaagcagt tcttctcact gacattttag   6960

ttttccttca agaaaaagac cagaagtaca tctttgcatc attggaccag aagtcaacag   7020

tgatctcttt aaagaagctg attgtgagag aagtggcaca tgaggagaaa ggtttattcc   7080

tgatcagcat ggggatgaca gatccagaga tggtagaagt ccatgccagc tccaaagagg   7140

aacgaaacag ctggattcag atcattcagg acacaatcaa caccctgaac agagatgaag   7200

atgaaggaat tcctagtgag aatgaggaag aaaagaaaat gttggacacc agagcccgag   7260

aattaaaaga acaacttcac cagaaggacc aaaaaatcct actcttgttg gaagagaagg   7320

agatgatttt ccgggacatg gctgagtgca gcacccctct cccagaggat tgctccccaa   7380

cacatagccc tagagttctc ttccgctcca acacagaaga ggctctcaaa ggaggacctt   7440

taatgaaaag tgcaataaat gaggtggaga tccttcaggg tttggtgagt ggaaatctgg   7500

gaggcacact tgggccgact gtcagcagcc ccattgagca agatgtggtc ggtcccgttt   7560

ccctgccccg gagagcagag acctttggag gatttgacag ccatcagatg aatgcttcaa   7620

aaggaggcga gaaggaagag ggagatgatg gccaagatct taggagaacg gaatcagata   7680

gtggcctaaa aaagggtgga aatgctaacc tggtatttat gcttaaaaga aacagtgagc   7740

aggttgtcca gagcgttgtt catctctacg agctcctcag cgctctgcag ggtgtggtgc   7800

tgcagcagga cagctacatt gaggaccaga aactggtgct gagcgagagg gcgctcactc   7860

gcagcttgtc ccgcccgagc tccctcattg agcaggagaa gcagcgcagc ctggagaagc   7920

agcgccagga cctggccaac ctgcagaagc agcaggccca gtacctcgag gagaagcgca   7980

ggcgcgagcg tgagtgggaa gctcgtgaga gggagctgcg ggagcgggag gccctcctgg   8040

cccagcgcga ggaggaggtg cagcaggggc agcaggacct ggaaaaggag cgggaggagc   8100

tccagcagaa gaagggcaca taccagtatg acctggagcg actgcgtgct gcccagaaac   8160

agcttgagag ggaacaggag cagctgcgcc gggaggcaga gcggctcagc cagcggcaga   8220

cagaacggga cctgtgtcag gtttcccatc cacataccaa gctgatgagg atcccatcgt   8280

tcttccccag tcctgaggag ccccccctcgc catctgcacc ttccatagcc aaatcagggt   8340

cattggactc agaactttca gtgtccccaa aaaggaacag catctctcgg acacacaaag   8400

ataaggggcc ttttcacata ctgagttcaa ccagccagac aaacaaagga ccagaagggc   8460
```

-continued

```
agagccaggc ccctgcgtcc acctctgcct ctacccgcct gtttgggtta acaaagccaa   8520
aggaaaagaa ggagaaaaaa aagaagaaca aaaccagccg ctctcagccc ggtgatggtc   8580
ccgcgtcaga agtatcagca gagggtgaag agatcttctg ctgaccctct tcctctctgc   8640
tgaggcagct gcctcctgat cctggccagc ccacctctcc tgctgtcccc gcgtgcacaa   8700
gtctcttaca ctggacgccc actgctcctc agcgtccagt cctcctgggc ggccccaggt   8760
cctggacaat aagcaacaga tgatattgag tgtcgggtgg ggaaggaggc ccagactctg   8820
cttcggccat gatttgtgac tgcccaggac tctcaggttg ggctggccct actcaggatt   8880
acactgaaag taatggcctc gtaagtacag gtgatggttt tggacacgtc aggaattcct   8940
aaaggctgaa agagtgtatc caagtaaggt ctgaacctcc gaatgccttt tatttggggg   9000
aacacaaaac caaacagcag atgttttgga cttgatctgt gtacgtacat ggggacctgt   9060
ctgcatatac acacggggaa tgccagaaga aggcccagtc tgcaccaggc gtctggtcaa   9120
cttagcacaa gggcagtgcc tggacggacc cggagccccc gcatatcagc agttcaccca   9180
gtactcctca gagactggtt tccctctaaa cccatcccgg gcacatacca cccgtgtttt   9240
gcatgtattt ctcatttcat tttagggatg acaaacattt gtgaaaccag tgagagaagg   9300
cttgatgtgt ataaaagacg tgatgtgcac cacctcgatc tcggtgtttc aggcactaaa   9360
gcaacaaaac aacccatagt atctcattct gtcatcagat ccagaagaaa tatcctggtt   9420
ttccagcatg tttacccaca tgttttggcc atggataaag tgaagaggcc tactcaccat   9480
tatccctgca gcgtgacacc ttttgattgt cactgaccac tcagaagggg ccacggcctc   9540
ctggctgtgt tcctgagccc ccgtcgtgcc tctcccagac agcagctgtc tggcccttgc   9600
tgggtgaggg cacaccactg ccaggggtca gcctcgcacc caggccaggc agaagctgtg   9660
ctctgaagct aggacagctg gctgagaagt gggttcaggc gaagggtgaa gccatgtgta   9720
gcagttcctg ccagtgcaga tctggagagg agctggcccg gaaggcgtgg ttgtgaaagc   9780
gcccttctta tgttaggagg ccttggcaaa attggatttc ttcaaaaata catgtaaagg   9840
tctgttgttg aattgtactc tgcccctgga agcagataca gatggctgcc tgctgctcgg   9900
ctttgctttt gcttttccca ccgtgttttc atctttgttc acttgaggct ttccccagct   9960
ggtgtgtgca ggacagttca tggtaatgtt gccctctgag gccccgtaca ccagaaggga  10020
ggccctggaa aattttgtgc ttccaacgtg gccttcaatt cttgcttttt tgcccctcgg  10080
aagcatgggg cttttgagca cacttaaaaa aagaaaaatc tgtaacttgg tgcttattga  10140
tgaattgcaa gctggccttg cagatggaga tatttatctt tcagtttatt tgaaagaggt  10200
ctggtttaaa atttgtagcc tacatttgtt ttatttattg tatttgtgtg tttgtgtttg  10260
ttttttttta agggtgagcc aggtctagcc caacagtcta aactatccag tcaataccga  10320
gtgaagtggc agccagcact gttcactctg tgtcttttga agtgccttga aggcccagat  10380
gaaattttaa agggaggggg tccatgtcct tccctccccc accccgcctc attctttaat  10440
caaaggatgt cttctccctt gtttgagaat gaagaaactc gccacctctg acctaccttt  10500
gcctttttct gtcatggaga atactcaccc ttcagaaaca gaccaaaggc caaaacctgc  10560
tgatttttct attgaaaata tgtccccttg caaagaccct aaacaaaaag ttaagtttct  10620
ttctttcacc tatttgtaca actccaagtt acagctgaat ctgtcgtgac tttcctgaga  10680
tctacccggg gcttggctgt ctgttctggg cactggctcc gagttcccct cctgggattt  10740
gcaggagggc agtactgaac ctgcattctt ctccttgtaa atgtaggccg ggtgcccctg  10800
ttctccgggt ttggaacaat acgaggttgg tgctgatggg atttacttgc gtacgtgctc  10860
```

```
ttcacaaaaa caccgtggat gctgaagtta gagcacgtcg ccacagagct tgacatcaat  10920
gttagagggt ctcttactcc ccgcccagct gtgatgtttc atctgctttg gttgttttgg  10980
tggtcttttt taaaaataga gatttcacat ctgcccagac cccactcaaa acgatttggt  11040
caggttctgg ttggacaagt ttaaaatcaa agtagtgccc ggaattccct caaaccaccc  11100
aacttcatcc aggaatacag tctgcagtgc agcaacagaa ccgcttacca agaactgtgc  11160
ttacatacct ttgtcatctc tcttcccccc ttggaagttg tcctcagggg gatttgttcc  11220
tgtcctgggg atttacctgg gatggtggct gcctgtgctt ttgctcatgg ccttgacagt  11280
gctctagttg ctggatctaa tggcctgtct tggtttctat cacatgagaa ggggttgttt  11340
ttttggggtg actcggactg aattccccat actgtttcca cgccgggaca ccatgttctc  11400
catcaagcta aagaaatcac gtgcctgaaa ctgtgcttaa gttttggggg aaagatggag  11460
ttcctatcca gagcccccag atttccagaa tcgagtgagc ttcctggaag gagactgcgt  11520
cttctctcaa ttccagtcat ctcagtcgtt gtcgttaggt gacatgtgca ctttaaatgc  11580
tctcatcggt tggcttcatt ttcaagacaa tcaaatgtat tgactgtgtt ttcttcttag  11640
aaaatggaga gggttaaaaa catgcaaact gccactttca acctttgcca gtattccctc  11700
tacccccgtg agagctatct ggggggaaga atccttacca aggttttttt ggaaaggtac  11760
gaatcttaac ttttttcccc ttctgtgtct cagggtaata ctattcagag tcgccccttt  11820
gctcattttc tcccgtattt gttaccttcc tgaggcctca gtattagtcg tgagcacaaa  11880
gttttgagac ctttggcgtt gtttcttgat gtgggagggg aggtgttagt gcatgcaagg  11940
gttgaactag atagaccctg ccttagtaga gggtgggact ataaccttag aggccagaac  12000
ttgatccaga agttgctgtc cacagaagtg ctttctattt catcattttt gtttctaggg  12060
ctctttttct gtagccaggt cttcccaagg attttagtat ttgcattgga gttgaggttt  12120
actctaatga tggtggccca gctgtgccca gaggacagcc aggcaggccc tgggagggag  12180
tttagaaaga cagtcctggt gaatgggctt caagtggtca caaagagggt ggctgtgagg  12240
tgaccccaga cactgcagaa cgatgtgcac cctctgcgtt ttggatgtcc ttggaatgtg  12300
ggagcctaga aataaccctg tggatggaat tggggcagcg gctgctggag atctgtgtgc  12360
cttgccttcc ttcagcagga ccgtctaggt gcgcagccac ctatggatgc gtcccagcca  12420
gccccgtcgc tctcgtccat cctcagagac aaagaagagg gcagggagtt tgggcttggt  12480
tttgaacttt cctttcaatg tagcaaagca ttcctagtta accagagcct tggaatctac  12540
tgcctgctgg ccaggcttta aaatgaaaag tgttttaatg ctgccataaa agggaggcgg  12600
gggggaggaa gggaaaataa aggcatcttt ccaagtactc atctaattta attgtcaaaa  12660
gattgatagg ccatgaatta cttctccatc tcactaaggg ttaaaggcgt gcaacccccc  12720
actggctgtg tcccctgcca ccgaagtgag tgacctgccc tacaaccagg tgggaccacc  12780
tgtgctgcag tccggagggg cttctgcagg aagcactcac cccccacacc ttccccggcc  12840
tgagcttccc ctacctttcg tcaccacctg agggcatgag cacaggccat ggggcgtgcc  12900
tggtgagtct gcctgtggtt caggcttagc ctgtggtctc ctgtgtgctg ctgcccgcat  12960
gggatgcgca ggggaggcgt ggggatccgc aggagggtgg ttgggataca ccggatacct  13020
ctgctctcat tgcttgtttg caaatgctct atggacattt gtgtgctaaa tcctattaaa  13080
taaaaaagac gggttaaaac ccagatgctg tatattcatt tgtaattatg tataaagtga  13140
agcagtttta aactgtaaag atttttttca gtgtgttttc tcgaattttg ccacaacata  13200
ctggcttcgt attttattta tctttctttc tagttaccag cttcagaccc ttgtaaagtc  13260
```

tccctcagcc ctttcaaaaa ataataaatt tcctgtgaag tt 13302

<210> SEQ ID NO 24
<211> LENGTH: 13290
<212> TYPE: DNA
<213> ORGANISM: Homo sapiens
<300> PUBLICATION INFORMATION:
<308> DATABASE ACCESSION NUMBER: NM_007200
<309> DATABASE ENTRY DATE: 2006-08-20
<313> RELEVANT RESIDUES IN SEQ ID NO: (1)..(13290)

<400> SEQUENCE: 24
gaagcgcctg tgctctgccg agactgccgt gcccattgct cgcctcggtc gccgccgctt 60
tagccgcctc cgggggagcg gccgcctatt gtctttctcc gcggcgaagg tgaagagttg 120
tcccagctcg gcccgcgggg gagccccggg agccgcacgt gtcctgggtc atgaaactta 180
atccacagca agctccctta tatggtgatt gtgttgttac agtgctgctt gctgaagagg 240
acaaagctga agatgatgta gtgttttact tggtattttt gggttccacc ctccgtcact 300
gtacaagtac tcggaaggtc agttctgata cattggagac cattgctcct ggtcatgatt 360
gttgtgaaac agtgaaggtg cagctctgtg cttccaaaga gggccttccc gtgtttgtgg 420
tggctgaaga agactttcat ttcgtccagg atgaagcgta tgatgcagct caattcctag 480
caaccagtgc tggaaatcag caggctttga actttacccg ttttcttgac cagtcaggac 540
ccccatctgg ggatgtgaat tcccttgata agaagttggt gctggcattc aggcacctga 600
agctgcccac ggagtggaat gtattgggga cagatcagag tttgcatgat gctggcccgc 660
gagagacatt gatgcatttt gctgtgcggc tgggactgct gaggttgacg tggttcctgt 720
tgcagaagcc aggtggccgc ggagctctca gtatccacaa ccaggaaggg gcgacgcctg 780
tgagcttggc cttggagcga ggctatcaca agctgcacca gcttctaacc gaggagaatg 840
ctggagaacc agactcctgg agcagtttat cctatgaaat accgtatgga gactgttctg 900
tgaggcatca tcgagagttg gacatctata cattaacctc tgagtctgat tcacatcatg 960
aacacccatt tcctggagac ggttgcactg gaccaatttt taaacttatg aacatccaac 1020
agcaactaat gaaaacaaac ctcaagcaga tggacagtct tatgccctta atgatgacag 1080
cacaggatcc ttccagtgcc ccagagacag atggccagtt tcttccctgt gcaccggagc 1140
ccacggaccc tcagcgactt tcttcttctg aagagactga gagcactcag tgctgcccag 1200
ggagccctgt tgcacagact gaaagtccct gtgatttgtc aagcatagtt gaggaggaga 1260
atacagaccg ttcctgtagg aagaaaaata aaggcgtgga aagaaaaggg gaagaggtgg 1320
agccagcacc tattgtggac tctggaactg tatctgatca agacagctgc cttcagagct 1380
tgcctgattg tggagtaaag ggcacggaag gcctttcgtc ctgtggaaac agaaatgaag 1440
aaactggaac aaaatcttct ggaatgccca cagaccagga gtccctgagc agtggagatg 1500
ctgtgcttca gagagacttg gtcatggagc caggcacagc ccagtattcc tctggaggtg 1560
aactgggagg catttcaaca acaaatgtca gtaccccaga cactgcaggg gaaatggaac 1620
atgggctcat gaacccagat gccactgttt ggaagaatgt gcttcaggga ggggaaagta 1680
caaaggaaag atttgagaac tctaatattg gcacagctgg agcctctgac gtgcacgtca 1740
caagtaagcc tgtggataaa atcagtgttc caaactgtgc ccctgctgcc agttccctgg 1800
atggtaacaa acctgctgag tcttcacttg catttagtaa tgaagaaacc tccactgaaa 1860
aaacagcaga aacggaaact tcacgaagtc gtgaggagag tgctgatgct ccagtagatc 1920
agaattctgt ggtgattcca gctgctgcaa aagacaagat ttcagatgga ttagaacctt 1980

```
atactctctt agcagcaggc ataggtgagg caatgtcacc ctcagattta gcccttcttg   2040
ggctggaaga agatgtaatg ccacaccaga actcagaaac aaattcatct catgctcaaa   2100
gccaaaaggg caaatcctca cccatttgtt ctacaactgg agacgataaa ctttgtgcag   2160
actctgcatg tcaacagaac acagtgactt ctagtggcga tttggttgca aaactgtgtg   2220
ataacatagt tagcgagtcc gaaagcacca cagcaaggca acccagctca caagatccac   2280
ccgatgcctc ccactgtgaa gacccacagg ctcatacagt cacctctgac cctgtaaggg   2340
atacccagga acgtgcggat ttttgtcctt tcaaagtggt ggataacaaa ggccaacgaa   2400
aagatgtgaa actagataaa cctttaacaa atatgcttga ggtggtttca catccacatc   2460
cagttgtccc taaaatggag aaagaactgg tgccagacca ggcagtaata tcagacagta   2520
ctttctctct ggcaaacagt ccaggcagtg aatcagtaac caaggatgac gcactttctt   2580
ttgtcccctc ccagaaagaa aagggaacag caactcctga actacataca gctacagatt   2640
atagagatgg cccagatgga aattcgaatg agcctgatac gcggccacta gaagacaggg   2700
cagtaggcct gtccacatcc tccactgctg cagagcttca gcacgggatg gggaatacca   2760
gtctcacagg acttggtgga gagcatgagg gtcccgcccc tccagcaatc ccagaagctc   2820
tgaatatcaa ggggaacact gactcttccc tgcaaagtgt gggtaaggcc actttggctt   2880
tagattcagt tttgactgaa gaaggaaaac ttctggtggt ttcagaaagc tctgcagctc   2940
aggaacaaga taaggataaa gcggtgacct gttcctctat taaggaaaat gctctctctt   3000
caggaacttt gcaggaagag cagagaacac cacctcctgg acaagatact caacaatttc   3060
atgaaaaatc aatctcagct gactgtgcca aggacaaagc acttcagcta agtaattcac   3120
cgggtgcatc ctctgccttt cttaaggcag aaactgaaca taacaaggaa gtggccccac   3180
aagtctcact gctgactcaa ggtggggctg cccagagcct ggtgccacca ggagcaagtc   3240
tggccacaga gtcaaggcag gaagccttgg gggcagagca caacagctcc gctctgttgc   3300
catgtctgtt gccagatggg tctgatgggt ccgatgctct taactgcagt cagccttctc   3360
ctctggatgt tggagtgaag aacactcaat cccagggaaa aactagtgcc tgtgaggtga   3420
gtggagatgt gacggtggat gttacagggg ttaatgctct acaaggtatg gctgagccca   3480
gaagagagaa tatatcacac aacacccaag acatcctgat tccaaacgtc ttgttgagcc   3540
aagagaagaa tgccgttcta ggtttgccag tggctctaca ggacaaagct gtgactgacc   3600
cacagggagt tggaacccca gagatgatac ctcttgattg ggagaaaggg aagctggagg   3660
gagcagacca cagctgtacc atgggtgacg ctgaggaagc ccaaatagac gatgaagcac   3720
atcctgtcct actgcagcct gttgccaagg agctccccac agacatggag ctctcagccc   3780
atgatgatgg ggccccagct ggtgtgaggg aagtcatgcg agccccgcct tcaggcaggg   3840
aaaggagcac tccctctcta ccttgcatgg tctctgccca ggacgcacct ctgcctaagg   3900
gggcagactt gatagaggag gctgccagcc gtatagtgga tgctgtcatc gaacaagtca   3960
aggccgctgg agcactgctt actgaggggg aggcctgtca catgtcactg tccagccctg   4020
agttgggtcc tctcactaaa ggactagaga gtgcttttac agaaaaagtg agtactttcc   4080
cacctgggga gagcctacca atgggcagta ctcctgagga agccacgggg agccttgcag   4140
gatgttttgc tggaagggag gagccagaga agatcatttt acctgtccag gggcctgagc   4200
cagcagcaga aatgccagac gtgaaagctg aagatgaagt ggattttaga gcaagttcaa   4260
tttctgaaga agtggctgta gggagcatag ctgctacact gaagatgaag caaggcccaa   4320
tgacccaggc gataaaccga gaaaactggt gtacaataga gccatgccct gatgcagcat   4380
```

```
ctcttctggc ttccaagcag agcccagaat gtgagaactt cctggatgtt ggactgggca   4440

gagagtgtac ctcaaaacaa ggtgtactta aaagagaatc tgggagtgat tctgacctct   4500

ttcactcacc cagtgatgac atggacagca tcatcttccc aaagccagag gaagagcatt   4560

tggcctgtga tatcaccgga tccagttcat ccaccgatga cacggcttca ctggaccgac   4620

attcttctca tggcagtgat gtgtctctct cccagatttt aaagccaaac aggtcaagag   4680

atcggcaaag ccttgatgga ttctacagcc atgggatggg agctgagggt cgagaaagtg   4740

agagtgagcc tgctgaccca ggcgacgtgg aggaggagga gatggacagt atcactgaag   4800

tgcctgcaaa ctgctctgtc ctaaggagct ccatgcgctc tctttctccc ttccggaggc   4860

acagctgggg gcctgggaaa aatgcagcca gcgatgcaga aatgaaccac cggagttcaa   4920

tgcgagttct tggggatgtt gtcaggagac ctcccattca taggagaagt ttcagtctag   4980

aaggcttgac aggaggagct ggtgtcggaa acaagccatc ctcatctcta gaagtaagct   5040

ctgcaaatgc cgaagagctc agacacccat tcagtggtga ggaacgggtt gactctttgg   5100

tgtcactttc agaagaggat ctggagtcag accagagaga acataggatg tttgatcagc   5160

agatatgtca cagatctaag cagcagggat ttaattactg tacatcagcc atttcctctc   5220

cattgacaaa atccatctca ttaatgacaa tcagccatcc tggattggac aattcacggc   5280

ccttccacag taccttccac aataccagtg ctaatctgac tgagagtata acagaagaga   5340

actataattt cctgccacat agcccctcca agaaagattc tgaatggaag agtggaacaa   5400

aagtcagtcg tacattcagc tacatcaaga ataaaatgtc tagcagcaag aagagcaaag   5460

aaaaggaaaa agaaaaagat aagattaagg agaaggagaa agattctaaa gacaaggaga   5520

aagataagaa gactgtcaac gggcacactt tcagttccat tcctgttgtg ggtcccatca   5580

gctgtagcca gtgtatgaag cccttcacca acaaagatgc ctatacttgt gcaaattgca   5640

gtgcttttgt ccacaaaggc tgccgagaaa gtctagcctc ctgtgcaaag gtcaaaatga   5700

agcagcccaa agggagcctt caggcacatg acacatcatc actgcccacg gtcattatga   5760

gaaacaagcc ctcacagccc aaggagcgtc ctcggtccgc agtcctcctg gtggatgaaa   5820

ccgctaccac cccaatattt gccaatagac gatcccagca gagtgtctcg ctctccaaaa   5880

gtgtctccat acagaacatt actggagttg gcaatgatga gaacatgtca aacacctgga   5940

aattcctgtc tcattcaaca gactcactaa ataaaatcag caaggtcaat gagtcaacag   6000

aatcacttac tgatgaggga gtaggtacag acatgaatga aggacaacta ctgggagact   6060

ttgagattga gtccaaacag ctggaagcag agtcttggag tcggataata gacagcaagt   6120

ttctaaaaca gcaaaagaaa gatgtggtca aacggcaaga agtaatatat gagttgatgc   6180

agacagagtt tcatcatgtc cgcactctca agatcatgag tggtgtgtac agccagggga   6240

tgatggcgga tctgcttttt gagcagcaga tggtagaaaa gctgttcccc tgtttggatg   6300

agctgatcag tatccatagc caattcttcc agaggattct ggagcggaag aaggagtctc   6360

tggtggataa aagtgaaaag aactttctca tcaagaggat aggggatgtg cttgtaaatc   6420

agttttcagg tgagaatgca gaacgtttaa agaagacata tggcaagttt tgtgggcaac   6480

ataaccagtc tgtaaactac ttcaaagacc tttatgccaa ggataagcgt tttcaagcct   6540

ttgtaaagaa gaagatgagc agttcagttg ttagaaggct tggaattcca gagtgcatat   6600

tgcttgtaac tcagcggatt accaagtacc cagttttatt ccaaagaata ttgcagtgta   6660

ccaaagacaa tgaagtggag caggaagatc tagcacagtc cttgagcctg gtgaaggatg   6720

tgattggagc tgtagacagc aaagtggcaa gttatgaaaa gaaagtgcgt ctcaatgaga   6780
```

```
tttatacaaa gacagatagc aagtcaatca tgaggatgaa gagtggtcag atgtttgcca   6840
aggaagattt gaaacggaag aagcttgtac gtgatgggag tgtgtttctg aagaatgcag   6900
caggaaggtt gaaagaggtt caagcagttc ttctcactga cattttagtt ttccttcaag   6960
aaaaagacca gaagtacatc tttgcatcat tggaccagaa gtcaacagtg atctctttaa   7020
agaagctgat tgtgagagaa gtggcacatg aggagaaagg tttattcctg atcagcatgg   7080
ggatgacaga tccagagatg gtagaagtcc atgccagctc caaagaggaa cgaaacagct   7140
ggattcagat cattcaggac acaatcaaca ccctgaacag agatgaagat gaaggaattc   7200
ctagtgagaa tgaggaagaa aagaaaatgt tggacaccag agcccgagaa ttaaaagaac   7260
aacttcacca gaaggaccaa aaaatcctac tcttgttgga agagaaggag atgatttttcc  7320
gggacatggc tgagtgcagc acccctctcc cagaggattg ctccccaaca catagcccta   7380
gagttctctt ccgctccaac acagaagagg ctctcaaagg aggaccttta atgaaaagtg   7440
caataaatga ggtggagatc cttcagggtt tggtgagtgg aaatctggga ggcacacttg   7500
ggccgactgt cagcagcccc attgagcaag atgtggtcgg tcccgtttcc ctgccccgga   7560
gagcagagac ctttggagga tttgacagcc atcagatgaa tgcttcaaaa ggaggcgaga   7620
aggaagaggg agatgatggc caagatctta ggagaacgga atcagatagt ggcctaaaaa   7680
agggtggaaa tgctaacctg gtatttatgc ttaaaagaaa cagtgagcag gttgtccaga   7740
gcgttgttca tctctacgag ctcctcagcg ctctgcaggg tgtggtgctg cagcaggaca   7800
gctacattga ggaccagaaa ctggtgctga gcgagagggc gctcactcgc agcttgtccc   7860
gcccgagctc cctcattgag caggagaagc agcgcagcct ggagaagcag cgccaggacc   7920
tggccaacct gcagaagcag caggcccagt acctcgagga gaagcgcagg cgcgagcgtg   7980
agtgggaagc tcgtgagagg gagctgcggg agcgggaggc cctcctggcc cagcgcgagg   8040
aggaggtgca gcaggggcag caggacctgg aaaaggagcg ggaggagctc cagcagaaga   8100
agggcacata ccagtatgac ctggagcgac tgcgtgctgc ccagaaacag cttgagaggg   8160
aacaggagca gctgcgccgg gaggcagagc ggctcagcca gcggcagaca gaacgggacc   8220
tgtgtcaggt ttcccatcca cataccaagc tgatgaggat cccatcgttc ttccccagtc   8280
ctgaggagcc cccctcgcca tctgcacctt ccatagccaa atcagggtca ttggactcag   8340
aactttcagt gtccccaaaa aggaacagca tctctcggac acacaaagat aaggggcctt   8400
ttcacatact gagttcaacc agccagacaa acaaaggacc agaagggcag agccaggccc   8460
ctgcgtccac ctctgcctct acccgcctgt ttgggttaac aaagccaaag gaaaagaagg   8520
agaaaaaaaa gaagaacaaa accagccgct ctcagcccgg tgatggtccc gcgtcagaag   8580
tatcagcaga gggtgaagag atcttctgct gaccctcttc ctctctgctg aggcagctgc   8640
ctcctgatcc tggccagccc acctctcctg ctgtccccgc gtgcacaagt ctcttacact   8700
ggacgcccac tgctcctcag cgtccagtcc tcctgggcgg ccccaggtcc tggacaataa   8760
gcaacagatg atattgagtg tcgggtgggg aaggaggccc agactctgct tcggccatga   8820
tttgtgactg cccaggactc tcaggttggg ctggccctac tcaggattac actgaaagta   8880
atggcctcgt aagtacaggt gatggttttg gacacgtcag gaattcctaa aggctgaaag   8940
agtgtatcca agtaaggtct gaacctccga atgcctttta tttgggggaa cacaaaacca   9000
aacagcagat gttttggact tgatctgtgt acgtacatgg ggacctgtct gcatatacac   9060
acggggaatg ccagaagaag gcccagtctg caccaggcgt ctggtcaact tagcacaagg   9120
gcagtgcctg gacggacccg gagcccccgc atatcagcag ttcacccagt actcctcaga   9180
```

```
gactggtttc cctctaaacc catcccgggc acataccacc cgtgttttgc atgtatttct   9240
catttcattt tagggatgac aaacatttgt gaaaccagtg agagaaggct tgatgtgtat   9300
aaaagacgtg atgtgcacca cctcgatctc ggtgtttcag gcactaaagc aacaaaacaa   9360
cccatagtat ctcattctgt catcagatcc agaagaaata tcctggtttt ccagcatgtt   9420
tacccacatg ttttggccat ggataaagtg aagaggccta ctcaccatta tccctgcagc   9480
gtgacacctt ttgattgtca ctgaccactc agaaggggcc acggcctcct ggctgtgttc   9540
ctgagccccc gtcgtgcctc tcccagacag cagctgtctg gcccttgctg ggtgagggca   9600
caccactgcc aggggtcagc ctcgcaccca ggccaggcag aagctgtgct ctgaagctag   9660
gacagctggc tgagaagtgg gttcaggcga agggtgaagc catgtgtagc agttcctgcc   9720
agtgcagatc tggagaggag ctggcccgga aggcgtggtt gtgaaagcgc ccttcttatg   9780
ttaggaggcc ttggcaaaat tggatttctt caaaaataca tgtaaaggtc tgttgttgaa   9840
ttgtactctg cccctggaag cagatacaga tggctgcctg ctgctcggct ttgcttttgc   9900
ttttcccacc gtgttttcat ctttgttcac ttgaggcttt ccccagctgg tgtgtgcagg   9960
acagttcatg gtaatgttgc cctctgaggc cccgtacacc agaagggagg ccctggaaaa  10020
ttttgtgctt ccaacgtggc cttcaattct tgctttttg cccctcggaa gcatggggct  10080
tttgagcaca cttaaaaaaa gaaaaatctg taacttggtg cttattgatg aattgcaagc  10140
tggccttgca gatggagata tttatctttc agtttatttg aaagaggtct ggtttaaaat  10200
ttgtagccta catttgtttt atttattgta tttgtgtgtt tgtgtttgtt ttttttaag  10260
ggtgagccag gtctagccca acagtctaaa ctatccagtc aataccgagt gaagtggcag  10320
ccagcactgt tcactctgtg tcttttgaag tgccttgaag gcccagatga aattttaaag  10380
ggagggggtc catgtccttc cctcccccac cccgcctcat tctttaatca aaggatgtct  10440
tctcccttgt ttgagaatga agaaactcgc cacctctgac ctacctttgc ctttttctgt  10500
catggagaat actcaccctt cagaaacaga ccaaaggcca aaacctgctg atttttctat  10560
tgaaaatatg tccccttgca aagaccctaa acaaaaagtt aagtttcttt ctttcaccta  10620
tttgtacaac tccaagttac agctgaatct gtcgtgactt tcctgagatc tacccggggc  10680
ttggctgtct gttctgggca ctggctccga gttcccctcc tgggatttgc aggagggcag  10740
tactgaacct gcattcttct ccttgtaaat gtaggccggg tgcccctgtt ctccgggttt  10800
ggaacaatac gaggttggtg ctgatgggat ttacttgcgt acgtgctctt cacaaaaaca  10860
ccgtggatgc tgaagttaga gcacgtcgcc acagagcttg acatcaatgt tagagggtct  10920
cttactcccc gcccagctgt gatgtttcat ctgctttggt tgttttggtg gtctttttta  10980
aaaatagaga tttcacatct gcccagaccc cactcaaaac gatttggtca ggttctggtt  11040
ggacaagttt aaaatcaaag tagtgcccgg aattccctca aaccacccaa cttcatccag  11100
gaatacagtc tgcagtgcag caacagaacc gcttaccaag aactgtgctt acataccttt  11160
gtcatctctc ttcccccctt ggaagttgtc ctcaggggga tttgttcctg tcctggggat  11220
ttacctggga tggtggctgc ctgtgctttt gctcatggcc ttgacagtgc tctagttgct  11280
ggatctaatg gcctgtcttg gtttctatca catgagaagg ggttgttttt ttggggtgac  11340
tcggactgaa ttccccatac tgtttccacg ccgggacacc atgttctcca tcaagctaaa  11400
gaaatcacgt gcctgaaact gtgcttaagt tttgggggaa agatggagtt cctatccaga  11460
gcccccagat ttccagaatc gagtgagctt cctggaagga gactgcgtct tctctcaatt  11520
ccagtcatct cagtcgttgt cgttaggtga catgtgcact ttaaatgctc tcatcggttg  11580
```

gcttcatttt caagacaatc aaatgtattg actgtgtttt cttcttagaa aatggagagg 11640
gttaaaaaca tgcaaactgc cactttcaac ctttgccagt attccctcta cccccgtgag 11700
agctatctgg ggggaagaat ccttaccaag gtttttttgg aaaggtacga atcttaactt 11760
ttttcccctt ctgtgtctca gggtaatact attcagagtc gcccctttgc tcattttctc 11820
ccgtatttgt taccttcctg aggcctcagt attagtcgtg agcacaaagt tttgagacct 11880
ttggcgttgt ttcttgatgt gggaggggag gtgttagtgc atgcaagggt tgaactagat 11940
agaccctgcc ttagtagagg gtgggactat aaccttagag gccagaactt gatccagaag 12000
ttgctgtcca cagaagtgct ttctatttca tcatttttgt ttctagggct ctttttctgt 12060
agccaggtct tcccaaggat tttagtattt gcattggagt tgaggtttac tctaatgatg 12120
gtggcccagc tgtgcccaga ggacagccag gcaggccctg ggagggagtt tagaaagaca 12180
gtcctggtga atgggcttca agtggtcaca aagagggtgg ctgtgaggtg accccagaca 12240
ctgcagaacg atgtgcaccc tctgcgtttt ggatgtcctt ggaatgtggg agcctagaaa 12300
taaccctgtg gatggaattg gggcagcggc tgctggagat ctgtgtgcct tgccttcctt 12360
cagcaggacc gtctaggtgc gcagccacct atggatgcgt cccagccagc cccgtcgctc 12420
tcgtccatcc tcagagacaa agaagagggc agggagtttg ggcttggttt tgaactttcc 12480
tttcaatgta gcaaagcatt cctagttaac cagagccttg gaatctactg cctgctggcc 12540
aggctttaaa atgaaaagtg ttttaatgct gccataaaag ggaggcgggg gggaggaagg 12600
gaaaataaag gcatctttcc aagtactcat ctaatttaat tgtcaaaaga ttgataggcc 12660
atgaattact tctccatctc actaagggtt aaaggcgtgc aaccccccac tggctgtgtc 12720
ccctgccacc gaagtgagtg acctgcccta caaccaggtg ggaccacctg tgctgcagtc 12780
cggaggggct tctgcaggaa gcactcaccc cccacacctt ccccggcctg agcttcccct 12840
acctttcgtc accacctgag ggcatgagca caggccatgg ggcgtgcctg gtgagtctgc 12900
ctgtggttca ggcttagcct gtggtctcct gtgtgctgct gcccgcatgg gatgcgcagg 12960
ggaggcgtgg ggatccgcag gagggtggtt gggatacacc ggatacctct gctctcattg 13020
cttgtttgca aatgctctat ggacatttgt gtgctaaatc ctattaaata aaaaagacgg 13080
gttaaaaccc agatgctgta tattcatttg taattatgta taaagtgaag cagttttaaa 13140
ctgtaaagat ttttttcagt gtgttttctc gaattttgcc acaacatact ggcttcgtat 13200
tttatttatc tttctttcta gttaccagct tcagaccctt gtaaagtctc cctcagccct 13260
ttcaaaaaat aataaatttc ctgtgaagtt 13290

<210> SEQ ID NO 25
<211> LENGTH: 8081
<212> TYPE: DNA
<213> ORGANISM: Homo sapiens
<300> PUBLICATION INFORMATION:
<308> DATABASE ACCESSION NUMBER: NM_144767
<309> DATABASE ENTRY DATE: 2006-08-20
<313> RELEVANT RESIDUES IN SEQ ID NO: (1)..(8081)

<400> SEQUENCE: 25
gtctaaaact ctcttttctc ttggctcttc ttattcgagt gatgaggagg aggagttgca 60
taattcacgg cccttccaca gtaccttcca caataccagt gctaatctga ctgagagtat 120
aacagaagag aactataatt tcctgccaca tagcccctcc aagaaagatt ctgaatggaa 180
gagtggaaca aaagtcagtc gtacattcag ctacatcaag aataaaatgt ctagcagcaa 240
gaagagcaaa gaaaaggaaa aagaaaaaga taagattaag gagaaggaga aagattctaa 300

```
agacaaggag aaagataaga agactgtcaa cgggcacact ttcagttcca ttcctgttgt    360
gggtcccatc agctgtagcc agtgtatgaa gcccttcacc aacaaagatg cctatacttg    420
tgcaaattgc agtgcttttg tccacaaagg ctgccgagaa agtctagcct cctgtgcaaa    480
ggtcaaaatg aagcagccca aagggagcct tcaggcacat gacacatcat cactgcccac    540
ggtcattatg agaaacaagc cctcacagcc caaggagcgt cctcggtccg cagtcctcct    600
ggtggatgaa accgctacca ccccaatatt tgccaataga cgatcccagc agagtgtctc    660
gctctccaaa agtgtctcca tacagaacat tactggagtt ggcaatgatg agaacatgtc    720
aaacacctgg aaattcctgt ctcattcaac agactcacta aataaaatca gcaaggtcaa    780
tgagtcaaca gaatcactta ctgatgaggg agtaggtaca gacatgaatg aaggacaact    840
actgggagac tttgagattg agtccaaaca gctggaagca gagtcttgga gtcggataat    900
agacagcaag tttctaaaac agcaaaagaa agatgtggtc aaacggcaag aagtaatata    960
tgagttgatg cagacagagt ttcatcatgt ccgcactctc aagatcatga gtggtgtgta   1020
cagccagggg atgatggcgg atctgctttt tgagcagcag atggtagaaa agctgttccc   1080
ctgtttggat gagctgatca gtatccatag ccaattcttc cagaggattc tggagcggaa   1140
gaaggagtct ctggtggata aaagtgaaaa gaactttctc atcaagagga taggggatgt   1200
gcttgtaaat cagttttcag gtgagaatgc agaacgttta aagaagacat atggcaagtt   1260
ttgtgggcaa cataaccagt ctgtaaacta cttcaaagac ctttatgcca aggataagcg   1320
ttttcaagcc tttgtaaaga agaagatgag cagttcagtt gttagaaggc ttggaattcc   1380
agagtgcata ttgcttgtaa ctcagcggat taccaagtac ccagttttat tccaaagaat   1440
attgcagtgt accaaagaca atgaagtgga gcaggaagat ctagcacagt ccttgagcct   1500
ggtgaaggat gtgattggag ctgtagacag caaagtggca agttatgaaa agaaagtgcg   1560
tctcaatgag atttatacaa agacagatag caagtcaatc atgaggatga agagtggtca   1620
gatgtttgcc aaggaagatt tgaaacggaa gaagcttgta cgtgatggga gtgtgtttct   1680
gaagaatgca gcaggaaggt tgaaagaggt tcaagcagtt cttctcactg acattttagt   1740
tttccttcaa gaaaaagacc agaagtacat ctttgcatca ttggaccaga agtcaacagt   1800
gatctcttta aagaagctga ttgtgagaga agtggcacat gaggagaaag gtttattcct   1860
gatcagcatg gggatgacag atccagagat ggtagaagtc catgccagct ccaaagagga   1920
acgaaacagc tggattcaga tcattcagga cacaatcaac accctgaaca gagatgaaga   1980
tgaaggaatt cctagtgaga atgaggaaga aaagaaaatg ttggacacca gagcccgaga   2040
attaaaagaa caacttcacc agaaggacca aaaaatccta ctcttgttgg aagagaagga   2100
gatgattttc cgggacatgg ctgagtgcag cacccctctc ccagaggatt gctccccaac   2160
acatagccct agagttctct tccgctccaa cacagaagag gctctcaaag gaggaccttt   2220
aatgaaaagt gcaataaatg aggtggagat ccttcagggt ttggtgagtg gaaatctggg   2280
aggcacactt gggccgactg tcagcagccc cattgagcaa gatgtggtcg gtcccgtttc   2340
cctgccccgg agagcagaga cctttggagg atttgacagc catcagatga atgcttcaaa   2400
aggaggcgag aaggaagagg gagatgatgg ccaagatctt aggagaacgg aatcagatag   2460
tggcctaaaa aagggtggaa atgctaacct ggtatttatg cttaaaagaa acagtgagca   2520
ggttgtccag agcgttgttc atctctacga gctcctcagc gctctgcagg gtgtggtgct   2580
gcagcaggac agctacattg aggaccagaa actggtgctg agcgagaggg cgctcactcg   2640
cagcttgtcc cgcccgagct ccctcattga gcaggagaag cagcgcagcc tggagaagca   2700
```

```
gcgccaggac ctggccaacc tgcagaagca gcaggcccag tacctcgagg agaagcgcag   2760
gcgcgagcgt gagtgggaag ctcgtgagag ggagctgcgg gagcgggagg ccctcctggc   2820
ccagcgcgag gaggaggtgc agcaggggca gcaggacctg gaaaaggagc gggaggagct   2880
ccagcagaag aagggcacat accagtatga cctggagcga ctgcgtgctg cccagaaaca   2940
gcttgagagg gaacaggagc agctgcgccg ggaggcagag cggctcagcc agcggcagac   3000
agaacgggac ctgtgtcagg tttcccatcc acataccaag ctgatgagga tcccatcgtt   3060
cttccccagt cctgaggagc ccccctcgcc atctgcacct tccatagcca aatcagggtc   3120
attggactca gaactttcag tgtccccaaa aaggaacagc atctctcgga cacacaaaga   3180
taaggggcct tttcacatac tgagttcaac cagccagaca aacaaaggac cagaagggca   3240
gagccaggcc cctgcgtcca cctctgcctc tacccgcctg tttgggttaa caaagccaaa   3300
ggaaaagaag gagaaaaaaa agaagaacaa aaccagccgc tctcagcccg gtgatggtcc   3360
cgcgtcagaa gtatcagcag agggtgaaga gatcttctgc tgaccctctt cctctctgct   3420
gaggcagctg cctcctgatc ctggccagcc cacctctcct gctgtccccg cgtgcacaag   3480
tctcttacac tggacgccca ctgctcctca gcgtccagtc ctcctgggcg gccccaggtc   3540
ctggacaata agcaacagat gatattgagt gtcgggtggg gaaggaggcc cagactctgc   3600
ttcggccatg atttgtgact gcccaggact ctcaggttgg gctggcccta ctcaggatta   3660
cactgaaagt aatggcctcg taagtacagg tgatggtttt ggacacgtca ggaattccta   3720
aaggctgaaa gagtgtatcc aagtaaggtc tgaacctccg aatgcctttt atttgggga   3780
acacaaaacc aaacagcaga tgttttggac ttgatctgtg tacgtacatg ggacctgtc   3840
tgcatataca cacggggaat gccagaagaa ggcccagtct gcaccaggcg tctggtcaac   3900
ttagcacaag ggcagtgcct ggacggaccc ggagcccccg catatcagca gttcacccag   3960
tactcctcag agactggttt ccctctaaac ccatcccggg cacataccac ccgtgttttg   4020
catgtatttc tcatttcatt ttagggatga caaacatttg tgaaaccagt gagagaaggc   4080
ttgatgtgta taaaagacgt gatgtgcacc acctcgatct cggtgtttca ggcactaaag   4140
caacaaaaca acccatagta tctcattctg tcatcagatc cagaagaaat atcctggttt   4200
tccagcatgt ttacccacat gttttggcca tggataaagt gaagaggcct actcaccatt   4260
atccctgcag cgtgacacct tttgattgtc actgaccact cagaaggggc cacggcctcc   4320
tggctgtgtt cctgagcccc cgtcgtgcct ctcccagaca gcagctgtct ggcccttgct   4380
gggtgagggc acaccactgc caggggtcag cctcgcaccc aggccaggca gaagctgtgc   4440
tctgaagcta ggacagctgg ctgagaagtg ggttcaggcg aagggtgaag ccatgtgtag   4500
cagttcctgc cagtgcagat ctggagagga gctggcccgg aaggcgtggt tgtgaaagcg   4560
cccttcttat gttaggaggc cttggcaaaa ttggatttct tcaaaaatac atgtaaaggt   4620
ctgttgttga attgtactct gcccctggaa gcagatacag atggctgcct gctgctcggc   4680
tttgcttttg cttttcccac cgtgttttca tctttgttca cttgaggctt tccccagctg   4740
gtgtgtgcag gacagttcat ggtaatgttg ccctctgagg ccccgtacac cagaagggag   4800
gccctggaaa attttgtgct tccaacgtgg ccttcaattc ttgctttttt gcccctcgga   4860
agcatggggc ttttgagcac acttaaaaaa agaaaaatct gtaacttggt gcttattgat   4920
gaattgcaag ctggccttgc agatggagat atttatcttt cagtttattt gaaagaggtc   4980
tggtttaaaa tttgtagcct acatttgttt tatttattgt atttgtgtgt ttgtgtttgt   5040
ttttttttaa gggtgagcca ggtctagccc aacagtctaa actatccagt caataccgag   5100
```

```
tgaagtggca gccagcactg ttcactctgt gtcttttgaa gtgccttgaa ggcccagatg   5160
aaattttaaa gggagggggt ccatgtcctt ccctccccca ccccgcctca ttctttaatc   5220
aaaggatgtc ttctcccttg tttgagaatg aagaaactcg ccacctctga cctacctttg   5280
ccttttctg tcatggagaa tactcaccct tcagaaacag accaaaggcc aaaacctgct   5340
gatttttcta ttgaaaatat gtccccttgc aaagacccta aacaaaaagt taagtttctt   5400
tctttcacct atttgtacaa ctccaagtta cagctgaatc tgtcgtgact ttcctgagat   5460
ctacccgggg cttggctgtc tgttctgggc actggctccg agttcccctc ctgggatttg   5520
caggagggca gtactgaacc tgcattcttc tccttgtaaa tgtaggccgg gtgcccctgt   5580
tctccgggtt tggaacaata cgaggttggt gctgatggga tttacttgcg tacgtgctct   5640
tcacaaaaac accgtggatg ctgaagttag agcacgtcgc cacagagctt gacatcaatg   5700
ttagagggtc tcttactccc cgcccagctg tgatgtttca tctgctttgg ttgttttggt   5760
ggtctttttt aaaaatagag atttcacatc tgcccagacc ccactcaaaa cgatttggtc   5820
aggttctggt tggacaagtt taaaatcaaa gtagtgcccg gaattccctc aaaccaccca   5880
acttcatcca ggaatacagt ctgcagtgca gcaacagaac cgcttaccaa gaactgtgct   5940
tacataccttt tgtcatctct cttccccct tggaagttgt cctcaggggg atttgttcct   6000
gtcctgggga tttacctggg atggtggctg cctgtgcttt tgctcatggc cttgacagtg   6060
ctctagttgc tggatctaat ggcctgtctt ggtttctatc acatgagaag ggttgtttt   6120
tttggggtga ctcggactga attccccata ctgtttccac gccgggacac catgttctcc   6180
atcaagctaa agaaatcacg tgcctgaaac tgtgcttaag ttttggggga aagatggagt   6240
tcctatccag agcccccaga tttccagaat cgagtgagct tcctggaagg agactgcgtc   6300
ttctctcaat tccagtcatc tcagtcgttg tcgttaggtg acatgtgcac tttaaatgct   6360
ctcatcggtt ggcttcattt tcaagacaat caaatgtatt gactgtgttt tcttcttaga   6420
aaatggagag ggttaaaaac atgcaaactg ccactttcaa cctttgccag tattccctct   6480
acccccgtga gagctatctg gggggaagaa tccttaccaa ggttttttg gaaaggtacg   6540
aatcttaact tttttcccct tctgtgtctc agggtaatac tattcagagt cgcccctttg   6600
ctcattttct cccgtatttg ttaccttcct gaggcctcag tattagtcgt gagcacaaag   6660
ttttgagacc tttggcgttg tttcttgatg tgggagggga ggtgttagtg catgcaaggg   6720
ttgaactaga tagaccctgc cttagtagag ggtgggacta taaccttaga ggccagaact   6780
tgatccagaa gttgctgtcc acagaagtgc tttctatttc atcatttttg tttctagggc   6840
tctttttctg tagccaggtc ttcccaagga ttttagtatt tgcattggag ttgaggttta   6900
ctctaatgat ggtggcccag ctgtgcccag aggacagcca ggcaggccct gggagggagt   6960
ttagaaagac agtcctggtg aatgggcttc aagtggtcac aaagagggtg gctgtgaggt   7020
gaccccagac actgcagaac gatgtgcacc ctctgcgttt tggatgtcct tggaatgtgg   7080
gagcctagaa ataaccctgt ggatggaatt ggggcagcgg ctgctggaga tctgtgtgcc   7140
ttgccttcct tcagcaggac cgtctaggtg cgcagccacc tatggatgcg tcccagccag   7200
ccccgtcgct ctcgtccatc ctcagagaca aagaagaggg cagggagttt gggcttggtt   7260
ttgaactttc ctttcaatgt agcaaagcat tcctagttaa ccagagcctt ggaatctact   7320
gcctgctggc caggctttaa aatgaaaagt gttttaatgc tgccataaaa gggaggcggg   7380
ggggaggaag ggaaaataaa ggcatctttc caagtactca tctaatttaa ttgtcaaaag   7440
attgataggc catgaattac ttctccatct cactaagggt taaaggcgtg caacccccca   7500
```

```
ctggctgtgt cccctgccac cgaagtgagt gacctgccct acaaccaggt gggaccacct   7560

gtgctgcagt ccggaggggc ttctgcagga agcactcacc ccccacacct tccccggcct   7620

gagcttcccc tacctttcgt caccacctga gggcatgagc acaggccatg gggcgtgcct   7680

ggtgagtctg cctgtggttc aggcttagcc tgtggtctcc tgtgtgctgc tgcccgcatg   7740

ggatgcgcag gggaggcgtg gggatccgca ggagggtggt tgggatacac cggatacctc   7800

tgctctcatt gcttgtttgc aaatgctcta tggacatttg tgtgctaaat cctattaaat   7860

aaaaaagacg ggttaaaacc cagatgctgt atattcattt gtaattatgt ataaagtgaa   7920

gcagttttaa actgtaaaga ttttttcag tgtgttttct cgaattttgc cacaacatac   7980

tggcttcgta ttttatttat ctttctttct agttaccagc ttcagaccct tgtaaagtct   8040

ccctcagccc tttcaaaaaa taataaattt cctgtgaagt t                       8081
```

<210> SEQ ID NO 26
<211> LENGTH: 4784
<212> TYPE: DNA
<213> ORGANISM: Homo sapiens
<300> PUBLICATION INFORMATION:
<308> DATABASE ACCESSION NUMBER: NM_000922
<309> DATABASE ENTRY DATE: 2006-07-30
<313> RELEVANT RESIDUES IN SEQ ID NO: (1)..(4784)

<400> SEQUENCE: 26

```
gaggcgacac tgagtctcca agtccggaga ggtgcccgag ggaaaagagg cggcagctaa     60

actggtcctg gagagaagcc ccttccgccc ctctcctcag ccagcatgtc ccggactccg    120

ccgctcctca gtccgcgcgg tggggacccc gggccgtggc ggccggcgca gccctgacgg    180

gttgcgaacc agggggcgcc ccgaacgcgg gggttggggt ctgggagcgc gagcggccgc    240

tacggtacga gcggggtgtg ctgagtcccg tggccacccc cggcccccagc catgaggagg    300

gacgagcgag acgccaaagc catgcggtcc ctgcagccgc cggatggggc cggctcgccc    360

cccgagagtc tgaggaacgg ctacgtgaag agctgcgtga gccccttgcg gcaggaccct    420

ccgcgcggct tcttcttcca cctctgccgc ttctgcaacg tggagctgcg gccgccgccg    480

gcctctcccc agcagccgcg gcgctgctcc cccttctgcc gggcgcgcct ctcgctgggc    540

gccctggctg cctttgtcct cgccctgctg ctgggcgcgg aacccgagag ctgggctgcc    600

ggggccgcct ggctgcggac gctgctgagc gtgtgttcgc acagcttgag ccccctcttc    660

agcatcgcct gtgccttctt cttcctcacc tgcttcctca cccggaccaa gcggggaccc    720

ggcccgggcc ggagctgcgg ctcctggtgg ctgctggcgc tgcccgcctg ctgttacctg    780

ggggacttct tggtgtggca gtggtggtct tggccttggg gggatggcga cgcagggtcc    840

gcggccccgc acacgccccc ggaggcggca gcgggcaggt tgctgctggt gctgagctgc    900

gtagggctgc tgctgacgct cgcgcacccg ctgcggctcc ggcactgcgt tctggtgctg    960

ctcctggcca gcttcgtctg gtgggtctcc ttcaccagcc tcgggtcgct gccctccgcc   1020

ctcaggccgc tgctctccgg cctggtgggg ggcgctggct gcctgctggc cctggggttg   1080

gatcacttct ttcaaatcag ggaagcgcct cttcatcctc gactgtccag tgccgccgaa   1140

gaaaaagtgc ctgtgatccg accccggagg aggtccagct gcgtgtcgtt aggagaaact   1200

gcagccagtt actatggcag ttgcaaaata ttcaggagac cgtcgttgcc ttgtatttcc   1260

agagaacaga tgattctttg ggattgggac ttaaaacaat ggtataagcc tcattatcaa   1320

aattctggag gtggaaatgg agttgatctt tcagtgctaa atgaggctcg caatatggtg   1380

tcagatcttc tgactgatcc aagccttcca ccacaagtca tttcctctct acggagtatt   1440
```

```
agtagcttaa tgggtgcttt ctcaggttcc tgtaggccaa agattaatcc tctcacacca   1500
tttcctggat tttacccctg ttctgaaata gaggacccag ctgagaaagg ggatagaaaa   1560
cttaacaagg gactaaatag gaatagtttg ccaactccac agctgaggag aagctcagga   1620
acttcaggat tgctacctgt tgaacagtct tcaaggtggg atcgtaataa tggcaaaagg   1680
cctcaccaag aatttggcat ttcaagtcaa ggatgctatc taaatgggcc ttttaattca   1740
aatctactga ctatcccgaa gcaaaggtca tcttctgtat cactgactca ccatgtaggt   1800
ctcagaagag ctggtgtttt gtccagtctg agtcctgtga attcttccaa ccatggacca   1860
gtgtctactg gctctctaac taatcgatca cccatagaat ttcctgatac tgctgatttt   1920
cttaataagc caagcgttat cttgcagaga tctctgggca atgcacctaa tactccagat   1980
ttttatcagc aacttagaaa ttctgatagc aatctgtgta acagctgtgg acatcaaatg   2040
ctgaaatatg tttcaacatc tgaatcagat ggtacagatt gctgcagtgg aaaatcaggt   2100
gaagaagaaa acattttctc gaaagaatca ttcaaactta tggaaactca acaagaagag   2160
gaaacagaga agaaagacag cagaaaatta tttcaggaag gtgataagtg gctaacagaa   2220
gaggcacaga gtgaacagca aacaaatatt gaacaggaag tatcactgga cctgatttta   2280
gtagaagagt atgactcatt aatagaaaag atgagcaact ggaattttcc aatttttgaa   2340
cttgtagaaa agatgggaga gaaatcagga aggattctca gtcaggttat gtatacctta   2400
tttcaagaca ctggtttatt ggaaatattt aaaattccca ctcaacaatt tatgaactat   2460
tttcgtgcat tagaaaatgg ctatcgagac attccttatc acaatcgtat acatgccaca   2520
gatgtgctac atgcagtttg gtatctgaca acacggccag ttcctggctt acagcagatc   2580
cacaatggtt gtggaacagg aaatgaaaca gattctgatg gtagaattaa ccatgggcga   2640
attgcttata tttcttcgaa gagctgctct aatcctgatg agagttatgg ctgcctgtct   2700
tcaaacattc ctgcattaga attgatggct ctatacgtgg cagctgccat gcatgattat   2760
gatcacccag ggaggacaaa tgcatttcta gtggctacaa atgcccctca ggcagtttta   2820
tacaatgaca gatctgttct ggaaaatcat catgctgcgt cagcttggaa tctatatctt   2880
tctcgcccag aatacaactt ccttcttcat cttgatcatg tggaattcaa gcgctttcgt   2940
tttttagtca ttgaagcaat ccttgctacg gatcttaaaa agcattttga ttttctcgca   3000
gaattcaatg ccaaggcaaa tgatgtaaat agtaatggca tagaatggag taatgaaaat   3060
gatcgcctct tggtatgcca ggtgtgcatc aaactggcag atataaatgg cccagcaaaa   3120
gttcgagact tgcatttgaa atggacagaa ggcattgtca atgaatttta tgagcaggga   3180
gatgaagaag caaatcttgg tctgcccatc agtccattca tggatcgttc ttctcctcaa   3240
ctagcaaaac tccaagaatc ttttatcacc cacatagtgg gtcccctgtg taactcctat   3300
gatgctgctg gtttgctacc aggtcagtgg ttagaagcag aagaggataa tgatactgaa   3360
agtggtgatg atgaagacgg tgaagaatta gatacagaag atgaagaaat ggaaaacaat   3420
ctaaatccaa aaccaccaag aaggaaaagc agacggcgaa tattttgtca gctaatgcac   3480
cacctcactg aaaaccacaa gatatggaag gaaatcgtag aggaagaaga aaaatgtaaa   3540
gctgatggga ataaactgca ggtggagaat tcctccttac ctcaagcaga tgagattcag   3600
gtaattgaag aggcagatga agaggaatag cgacagtttg agtaaaagaa aagtcatatt   3660
gaagaagccc agagggttgt gcccaggggc agaaatcatt gcctagtgtt caccggctga   3720
ctctcaactg accattccca tgtggacagg ccttaatact gtgagaggat ccttgctctg   3780
ctggcagttt cccactccta tgcactttca caggaactag aaaactattc ttaaaccaaa   3840
```

```
aataccatcc gtgttgaccc atgttgcaga gcccttactt aaatccttca ctggtgtatg   3900

aatactttgt cataatgctg ctttgctggg tagtgagctc ttatttttca ctgggggtca   3960

gctataacta aaaactcaag tgacatattt cagttaccaa agtggccagg aactttttgc   4020

ttttatgaaa atagattcat attgtatttc ccagtgtgtc ttttatgtct ttgaatgttt   4080

tggagaaaag tctatgcctg tctaaaaatg aatccagtgt tgcctttctg agggatttct   4140

gctcaatgca atacactgtt cagtgctatt ctcccagcta ggtttatcca tgaaggactg   4200

agtgaccttt gttgtattta acaaaatcca ggtgcatcaa tttctgatgc tttttactat   4260

tgtgtattat ctactatgtg tgttttattt ctgctgagag tattcaggtt tgccatggac   4320

atcagaagtt tgaattccag tcttatctta tgttccatgg ctgaatttta aagctgttta   4380

ggtttaacaa tgaagggatt tattctttag tcaaaattgt tgtttttact ctagctcagg   4440

attcgtattt ttaaagattt agttaatata aacacagcac agatttgtca gaagaaaaaa   4500

aatttgctgt aataccaaaa ctaacctcat caaagataca gaaaaaaaga aatatagtga   4560

gccctaaagg acacatacat tgaataaata attggaacat gtggttatct ttagatccac   4620

atcttagctg tcatttgttc actctaaaac tgatgttcat ctttctgtta atttccctct   4680

gcctaaagag tacatgacag aaatgaccta tcactactta ttatttctga agcctaactg   4740

caagagtgat ttcttgagaa caagtaaaga actggctcgt gccg                    4784


<210> SEQ ID NO 27
<211> LENGTH: 4693
<212> TYPE: DNA
<213> ORGANISM: Homo sapiens
<300> PUBLICATION INFORMATION:
<308> DATABASE ACCESSION NUMBER: NM_005104
<309> DATABASE ENTRY DATE: 2006-08-20
<313> RELEVANT RESIDUES IN SEQ ID NO: (1)..(4693)

<400> SEQUENCE: 27

ggactgcggg ataggaagct ggggatatgg acaagcagca gcgttatagc gctctgggtt     60

tcgggacata ggcctgggcc atgcggcccc cttggcccct tggcgcgacc cccaggaacg    120

ttcggaaagc tggtcctcgt ggctggggga aaggcggggg gtgggggga agcgggcacg     180

tgaccccggt cagccaatct gggtgctgct gacgtggccg cgcggccccg atgctctccc    240

caccccccca gcccgttccg gaagggaggg gctgggggct acgccccctc ccccagcacg    300

gcttcgtttt ctgggggggg gttgacaccc cggattacat accccgtacc aagccgaggg    360

caactttgga ggcccccctgg aaggctttag gatccagatt cttcgctgct gctgccttac   420

cgccgagaac caccacccgc caggcgtctt gcggccacac ccctggcggg ttcaggcagg    480

ctacgcccac gcgacccctc ccgtttccct gctttggcca atggaggagc tacgaatggc    540

acgacctgct cgagcttggc agtctccagt tgggctgtgc atggaagctt gggaagactt    600

tgttggaagg ggaggcgggg agagagtgct ggaggctctg ggcgatggc ttccgcacct     660

cttccaacca ccctctttcc ctggagtcgg cggaccacag ctcagccaat tggcttggag    720

atgtggcggg ttgccacttc cctgtgggtc tctgcggcac tcttctgcct ggtgactgac    780

accttggaaa tgaagtttat gacgtcatcg ctgcggctgg ccaatagaaa aagctcccgc    840

ggagaggtgt tccttcccct tcgactcagc ttcttcaccc gcgtgagcga gcgcgcgcgc    900

gcggaggggg tggggaaaat ctcaagcagg gtggcgcgca tgagcggcga agctcctcct    960

ccccgcctat atataaaggg ctggcgcggg gctcggcggc gccatttcgt gctggagtgg   1020

agcagcctct agaacgagct ggaggattct gcctaccgat acagagcctt cgagtcgtcc   1080
```

```
ggggccgcca ttacaatcca cctccatccg cttggaaatg gccttcgtcc cggcctatga   1140

ctggtcccag cgggcagtac agacccccta gaagcccctg gagctcccct ttttcgggcc   1200

ccgcccaatc ctcggagtct gtccaccccc tctactccgc cctcaagagg atttcaaaga   1260

tggaggcggc ggctccctaa accacttttc gtgttcatcc gcctccatcc gagatcgaaa   1320

cgggacctcg tcggccccgt aggggcccga caagaagagg gaatccctgc agaccaacag   1380

cgggctatat tgacgacggt gtctgagatc ggggaccgtc ttttgaagag tcagtccctc   1440

cttagttgcc cgcctcagct gaggccgccg ccattttctt gctgtccgcc gtctgcagag   1500

cgcgccaagc tgcccggagc tctccgagag gccccaaaga gactgctttc gtgccggcca   1560

ggcagggggt ttgtcgcctg gaggcccaag aggaacggcc tccccccaac ttagcgggtt   1620

atgctggacc gggcggtgag ggaaaccgag gccacccgga ctttccgcgg ctgagggcag   1680

cgccggttcc ttgcggtcaa gatgctgcaa aacgtgactc cccacaataa gctccctggg   1740

gaagggaatg cagggttgct ggggctgggc ccagaagcag cagcaccagg gaaaaggatt   1800

cgaaaaccct ctctcttgta tgagggcttt gagagcccca caatggcttc ggtgcctgct   1860

ttgcaactta cccctgccaa cccaccaccc ccggaggtgt ccaatcccaa aaagccagga   1920

cgagttacca accagctgca atacctacac aaggtagtga tgaaggctct gtggaaacat   1980

cagttcgcat ggccattccg gcagcctgtg gatgctgtca aactgggtct accggattat   2040

cacaaaatta taaaacagcc tatggacatg ggtactatta agaggagact tgaaaacaat   2100

tattattggg ctgcttcaga gtgtatgcaa gattttaata ccatgttcac caactgttac   2160

atttacaaca agcccactga tgatattgtc ctaatggcac aaacgctgga aaagatattc   2220

ctacagaagg ttgcatcaat gccacaagaa gaacaagagc tggtagtgac catccctaag   2280

aacagccaca agaagggggc caagttggca gcgctccagg gcagtgttac cagtgcccat   2340

caggtgcctg ccgtctcttc tgtgtcacac acagccctgt atactcctcc acctgagata   2400

cctaccactg tcctcaacat tccccaccca tcagtcattt cctctccact tctcaagtcc   2460

ttgcactctg ctggaccccc gctccttgct gttactgcag ctcctccagc ccagcccctt   2520

gccaagaaaa aaggcgtaaa gcggaaagca gatactacca cccctacacc tacagccatc   2580

ttggctcctg gttctccagc tagccctcct gggagtcttg agcctaaggc agcacggctt   2640

ccccctatgc gtagagagag tggtcgcccc atcaagcccc cacgcaaaga cttgcctgac   2700

tctcagcaac aacaccagag ctctaagaaa ggaaagcttt cagaacagtt aaaacattgc   2760

aatggcattt tgaaggagtt actctctaag aagcatgctg cctatgcttg gcctttctat   2820

aaaccagtgg atgcttctgc acttggcctg catgactacc atgacatcat taagcacccc   2880

atggacctca gcactgtcaa gcggaagatg gagaaccgtg attaccggga tgcacaggag   2940

tttgctgctg atgtacggct tatgttctcc aactgctata agtacaatcc cccagatcac   3000

gatgttgtgg caatggcacg aaagctacag gatgtatttg agttccgtta tgccaagatg   3060

ccagatgaac cactagaacc agggccttta ccagtctcta ctgccatgcc ccctggcttg   3120

gccaaatcgt cttcagagtc ctccagtgag gaaagtagca gtgagagctc ctctgaggaa   3180

gaggaggagg aagatgagga ggacgaggag gaagaagaga gtgaaagctc agactcagag   3240

gaagaaaggg ctcatcgctt agcagaacta caggaacagc ttcgggcagt acatgaacaa   3300

ctggctgctc tgtcccaggg tccaatatcc aagcccaaga ggaaaagaga gaaaaaagag   3360

aaaaagaaga aacggaaggc agagaagcat cgaggccgag ctggggccga tgaagatgac   3420

aaggggccta gggcaccccg cccacctcaa cctaagaagt ccaagaaagc aagtggcagt   3480
```

```
gggggtggca gtgctgcttt aggcccttct ggctttggac cttctggagg aagtggcacc   3540

aagctcccca aaaaggccac aaagacagcc ccacctgccc tgcctacagg ttatgattca   3600

gaggaggagg aagagagcag gcccatgagt tacgatgaga agcggcagct gagcctggac   3660

atcaacaaat tacctgggga gaagctgggc cgagttgtgc atataatcca agccagggag   3720

ccctctttac gtgattcaaa cccagaagag attgagattg attttgaaac actcaagcca   3780

tccacactta gagagcttga gcgctatgtc ctttcctgcc tacgtaagaa accccggaag   3840

ccctacacca ttaagaagcc tgtgggaaag acaaaggagg aactggcttt ggagaaaaag   3900

cgggaattag aaaagcggtt acaagatgtc agcggacagc tcaattctac taaaaagccc   3960

cccaagaaag cgaatgagaa aacagagtca tcctctgcac agcaagtagc agtgtcacgc   4020

cttagcgctt ccagctccag ctcagattcc agctcctcct cttcctcgtc gtcgtcttca   4080

gacaccagtg attcagactc aggctaaggg gtcaggccag atggggcagg aaggctccgc   4140

aggaccggac ccctagacca ccctgcccca cctgcccctt ccccctttgc tgtgacactt   4200

cttcatctca cccccccccg ccccccctcta ggagagctgg ctctgcagtg ggggagggat   4260

gcagggacat ttactgaagg agggacatgg acaaaacaac attgaattcc cagccccatt   4320

ggggagtgat ctcttggaca cagagccccc attcaaaatg gggcagggca agggtgggag   4380

tgtgcaaagc cctgatctgg agttacctga ggccatagct gccctattca cttctaaggg   4440

ccctgttttg agattgtttg ttctaattta ttttaagcta ggtaaggctg gggggagggt   4500

ggggccgtgg tcccctcagc ctccatgggg agggaagaag gggagctctt ttttttacgt   4560

tgattttttt ttttctactc tgttttccct ttttccttcc gctccatttg ggccctggg    4620

ggtttcagtc atctccccat ttggtcccct ggactgtctt tgttgattct aacttgtaaa   4680

taaagaaaat att                                                      4693
```

```
<210> SEQ ID NO 28
<211> LENGTH: 3497
<212> TYPE: DNA
<213> ORGANISM: Homo sapiens
<300> PUBLICATION INFORMATION:
<308> DATABASE ACCESSION NUMBER: NM_001712
<309> DATABASE ENTRY DATE: 2006-08-20
<313> RELEVANT RESIDUES IN SEQ ID NO: (1)..(3497)

<400> SEQUENCE: 28

aggctcagca cagagagtgg aaaacagcag aggtgacaga gcagccgtgc tcgaagcgtt     60

cctggagccc aagctctcct ccacaggtga agacagggcc agcaggagac accatggggc    120

acctctcagc cccacttcac agagtgcgtg taccctggca ggggcttctg ctcacagcct    180

cacttctaac cttctggaac ccgcccacca ctgcccagct cactactgaa tccatgccat    240

tcaatgttgc agaggggaag gaggttcttc tccttgtcca caatctgccc cagcaacttt    300

ttggctacag ctggtacaaa ggggaaagag tggatggcaa ccgtcaaatt gtaggatatg    360

caataggaac tcaacaagct accccagggc ccgcaaacag cggtcgagag acaatatacc    420

ccaatgcatc cctgctgatc cagaacgtca cccagaatga cacaggattc tacaccctac    480

aagtcataaa gtcagatctt gtgaatgaag aagcaactgg acagttccat gtatacccgg    540

agctgcccaa gccctccatc tccagcaaca actccaaccc tgtggaggac aaggatgctg    600

tggccttcac ctgtgaacct gagactcagg acacaaccta cctgtggtgg ataaacaatc    660

agagcctccc ggtcagtccc aggctgcagc tgtccaatgg caacaggacc ctcactctac    720

tcagtgtcac aaggaatgac acaggaccct atgagtgtga aatacagaac ccagtgagtg    780
```

```
cgaaccgcag tgacccagtc accttgaatg tcacctatgg cccggacacc cccaccattt    840
ccccttcaga cacctattac cgtccagggg caaacctcag cctctcctgc tatgcagcct    900
ctaacccacc tgcacagtac tcctggctta tcaatggaac attccagcaa agcacacaag    960
agctctttat ccctaacatc actgtgaata atagtggatc ctatacctgc cacgccaata   1020
actcagtcac tggctgcaac aggaccacag tcaagacgat catagtcact gagctaagtc   1080
cagtagtagc aaagccccaa atcaaagcca gcaagaccac agtcacagga gataaggact   1140
ctgtgaacct gacctgctcc acaaatgaca ctggaatctc catccgttgg ttcttcaaaa   1200
accagagtct cccgtcctcg gagaggatga agctgtccca gggcaacacc accctcagca   1260
taaaccctgt caagagggag gatgctggga cgtattggtg tgaggtcttc aacccaatca   1320
gtaagaacca aagcgacccc atcatgctga acgtaaacta taatgctcta ccacaagaaa   1380
atggcctctc acctggggcc attgctggca ttgtgattgg agtagtggcc ctggttgctc   1440
tgatagcagt agccctggca tgttttctgc atttcgggaa gaccggcagg gcaagcgacc   1500
agcgtgatct cacagagcac aaaccctcag tctccaacca cactcaggac cactccaatg   1560
acccacctaa caagatgaat gaagttactt attctaccct gaactttgaa gcccagcaac   1620
ccacacaacc aacttcagcc tccccatccc taacagccac agaaataatt tattcagaag   1680
taaaaaagca gtaatgaaac ctgtcctgct cactgcagtg ctgatgtatt tcaagtctct   1740
caccctcatc actaggagat tcctttcccc tgtaggggta gaggggtggg gacagaaaca   1800
actttctcct actcttcctt cctaataggc atctccaggc tgcctggtca ctgcccctct   1860
ctcagtgtca atagatgaaa gtacattggg agtctgtagg aaacccaacc ttcttgtcat   1920
tgaaatttgg caaagctgac tttgggaaag agggaccaga acttcccctc ccttcccctt   1980
ttcccaacct ggacttgttt taaacttgcc tgttcagagc actcattcct tcccaccccc   2040
agtcctgtcc tatcactcta attcggattt gccatagcct tgaggttatg tccttttcca   2100
ttaagtacat gtgccaggaa acaagagaga gagaaagtaa aggcagtaat gccttctcct   2160
atttctccaa agccttgtgt gaactcacca aacacaagaa aatcaaatat ataaccaata   2220
gtgaaatgcc acacctttgt ccactgtcag ggttgtctac ctgtaggatc agggtctaag   2280
caccttggtg cttagctaga ataccaccta atccttctgg caagcctgtc ttcagagaac   2340
ccactagaag caactaggaa aatcacttgc caaaatccaa ggcaattcct gatggaaaat   2400
gcaaaagcac atatatgttt taatatcttt atgggctctg ttcaaggcag tgctgagagg   2460
gaggggttat agcttcagga gggaaccagc ttctgataaa cacaatctgc taggaacttg   2520
ggaaaggaat cagagagctg cccttcagcg attatttaaa ttattgttaa agaatacaca   2580
atttggggta ttgggatttt tctccttttc tctgagacat tccaccattt taatttttgt   2640
aactgcttat ttatgtgaaa agggttattt ttacttagct tagctatgtc agccaatccg   2700
attgccttag gtgaaagaaa ccaccgaaat ccctcaggtc ccttggtcag gagcctctca   2760
agattttttt tgtcagaggc tccaaataga aaataagaaa aggttttctt cattcatggc   2820
tagagctaga tttaactcag tttctaggca cctcagacca atcatcaact accattctat   2880
tccatgtttg cacctgtgca ttttctgttt gcccccattc actttgtcag gaaaccttgg   2940
cctctgctaa ggtgtatttg gtccttgaga agtgggagca ccctacaggg acactatcac   3000
tcatgctggt ggcattgttt acagctagaa agctgcactg gtgctaatgc cccttgggga   3060
aatggggctg tgaggaggag gattataact taggcctagc ctcttttaac agcctctgaa   3120
atttatcttt tcttctatgg ggtctataaa tgtatcttat aataaaaagg aaggacagga   3180
```

ggaagacagg caaatgtact tctcacccag tcttctacac agatggaatc tctttggggc 3240
taagagaaag gttttattct atattgctta cctgatctca tgttaggcct aagaggcttt 3300
ctccaggagg attagcttgg agttctctat actcaggtac ctctttcagg gttttctaac 3360
cctgacacgg actgtgcata ctttccctca tccatgctgt gctgtgttat ttaatttttc 3420
ctggctaaga tcatgtctga attatgtatg aaaattattc tatgttttta taataaaaat 3480
aatatatcag acatcga 3497

<210> SEQ ID NO 29
<211> LENGTH: 2466
<212> TYPE: DNA
<213> ORGANISM: Homo sapiens
<300> PUBLICATION INFORMATION:
<308> DATABASE ACCESSION NUMBER: NM_001008860
<309> DATABASE ENTRY DATE: 2006-08-15
<313> RELEVANT RESIDUES IN SEQ ID NO: (1)..(2466)

<400> SEQUENCE: 29
gttttccggc gccggcccta ggtcccggca gcggtggtga cggcggtgcc ggaggttgtc 60
cttggcaggt tttcctcggc gcttctccat ggaggaggcg gtgcgaacgg cttcagcccc 120
gaatgctcgc atctcccact ggacggcgac gaaggcggtg gccgtgcgag cgcaggactg 180
ggcggcctgt gtgggggtgt gagccgcggt gcccaaggct gcgccggcga ggggaagccg 240
cgcggccggc cggccgacta gggctggagc tactcggcca gggtttaaga ctttaaatga 300
gaataaaggg tggtatttac gaggaaatga gagtgaataa gtcatctcta acctctccca 360 gcctttttt cataagagag accatattaa acttacatgt ttgaagactg cttcattctg 420
cctctagtac cagcggtttc tctgttctgt gatcaatgtg attcacagga actccttaag 480
taacaaacga aatgagccag gggcgtggaa aatatgactt ctatattggt ctgggattgg 540
ctatgagctc cagcattttc attggaggaa gtttcatttt gaaaaaaaag ggcctccttc 600
gacttgccag gaaaggctct atgagagcag gtcaaggtgg ccatgcatat cttaaggaat 660
ggttgtggtg ggctggactg ctgtcaatgg gagctggtga ggtggccaac ttcgctgcgt 720
atgcgtttgc accagccact ctagtgactc cactaggagc tctcagcgtg ctagtaagtg 780
ccattctttc ttcatacttt ctcaatgaaa gacttaatct tcatgggaaa attgggtgtt 840
tgctaagtat tctaggatct acagttatgg tcattcatgc tccaaaggaa gaggagattg 900
agactttaaa tgaaatgtct cacaagctag gtgatccagg ttttgtggtc tttgcaaccc 960
ttgtggtcat tgtggccttg atattaatct tcgtggtggg tcctcgccat ggacagacaa 1020
acattcttgt gtacataaca atctgctctg taatcggcgc gttttcagtc tcctgtgtga 1080
agggcctggg cattgctatc aaggagctgt ttgcagggaa gcctgtgctg cggcatcccc 1140
tggcttggat tctgctgctg agcctcatcg tctgtgtgag cacacagatt aattacctaa 1200
atagggccct ggatatattc aacacttcca ttgtgactcc aatatattat gtattcttta 1260
caacatcagt tttaacttgt tcagctattc tttttaagga gtggcaagat atgcctgttg 1320
acgatgtcat tggtactttg agtggcttct ttacaatcat tgtggggata ttcttgttgc 1380
atgcctttaa agacgtcagc tttagtctag caagtctgcc tgtgtctttt cgaaaagacg 1440
agaaagcaat gaatggcaat ctctctaata tgtatgaagt tcttaataat aatgaagaaa 1500
gcttaacctg tggaatcgaa caacacactg gtgaaaatgt ctcccgaaga aatggaaatc 1560
tgacagcttt ttaagaaagg tgtaattaaa ggttaatctg tgattgttat gaagtgaatt 1620
tgaatatcat cagaatgtgt ctgaaaaaac attgtcctca aataatgttc tttaaaggca 1680

```
atctttttaa agatttcact aatttggacc aagaaattac ttttcttgta tttaaacaaa   1740

caatggtagc tcactaaaat gacctcagca catgacgatt tctattaaca ttttattgtt   1800

gtagaagtat tttacatttt catcccttct ccaaaagccg aatgcactaa tgacagtttt   1860

aagtctatga aaatgcttta ttttttcatt ggtgatgaaa gtctgaaatg tgcatttgtc   1920

atccccactc catcaatccc tgaccatgta aggctttttt attttaaaaa aacagagtta   1980

tcccaataca ttatcctgtg atttacctta cctacaaaag tggctcctgt ttgtttgatg   2040

atgattggtt ttatttttga aatatttatt aagggaaaac taagttactg aatgaaggaa   2100

cctctttctt acaaaacaaa aaaaagggca gaaatcaccc caaggaacga tttctcaggt   2160

tgagatgatc accgtgaatc cggcttcctc tgagcattcg atggccttag cacctcatca   2220

agccagcaca tcctgcctgc tgttgcagcc tggctgggtt tattcttcag ttaccctaat   2280

cccatgatgc ctggaacctt gattaccgtt ttacatcagc tcttgtactt ttcagtatat   2340

tttcataatg agttatattg tcatttagac tttgaacagc tctgggaaat agaagactag   2400

ggttgtttct taaatttagc tcatgttata ataaaaagtt gaaatgaaaa aaaaaaaaaa   2460

aaaaaa                                                              2466
```

<210> SEQ ID NO 30
<211> LENGTH: 2330
<212> TYPE: DNA
<213> ORGANISM: Homo sapiens
<300> PUBLICATION INFORMATION:
<308> DATABASE ACCESSION NUMBER: NM_001008892
<309> DATABASE ENTRY DATE: 2006-10-15
<313> RELEVANT RESIDUES IN SEQ ID NO: (1)..(2330)

<400> SEQUENCE: 30

```
gttttccggc gccggcccta ggtcccggca gcggtggtga cggcggtgcc ggaggttgtc     60

cttggcaggt tttcctcggc gcttctccat ggaggaggcg gtgcgaacgg cttcagcccc    120

gaatgctcgc atctcccact ggacggcgac gaaggcggtg gccgtgcgag cgcaggactg    180

ggcggcctgt gtgggggtgt gagccgcggt gcccaaggct gcgccggcga ggggaagccg    240

cgcggccggc cggccgacta gggtttgaag actgcttcat tctgcctcta gtaccagcgg    300

tttctctgtt ctgtgatcaa tgtgattcac aggaactcct taagtaacaa acgaaatgag    360

ccaggggcgt ggaaaatatg acttctatat tggtctggga ttggctatga gctccagcat    420

tttcattgga ggaagtttca ttttgaaaaa aaagggcctc cttcgacttg ccaggaaagg    480

ctctatgaga gcaggtcaag gtggccatgc atatcttaag gaatggttgt ggtgggctgg    540

actgctgtca atgggagctg gtgaggtggc caacttcgct gcgtatgcgt ttgcaccagc    600

cactctagtg actccactag gagctctcag cgtgctagta agtgccattc tttcttcata    660

ctttctcaat gaaagactta atcttcatgg gaaaattggg tgtttgctaa gtattctagg    720

atctacagtt atggtcattc atgctccaaa ggaagaggag attgagactt taaatgaaat    780

gtctcacaag ctaggtgatc caggttttgt ggtctttgca acccttgtgg tcattgtggc    840

cttgatatta atcttcgtgg tgggtcctcg ccatggacag acaaacattc ttgtgtacat    900

aacaatctgc tctgtaatcg gcgcgttttc agtctcctgt gtgaagggcc tgggcattgc    960

tatcaaggag ctgtttgcag ggaagcctgt gctgcggcat cccctggctt ggattctgct   1020

gctgagcctc atcgtctgtg tgagcacaca gattaattac ctaaataggg ccctggatat   1080

attcaacact tccattgtga ctccaatata ttatgtattc tttacaacat cagttttaac   1140

ttgttcagct attcttttta aggagtggca agatatgcct gttgacgatg tcattggtac   1200
```

```
tttgagtggc ttctttacaa tcattgtggg gatattcttg ttgcatgcct ttaaagacgt   1260

cagctttagt ctagcaagtc tgcctgtgtc ttttcgaaaa gacgagaaag caatgaatgg   1320

caatctctct aatatgtatg aagttcttaa taataatgaa gaaagcttaa cctgtggaat   1380

cgaacaacac actggtgaaa atgtctcccg aagaaatgga aatctgacag ctttttaaga   1440

aaggtgtaat taaaggttaa tctgtgattg ttatgaagtg aatttgaata tcatcagaat   1500

gtgtctgaaa aaacattgtc ctcaaataat gttctttaaa ggcaatcttt ttaaagattt   1560

cactaatttg gaccaagaaa ttacttttct tgtatttaaa caaacaatgg tagctcacta   1620

aaatgacctc agcacatgac gatttctatt aacattttat tgttgtagaa gtattttaca   1680

ttttcatccc ttctccaaaa gccgaatgca ctaatgacag ttttaagtct atgaaaatgc   1740

tttatttttt cattggtgat gaaagtctga aatgtgcatt tgtcatcccc actccatcaa   1800

tccctgacca tgtaaggctt ttttatttta aaaaaacaga gttatcccaa tacattatcc   1860

tgtgatttac cttacctaca aaagtggctc ctgtttgttt gatgatgatt ggttttattt   1920

ttgaaatatt tattaaggga aaactaagtt actgaatgaa ggaacctctt tcttacaaaa   1980

caaaaaaaag ggcagaaatc accccaagga acgatttctc aggttgagat gatcaccgtg   2040

aatccggctt cctctgagca ttcgatggcc ttagcacctc atcaagccag cacatcctgc   2100

ctgctgttgc agcctggctg ggtttattct tcagttaccc taatcccatg atgcctggaa   2160

ccttgattac cgttttacat cagctcttgt acttttcagt atattttcat aatgagttat   2220

attgtcattt agactttgaa cagctctggg aaatagaaga ctagggttgt ttcttaaatt   2280

tagctcatgt tataataaaa agttgaaatg aaaaaaaaaa aaaaaaaaaa              2330
```

```
<210> SEQ ID NO 31
<211> LENGTH: 2273
<212> TYPE: DNA
<213> ORGANISM: Homo sapiens
<300> PUBLICATION INFORMATION:
<308> DATABASE ACCESSION NUMBER: NM_001008894
<309> DATABASE ENTRY DATE: 2006-10-15
<313> RELEVANT RESIDUES IN SEQ ID NO: (1)..(2273)

<400> SEQUENCE: 31

gttttccggc gccggcccta ggtcccggca gcggtggtga cggcggtgcc ggaggttgtc     60

cttggcaggt tttcctcggc gcttctccat ggaggaggcg gtgcgaacgg cttcagcccc    120

gaatgctcgc atctcccact ggacggcgac gaaggcggtg gccgtgcgag cgcaggactg    180

ggcggcctgt gtgggggtgt gagccgcggt gcccaaggct gcgccggcga ggggaagccg    240

cgcggccggc cggccgacta gggtttgaag actgcttcat tctgcctcta gtaccagcgg    300

tttctctgtt ctgtgatcaa tgtgattcac aggaactcct taagtaacaa acgaaatgag    360

ccaggggcgt ggaaaatatg acttctatat tggtctggga ttggctatga gctccagcat    420

tttcattgga ggaagtttca ttttgaaaaa aaagggcctc cttcgacttg ccaggaaagg    480

ctctatgaga gcagtgggag ctggtgaggt ggccaacttc gctgcgtatg cgtttgcacc    540

agccactcta gtgactccac taggagctct cagcgtgcta gtaagtgcca ttctttcttc    600

atactttctc aatgaaagac ttaatcttca tgggaaaatt gggtgtttgc taagtattct    660

aggatctaca gttatggtca ttcatgctcc aaaggaagag gagattgaga ctttaaatga    720

aatgtctcac aagctaggtg atccaggttt tgtggtcttt gcaacccttg tggtcattgt    780

ggccttgata ttaatcttcg tggtgggtcc tcgccatgga cagacaaaca ttcttgtgta    840

cataacaatc tgctctgtaa tcggcgcgtt ttcagtctcc tgtgtgaagg gcctgggcat    900
```

```
tgctatcaag gagctgtttg cagggaagcc tgtgctgcgg catcccctgg cttggattct    960

gctgctgagc ctcatcgtct gtgtgagcac acagattaat tacctaaata gggccctgga   1020

tatattcaac acttccattg tgactccaat atattatgta ttctttacaa catcagtttt   1080

aacttgttca gctattcttt ttaaggagtg gcaagatatg cctgttgacg atgtcattgg   1140

tactttgagt ggcttcttta caatcattgt ggggatattc ttgttgcatg cctttaaaga   1200

cgtcagcttt agtctagcaa gtctgcctgt gtcttttcga aaagacgaga aagcaatgaa   1260

tggcaatctc tctaatatgt atgaagttct taataataat gaagaaagct taacctgtgg   1320

aatcgaacaa cacactggtg aaaatgtctc ccgaagaaat ggaaatctga cagcttttta   1380

agaaaggtgt aattaaaggt taatctgtga ttgttatgaa gtgaatttga atatcatcag   1440

aatgtgtctg aaaaaacatt gtcctcaaat aatgttcttt aaaggcaatc tttttaaaga   1500

tttcactaat ttggaccaag aaattacttt tcttgtattt aaacaaacaa tggtagctca   1560

ctaaaatgac ctcagcacat gacgatttct attaacattt tattgttgta gaagtatttt   1620

acattttcat cccttctcca aaagccgaat gcactaatga cagttttaag tctatgaaaa   1680

tgctttattt tttcattggt gatgaaagtc tgaaatgtgc atttgtcatc cccactccat   1740

caatccctga ccatgtaagg ctttttttatt ttaaaaaaac agagttatcc caatacatta  1800

tcctgtgatt taccttacct acaaaagtgg ctcctgtttg tttgatgatg attggtttta   1860

tttttgaaat atttattaag ggaaaactaa gttactgaat gaaggaacct ctttcttaca   1920

aaacaaaaaa aagggcagaa atcaccccaa ggaacgattt ctcaggttga gatgatcacc   1980

gtgaatccgg cttcctctga gcattcgatg gccttagcac ctcatcaagc cagcacatcc   2040

tgcctgctgt tgcagcctgg ctgggtttat tcttcagtta ccctaatccc atgatgcctg   2100

gaaccttgat taccgtttta catcagctct tgtacttttc agtatatttt cataatgagt   2160

tatattgtca tttagacttt gaacagctct gggaaataga agactagggt tgtttcttaa   2220

atttagctca tgttataata aaaagttgaa atgaaaaaaa aaaaaaaaaa aaa          2273
```

<210> SEQ ID NO 32
<211> LENGTH: 2588
<212> TYPE: DNA
<213> ORGANISM: Homo sapiens
<300> PUBLICATION INFORMATION:
<308> DATABASE ACCESSION NUMBER: NM_030922
<309> DATABASE ENTRY DATE: 2006-10-15
<313> RELEVANT RESIDUES IN SEQ ID NO: (1)..(2588)

<400> SEQUENCE: 32

```
gttttccggc gccggcccta ggtcccggca gcggtggtga cggcggtgcc ggaggttgtc     60

cttggcaggt tttcctcggc gcttctccat ggaggaggcg gtgcgaacgg cttcagcccc    120

gaatgctcgc atctcccact ggacggcgac gaaggcggtg gccgtgcgag cgcaggactg    180

ggcggcctgt gtgggggtgt gagccgcggt gcccaaggct gcgccggcga ggggaagccg    240

cgcggccggc cggccgacta gggctggagc tactcggcca gggtttaaga ctttaaatga    300

gaataaaggg tggtatttac gaggaaatga gagtgaataa gtcatctcta acctctccca    360

gccttttttt cataagagag accatattaa acttacatgc tctcccggct gtgatagacc    420

ttcagttaca gagagaggga gcagagtggg accaggtctg agaatagtga agcaactcat    480

tcctttcagg acattccctc tgatgtccta ttttcaaact gtttgaagac tgcttcattc    540

tgcctctagt accagcggtt tctctgttct gtgatcaatg tgattcacag gaactcctta    600

agtaacaaac gaaatgagcc aggggcgtgg aaaatatgac ttctatattg gtctgggatt    660
```

```
ggctatgagc tccagcattt tcattggagg aagtttcatt ttgaaaaaaa agggcctcct    720
tcgacttgcc aggaaaggct ctatgagagc aggtcaaggt ggccatgcat atcttaagga    780
atggttgtgg tgggctggac tgctgtcaat gggagctggt gaggtggcca acttcgctgc    840
gtatgcgttt gcaccagcca ctctagtgac tccactagga gctctcagcg tgctagtaag    900
tgccattctt tcttcatact ttctcaatga aagacttaat cttcatggga aaattgggtg    960
tttgctaagt attctaggat ctacagttat ggtcattcat gctccaaagg aagaggagat   1020
tgagacttta aatgaaatgt ctcacaagct aggtgatcca ggttttgtgg tctttgcaac   1080
ccttgtggtc attgtggcct tgatattaat cttcgtggtg ggtcctcgcc atggacagac   1140
aaacattctt gtgtacataa caatctgctc tgtaatcggc gcgttttcag tctcctgtgt   1200
gaagggcctg ggcattgcta tcaaggagct gtttgcaggg aagcctgtgc tgcggcatcc   1260
cctggcttgg attctgctgc tgagcctcat cgtctgtgtg agcacacaga ttaattacct   1320
aaatagggcc ctggatatat tcaacacttc cattgtgact ccaatatatt atgtattctt   1380
tacaacatca gttttaactt gttcagctat tctttttaag gagtggcaag atatgcctgt   1440
tgacgatgtc attggtactt tgagtggctt ctttacaatc attgtgggga tattcttgtt   1500
gcatgccttt aaagacgtca gctttagtct agcaagtctg cctgtgtctt ttcgaaaaga   1560
cgagaaagca atgaatggca atctctctaa tatgtatgaa gttcttaata ataatgaaga   1620
aagcttaacc tgtggaatcg aacaacacac tggtgaaaat gtctcccgaa gaaatggaaa   1680
tctgacagct tttaagaaa ggtgtaatta aaggttaatc tgtgattgtt atgaagtgaa   1740
tttgaatatc atcagaatgt gtctgaaaaa acattgtcct caaataatgt tctttaaagg   1800
caatcttttt aaagatttca ctaatttgga ccaagaaatt acttttcttg tatttaaaca   1860
aacaatggta gctcactaaa atgacctcag cacatgacga tttctattaa cattttattg   1920
ttgtagaagt attttacatt ttcatccctt ctccaaaagc cgaatgcact aatgacagtt   1980
ttaagtctat gaaaatgctt tattttttca ttggtgatga aagtctgaaa tgtgcatttg   2040
tcatccccac tccatcaatc cctgaccatg taaggctttt ttattttaaa aaaacagagt   2100
tatcccaata cattatcctg tgatttacct tacctacaaa agtggctcct gtttgtttga   2160
tgatgattgg ttttattttt gaaatattta ttaagggaaa actaagttac tgaatgaagg   2220
aacctctttc ttacaaaaca aaaaaaaggg cagaaatcac cccaaggaac gatttctcag   2280
gttgagatga tcaccgtgaa tccggcttcc tctgagcatt cgatggcctt agcacctcat   2340
caagccagca catcctgcct gctgttgcag cctggctggg tttattcttc agttacccta   2400
atcccatgat gcctggaacc ttgattaccg ttttacatca gctcttgtac ttttcagtat   2460
attttcataa tgagttatat tgtcatttag actttgaaca gctctgggaa atagaagact   2520
agggttgttt cttaaattta gctcatgtta taataaaaag ttgaaatgaa aaaaaaaaaa   2580
aaaaaaaa                                                            2588
```

```
<210> SEQ ID NO 33
<211> LENGTH: 3331
<212> TYPE: DNA
<213> ORGANISM: Homo sapiens
<300> PUBLICATION INFORMATION:
<308> DATABASE ACCESSION NUMBER: NM_021950
<309> DATABASE ENTRY DATE: 2006-10-15
<313> RELEVANT RESIDUES IN SEQ ID NO: (1)..(3331)

<400> SEQUENCE: 33

gtctatcagc gatttcatct tcaggcctgg actacaccac tcaccctccc agtgtgcttg     60
```

```
agaaacaaac tgcacccact gaactccgca gctagcatcc aaatcagccc ttgagatttg    120
aggccttgga gactcaggag ttttgagagc aaaatgacaa cacccagaaa ttcagtaaat    180
gggactttcc cggcagagcc aatgaaaggc cctattgcta tgcaatctgg tccaaaacca    240
ctcttcagga ggatgtcttc actggtgggc cccacgcaaa gcttcttcat gagggaatct    300
aagactttgg gggctgtcca gattatgaat gggctcttcc acattgccct ggggggtctt    360
ctgatgatcc cagcagggat ctatgcaccc atctgtgtga ctgtgtggta ccctctctgg    420
ggaggcatta tgtatattat ttccggatca ctcctggcag caacggagaa aaactccagg    480
aagtgtttgg tcaaaggaaa aatgataatg aattcattga gcctctttgc tgccatttct    540
ggaatgattc tttcaatcat ggacatactt aatattaaaa tttcccattt tttaaaaatg    600
gagagtctga attttattag agctcacaca ccatatatta acatatacaa ctgtgaacca    660
gctaatccct ctgagaaaaa ctccccatct acccaatact gttacagcat acaatctctg    720
ttcttgggca ttttgtcagt gatgctgatc tttgccttct tccaggaact tgtaatagct    780
ggcatcgttg agaatgaatg gaaaagaacg tgctccagac ccaaatctaa catagttctc    840
ctgtcagcag aagaaaaaaa agaacagact attgaaataa aagaagaagt ggttgggcta    900
actgaaacat cttcccaacc aaagaatgaa gaagacattg aaattattcc aatccaagaa    960
gaggaagaag aagaaacaga gacgaacttt ccagaacctc cccaagatca ggaatcctca   1020
ccaatagaaa atgacagctc tccttaagtg atttcttctg ttttctgttt cctttttttaa  1080
acattagtgt tcatagcttc caagagacat gctgactttc atttcttgag gtactctgca   1140
catacgcacc acatctctat ctggcctttg catggagtga ccatagctcc ttctctctta   1200
cattgaatgt agagaatgta gccattgtag cagcttgtgt tgtcacgctt cttcttttga   1260
gcaactttct tacactgaag aaaggcagaa tgagtgcttc agaatgtgat ttcctactaa   1320
cctgttcctt ggataggctt tttagtatag tatttttttt tgtcattttc tccatcaaca   1380
accagggaga ctgcacctga tggaaaagat atatgactgc ttcatgacat tcctaaacta   1440
tctttttttt attccacatc tacgtttttg gtggagtccc ttttgcatca ttgttttaag   1500
gatgataaaa aaaaataaca actagggaca atacagaacc cattccattt atctttctac   1560
agggctgaca ttgtggcaca ttcttagagt taccacaccc catgagggaa gctctaaata   1620
gccaacaccc atctgttttt tgtaaaaaca gcatagctta tacatggaca tgtctctgcc   1680
ttaactttc ctaactccca ctctaggcta ttgtttgcat gtctacctac ttttagccat    1740
tatgcgagaa aagaaaaaaa tgaccataga aaatgccacc atgaggtgcc caaatttcaa   1800
ataataatta acatttagtt atatttataa tttccagatg acaaagtatt tcatcaaata   1860
acttcatttg atgttccatg atcaagaaag aatccctatc tctattttac aagtaattca   1920
aagaggccaa ataacttgta aacaagaaaa ggtaacttgt caacagtcat aactagtaat   1980
tatgagagcc ttgtttcata accaggtctt cttactcaaa tcctgtgatg tttgaaataa   2040
ccaaattgtc tctccaatgt ctgcataaac tgtgagagcc aagtcaacag cttttatcaa   2100
gaatttactc tctgaccagc aataaacaag cactgagaga cacagagagc cagattcaga   2160
ttttacccat ggggataaaa agactcagac tttcaccaca tttggaaaac tacttgcatc   2220
ataaatatat aataactggt agtttatatg aagcagacac taagtgctat agacactctc   2280
agaatatcat acttggaaac aatgtaatta aaatgccgaa tctgagtcaa cagctgccct   2340
acttttcaat tcagatatac tagtacctta cctagaaata atgttaacct agggtgaagt   2400
cactataatc tgtagtctat tatttgggca tttgctacat gatgagtgct gccagattgt   2460
```

```
ggcaggtaaa gagacaatgt aatttgcact ccctatgata tttctacatt tttagcgacc   2520

actagtggaa gacattcccc aaaattagaa aaaaaggaga tagaagattt ctgtctatgt   2580

aaagttctca aaatttgttc taaattaata aaactatctt tgtgttcttt tctgcaacag   2640

atgattccaa catgggtgtt tgtctattct tctttactct tgaaacatta gaccatggga   2700

ggctcttaca gccttgagtt gatatttata caacccaaat ctaggtttga acggtgaggt   2760

gtcaggtcat caaatattca tgtctatata gtcttacaca ggttctcaaa aaaaatgttc   2820

atgggatagg tcattgataa tggattcctt attctgagaa ctccagacga ctgaaatata   2880

tgagagaagg aaaaggacat agtaggagca ggcctgagaa aaaaatgaaa gtcagaaatc   2940

tttaaaaaaa tacaagatct tatttctatc ttattttttc tcctcttctg aaatatatat   3000

gaggattcct ctccaaaccc atggtttctc taagaatttt gagtcatttg tatgacctca   3060

aataattagt tttagctgac ctcacataac tccttataat aggagacatc tttaatgtct   3120

gctattaaag aaggatgaaa attcctatga ccttctcccc gattatccct ttggcaatat   3180

agagtcaaat aataacattg accaatagta aacatgcttt gccaagaagt agaagatata   3240

ttctctagcc ttagtttttc ctcccaattt gcatttttgt aaaaataatg ttgtatccac   3300

aaaggaaata aactttaaaa acccaagtgc a                                  3331
```

```
<210> SEQ ID NO 34
<211> LENGTH: 3594
<212> TYPE: DNA
<213> ORGANISM: Homo sapiens
<300> PUBLICATION INFORMATION:
<308> DATABASE ACCESSION NUMBER: NM_152866
<309> DATABASE ENTRY DATE: 2006-10-15
<313> RELEVANT RESIDUES IN SEQ ID NO: (1)..(2594)

<400> SEQUENCE: 34

gtctatcagc gatttcatct tcaggcctgg actacaccac tcaccctccc agtgtgcttg     60

agaaacaaac tgcacccact gaactccgca gctagcatcc aaatcagccc ttgagatttg    120

aggccttgga gactcagatc ctgaacaaga gagaacaaaa tctctacttt gatggaactt    180

ccattctgtg gggaagagac tgacaataag caattaaata aataagaact cagcagtagg    240

ccttgcctca gatccaaggt cactcggaag aggccatgtc taccctcaat gacactcatg    300

gaggaaatgc tgagagaagc attcagatgc atgacacaag gtaagactgc caaaaatctt    360

gttcttgctc tcctcatttt gttatttgtt ttatttttag gagttttgag agcaaaatga    420

caacacccag aaattcagta aatgggactt tcccggcaga gccaatgaaa ggccctattg    480

ctatgcaatc tggtccaaaa ccactcttca ggaggatgtc ttcactggtg ggccccacgc    540

aaagcttctt catgagggaa tctaagactt tgggggctgt ccagattatg aatgggctct    600

tccacattgc cctgggggt  cttctgatga tcccagcagg gatctatgca cccatctgtg    660

tgactgtgtg gtaccctctc tggggaggca ttatgtatat tatttccgga tcactcctgg    720

cagcaacgga gaaaaactcc aggaagtgtt tggtcaaagg aaaaatgata atgaattcat    780

tgagcctctt tgctgccatt tctggaatga ttctttcaat catggacata cttaatatta    840

aaatttccca ttttttaaaa atggagagtc tgaattttat tagagctcac acaccatata    900

ttaacatata caactgtgaa ccagctaatc cctctgagaa aaactcccca tctacccaat    960

actgttacag catacaatct ctgttcttgg gcattttgtc agtgatgctg atctttgcct   1020

tcttccagga acttgtaata gctggcatcg ttgagaatga atggaaaaga acgtgctcca   1080

gacccaaatc taacatagtt ctcctgtcag cagaagaaaa aaaagaacag actattgaaa   1140
```

```
taaaagaaga agtggttggg ctaactgaaa catcttccca accaaagaat gaagaagaca   1200
ttgaaattat tccaatccaa gaagaggaag aagaagaaac agagacgaac tttccagaac   1260
ctccccaaga tcaggaatcc tcaccaatag aaaatgacag ctctccttaa gtgatttctt   1320
ctgttttctg tttccttttt taaacattag tgttcatagc ttccaagaga catgctgact   1380
ttcatttctt gaggtactct gcacatacgc accacatctc tatctggcct ttgcatggag   1440
tgaccatagc tccttctctc ttacattgaa tgtagagaat gtagccattg tagcagcttg   1500
tgttgtcacg cttcttcttt tgagcaactt tcttacactg aagaaaggca gaatgagtgc   1560
ttcagaatgt gatttcctac taacctgttc cttggatagg ctttttagta tagtattttt   1620
ttttgtcatt ttctccatca acaaccaggg agactgcacc tgatggaaaa gatatatgac   1680
tgcttcatga cattcctaaa ctatcttttt tttattccac atctacgttt ttggtggagt   1740
ccctttgca tcattgtttt aaggatgata aaaaaaaata acaactaggg acaatacaga   1800
acccattcca tttatctttc tacagggctg acattgtggc acattcttag agttaccaca   1860
ccccatgagg gaagctctaa atagccaaca cccatctgtt ttttgtaaaa acagcatagc   1920
ttatacatgg acatgtctct gccttaactt ttcctaactc ccactctagg ctattgtttg   1980
catgtctacc tacttttagc cattatgcga gaaaagaaaa aaatgaccat agaaaatgcc   2040
accatgaggt gcccaaattt caaataataa ttaacattta gttatattta taatttccag   2100
atgacaaagt atttcatcaa ataacttcat ttgatgttcc atgatcaaga aagaatccct   2160
atctctattt tacaagtaat tcaaagaggc caaataactt gtaaacaaga aaaggtaact   2220
tgtcaacagt cataactagt aattatgaga gccttgtttc ataaccaggt cttcttactc   2280
aaatcctgtg atgtttgaaa taaccaaatt gtctctccaa tgtctgcata aactgtgaga   2340
gccaagtcaa cagcttttat caagaattta ctctctgacc agcaataaac aagcactgag   2400
agacacagag agccagattc agattttacc catggggata aaaagactca gactttcacc   2460
acatttggaa aactacttgc atcataaata tataataact ggtagtttat atgaagcaga   2520
cactaagtgc tatagacact ctcagaatat catacttgga aacaatgtaa ttaaaatgcc   2580
gaatctgagt caacagctgc cctacttttc aattcagata tactagtacc ttacctagaa   2640
ataatgttaa cctagggtga agtcactata atctgtagtc tattatttgg gcatttgcta   2700
catgatgagt gctgccagat tgtggcaggt aaagagacaa tgtaatttgc actccctatg   2760
atatttctac atttttagcg accactagtg gaagacattc cccaaaatta gaaaaaaagg   2820
agatagaaga tttctgtcta tgtaaagttc tcaaaatttg ttctaaatta ataaaactat   2880
ctttgtgttc ttttctgcaa cagatgattc caacatgggt gtttgtctat tcttctttac   2940
tcttgaaaca ttagaccatg ggaggctctt acagccttga gttgatattt atacaaccca   3000
aatctaggtt tgaacggtga ggtgtcaggt catcaaatat tcatgtctat atagtcttac   3060
acaggttctc aaaaaaaatg ttcatgggat aggtcattga taatggattc cttattctga   3120
gaactccaga cgactgaaat atatgagaga aggaaaagga catagtagga gcaggcctga   3180
gaaaaaaatg aaagtcagaa atctttaaaa aaatacaaga tcttatttct atcttatttt   3240
ttctcctctt ctgaaatata tatgaggatt cctctccaaa cccatggttt ctctaagaat   3300
tttgagtcat ttgtatgacc tcaaataatt agttttagct gacctcacat aactccttat   3360
aataggagac atctttaatg tctgctatta aagaaggatg aaaattccta tgaccttctc   3420
cccgattatc cctttggcaa tatagagtca aataataaca ttgaccaata gtaaacatgc   3480
tttgccaaga agtagaagat atattctcta gccttagttt ttcctcccaa tttgcatttt   3540
```

tgtaaaaata atgttgtatc cacaaaggaa ataaacttta aaaacccaag tgca 3594

<210> SEQ ID NO 35
<211> LENGTH: 4141
<212> TYPE: DNA
<213> ORGANISM: Homo sapiens
<300> PUBLICATION INFORMATION:
<308> DATABASE ACCESSION NUMBER: NM_003618
<309> DATABASE ENTRY DATE: 2006-08-20
<313> RELEVANT RESIDUES IN SEQ ID NO: (1)..(4141)

<400> SEQUENCE: 35
gagccggccg cggcgccctc tctccgtgtg gccccctgag cggccccccct cccctgcccg 60 ggagggaggc ggggggcacc tggggcccgc catgaacccc ggcttcgatt tgtcccgccg 120
gaacccgcag gaggacttcg agctgattca gcgcatcggc agcggcacct acggcgacgt 180
ctacaaggca cggaatgtta acactggtga attagcagca attaaagtaa taaaattgga 240
accaggagaa gactttgcag ttgtgcagca agaaattatt atgatgaaag actgtaaaca 300
cccaaatatt gttgcttatt ttggaagcta tctcaggcga gataagcttt ggatttgcat 360
ggagttttgt ggaggtggtt ctttacagga tatttatcac gtaactggac ctctgtcaga 420
actgcaaatt gcatatgtta gcagagaaac actgcaggga ttatattatc ttcacagtaa 480
aggaaaaatg cacagagata taaagggagc taacattcta ttaacggata atggtcatgt 540
gaaattggct gattttggag tatctgcaca gataacagct acaattgcca aacggaagtc 600
tttcattggc acaccatatt ggatggctcc agaagttgca gctgttgaga ggaagggggg 660
ttacaatcaa ctctgtgatc tctgggcagt gggaatcact gccatagaac ttgcagagct 720
tcagcctcct atgtttgact tacacccaat gagagcatta tttctaatga caaaaagcaa 780
ttttcagcct cctaaactaa aggataaaat gaaatggtca aatagttttc atcactttgt 840
gaaaatggca cttaccaaaa atccgaaaaa aagacctact gctgaaaaat tattacagca 900
tccttttgta acacaacatt tgacacggtc tttggcaatc gagctgttgg ataaagtaaa 960
taatccagat cattccactt accatgattt cgatgatgat gatcctgagc ctcttgttgc 1020
tgtaccacat agaattcact caacaagtag aaacgtgaga gaagaaaaaa cacgctcaga 1080
gataaccttt ggccaagtga aatttgatcc acccttaaga aaggagacag aaccacatca 1140
tgaacttccc gacagtgatg gtttttgga cagttcagaa gaaatatact acactgcaag 1200
atctaatctg gatctgcaac tggaatatgg acaaggacac caaggtggtt actttttagg 1260
tgcaaacaag agtcttctca agtctgttga agaagaattg catcagcgag gacacgtcgc 1320
acatttagaa gatgatgaag gagatgatga tgaatctaaa cactcaactc tgaaagcaaa 1380
aattccacct cctttgccac caaagcctaa gtctatcttc ataccacagg aaatgcattc 1440
tactgaggat gaaaatcaag gaacaatcaa gagatgtccc atgtcaggga gcccagcaaa 1500
gccatcccaa gttccaccta gaccaccacc tcccagatta cccccacaca aacctgttgc 1560
cttaggaaat ggaatgagct ccttccagtt aaatggtgaa cgagatggct cattatgtca 1620
acaacagaat gaacatagag gcacaaacct ttcaagaaaa gaaaagaaag atgtaccaaa 1680
gcctattagt aatggtcttc ctccaacacc taaagtgcat atgggtgcat gtttttcaaa 1740
agtttttaat gggtgtccct tgaaaattca ctgtgcatca tcatggataa acccagatac 1800
aagagatcag tacttgatat ttggtgccga agaagggatt tataccctca atcttaatga 1860
acttcatgaa acatcaatgg aacagctatt ccctcgaagg tgtacatggt tgtatgtaat 1920
gaacaattgc ttgctatcaa tatctggtaa agcttctcag ctttattccc ataatttacc 1980

```
agggcttttt gattatgcaa gacaaatgca aaagttacct gttgctattc cagcacacaa   2040

actccctgac agaatactgc caaggaaatt ttctgtatca gcaaaaatcc ctgaaaccaa   2100

atggtgccag aagtgttgtg ttgtaagaaa tccttacacg ggccataaat acctatgtgg   2160

agcacttcag actagcattg ttctattaga atgggttgaa ccaatgcaga aatttatgtt   2220

aattaagcac atagattttc ctataccatg tccacttaga atgtttgaaa tgctggtagt   2280

tcctgaacag gagtaccctt tagtttgtgt tggtgtcagt agaggtagag acttcaacca   2340

agtggttcga tttgagacgg tcaatccaaa ttctacctct tcatggttta cagaatcaga   2400

taccccacag acaaatgtta ctcatgtaac ccaactggag agagatacca tccttgtatg   2460

cttggactgt tgtataaaaa tagtaaatct ccaaggaaga ttaaaatcta gcaggaaatt   2520

gtcatcagaa ctcacctttg atttccagat tgaatcaata gtgtgcctac aagacagtgt   2580

gctagctttc tggaaacatg gaatgcaagg tagaagtttt agatctaatg aggtaacaca   2640

agaaatttca gatagcacaa gaattttcag gctgcttgga tctgacaggg tcgtggtttt   2700

ggaaagtagg ccaactgata accccacagc aaatagcaat ttgtacatcc tggcgggtca   2760

tgaaaacagt tactgagaat tgttgtgctt tgacagttaa ctctagaaag aaagaacact   2820

accactgcaa cattaatgga tgcttgaagc tgtacaaaag ctgcagtaac ctgtcttcag   2880

ttactttgta atttattgtg gcatgagata agatggggaa aattttgttt taagtggtat   2940

ggatatattt agcatattga accacacaag tgcttaattc attgttatgt aatctttgta   3000

catataggca gtatttttttc tgtgaaactt catattgctg aagacataca ctaagaattt   3060

atgtagataa tgtactttta tgagatgtac aagtaagtgt cttatctgta cagatgtaaa   3120

tgttgatgaa aatgcaattg gggttaatat tttaagaatt ctttagtata ttcttgggtg   3180

tggctatatt acaaaatggg atgctggcaa tgaaacaata catttaacac tattgtattt   3240

ttattatatg taatttagta atatgaatat aaatcttgta acttttaaaa ttgtaatgga   3300

ggctgtaatc attttataat ctttttaatt ttaatgcaag tacactggtg tttatatttg   3360

cacaaagtat tgatatgtga tgtattaagt cacaaaagta agctgtgaca ttgtctataa   3420

gcatttggct ccacaaatgt atttggattg ttttctatgt gaagcaaacc aattataatt   3480

aaccacatgt tgtagtaact ggtcttttta tatttaagca gaatcctgta agattgcttg   3540

tctttgctta aaaacaatac ctttgaacat ttttgaatca cagaatagcg gtaccatgat   3600

agaatactgc aattgtggtc agaattacag tatgcacaaa gaattaatta gcattattaa   3660

agagtcctca ctaaacattt catatgatca cactgaagaa ctgtaacatt ccatagagtg   3720

aagtggttca aatttctctt ggaattttta cttttgttgg ccttatttta tgatcctttt   3780

catatttctt ttgacttaga gtattaatac atggccaaaa taatttagtt actacctcat   3840

acaaacaata taatggttac tacacatcac aggaacttag ttttggttta agtcattttt   3900

gattgctttt ttccaatgga atatgtatat accaggtttt agcaaaatgc acacttttgg   3960

ctctttttgg tatatgttct ttatatttta atgtgagtat atacactaag aacaaactaa   4020

attgtgattt atgatcttca tttattttaa tgataatggt tttaaaatat gttcctgatt   4080

gtacatattg taaaataaac atgtttttta acaaaaaaaa aaaaaaaaaa aaaaaaaaaa   4140

a                                                                  4141
```

<210> SEQ ID NO 36
<211> LENGTH: 3938
<212> TYPE: DNA
<213> ORGANISM: Homo sapiens <300> PUBLICATION INFORMATION:
<308> DATABASE ACCESSION NUMBER: NM_017784
<309> DATABASE ENTRY DATE: 2005-09-24
<313> RELEVANT RESIDUES IN SEQ ID NO: (1)..(3938)

<400> SEQUENCE: 36

```
tgagcctgtc aggctgggcg ggtccatatc cgggtggacc gggtgggtga ggctgcccct      60
ccctccaggt cccgaggtgg ataaggggtg gggagtgacg tgcagagatt ccctttcgcc     120
ccttcggatc caagagaggg tggcagaagg aatgcgtggg tgacttggcg tggatttagg     180
gcgtgcccac cctgcagatc ggcctcctag agtgtcccga gggcctgaga ggccgcaggg     240
acacgaagga agagaaggca tttcccgggg atttggagca ggcacgcgcg gcccgggcgt     300
ccggagctgt agcagcagca gcagccgccg tgccggggcc gccaccgcgg cgggcacccg     360
cgtcccgggc gcccacggac catggagagg gcagtccagg gcacagacgg cggcgggggt     420
agcaacagca gcagccgcag cagcagccgt gctacctcgg cgggctcctc gccctcctgc     480
tctctggcgg gccgggggt ctccagccgg tcggcggcgg ccgggctcgg cggcgggga      540
agccgcagca gcccgggctc tgtggccgct agcccgtccg ggggaggcgg ccgcaggagg     600
gagccggcgc tcgagggcgt gctcagcaaa tacaccaacc tcctccaggg ctggcagaac     660
aggtacttcg tactggattt cgaggctggc atcctgcagt attttgtgaa tgagcaaagc     720
aaacaccaga agcctcgagg agtcctgtct ttatctggag ccatagtgtc cctgagcgat     780
gaagctcccc acatgctggt ggtgtactct gctaatggag agatgtttaa actgagagct     840
gctgatgcaa aagagaaaca attctgggtg actcagcttc gagcttgtgc caaataccac     900
atggaaatga attctaagag tgctccaagc tcccgaagcc gaagtctcac tttgctccca     960
catggaacac ccaattctgc gtctccctgt agccagagac acctcagtgt gggggccccc    1020
ggtgttgtca caatcacgca tcacaagtcg cctgcagccg cccgaagagc caagagtcag    1080
tattccggcc agcttcacga agtcagagag atgatgaacc aggtggaagg gcagcagaag    1140
aaccttgtgc acgccattga gtccctgcca gggtccggcc ccctcactgc cttggaccag    1200
gacctgctgc tcctgaaagc tacctctgct gccaccctca gctgccttgg ggagtgcctc    1260
aacttgttac agcagagtgt gcaccaggcg ggccagccca gccagaagcc aggagcctcg    1320
gaaaacatcc tgggatggca cgggtccaag tcacattcca cagagcagct gaaaaatggg    1380
acacttggct ctttgccatc agccagtgcc aacataacct gggcaatttt accaaactct    1440
gctgaagacg aacaaacctc acagccagag ccagagccaa actcaggctc tgaattggtt    1500
ttgtctgaag atgaaaaaag tgacaatgaa gataaggaag agacggaatt gggcgtcatg    1560
gaggatcagc gtagtataat tcttcatctc atttcacaac tcaaacttgg aatggatttg    1620
accaaggtgg tgcttcccac ctttatcctg gagaagcgat ctttgctgga gatgtatgca    1680
gatttcatgg cgcacccaga cctactgctg gccatcaccg ctggggccac accagaggag    1740
agagtcattt gcttcgttga gtattatctc acagcctttc acgagggccg caagggcgct    1800
ttagccaaga agccctacaa ccccatcata ggcgagacat ttcactgctc ctgggaagtt    1860
cccaaggaca gggtcaagcc taagaggact gcttcccgct ctcctgccag ctgtcacgaa    1920
cacccaatgg ccgatgaccc ttccaaaagc tacaaactaa ggtttgtggc tgagcaagtg    1980
tcccatcacc cacccatctc ctgcttctac tgtgagtgcg aggagaagag actgtgcgtc    2040
aacactcatg tatggaccaa aagcaagttc atgggcatgt ccgtgggggt ctctatgata    2100
ggggaaggtg tgttgaggct cctggaacac ggggaggagt acgtattcac cctgcctagt    2160
gcctacgccc ggtccattct caccatcccg tgggtggagc tcggaggaaa agtcagcatc    2220
```

```
aactgtgcca agactgggta ctcagcgaca gtgatattcc acacgaagcc tttctatgga   2280

gggaaagtcc acagggttac cgcagaagtg aagcacaacc caaccaacac cattgtttgt   2340

aaagcccatg ggaatggaa tggtacttta gagttcacct acaacaatgg agaaaccaaa   2400

gtcatcgaca caaccacact gccagtgtat cccaagaaga tcagacctct tgagaagcag   2460

ggacccatgg agtccaggaa cctctggcgg gaggtgaccc gatacctgcg gctgggggac   2520

attgacgcag ccaccgagca gaagcggcac ctggaggaga agcaacgggt ggaggaacgg   2580

aagcgcgaga acctccgcac accatggaag cccaaatatt ttatccagga gggcgatggc   2640

tgggtatact tcaatcccct ctggaaagca cactgatggg gtggaggtgc agagctttcc   2700

agtatagccc tgtttttgta ggaatattaa agtagtagag tatcagggtt ttgttggcat   2760

tcactgagac cttgtattag catccaagaa atgatgagag agagagaaat tatatactat   2820

gaaaagtgca cccccacact ctgctagagg aatgaattta ttcaagagcc attcggggca   2880

cgtgtgtgta cacaccgtat acgttcacac acatgcacta tgtaaacatc tgagtatgat   2940

tacacattta aatactgcac tcaccaaggt taaagtgggt aatcataagc tcctttttat   3000

caatgaagtt tgaagttttt ctatttttca ctttgccaaa aatgttttac actcacaaag   3060

atattctcac ttagtcaact cctgtcaaaa tgaaggtgaa ctggcatggc ccgatcactg   3120

tccataaggg agaaagtggc tcattcctgg tagaagtatg ggtggttatc atttcaaaat   3180

tattgtgatt ctcacctccc tccccacctc agtgttttgt ctgtccgcgc ccaagaaaga   3240

taagcaagta tttcctgctg gatgggggtt ggcaggaagc tgttaaagat ttatgccaga   3300

gccttgcagg atggagcacc tctgggacaa ctaagagcca aggcccacca aggagttttc   3360

cacccgtctc tcatggtcac agcgctagtc attcattttt gagaagttgc ttcttttaca   3420

tcagaaaacc agtcaatcat atggagactt cttttgtgat gaaaaagggc tttagaagtt   3480

aaatacatgc atgcacatga aaacatgcac aaccacagcc tcaatcttgt atttagtttg   3540

gggaaagaga agagaatttc ctgtggatta tttttcctc aagtgcacct ctctggttaa   3600

cccaaactct gcaagaaagc actgtgacta aaacatacat aacgcctgca taaatattcc   3660

atggtttcag ttaaatttca gtttttagcc tttacacatg aggtcaaagg agtgacgaaa   3720

atacaaagca aggaaaaaat gaaatatctg gtttttgctg aatgcttaat ttatttttta   3780

ctgtgccact ccaatattta tcaaatccaa atagcatgaa tgcttctctg tagtaatact   3840

aattttgtgc cttttgtctg ctttcttaag accagttgtt cacactttgt agatattaga   3900

caaatatatt tcgattgaat acaaaaaaaa aaaaaaaa                          3938
```

```
<210> SEQ ID NO 37
<211> LENGTH: 3239
<212> TYPE: DNA
<213> ORGANISM: Homo sapiens
<300> PUBLICATION INFORMATION:
<308> DATABASE ACCESSION NUMBER: NM_017935
<309> DATABASE ENTRY DATE: 2006-08-20
<313> RELEVANT RESIDUES IN SEQ ID NO: (1)..(3239)

<400> SEQUENCE: 37

ccgcagcctc cgcgggtggc aagcgggctg gggagagccg agggccaaag gaagagaaaa     60

tcgcggggag tctctggccg ggagagtcca ggtagcgctc ggcgggcagc agtgcgcagg    120

cccctcggct tcaaccgcca caatgctgcc agcagcgcca ggcaaggggc ttgggagccc    180

ggaccccgcc ccctgcggcc cagcgccccc aggaaataca aaagatataa taatgatata    240

tgaagaagat gctgaggaat gggctctgta cttgacagaa gtatttttac atgttgtgaa    300
```

aagggaagcc atcctgttat atcgcttgga gaatttctct tttcggcatt tggagttgct 360
gaacttaacg tcttacaaat gtaaactttt gatattatca aatagcctgc ttagagacct 420
aactccaaag aaatgtcagt ttctggaaaa gatacttcat tcaccaaaaa gtgtagttac 480
tttgctttgt ggagtgaaga gttcagatca gctctatgaa ttactaaata tctctcaaag 540
cagatgggag atctcaactg aacaggaacc tgaagactac atctctgtaa tccagagtat 600
catattcaaa gattctgaag actactttga ggtcaacatt ccaacagacc tacgagcaaa 660
acattctggg gaaataagtg agagaaagga aattgaagaa ctatcagaag cttcaagaaa 720
caccatacca ctagcagtgg tgcttcccac tgaaattcca tgtgagaatc ctggtgaaat 780
attcataatt ttgagagatg aagtaattgg tgatactgta gaggttgaat ttacatcaag 840
taataagcgc attagaacac ggccagccct ttggaataag aaagtctggt gcatgaaagc 900
tttagagttt cctgctggtt cagtccatgt caatgtctac tgtgatggaa tcgttaaagc 960
tacaaccaaa attaagtact acccaacagc aaaggcaaag gaatgcctat tcagaatggc 1020
agattcagga gagagtttgt gccagaatag cattgaagaa cttgatggtg tccttacatc 1080
catattcaaa catgagatac catattatga gttccagtct cttcaaactg aaatttgttc 1140
tcaaaacaaa tatactcatt tcaaagaact tccaactctt ctccactgtg cagcaaaatt 1200
tggcttaaag aacctggcta ttcatttgct tcaatgttca ggagcaacct gggcatctaa 1260
gatgaaaaat atggagggtt cagaccccgc acatattgct gaaaggcatg gtcacaaaga 1320
actcaagaaa atcttcgaag acttttcaat ccaagaaatt gacataaata atgagcaaga 1380
aaatgattat gaagaggata ttgcctcatt ttccacatat attccttcca cacagaaccc 1440
agcatttcat catgaaagca ggaagacata cgggcagagt gcagatggag ctgaggcaaa 1500
tgaaatggaa ggggaaggaa aacagaatgg atcaggcatg gagaccaaac acagcccact 1560
agaggttggc agtgagagtt ctgaagacca gtatgatgac ttgtatgtgt tcattcctgg 1620
tgctgatcca gaaaataatt cacaagagcc actcatgagc agcagacctc ctctcccccc 1680
gccgcgacct gtagctaatg ccttccaact ggaaagacct cacttcacct taccagggac 1740
aatggtggaa ggccaaatgg aaagaagtca aaactggggt catcctggtg ttagacaaga 1800
aacaggagat gaacccaaag gagaaaaaga gaagaaagaa gaggaaaaag agcaggagga 1860
ggaagaagac ccatatactt ttgctgagat tgatgacagt gaatatgaca tgatattggc 1920
caatctgagt ataaagaaaa aaactgggag tcggtctttc attataaata gacctcctgc 1980
ccccacaccc cgacccacaa gtatacctcc aaaagaggaa actacacctt acatagctca 2040
agtgtttcaa caaaagacag ccagaagaca atctgatgat gacaagttcc gtggtcttcc 2100
taagaaacaa gacagagctc ggatagagag tccagccttt tctactctca ggggctgtct 2160
aactgatggt caggaagaac tcatcctcct gcaggagaaa gtaaagaatg ggaaaatgtc 2220
tatggatgaa gctctggaga aatttaaaca ctggcagatg ggaaaaagtg gcctggaaat 2280
gattcagcag gagaaattac gacaactacg agactgcatt attgggaaaa ggccagaaga 2340
agaaaatgtc tataataaac tcaccattgt gcaccatcca ggtggtaagg aaactgccca 2400
caatgaaaat aagttttata atgtacactt cagcaataag cttcctgctc gaccccaagt 2460
tgaaaaggaa tttggtttct gttgcaagaa agatcattaa agaaggttat tataatgaaa 2520
ctcacgaatc tacggacatt ttgctttcag ggtgaagcaa gcttgaattt ggattgcctg 2580
ctctctttaa agcgaattca tactatgaca gcagaaacaa aacttcagat ttcagaattt 2640
gttattggca aaatttattc tcattatacc tgcttcatat gggtatatta ctattaaaac 2700
agaataccat agagtaattg cattatttga aaattctctc attttacaat gcacttcacc 2760
aatgaaacag ctaatttcca ttttgaaaat taaaagaaaa cagcacagag aagttaaatg 2820
cggtgtagca aagttatggg gtctgcttga gggcactaac ctcaacagat tattcctcct 2880
ctccttagaa taaccatgaa aatacaaatt tacttagcac atttttgctt tttaagtagc 2940
tggttcattt tctgaatttc tcacattcag agttccagtc attattgtta catcatgttt 3000
gcagaaacct tgtcttattt agtgtctatt tgcatataac cctgaaaaca ttattatttg 3060
aaaacttttc tatatctcaa attaatatac attttcataa cctacctttg tattaagact 3120
tgcaatttta tcaatctatt atttcttaga aacaatttac tagcttagaa tagaaagcaa 3180
tgttatcgtc atataatttt catgtacaaa tgccacaaat aaattgaatg tttaaagct 3239

<210> SEQ ID NO 38
<211> LENGTH: 4064
<212> TYPE: DNA
<213> ORGANISM: Homo sapiens
<300> PUBLICATION INFORMATION:
<308> DATABASE ACCESSION NUMBER: NM_021070
<309> DATABASE ENTRY DATE: 2006-08-20
<313> RELEVANT RESIDUES IN SEQ ID NO: (1)..(4064)

<400> SEQUENCE: 38
atgcccgggc cccgaggggc tgctggcggc ctggcccctg agatgcgcgg ggcgggggcg 60
gcggggctgc tggcgctgct gctgctgctg ctgctgctgc tgctgggcct gggcggcagg 120
gtcgaggggg ggccggccgg cgagcggggc gcaggcgggg gcggggcgct ggcccgcgag 180
cgcttcaagg tggtctttgc gccggtgatc tgcaagcgga cctgtctcaa gggccagtgt 240
cgggacagtt gtcagcaggg ctccaacatg acgctcatcg gagagaacgg ccacagcaca 300
gacacgctca cgggctccgg cttccgcgtg gtggtgtgcc ctctcccctg catgaatggc 360
ggccagtgct cctcgcgaaa ccagtgcctg tgtcccccgg acttcactgg gcgcttctgc 420
caggtgcccg caggaggagc cggtgggggt accggcggct caggccccgg cctgagcagg 480
acaggggccc tgtccacagg ggcgctgccg cccctggctc cggagggcga ctctgtggcc 540
agcaagcacg ccatctacgc cgtccaggtg atcgctgacc ctcctgggcc cggggagggg 600
cctcctgccc agcacgcagc cttcctggtg cccctaggcc cgggacagat ctcagcagaa 660
gtgcaggccc cgcccccgt ggtgaatgtg cgcgtccatc acccgcccga ggcctcagtc 720
caggtgcacc gcattgagag ctcgaacgcc gagagcgcag ccccctccca gcacctgctg 780
ccgcacccca agccctcgca cccccggccg cccacccaga agcccctggg ccgctgcttt 840
caggacactc tgcccaagca gccgtgtggc agcaaccccc tccccggcct caccaagcag 900
gaagactgct gcggtagcat cggcactgcc tggggccaga gcaagtgcca caagtgtccc 960
cagctgcagt acacaggagt gcagaagcca gggcctgtac gtggggaagt gggcgctgac 1020
tgtccccagg gctacaagag gcttaacagc acccactgcc aggacatcaa cgagtgcgca 1080
atgccgggcg tgtgtcgcca tggtgactgc ctcaacaacc ctggctccta tcgctgtgtc 1140
tgcccacctg gccatagttt aggcccctcc cgtacacagt gcattgcaga caaaccggag 1200
gagaagagcc tgtgtttccg cctggtgagc cctgagcacc agtgccagca cccactgacc 1260
acccgcctga cccgccagct ctgctgctgc agtgtcggca aggcctgggg cgcgcggtgt 1320
cagcgctgcc caacagatgg caccgctgcg ttcaaggaga tctgcccagc tgggaaggga 1380
taccacattc tcacctccca ccagacgctc accattcagg gcgagagtga cttttccctt 1440
ttcctgcacc ctgacgggcc acccaagccc cagcagcttc cggagagccc tagccaggct 1500

```
ccaccacctg aggacacaga ggaagagaga ggggtgacca cggactcacc ggtgagtgag   1560
gagaggtcag tgcagcagag ccacccaact gccaccacga ctcctgcccg gccctacccc   1620
gagctgatct cccgtccctc gcccccgacc atgcgctggt tcctgccgga cttgcctcct   1680
tcccgcagcg ccgtagagat cgctcccact caggtcacag agactgatga gtgccgactg   1740
aaccagaaca tctgtggcca cggagagtgc gtgccgggcc cccctgacta ctcctgccac   1800
tgcaaccccg gctaccggtc acatccccag caccgctact gcgtggatgt gaacgagtgc   1860
gaggcagagc cctgtggccc ggggagggc atctgcatga acaccggcgg ctcctacaat   1920
tgccactgca accgcggcta ccgcctgcac gtgggcgccg gggggcgctc gtgcgtggac   1980
ctgaacgaat gcgccaagcc ccacctgtgc ggcgacggcg gcttctgcat caactttccc   2040
ggtcactaca agtgcaactg ctaccccggc taccggctca aagcctcccg gcctcctgtg   2100
tgcgaagaca tcgacgagtg ccgggaccca agctcttgcc cggatggcaa atgcgagaac   2160
aagcccggga gcttcaagtg catcgcctgt cagcctggct accgcagcca ggggggcggg   2220
gcctgtcgcg acgtgaacga gtgcgccgag ggcagcccct gctcgcctgg ctggtgcgag   2280
aacctcccgg gctccttccg ctgcacctgt gcccagggct acgcgcccgc gcccgacggc   2340
cgcagttgct tggatgtgga cgagtgtgag gctggggacg tgtgtgacaa tggcatctgc   2400
agcaacacgc caggatcttt ccagtgtcag tgcctctctg gctaccatct gtccagggac   2460
cggagccact gcgaggacat tgatgagtgt gacttccctg cagcctgcat tgggggtgac   2520
tgcatcaata ccaatggctc ctacagatgt ctttgccccc aggggcatcg gctggtgggt   2580
ggcaggaaat gccaagacat agatgagtgc agccaggacc cgagcctgtg ccttccccat   2640
ggggcctgca agaaccttca gggctcctat gtgtgtgtct gcgatgaggg cttcactccc   2700
acccaggacc agcacggttg tgaggaggtg gagcagcccc accacaagaa ggagtgctac   2760
ctgaacttcg atgacacagt gttctgcgac agcgtattgg ccaccaacgt gacccagcag   2820
gagtgctgct gctctctggg ggccggctgg ggcgaccact gcgaaatcta cccctgccca   2880
gtctacagct cagccgagtt ccacagcctc tgcccagacg gaaagggcta cacccaggac   2940
aacaacatcg tcaactacgg catcccagcc caccgtgaca tcgacgagtg catgttgttc   3000
gggtcggaga tttgcaagga gggcaagtgc gtgaacacgc agcctggcta cgagtgctac   3060
tgcaagcagg gcttctacta cgacgggaac ctgctggaat gcgtggacgt ggacgagtgc   3120
ctggacgagt ccaactgccg gaacggagtg tgtgagaaca cgcgcggcgg ctaccgctgt   3180
gcctgcacgc cccctgccga gtacagtccc gcgcagcgcc agtgcctgag cccggaagag   3240
atggagcgtg ccccggagcg gcgcgacgtg tgctggagcc agcgcggaga ggacggcatg   3300
tgcgctggcc ccctggccgg gcctgccctc accttcgacg actgctgctg ccgccagggc   3360
cgcggctggg gcgcccaatg ccgaccgtgc ccgccgcgcg gcgcggggtc ccattgcccg   3420
acatcgcaga gcgagagcaa ttccttctgg gacacaagcc ccctgctgtt ggggaagccc   3480
ccaagagatg aggacagttc agaggaggat tcagacgagt gtcgctgcgt gagtggccgc   3540
tgcgtgccgc ggccgggcgg cgccgtgtgc gagtgtcccg gcggcttcca gctcgacgcc   3600
tcccgcgccc gctgcgtgga tatcgacgag tgccgagagc tgaaccagcg cgggctgctg   3660
tgcaagagcg agcgctgcgt gaacaccagc ggctccttcc gctgcgtctg caaagccggc   3720
ttcgcgcgca gccgcccgca cggggcctgc gttccccagc gccgccgctg acgccgccga   3780
cgccgccctc ggcccagacc tcggtgatca ctgagggatt tccgcgagct cggcctcact   3840
tctgccccga cttgtggctc ggacccaggg accttcaggg cccgcagacc ctcccggcgc   3900
```

cttgagaccc gaggcgcccc taccggcccc cctccccggt tagcgggcgg ttgtaaggtc 3960
tccggcgggc gctgcctgcc ttcctcccag agggtgtttc ctagaaactg ataaatcaga 4020
tcgtgcctct ttacccttgg ctttcgaaaa aaaaaaaaaa aaaa 4064

<210> SEQ ID NO 39
<211> LENGTH: 558
<212> TYPE: DNA
<213> ORGANISM: Homo sapiens
<300> PUBLICATION INFORMATION:
<308> DATABASE ACCESSION NUMBER: NM_006786
<309> DATABASE ENTRY DATE: 2006-10-08
<313> RELEVANT RESIDUES IN SEQ ID NO: (1)..(558)

<400> SEQUENCE: 39
ccaagaagga agccgtctat cttgtggcga tcatgtataa gctggcctcc tgctgtttgc 60
ttttcatagg attcttaaat cctctcttat ctcttcctct ccttgactcc agggaaatat 120
cctttcaact ctcagcacct catgaagacg cgcgcttaac tccggaggag ctagaaagag 180
cttcccttct acagatactg ccagagatgc tgggtgcaga aagaggggat attctcagga 240
aagcagactc aagtaccaac atttttaacc caagaggaaa tttgagaaag tttcaggatt 300
tctctggaca agatcctaac attttactga gtcatctttt ggccagaatc tggaaaccat 360
acaagaaacg tgagactcct gattgcttct ggaaatactg tgtctgaagt gaaataagca 420
tctgttagtc agctcagaaa cacccatctt agaatatgaa aaataacaca atgcttgatt 480
tgaaaacagt gtggagaaaa actaggcaaa ctacaccctg ttcattgtta cctggaaaat 540
aaatcctcta tgttttgc 558

<210> SEQ ID NO 40
<211> LENGTH: 652
<212> TYPE: DNA
<213> ORGANISM: Homo sapiens
<300> PUBLICATION INFORMATION:
<308> DATABASE ACCESSION NUMBER: NM_021995
<309> DATABASE ENTRY DATE: 2006-10-08
<313> RELEVANT RESIDUES IN SEQ ID NO: (1)..(652)

<400> SEQUENCE: 40
tccccagatt gtcattcttc agggatggca gccctaaaca cagcatggca actcatctac 60
tcactcatga aagattaaaa aatggaaacc aacgtatttc atcttatgct ctgcgtcact 120
tctgctcgga ctcataaatc cacgtctctt tgctttggcc acttcaactc atatccaagc 180
cttcctttaa ttcatgattt attgctggaa atatcctttc aactctcagc acctcatgaa 240
gacgcgcgct taactccgga ggagctagaa agagcttccc ttctacagat actgccagag 300
atgctgggtg cagaaagagg ggatattctc aggaaagcag actcaagtac caacattttt 360
aacccaagag gaaatttgag aaagtttcag gatttctctg gacaagatcc taacatttta 420
ctgagtcatc ttttggccag aatctggaaa ccatacaaga aacgtgagac tcctgattgc 480
ttctggaaat actgtgtctg aagtgaaata agcatctgtt agtcagctca gaaacaccca 540
tcttagaata tgaaaaataa cacaatgctt gatttgaaaa cagtgtggag aaaaactagg 600
caaactacac cctgttcatt gttacctgga aaataaatcc tctatgtttt gc 652

<210> SEQ ID NO 41
<211> LENGTH: 4182
<212> TYPE: DNA
<213> ORGANISM: Homo sapiens
<300> PUBLICATION INFORMATION:
<308> DATABASE ACCESSION NUMBER: NM_021998

<309> DATABASE ENTRY DATE: 2006-07-07
<313> RELEVANT RESIDUES IN SEQ ID NO: (1)..(4182)

<400> SEQUENCE: 41

```
agacgcagag tagattgtga ttggctcggg ctgcggaacc tcggaaaccc gaatgtgagg     60

accttaaggg atccacagct gccgcccccc gcagccatcc agagcgcggt cacagtccga    120

ctggcggcac ggaggcggcg gcggcggcgg cggcggcagc ggcggcggca gcggcggcgg    180

cagctgtagc tgcagcagca ggtaaagaga gcgttttccc aaagaaaata acatagcaca    240

gaaggaaaaa taaaaagaaa ttgctgcaga ttttacttta tgtgagaaaa tctacaattt    300

cttcgagaca ctcatataaa gatattggtg aatgaacttt gctaagtatg gattcaggcg    360

gtggaagtct tggattgcac acgccagact ctagaatggc ccataccatg attatgcaag    420

attttgtggc tggaatggct ggtactgcac atatcgatgg agaccatatt gttgtttcag    480

ttcctgaagc tgttttagtt tctgatgttg tcacagatga tgggataact cttgatcatg    540

gccttgcagc tgaagttgtc catggacctg atatcatcac agagactgat gtagtaacag    600

aaggtgtgat tgttcctgaa gcggtacttg aagctgatgt tgccattgaa gaggatttag    660

aggaagatga tggtgatcac atcttgactt ctgaactaat tacagaaacc gttagggtac    720

cagagcaggt tttcgtggct gaccttgtta ctggtcctaa tggacactta gaacatgtgg    780

tccaagattg tgtttcagga gtcgactctc ccacaatggt atcagaggag gttcttgtaa    840

ctaattcaga tacagaaact gtgattcaag cagctggagg tgttcctggt tctacagtta    900

ctataaaaac cgaagatgat gatgatgatg atgtcaagag cacttctgaa gactacttaa    960

tgatatcttt ggatgatgtt ggagaaaaat tagagcatat ggggaataca ccattaaaaa   1020

ttggcagtga tggttcacaa gaagatgcta aagaagatgg gtttggttct gaagttataa   1080

aagtgtatat atttaaagcg gaggctgaag atgatgttga aataggtgga acagaaattg   1140

tcacagagag tgagtacacc agtggacatt cagtagctgg agtgcttgac cagagccgaa   1200

tgcagcggga gaagatggtt tacatggcag ttaaagattc ttctcaagaa gaagatgata   1260

tcagagatga aagaagagtt tcccgaaggt atgaagattg tcaagcatca ggaaatactt   1320

tggactcagc attagaaagc agaagtagta cagcagcaca gtaccttcaa atttgtgacg   1380

gcattaatac aaataaagta cttaaacaaa aagccaaaaa gaggagaagg ggagaaacca   1440

ggcagtggca aacagctgtt ataataggtc ctgatggaca gcccctcaca gtgtacccct   1500

gccatatttg cacaaaaaag tttaaatcca ggggattctt aaaaagacac atgaagaatc   1560

atcctgatca tttaatgaga aaaaaatatc agtgtacaga ttgtgacttt acaactaaca   1620

agaaagtgag tttccataac cacttagaaa gccataagct cataaacaaa gtcgacaaaa   1680

cccatgaatt tacagaatac acacgaagat acagagaggc tagtccactg agttccaata   1740

aacttatttt aagagacaag gagccgaaga tgcacaagtg caaatactgt gactatgaaa   1800

ctgcagaaca aggactgtta aacaggcatt tgttggccgt tcacagcaag aattttcctc   1860

atgtttgtgt tgagtgtggg aagggttttc gacatccttc tgaactcaag aaacatatga   1920

gaacccatac tggtgagaag ccatatcagt gtcagtattg tattttcagg tgtgcagatc   1980

aatcaaatct gaaaactcac attaagtcta aacatggtaa caatttgcca tataaatgtg   2040

agcattgtcc ccaagcattt ggtgatgaga gggagcttca acgccatctg gatttgtttc   2100

aaggacataa gacacaccag tgtcctcatt gtgaccataa gagcaccaat tcaagtgacc   2160

ttaagcggca catcatatct gtccatacta aggattttcc tcacaaatgt gaggtctgtg   2220

ataaaggttt tcatcgtcct tctgagctca aaaagcatag tgatatccat aagggtagga   2280
```

```
agattcatca gtgcaggcac tgtgacttta aaacatccga tccatttatt cttagtggcc   2340

atatcctttc agttcatact aaagatcagc cattgaaatg taaaaggtgc aagagaggat   2400

tcagacaaca aaatgagcta aaaaaacata tgaagaccca tactggaagg aagatttacc   2460

aatgtgagta ttgtgaatac agcactacag atgcatctgg ctttaaacga catgtgatat   2520

caatacatac aaaagactat ccacacaggt gtgaattctg caagaaggga ttccgaagac   2580

catcagaaaa aaatcagcat attatgaggc accacaaaga ggctcttatg taataagatc   2640

aatataaaga aagaagctat ttaggagata tgatatgcta cttgggagaa aactctcact   2700

aactgtctca ccgggtttca aagcttgata ctaaaccatg actttacatt ctttgtatta   2760

aagatcttaa aatatttgaa ttcacagggg atcccatagc cctttgaaaa ttacttaaag   2820

aatttaagaa gcactataga atggttacag aaaaacttct taagtatctg tgtaatagta   2880

ttatatgcat acttaaacta cagaggggaa aagcaaagac aaatacttta tttggctgat   2940

tatgttagat acaaatgttt ctgagaagag aatacataat tgagtttagt gatgctttgc   3000

tatagcaagc aaacccactt ttatgcaatt ttagaaatgg ggcagggaaa caaaatgtgg   3060

tcattcatca gtcacttagt cattgagcct tttatattgt acctggaaat taaattccag   3120

caatgacaaa agttttgtgt attcattaaa agaaaactaa ctggaaaaca ggttagatta   3180

attcagtact attaaaaaag aattcagagc tgttaatatt ttatcacagg ataggatact   3240

taaaatatag cattctgtgc tgagatctaa ggtgaagtct ataaagatta aagttccctt   3300

ttttctgatg ttcaagttga ttgttgttca gtatggcata tatgacaaaa gtatatttga   3360

gtcaaatgtg gctttctaaa atggatgcaa cattagcgtt gcaaacaaaa tcagcactat   3420

atttcttaat gatctaaaga ttaatttgag agaacacagt tttcttaaat attataatgt   3480

ctagagtttt tttaggacag tcttagcaag tatgattgtt ctagtcttac ttgctctaat   3540

gtttaaaggt gcaattttat gccattattg aaattgattt ttaaaatcta tataccatat   3600

gattaacatg cattttcaat atgaggcagt gtttatgcag tatttaacag agcaatctgc   3660

tgccaataga gtttggaggt ggatatttag tttacagtgt ataaacttaa aatatgcatc   3720

cctttaacaa cgctttgtgt tagcatgctg caaatcaaaa tggcacttaa tattaaaagc   3780

tggtttaggg aaattttatg aaaatcctgt tcataaatgt aatgcatatg atatgtactt   3840

ttaagtttta gttgcttcat gtttacattc agctgttcaa cataattaaa atgtaatttt   3900

acttcatgct atattgtggc tttgtgtttc aaataatgtt cacctttctg tttttgcacc   3960

agataagaat cagttccttg agaataaatt ttttatcttt cttaacttca gaatattaaa   4020

tttggaatat ctactaaaat tgtgtgttat gtggctgtaa atgatgtaca cgctgtaaaa   4080

taagatcgct actgttatgt gggattatta tttctaaatg ttactcattg aaatgagcat   4140

acaataaaaa gcatttattg cacttaaaaa aaaaaaaaaa aa                      4182
```

<210> SEQ ID NO 42
<211> LENGTH: 3899
<212> TYPE: DNA
<213> ORGANISM: Homo sapiens
<300> PUBLICATION INFORMATION:
<308> DATABASE ACCESSION NUMBER: NM_003178
<309> DATABASE ENTRY DATE: 2006-08-20
<313> RELEVANT RESIDUES IN SEQ ID NO: (1)..(3899)

<400> SEQUENCE: 42

```
tccgccgctg ctgtctgcgg ggtctggcgc cggggtctga gtctctgctg gctaagccgc     60

cgcctcagcc gcctcagtcg cctcaatctc gccttccgcc ctcgctctcc ctccgcgcca    120
```

-continued

```
ccagaccccg tagccccgcg cgcccccagc cctttaagcc agatgatgaa cttcctgcgg    180
cgccggctgt cggacagcag cttcatcgcc aacctgccca acggctacat gaccgacctg    240
cagcggcccg agccccagca gccgccgccg ccgccgcccc ccggtccggg cgccgcctcg    300
gcctcggcgg cgcccccgac cgcctcgccg ggcccggagc ggaggccgcc gcccgcctcg    360
gcgcccgcgc cgcagcccgc gccgacgccg tcggtgggca gcagcttctt cagctcgctg    420
tcccaagccg tgaagcagac ggccgcctcg gctggcctgg tggacgcgcc cgctcccgcg    480
cccgcagccg ccaggaaggc caaggtgctg ctggtggtcg acgagccgca cgccgactgg    540
gccaagtgct ttcggggcaa aaaagtcctt ggagattatg atatcaaggt ggaacaggca    600
gaattttcag agctcaacct ggtggcccat gcagatggca cctatgctgt ggatatgcag    660
gttctccgga atggcacaaa ggttgtccgg tccttccggc cagacttcgt gctcatccgg    720
cagcatgcat ttggcatggc ggagaatgag gacttccgcc acctgatcat tggtatgcag    780
tatgcaggcc tccccagcat caactcactg gaatccatat acaacttctg tgacaagcca    840
tgggtgtttg cccagctggt cgctatctat aagacactgg gaggagaaaa gttccctctc    900
attgaacaga catactaccc caaccacaaa gagatgctga cactgcccac gttccctgtg    960
gtggtgaaga ttggccacgc tcactcaggc atgggcaagg tcaaagtgga aaaccactac   1020
gacttccagg acattgccag cgtggtggct ctcacccaga cctatgccac tgcagagcct   1080
ttcattgact ccaagtatga catccgggtc cagaagattg gcaacaacta caaggcttac   1140
atgaggacat cgatctcagg gaactggaag acgaacactg gctctgcgat gctggagcag   1200
attgccatgt cagacaggta caaactgtgg gtggacacct gctctgagat gtttggcggc   1260
ctggacatct gtgctgtcaa agctgtacat ggcaaagatg ggaaagacta catttttgag   1320
gtcatggact gtagcatgcc actgattggg gaacatcagg tggaggacag gcaactcatc   1380
accgaactag tcatcagcaa gatgaaccag ctgctgtcca ggactcctgc cctgtctcct   1440
cagagacccc taacaaccca gcagccacag agcggaacac ttaaggatcc ggactcaagc   1500
aagaccccac ctcagcggcc accccctcaa ggttgtttac agtatattct cgactgtaat   1560
ggcattgcag tagggccaaa acaagtccaa gcttcttaaa atgattggtg gttaattttt   1620
caaagcagaa attttaagcc aaaaacaaac gaaaggaaag cggggagggg aaaacagacc   1680
ctcccactgg tgccgttgct gcgttctttc aatgctgact ggactgtgtt tttcctatgc   1740
agtgtcagct cctctgtctg gttgtttacc tgttcctgtt cgtgcttgta atgctcactt   1800
atgttttctc tgtataactt gtgattccag ggctgtttgt caacagtata caaaagaatt   1860
gtgcctctcc caagtccagt gtgactttat cttctgggtg gtttgatagt gtttttaaaa   1920
gtaatatata atgtggggtg aaatgggagt aggggggtgg acaggggaga aacgaaaacc   1980
acaaaaagaa aacccaactc ctctcctccc cccaagctca gttaaatccc ccacctccaa   2040
ctttccctcc accagtgtgc ttgggatctt caatgaactg tgcttttcgc tttctttctg   2100
catgactatt gtaactagat agaacattaa gagattttca agatcaaact tccatagctt   2160
catccactga atttgaaggc atccaccttt ttctccattt gctaaaattt ggtgcagttt   2220
gagtttatgt gaataggctg gctgtgcctg tagagctctt gtgtttttag tgatgacatg   2280
aaatacaaag aacaagctat ttccaggaat gtgttctgta ttttacatcc cagtgtaccc   2340
tttattttat tattaactaa ttaactatga gatttttaaa aaatggggcc gctgatgtgc   2400
aatatcaaag tgaacttgtg agtattttgt gtgtgttgat ctcagttgtt tcttcattgt   2460
tgctgtttct ggatccagcc atgtgtgcgc ttgtgtggac ctgaggctgc tttctgttcc   2520
```

caaagcttga cctgtgtaca gagataattc cttggcaatg ttggacatag aatgcaggga 2580
gctactgaag gtctgtcagg gatttgtcca ttctgctctt ggcctctcct gaggcctcat 2640
aatgggagac caaatcaaaa atgtcccatg tcacttgagt gggtacactg cctacagaac 2700
cttgaggttg actcctgctt cagttctcag ctgtttacca cagccctcca gggtccaaag 2760
attgaggagc tttctctttc ctgggaggaa ctgtctcaga tttagcttgt gtgtgttttg 2820
gacagaggct ccacagcggt ggctcttgag gaatcctcac cagtttgttc tcttccctct 2880
gacaagcagc acctgagcag atgctgaggc agttcattaa accaggcctc agcttcagtg 2940
cctcatcttg ccatctcccg gccaggctgg gaacgggcac caagcagccg cctctaacaa 3000
acaccatggt ccgtggaagt tcatgccagc agcttgcctt tgagaagaaa tgctgctggc 3060
tctattttta cattcccttc cacctctata ctgtcatgtc accgttctga actcccagat 3120
ctgagaagga actagtgttg gtggtatgta acaagagtta cgtatccagg ggcttgtgcc 3180
ttggtttctc ctttgattgc tggtaaattc tgaggccaca gagaaatgca ttgagtgtga 3240
atgttgtcat ctgtaatccc tccctcagct gataatggta gttgatctgt tgtaaatata 3300
tacatatatg catatttgca cttccagatg ggttgcataa gaatcaggtc cttaaatacc 3360
tcccaatctg atgaaacgat agaataaagt aacatttccc agaatggagg aatacattat 3420
tttatcgtat atttttgtcc aagcgataag ctgacggtgg tattgcttct ctgcatgtta 3480
tcagtgtgta catctggtgc ttttcatgtg tcatttgtga gccacaaatg caaagttgcc 3540
atttgaattc agtcaggcta cagggtggtg tcagtcaagg tctttcaggt gggggagaaa 3600
ttggttaggg ctcccactgc caaatgcaag cagatagcat aacctgactg ttatgtgccc 3660
tcaggcagca tgcttaggga caactctgtg gcctgggggga catctgtgtc acagtatagg 3720
attgccattc aggtgttttg tacctatttc tttcctgacg ttgtcccctt tttttgtact 3780
gatccaactg ggagaacctc agccaatgct ggaagtatga ttgaagtacc tctcttttgt 3840
gactcttgta cagcttaatg tgcaataaag gaaaagttat atctgaaaaa aaaaaaaaa 3899

<210> SEQ ID NO 43
<211> LENGTH: 2340
<212> TYPE: DNA
<213> ORGANISM: Homo sapiens
<300> PUBLICATION INFORMATION:
<308> DATABASE ACCESSION NUMBER: NM_173544
<309> DATABASE ENTRY DATE: 2006-03-17
<313> RELEVANT RESIDUES IN SEQ ID NO: (1)..(2340)

<400> SEQUENCE: 43
gctgagcagg agatgggaat tgaaacctgc gcagaggcgg ctgtgcaggg tgagagtgga 60
gccgaaacca cagaaagtga agtttgcttc aacgtcttgt cccggcaggc cactcagatg 120
tgagagtgag gaagtgggat ggggcctgac cggaaggagg tgcccctgag ccgaggaacg 180
caggcggtgg tcgtggggaa gggaagagga gccccgggag acgacagcag catgggtggg 240
cggccttcga gccctctgga caagcagcag cggcagcacc taaggggtca ggtggacacc 300
ctgctgagga acttcctgcc ttgctaccgt gggcagctgg cagcgtctgt cctgcggcag 360
atctctcgag agctgggccc tcaggagccg accggaagcc agttgctacg cagcaaaaag 420
ctgccccgag tccgtgagca ccgaggaccc ctgacccagc ttcggggcca cccaccccgg 480
tggcagccga tcttctgtgt tctgcgtggg gacggccgcc tagagtggtt cagccacaag 540
gaggaatatg aaaacggggg ccactgcctt ggctcaacag ccctgacagg atacacgctc 600
ctgacttccc agcgagaata tctccgcctt ttggatgctc tctgccctga atccttggga 660
gaccatactc aggaagagcc tgactccctc ttggaagtgc ctgtgagctt cccgctgttc 720
ctgcagcacc ccttccgccg gcacctctgc ttctctgcag ccaccaggga ggcacagcat 780
gcctggaggc tggccctgca gggtggcatc cggcttcagg gcacagtcct gcagcgaagc 840
caggcccctg ctgcccgggc cttcctggac gccgtccgac tctaccggca gcaccaaggc 900
cactttggcg acgacgacgt gaccctaggc tcagacgccg aggtgctgac cgcggtgctg 960
atgcgggagc aacttcccgc gctgcgagcc cagacccttc ctggcctgcg gggggcaggc 1020
cgcgcccgcg cctgggcctg gaccgagctt ctagacgccg ttcacgcagc tgtcctggcc 1080
ggggcctccg ccgggctctg cgccttccag cccgaaaagg acgagctgct tgcgtcgctg 1140
gagaagacga tccgcccgga cgtggaccag ctgctgcggc agcgggcgcg tgtggcgggg 1200
cggctgagga cggatatcag gggaccgctc gagtcgtgcc tgcgccggga ggtggacccg 1260
cagctgcccc gggtcgtgca gaccctgctg cgcaccgtgg aagcctcgct cgaggcggtg 1320
cggaccctcc tggctcaagg catggaccga ctgtcccacc gcctgcgcca gagcccctca 1380
ggcacgcggc tgcgcaggga ggtttactca tttggggaga tgccgtggga cttggcgctg 1440
atgcagacat gctaccgtga ggccgagcgg agccgggggc gcttggggca gctggcagca 1500
ccgtttggct ttctggggat gcagagcctc gtgtttgggg cccaagatct tgcacagcag 1560
ctcatggctg acgccgtggc caccttcctg cagctggctg accagtgtct gacgacggcc 1620
ctcaactgtg accaggctgc ccagaggctg gagagagtca gggggcgcgt gctgaagaaa 1680
ttcaaatcgg acagcgggtt ggcgcagagg aggttcatcc gaggctgggg tctctgcatc 1740
tttttacctt ttgtgctgag ccaactcgag ccaggctgca aaaaggagct gcctgagttc 1800
gagggggatg tccttgccgt gggcagccag gctctgacca ctgagggcat ctatgaggac 1860
gtcatccggg ggtgcttgct gcagaggatt gaccaagaat tgaaaaagac ccttggtgcc 1920
aatgatgtat cctgcactct ggacggctgc ttggaggtcc catgggaaca ggagggagca 1980
gctccaaatc ttaacttggt gtcaagtttc ctggctggga gacaagcttt taccgacttc 2040
ctctgcttgc cagcaaagtc atctgctaac tggatattgg cagcttctct gctgtcttgc 2100
agctgcttcc ggagtgggtt ccacagggat tcccgtgtgt tcttggttca gcttgcagag 2160
ggactttcac actccctgga gaccgtttcc tcccattctg tctggagttt tcggcctacc 2220
ccaagacaat gagatattcc tgccctttcc tcctatttcc ctccaacccc cccttccgaa 2280
atacatttgc tcaatcattt gcacttcata ggccaaaaaa aaaaaaaaaa aaaaaaaaaa 2340

<210> SEQ ID NO 44
<211> LENGTH: 5659
<212> TYPE: DNA
<213> ORGANISM: Homo sapiens
<300> PUBLICATION INFORMATION:
<308> DATABASE ACCESSION NUMBER: NM_020917
<309> DATABASE ENTRY DATE: 2006-07-07
<313> RELEVANT RESIDUES IN SEQ ID NO: (1)..(5659)

<400> SEQUENCE: 44
gtcggctccg agagctctgg cttatcagga ctccatagtt ctccaacaga gaaatcttga 60
aaaggactga ccagtttttg cagttctaaa accatggccc atggttcagt gacattcagg 120
gatgtggcca tagacttctc acaggaagaa tgggaattcc tggatcctgc tcagagggac 180
ttatataggg atgtaatgtg ggagaactac agcaacttca tttcactagg accttccatt 240
tctaaaccag atgtgattac cttattggat gaagaaagga aggaacctgg gatggttgtg 300
agggaaggga caagaagata ctgccctgat ttggagtcca gatacaggac caatacttta 360

```
tctccagaaa aggacattta tgaaatatat tcatttcagt gggatataat ggaaagaatt    420
aaaagctata gccttcaggg ttccattttt aggaatgatt gggaatgcaa aagcaagatt    480
gagggggaaa aggaacaaca agagggatat tttgggcaag tgaaaattac ctctgaaaaa    540
atgaccactt acaaaaggca caattttctt actgagtatc agatcgttca taatggagaa    600
aaggtgtatg agtgtaagga gtgtaggaag acctttattc gtcgctcaac acttagtcaa    660
cacctgagaa ttcatactgg tgagaaacct tataagtgta aggaatgtgg gcaggccttt    720
agacagcgtg cacatcttat tcgacatcac aaacttcaca ccggtgagaa accctatgaa    780
tgtaaggagt gtgggaaggc ctttacagtg ctccaagaac ttactcaaca tcagagactt    840
catacgggtg aaaaacccta tgaatgtaag gaatgtggaa aggcctttag agtacatcag    900
caactggctc gacatcagag aattcacact ggtgagaaac cctatgaatg taaggactgt    960
ggaaagacct ttagacagtg tacacacctt acacgccatc agagacttca tactgctgaa   1020
aagctctatg aatgtaagga atgtgggaaa gccttcgtat gtggtccaga ccttagagta   1080
catcagaaaa ttcattttgg tgagaaaccc tatgaatgta aggagtgtgg aaaggctttt   1140
agaatatgcc aacaacttac tgttcatcag agtattcata ctggtgagaa accctacgaa   1200
tgtaaggaat gtgggaagac ttttagatta agacaacaac tagttcgcca tcagagaata   1260
catactcgtg agaaacccta tgaatgtatg gaatgttgga agacctttag tagttactca   1320
cagcttattt cacaccagag cattcatatt ggtgagagac cctatgaatg tgaagagtgt   1380
ggaaaggcct ttagactgct ctcacaactt actcagcatc aaagtattca cactggtgag   1440
aaaccttatg aatgtaagga atgtagaaaa ccttttagac tgctctcaca acttacccaa   1500
catcagagta ttcacactgg tgagaaacct tatgaatgta aggaatgtgg taaggctttt   1560
agactttatt catttcttac tcaacaccag agaattcata ctggtgagaa gccctacaag   1620
tgtaaggagt gtaagaaggc ctttagacag cattcacacc ttactcagca tcagaagatt   1680
cataatggaa tttaatagaa gaaagccttc aaatgtatat gatgttacag aacatcagaa   1740
aattcatttt tgagaaaatg tgtttcatgc tcaattccaa gcataataaa ttttatatta   1800
gagaaagaat atgttgattt aaaagccttc caacaccatt taaacatggt ttatcttcag   1860
caaattccta tgagagaata atgtaatgaa tgtaggaaaa tctttagcct tatctgtcat   1920
tatctccctt tctccacttg attaccagtt tgatttattg gacaagatac taagcttctg   1980
tgcctcattt tgctgacttg taaaatggta ataatagtac ttatatgtat tagttattta   2040
ttgctgcgta ataaattacc acagacttag tagcataaaa taacatataa ttatatctta   2100
taatttggat caggagtata ggcatgactt agttgggtcc tctgcttcag ggtctcttgc   2160
aaggctacag atttcagcca gggctgaggt ctcatctgaa ggctcaactg gggaaggatc   2220
cacatccaga ctaacatagt tgttacccaa tgtatttccg tgaggcctgt tgcattgaga   2280
ttctcagttt ctagctggct gttggctgaa cgctgactgc agctcctggc cacaatagcc   2340
tcatcaacat ggctgcttgc ttcatcaagg catgcaagcc aaaagggagg acagtctgct   2400
agcaagatgg aagttaccat cttgtgtaat ctaatcatgg aagtaacatt ccctcacctt   2460
ctactggtag aagtaagtta ctaggatagt ccacactcaa gagaacggga tgatacaaga   2520
gtgtgaataa gtcctggaga caggaccact ggggggcctg tttagagtca gcctgccaca   2580
ctgtggaata ggattgttgc aaggagtaag tagttaatac ttggaggaat cacagtcata   2640
tagcatgtat tctgtaaata ttatctgtaa ttgttattat tgtcattagt attagtgaat   2700
tcacgtaaaa ggaagatctg tagacataat aaatgtagaa atgcctcctg tcacctctca   2760
```

```
gaaattatta aacataattt attctaggta aaatttagat tgtagtgaat gtaggaagtt   2820
cttcagcact tgagctgcat tagaaatttc atgccaaaaa tgaatttcat gaatgtgagg   2880
tcactagtaa tacagctgtt gaagaattag agggaaatag gaaatgattt tcccataatt   2940
ccagaaagca aaaggcttac aatccctgtt gtctgaccac agtttaaaat taattagaaa   3000
ctatcaaaaa tgtggcttaa aagaaattaa ccacctagga atttaatatt gttgtgtata   3060
tttatgtgtg tgtataaaac tcctgtggga aagaaacaaa acatcattct ataagtcagt   3120
atacttttgg atgctcaaaa tgccatatct tcaaccagta ggagttgttt caagttgagt   3180
ttttgatgtg atcccaccaa taatttgata gtttacttga ttgtggctgc ataatttggt   3240
aacctatgaa agatgctaga gcaccaatgt ataatttttt tgagacaggg tgtcactttg   3300
tcccccaggc tggagtgcag tggtacgagc acagttcact gtaccctgtt cctcctgggc   3360
tcaagtgatt cttccaccta aatttttttt tttttttag agaaagggtc tcactatgtt   3420
gcccaggctg gtcttgaact tctgggctca agtgatcctc cctccttggc ctccaaaggt   3480
gctggggtta caggtgtgag ccaccacacc cggcccaact cattattctt gaaatcaata   3540
aatcagagga aaaattgtca tttagtttcc ttttcccatg tgaaccaaat ttcagggtca   3600
ccagaagttc atcaaattca aatgaatttg gcctggcaca ggggtcacac ctgtaatccc   3660
agcactttgg gaggacaagg tgggtggatc acttgaggcc aggagtttga gaccaacctg   3720
gttaacatgg tgaaaccctg tctgtactaa aaatacaaaa tttagccggg cgtggtggca   3780
cacacctgta gtcccaggct gaggtgggag gatcacttga gcccaggagg cagagtttgc   3840
agtgagctgg gatcgtgcca ctgcactcca gcctgggtga cggagtgaga ccctgtctca   3900
aaaaaaaaat ttgtttttttg aatgggtttt tctttttga agaagtctaa taaatctaga   3960
aggaattaga ggattagaaa aatcaccatt ttctggacct taatggaata atgggtccag   4020
aaaacatgat cttcaatggg tactacaact aataggtgaa atattttata gcgagatttt   4080
tatggtggat ctatcaaact ggccacctct gaaccctttg atctgtttta accttaataa   4140
aaatgggtct atcagacaac acacttcctg acgtaatgca ataggaagtc cacaccacca   4200
tctacaaagc cttattgctg gaataatgaa ctgaaagcag acagggacta gatgaacagt   4260
atatggtcat cccttggtat ccatggggaa ttggttccag gatcctccac tgatggtaaa   4320
atctgaggat gctcaagtcc cttgtataaa atggcatagt atgtatttgc atattaccta   4380
ctcacatctt cctgtatact ttaaattatc tttagatcac ttatacctat cacaatgtaa   4440
atactatgta aatagttgtt atactgtatt tttcaatttg cattattttt attgtatttt   4500
atttttattg tttttttttg agtattttct atttgagatt ggttgaatct gcacatatgg   4560
agggctggct ataaagggca ccacaaggaa gaagccaaac agatccagaa tgtgtgaaat   4620
tctacagagc aaattacctg atttcttcaa ctaacaggta gcatgaaaat acaaggggaa   4680
gggcaaccat taacagatta aaagagactt aaagagacat atcaactaaa ttcagtatgt   4740
tggcattact tggacctggt ttgaacaaaa cataaaaagc cattttggag acagtgaggg   4800
aagtgtggac atggactaaa tattaaatga tatttacata tattaatttg gttagggatt   4860
atgtcagtgt gattataaaa aataaaagat cgtatgatat gagatacata ctatgaaatg   4920
aagatagaca catttggatt aaaatattct agcaaaagaa ataattggca aagagagctg   4980
gaaactaaat tggcaacatg ttgataattt aagtggagtg ttttgttcat ggagacttat   5040
tgttctaata tttctacttt tgtatgtgtt tgaaatttca ataataaaat gtttaaaatc   5100
aaaaccaaaa ttatagacta tgtagaaatg aatgacagtg agatgcctgc acatctaacc   5160
```

```
ttgtcagata taatcaaagt tctgttcagt gacaaattaa tgccctgtaa tgtggtaagg   5220

aaatcttatt tgtggataca gtcttcatct tcttcactta cccacagcag caacaccagg   5280

cctgtcacac agatgaatgt gttgagggaa tgaataagta tttccgtcaa gaaaaaggaa   5340

acaacaaaat aaaaccaacc caagtaaaga acagccaagt ggccaggtgc ggtggctcat   5400

gcctgtaatc ccagcacttt gggaggccat ggcaggtgga tcacctgagg tcgggatttt   5460

gagaccagcc tgaccaacac tgagaaaccc catctctatt aaagatacaa aattagccag   5520

gcatggtggt gcatgcctgt aatcccagct acttgggagg ctaaggcagg agaatcactt   5580

gaatccagga ggcggagttt gtggtgagtt gagatcgcgc cactgcactc cagcctgggt   5640

aacagagcaa gagtctgtc                                                5659
```

```
<210> SEQ ID NO 45
<211> LENGTH: 4607
<212> TYPE: DNA
<213> ORGANISM: Homo sapiens
<300> PUBLICATION INFORMATION:
<308> DATABASE ACCESSION NUMBER: NM_020830
<309> DATABASE ENTRY DATE: 2006-09-24
<313> RELEVANT RESIDUES IN SEQ ID NO: (1)..(4607)

<400> SEQUENCE: 45

gtcagctgat gggctgcctg ccgaggaggc cgcagcagtc gccgcgcgaa catggcggcc     60

gaaatccact ccaggccgca gagcagccgc ccggtgctgc tgagcaagat cgaggggcac    120

caggacgccg tcacggccgc gctgctcatc cccaaggagg acggcgtgat cacggccagc    180

gaggacagaa ccatccgggt atggctgaaa agagacagtg gtcaatactg gcccagcatt    240

taccacacaa tggcctctcc ttgctctgct atggcttacc atcatgacag cagacggata    300

tttgtgggcc aggataatgg agctgtaatg gaatttcacg tttctgaaga ttttaataaa    360

atgaacttta tcaagaccta cccagctcat cagaaccggg tgtctgcgat tatcttcagc    420

ttggccacag agtgggtgat cagtaccggc cacgacaagt gtgtgagctg gatgtgcacg    480

cggagcggga acatgctcgg gaggcacttc ttcacgtcct gggcttcgtg tctgcaatat    540

gactttgaca ctcagtatgc tttcgttggt gattattctg ggcagatcac cctgctgaag    600

cttgaacaga acacgtgttc agtcatcaca accctcaaag gacatgaagg tagtgtcgcc    660

tgcctctggt gggaccctat tcagcggtta ctcttctcag gagcatctga caacagcatc    720

atcatgtggg acatcggagg aaggaaaggc cggacgctgt tacttcaggg ccatcatgac    780

aaggtgcagt cgctgtgcta ccttcagctc accaggcagc tcgtctcctg ttcctcggac    840

ggcggaattg cagtgtggaa catggatgtt agcagagaag aggctcctca gtggttggaa    900

agtgattctt gtcagaaatg tgagcagcca tttttctgga acataaagca gatgtgggac    960

accaagacgc tggggctaag acaacatcac tgcaggaaat gcgggcaggc tgtctgcggg   1020

aagtgcagca gcaagcgctc aagttaccca gtcatgggct tcgagttcca agtccgggtt   1080

tgtgattctt gttacgactc catcaaagat gaagatcgga cttctctagc gacctttcat   1140

gaaggaaaac ataacatttc ccacatgtcc atggacattg ccaggggact gatggtgacc   1200

tgtgggaccg accgcattgt aaagatctgg gacatgacac ctgtggtggg ctgcagtctg   1260

gcgactgggt tttctccgca ctgatctgag agctgggcgg cgtccacacc taagaacagc   1320

agctccacca aatgaagtcc ctctcacgca gctccacagc gctgtctcgt gaatggacag   1380

tagccactta caaacaaatc aacattttta aaaagaaaat gtaaaggtgt gttttggggc   1440

atttgtggaa cttacccatg ggactaata tggaaaaggt ctgtccatag tggttccctg   1500
```

```
aagactggaa ttacttcagc aaaacttccc catgaacagc taatgtgtag tgaaagaatg   1560
agctagcaaa tgagttttag cggggacaaa aaatcaaaca aaaaagtgaa tgcttagaac   1620
cttctcaaag cagtcacaag tacagacact tcacttagcc tagggggcct tccagggttc   1680
ttgtggctgt tgtcagagca ggagctgggg gagggaagac ttgttctctc tttcttgagg   1740
ggtggcatta ggaacttacg aaaccagaga cctttcccta tgacttggca gtatgtgaat   1800
atcctctaca cttagttatt gataaacttc ttaaagagat ctgttatttt caggtagtgc   1860
cataatctgc acttagcatt ggcttgcttc agttgtttct cttcccagcc agtatgccac   1920
aggtgaactt tcggggttgt cattaagtaa gttgtgaaat ttctgtaata acaaaggcag   1980
tccgcattct tccctttccc ccaaattcct agggcaaaac tttttatgg tgctgttaac    2040
atgggagtca cacaagccgc ctgacttttt ctcattgcca ttagtaatga ctgatggaaa   2100
acccagccac cactgtgatg cgaaatgatc agtctgttgc ctgaaacagc ccagtcctct   2160
taactgaaac agcattctac ttcttgttcc aagatgagcc tctgcaatat tctggcaatt   2220
taatataccc cctacaaaag cactccacag cttttacact attttgactt tgagttataa   2280
ctagtattat tcatgttttc ataaaaagaa gttagtgacc cagagctata atcatccatc   2340
aagtcttcca caataattcc caactcataa attgctttcc taacaactag caaaagctat   2400
tgttcataat ggcatttcta aagcttttgg gcactgtgta ccaggatgag gaagagaaga   2460
aatgaggagc ctgtctttta atattccagt atttgtgtgt ttgatttttt ttgacaacag   2520
tacatatatc tatttctcta gggatatgga agtaagtgga gaagggccta cctttttaaa   2580
ggacaaatat aaaaatagca acagtatctt tgctaatctt actaatagat attgattaaa   2640
aaaaaaaaac ctcagtactg catcactgtg ttgggatcgt accaggacaa tagggtcatt   2700
ccatatgata aaactaaagg actaaatttg ttttataatg atgtcttaga gggactgaaa   2760
agtttaagga ggcgatcaaa ctaaaatgtc ttaatggctg tgtgacacac gtaaggaaag   2820
gaaagggggt cacgcacatc atgtactgga atgatctgca ttaaacattg acttgtcttc   2880
agaaataaga ctgaagggtt ttgttgttcc ttagagtttt cgtgttacat cacctaaaga   2940
gatttctttt aaaaactttc tagactcttt gcaaaatgta tattactaac atagtttgga   3000
agaaaaattg agtagtggta agttttgttc aagcacaatg ttgaatgtta agcttcctgt   3060
attaatttta gttcagttaa tggttcagcc catacaaagg tgctatccta gggattttat   3120
gaattcctga aaggaaaata gaatatgatc aattccttgc cctgtggaag agtgcagaac   3180
tgtggttttg ttttcctttg acttctgtaa aatgtgaccg tttgacatct gtggtagatt   3240
gaacggaata tcacagctgc tgagtttact ccatagcttt caaacctttt ttattttaag   3300
aaattcttga aaaaccctat gttccatggg aacataaagt tattatagtg cctcctaagg   3360
ggttaatata aatcaaggag gaagtttata tttaaggaag aattggagtg acgtatctta   3420
gaaaaggaaa ggctgatgtt tccatatagc ttgctctcca ccaggcctat catttttctt   3480
tttagagaca aacgtgacag gctagtcttg tctctctcat atgctaggta gcaaatgggg   3540
tgatattttt atagaagtgg gcaaaaatta ttttctcaat tttactgagt aggcacagaa   3600
gaaaagtaca gataggctga tggttattgc cttattttga ctgcatttct cttaaatgga   3660
tcatttaaat tagttcttca agtaacagtt tactggttgt tccattcctg aatatgcagg   3720
ctaatttgta cagataggga ttaaggaata cagactatta gagaagatcc ttatatttac   3780
atctagtata tatgtggtaa ggaaatgccg attcttcatt ataaacaagt tttaaaattg   3840
ttctttctta gttcaaatga tagcaatacc cctatagcat taggtagaaa caaattattc   3900
```

attacatcgt aaatctcttt actatgtcct agctctgtcc tgctacctaa aggatataaa 3960
gaaatactat tgctctagaa tgtattactt tgttctccca tgaaagaatt cagtttgtta 4020
gtacctatat ttttaaactg gtgaaactga cccaaatatg taataaatac catagtagct 4080
cagacccaag gagatatttt tctaaaatca gttttcgtta aagtacttct acttccgtta 4140
ttggatatgg tatctcctaa agtgtaaaaa aaatctgtta ctatatagtg ataaaccatc 4200
tgctcatcgt aagtgtaagg cttaacaaat aagtaataca tgctatattt attcaagtgt 4260
ctattgctta attgttaatt gtgagcagat ttattgaatg cctattctat tttctgcagt 4320
ttacaataca ataactcttt gagtaagttg aagtttaatt gtgcaacaaa tttgtattag 4380
agtacaattt aaagtgtttt tctctatagc ctttttttgac tggggaagca aggggtaatg 4440
ttaattagta cactttgttc ttgtactagc tatgtttcta taagatatgg tgccctgtgt 4500
atcccagaga tgctagaaaa ctgttctttg ctcctatttg tgggttctgt ttttgtgggt 4560 ttttttttt gagaaaatgt acacaataaa acattccttg cttgtta 4607

<210> SEQ ID NO 46
<211> LENGTH: 1502
<212> TYPE: DNA
<213> ORGANISM: Homo sapiens
<300> PUBLICATION INFORMATION:
<308> DATABASE ACCESSION NUMBER: NM_022788
<309> DATABASE ENTRY DATE: 2006-10-01
<313> RELEVANT RESIDUES IN SEQ ID NO: (1)..(1502)

<400> SEQUENCE: 46
atcacaatca gaagacagga gctgcagaac agaacacttt ctcatgtcca gggtcagatt 60
acaagagcac tcaagacttt actgacgaaa actcaggaaa tcctctatca caaagaggtt 120
tggcaactaa actaagacat taaaaggaaa ataccagatg ccactctgca ggttgcaata 180
actactactt actggataca ttcaaaccct ccagaatcaa cagttatcag gtaaccaaca 240
agaaatgcaa gccgtcgaca acctcacctc tgcgcctggt aacaccagtc tgtgcaccag 300
agactacaaa atcacccagg tcctcttccc actgctctac actgtcctgt tttttgttgg 360
acttatcaca aatggcctgg cgatgaggat tttctttcaa atccggagta aatcaaactt 420
tattattttt cttaagaaca cagtcatttc tgatcttctc atgattctga cttttccatt 480
caaaattctt agtgatgcca aactgggaac aggaccactg agaacttttg tgtgtcaagt 540
tacctccgtc atattttatt tcacaatgta tatcagtatt tcattcctgg gactgataac 600
tatcgatcgc taccagaaga ccaccaggcc atttaaaaca tccaaccccca aaaatctctt 660 gggggctaag attctctctg ttgtcatctg ggcattcatg ttcttactct ctttgcctaa 720
catgattctg accaacaggc agccgagaga caagaatgtg aagaaatgct ctttccttaa 780
atcagagttc ggtctagtct ggcatgaaat agtaaattac atctgtcaag tcattttctg 840
gattaatttc ttaattgtta ttgtatgtta tacactcatt acaaaagaac tgtaccggtc 900
atacgtaaga acgaggggtg taggtaaagt ccccaggaaa aaggtgaacg tcaaagtttt 960
cattatcatt gctgtattct ttatttgttt tgttcctttc cattttgccc gaattcctta 1020
caccctgagc caaacccggg atgtctttga ctgcactgct gaaaatactc tgttctatgt 1080
gaaagagagc actctgtggt taacttcctt aaatgcatgc ctggatccgt tcatctattt 1140
tttcctttgc aagtccttca gaaattcctt gataagtatg ctgaagtgcc ccaattctgc 1200
aacatctctg tcccaggaca ataggaaaaa agaacaggat ggtggtgacc caaatgaaga 1260
gactccaatg taaacaaatt aactaaggaa atatttcaat ctctttgtgt tcagaactcg 1320

```
ttaaagcaaa gcgctaagta aaaatattaa ctgacgaaga agcaactaag ttaataataa   1380

tgactctaaa gaaacagaag attacaaaag caattttcat ttacctttcc agtatgaaaa   1440

gctatcttaa aatatagaaa actaatctaa actgtagctg tattagcagc aaaacaaacg   1500

ac                                                                  1502
```

<210> SEQ ID NO 47
<211> LENGTH: 1474
<212> TYPE: DNA
<213> ORGANISM: Homo sapiens
<300> PUBLICATION INFORMATION:
<308> DATABASE ACCESSION NUMBER: NM_176876
<309> DATABASE ENTRY DATE: 2006-10-01
<313> RELEVANT RESIDUES IN SEQ ID NO: (1)..(1474)

<400> SEQUENCE: 47

```
tgaagccctc tttttctctc cttctatttc tctctagagc actcaagact ttactgacga     60

aaactcagga aatcctctat cacaaagagg tttggcaact aaactaagac attaaaagga    120

aaataccaga tgccactctg caggttgcaa taactactac ttactggata cattcaaacc    180

ctccagaatc aacagttatc aggtaaccaa caagaaatgc aagccgtcga caacctcacc    240

tctgcgcctg gtaacaccag tctgtgcacc agagactaca aaatcaccca ggtcctcttc    300

ccactgctct acactgtcct gtttttgtt ggacttatca caaatggcct ggcgatgagg    360

attttctttc aaatccggag taaatcaaac tttattattt ttcttaagaa cacagtcatt    420

tctgatcttc tcatgattct gacttttcca ttcaaaattc ttagtgatgc caaactggga    480

acaggaccac tgagaacttt tgtgtgtcaa gttacctccg tcatatttta tttcacaatg    540

tatatcagta tttcattcct gggactgata actatcgatc gctaccagaa gaccaccagg    600

ccatttaaaa catccaaccc caaaaatctc ttgggggcta agattctctc tgttgtcatc    660

tgggcattca tgttcttact ctctttgcct aacatgattc tgaccaacag gcagccgaga    720

gacaagaatg tgaagaaatg ctctttcctt aaatcagagt tcggtctagt ctggcatgaa    780

atagtaaatt acatctgtca agtcattttc tggattaatt tcttaattgt tattgtatgt    840

tatacactca ttacaaaaga actgtaccgg tcatacgtaa gaacgagggg tgtaggtaaa    900

gtccccagga aaaaggtgaa cgtcaaagtt ttcattatca ttgctgtatt ctttatttgt    960

tttgttcctt tccattttgc ccgaattcct tacaccctga gccaaacccg ggatgtcttt   1020

gactgcactg ctgaaaatac tctgttctat gtgaaagaga gcactctgtg gttaacttcc   1080

ttaaatgcat gcctggatcc gttcatctat tttttccttt gcaagtcctt cagaaattcc   1140

ttgataagta tgctgaagtg ccccaattct gcaacatctc tgtcccagga caataggaaa   1200

aaagaacagg atggtggtga cccaaatgaa gagactccaa tgtaaacaaa ttaactaagg   1260

aaatatttca atctctttgt gttcagaact cgttaaagca aagcgctaag taaaaatatt   1320

aactgacgaa gaagcaacta agttaataat aatgactcta aagaaacaga agattacaaa   1380

agcaattttc atttaccttt ccagtatgaa aagctatctt aaaatataga aaactaatct   1440

aaactgtagc tgtattagca gcaaaacaaa cgac                              1474
```

<210> SEQ ID NO 48
<211> LENGTH: 2537
<212> TYPE: DNA
<213> ORGANISM: Homo sapiens
<300> PUBLICATION INFORMATION:
<308> DATABASE ACCESSION NUMBER: NM_174938
<309> DATABASE ENTRY DATE: 2006-10-15
<313> RELEVANT RESIDUES IN SEQ ID NO: (1)..(2537)

<400> SEQUENCE: 48

```
gaggtggagg cgagcgaaca gagggaggga cccgcccgcc gcgccccggc cgctgggcat     60
gtgtgtccgc aggcgcccga cgctgccgat gtcccggggc tgagcagcgc ccaggtgtcc    120
cggacagtgc gtgcgagcgt gtgtgtccgc gcaggcgagc accgcgccgg ccctgagcct    180
cccgctcgct ccccacggcc gcggtgcatg ttcgcctcct gccactgtgt gccgagaggc    240
aggaggacca tgaaatgatc cactttcgga gctccagcgt caaatcgctc agccaggaga    300
tgagatgcac catccggctg ctggacgact cggagatctc ctgccacatc cagagggaaa    360
ccaaagggca gtttctcatt gaccacatct gcaactacta cagcctgctg gagaaggact    420
actttggcat tcgctatgtg gacccagaga agcaaaggca ctggcttgaa cctaacaagt    480
ccatcttcaa gcaaatgaaa actcatccac catacaccat gtgctttaga gtgaaattct    540
acccacatga acccttgaag attaaagaag agctcacaag atacctttta taccttcaga    600
ttaaaaggga catttttcat ggccacctgc tgtgctcctt ttctgatgct gcctacctgg    660
gtgcctgtat tgttcaagct gagcttggtg attacgatcc taatgagcat cctgagaatt    720
acatcagtga gtttgagatt ttccccaagc agtcacagaa gctggaaaga aaaatagtgg    780
aaattcataa aaatgaactc agggggcaga gcccaccagt tgctgaattt aacttgctcc    840
tgaaagctca cactttggaa acctacgggg tggatcctca cccatgcaag gattcaacag    900
gcacaacaac atttttagga ttcacagctg caggctttgt ggtctttcag ggaaataaga    960
gaatccattt gataaaatgg ccagatgtct gcaaattgaa gtttgaaggg aagacatttt   1020
atgtgattgg cacccagaag gagaaaaaag ccatgttggc attcaatact tcaacaccag   1080
ctgcctgcaa acatctttgg aagtgtggag tggaaaacca ggccttttat aagtatgcaa   1140
aatccagtca gatcaagact gtatcaagca gcaagatatt ttttaaagga agtagatttc   1200
gatatagtgg gaaagttgcc aaagaggtgg tggaggccag ttccaagatc cagagggagc   1260
ctcctgaggt gcacagagcc aacattactc agagccgcag ttcccactcc ttgaacaaac   1320
agctcatcat taacatggaa cccctgcagc ccctgcttcc ttcccccagc gagcaagaag   1380
aagaacttcc tctgggtgag ggtgttccat tgcctaaaga ggagaacatt tctgctccct   1440
tgatctccag ctccccagtg aaggcagccc gggagtatga agatcccccct agtgaagagg   1500
aagataaaat aaaagaagaa cctttaacca tctctgaact agtgtacaac ccaagtgcca   1560
gcctgctccc cacccctgtg gatgacgatg agattgacat gctctttgac tgtccttcta   1620
ggcttgagtt ggaaagagaa gacacagatt catttgagga tctggaagca gatgaaaacg   1680
cctttttgat tgctgaagaa gaggagctga aggaggctcg ccgtgctttg tcgtggagct   1740
acgacattct gactggccat attcgggtga acccactggt caagagtttt tccaggctcc   1800
ttgtggtggg cctgggactg ctgctctttg tatttcccct gctcctcctc cttttggagt   1860
caggtattga tctctccttc ttatgcgaaa tccgccagac accagagttt gagcagtttc   1920
actatgaata ctactgtccc ctcaaggagt gggtggctgg gaaagtccac ctcatcctct   1980
acatgctggg ttgctcatga agttaatctc tcacgtgact aagggctata ttcaatgcta   2040
gtgatttctt tttttcagca aatgcctggt tctgaagggt cacggggctg tcaacaggtg   2100
ttccttactc ataattgatt attcaaacct ttaagttagc tttccataat tcactgcact   2160
taaataagtt taaatcaaat acagttattt tagttacagg ttaggaagat ggtctttaaa   2220
taaccaaaaa tatgtttatt ttttattata gtgtagacat acccttcatc tattatatca   2280
taatacatgt tacattggac tgaattagat tttcccattt ctaatagttg gcaccattat   2340
```

aagctataag gttcagaatc agaattttag taacaactca agagaaagtt gttgaatata 2400
atccttagtg aagacagtgt cctctaacca atgcctatac aactaaattt atgctgggtt 2460
tttggttttg ttttttaaa aatattttta tgtgttcaaa ctattttggt aaatttttag 2520
caaaaaaaaa aaaaaaa 2537

<210> SEQ ID NO 49
<211> LENGTH: 3084
<212> TYPE: DNA
<213> ORGANISM: Homo sapiens

<400> SEQUENCE: 49
aagatctaaa aacggacatc tccaccgtgg gtggctcctt tttctttttc tttttttccc 60
acccttcagg aagtggacgt ttcgttatct tctgatcctt gcaccttctt ttggggaaac 120
ggggcccttc tgcccagatc ccctctcttt tctcggaaaa caaactacta agtcggcatc 180
cggggtaact acagtggaga gggtttccgc ggagacgcgc cgccggaccc tcctctgcac 240
tttggggagg cgtgctccct ccagaaccgg cgttctccgc gcgcaaatcc cggcgacgcg 300
gggtcgcggg gtggccgccg gggcagcctc gtctagcgcg cgccgcgcag acgcccccgg 360
agtcgccagc taccgcagcc ctcgccgccc agtgcccttc ggcctcgggg cgggcgcctg 420
cgtcggtctc cgcgaagcgg gaaagcgcgg cggccgccgg gattcgggcg ccgcggcagc 480
tgctccggct gccggccggc ggccccgcgc tcgcccgccc cgcttccgcc cgctgtcctg 540
ctgcacgaac ccttccaact ctcctttcct cccccaccct tgagttaccc ctctgtcttt 600
cctgctgttg cgcgggtgct cccacagcgg agcggagatt acagagccgc cgggatgccc 660
caactctccg gaggaggtgg cggcggcggg ggggacccgg aactctgcgc cacggacgag 720
atgatcccct tcaaggacga gggcgatcct cagaaggaaa agatcttcgc cgagatcagt 780
catcccgaag aggaaggcga tttagctgac atcaagtctt ccttggtgaa cgagtctgaa 840
atcatcccgg ccagcaacgg acacgaggtg gccagacaag cacaaacctc tcaggagccc 900
taccacgaca aggccagaga acaccccgat gacggaaagc atccagatgg aggcctctac 960
aacaagggac cctcctactc gagttattcc gggtacataa tgatgccaaa tatgaataac 1020
gacccataca tgtcaaatgg atctctttct ccacccatcc cgagaacatc aaataaagtg 1080
cccgtggtgc agccatccca tgcggtccat cctctcaccc ccctcatcac ttacagtgac 1140
gagcactttt ctccaggatc acacccgtca cacatcccat cagatgtcaa ctccaaacaa 1200
ggcatgtcca gacatcctcc agctcctgat atccctactt tttatccctt gtctccgggt 1260
ggtgttggac agatcacccc acctcttggc tggcaaggtc agcctgtata tcccatcacg 1320
ggtggattca ggcaacccta cccatcctca ctgtcagtcg acacttccat gtccaggttt 1380
tcccatcata tgattcccgg tcctcctggt ccccacacaa ctggcatccc tcatccagct 1440
attgtaacac ctcaggtcaa acaggaacat ccccacactg acagtgacct aatgcacgtg 1500
aagcctcagc atgaacagag aaaggagcag gagccaaaaa gacctcacat taagaagcct 1560
ctgaatgctt ttatgttata catgaaagaa atgagagcga atgtcgttgc tgagtgtact 1620
ctaaaagaaa gtgcagctat caaccagatt cttggcagaa ggtggcatgc cctctcccgt 1680
gaagagcagg ctaaatatta tgaattagca cggaaagaaa gacagctaca tatgcagctt 1740
tatccaggct ggtctgcaag agacaattat ggtaagaaaa agaagaggaa gagagagaaa 1800
ctacaggaat ctgcatcagg tacaggtcca agaatgacag ctgcctacat ctgaaacatg 1860
gtggaaaacg aagctcattc ccaacgtgca aagccaaggc agcgacccca ggacctcttc 1920

```
tggagatgga agcttgttga aaacccagac tgtctccacg gcctgcccag tcgacgccaa   1980

aggaacactg acatcaattt taccctgagg tcactgctag agacgctgat ccataaagac   2040

aatcactgcc aacccctctt tcgtctactg caagagccaa gttccaaaat aaagcataaa   2100

aaggtttttt aaaaggaaat gtaaaagcac atgagaatgc tagcaggctg tggggcagct   2160

gagcagcttt tctcccccca tatctgcgtg cacttcccag agcatcttgc atccaaacct   2220

gtaacctttc ggcaaggacg gtaacttggc tgcatttgcc tgtcatgcgc aactggagcc   2280

agcaaccagc tatccatcag caccccagtg gaggagttca tggaagagtt ccctctttgt   2340

ttctgcttca tttttctttc ttttcttttc tcctaaagct tttatttaac agtgcaaaag   2400

gatcgttttt ttttgctttt ttaaacttga attttttaa tttacacttt ttagttttaa   2460

ttttcttgta tattttgcta gctatgagct tttaaataaa attgaaagtt ctggaaaagt   2520

ttgaaataat gacataaaaa gaagccttct ttttctgaga cagcttgtct ggtaagtggc   2580

ttctctgtga attgcctgta acacatagtg gcttctccgc ccttgtaagg tgttcagtag   2640

agctaaataa atgtaatagc caaaccccac tctgttggta gcaattggca gccctatttc   2700

agtttatttt ttcttctgtt ttcttctttt cttttttaa acagtaaacc ttaacagatg   2760

cgttcagcag actggtttgc agtgaatttt catttctttc cttatcaccc ccttgttgta   2820

aaaagcccag cacttgaatt gttattactt taaatgttct gtatttgtat ctgtttttat   2880

tagccaatta gtgggatttt atgccagttg ttaaaatgag cattgatgta cccatttttt   2940

aaaaaagcaa gcacagcctt tgcccaaaac tgtcatccta acgtttgtca ttccagtttg   3000

agttaatgtg ctgagcattt ttttaaaaga agctttgtaa taaaacattt ttaaaaattg   3060

tcatttaaaa aaaaaaaaaa aaaa                                          3084
```

```
<210> SEQ ID NO 50
<211> LENGTH: 1973
<212> TYPE: DNA
<213> ORGANISM: Homo sapiens
<300> PUBLICATION INFORMATION:
<308> DATABASE ACCESSION NUMBER: NM_080387
<309> DATABASE ENTRY DATE: 2006-04-19
<313> RELEVANT RESIDUES IN SEQ ID NO: (1)..(1973)

<400> SEQUENCE: 50

ctttgaaaaa gacttctttt gagctaactt tcttatactg gtacctttct aatctcacta     60

caatatgtaa cattggtgtt cgatctcaag tatttctgaa tatattcccc tatccacaga    120

aatatactct gggggaaaaa aaatagaaca aattcttgcc gtcctgacca ttgaacaaga    180

gactaattag acaatggggc tagaaaaacc tcaaagtaaa ctggaaggag gcatgcatcc    240

ccagctgata ccttcggtta ttgctgtagt tttcatctta cttctcagtg tctgttttat    300

tgcaagttgt ttggtgactc atcacaactt ttcacgctgt aagagaggca caggagtgca    360

caagttagag caccatgcaa agctcaaatg catcaaagag aaatcagaac tgaaaagtgc    420

tgaagggagc acctggaact gttgtcctat tgactggaga gccttccagt ccaactgcta    480

ttttcctctt actgacaaca agacgtgggc tgagagtgaa aggaactgtt cagggatggg    540

ggcccatctg atgaccatca gcacggaagc tgagcagaac tttattattc agtttctgga    600

tagacggctt tcctatttcc ttggacttag agatgagaat gccaaaggtc agtggcgttg    660

ggtggaccag acgccattta acccacgcag agtattctgg cataagaatg aacccgacaa    720

ctctcaggga gaaaactgtg ttgttcttgt ttataaccaa gataaatggg cctggaatga    780

tgttccttgt aactttgaag caagtaggat ttgtaaaata cctggaacaa cattgaacta    840
```

```
gaaactcaga aagtggtcct tgtgatggaa agagaaaaga aaaaccaatt agaataaggc    900

agaatgtacg tgcgtcattg gaacacagaa aacatgctgg ttcatacagc gtttttagtc    960

ataatggtct tttttatttt gtttgattca ttcgagacaa catgtgtgta tgtgtgtgtg   1020

tgtgtgtgta gataatgtgg tttttgtatg gtgtttgatg gaaggaataa tctttctttg   1080

ctttcttagt agtatttcaa ggtgtttact tttcaattgg tgtgcactga atgcatgtat   1140

ggaagaatag cgtgaataat gcaatctctt tgtcattttt cccctctca gactcttagc   1200

tcttaaaatt caaagatggg atattctaac tggtagtggt gcatcatttt taacccaaat   1260

attgcaagca ctttaaagat ttgaaaccac atttttattg tttgatgttt cattttcaga   1320

ctttttaatg tcagtcatta caattacatt gcatgaggaa aatttttcca gaacaacagt   1380

gtggaatagt tctgaattat gctgttctac agatagaaaa aaagtccaaa tgcctttaaa   1440

aatttacttc ttactccacc caacacgttt ttgcaaagca agaagtcttt gtaagacacc   1500

ttaaacaaag tccttcaatt ctacagcaga ggaaataaaa tcccccagaa gccaaagggc   1560

tcaccttcac attgttagtt catgacagac ccaggtgtgc ttcattagag ataacataca   1620

ttccctttgg tatcacagga agttactggg gattactcga cctcattact tagctaacga   1680

ctggataaaa tttcttaatt gtttgaagta acattgtatt cgtgtttgca ttattaattt   1740

gaatagaaaa taatcacatt ttcaacccat ttatacaaat tgttaatgtt tctttagagc   1800

tgtataacta tagtttgaac tagcaaggaa gttattgttt tgacaaccag aaattatgct   1860

tttctggtgc atgaaacatt aattgcaaag ggcagtcaca tccaacttta ataaaatatg   1920

gtggtctttc ttaaaaaaaa aaaaaaaaaa aaaaaaaaaa aaaaaaaaaa aaa          1973
```

<210> SEQ ID NO 51
<211> LENGTH: 2263
<212> TYPE: DNA
<213> ORGANISM: Homo sapiens
<300> PUBLICATION INFORMATION:
<308> DATABASE ACCESSION NUMBER: NM_012387
<309> DATABASE ENTRY DATE: 2006-08-13
<313> RELEVANT RESIDUES IN SEQ ID NO: (1)..(2263)

<400> SEQUENCE: 51

```
agccagaggg acgagctagc ccgacgatgg cccaggggac attgatccgt gtgaccccag     60

agcagcccac ccatgccgtg tgtgtgctgg gcaccttgac tcagcttgac atctgcagct    120

ctgcccctga ggactgcacg tccttcagca tcaacgcctc cccaggggtg gtcgtggata    180

ttgcccacag ccctccagcc aagaagaaat ccacaggttc ctccacatgg cccctggacc    240

ctggggtaga ggtgaccctg acgatgaaag cggccagtgg tagcacaggc gaccagaagg    300

ttcagatttc atactacgga cccaagactc caccagtcaa agctctactc tacctcaccg    360

cggtggaaat ctccctgtgc gcagacatca cccgcaccgg caaagtgaag ccaaccagag    420

ctgtgaaaga tcagaggacc tggacctggg gcccttgtgg acagggtgcc atcctgctgg    480

tgaactgtga cagagacaat ctcgaatctt ctgccatgga ctgcgaggat gatgaagtgc    540

ttgacagcga agacctgcag gacatgtcgc tgatgaccct gagcacgaag acccccaagg    600

acttcttcac aaaccataca ctggtgctcc acgtggccag gtctgagatg gacaaagtga    660

gggtgtttca ggccacacgg ggcaaactgt cctccaagtg cagcgtagtc ttgggtccca    720

agtggccctc tcactacctg atggtccccg gtggaaagca caacatggac ttctacgtgg    780

aggccctcgc tttcccggac accgacttcc cggggctcat taccctcacc atctccctgc    840

tggacacgtc caacctggag ctccccgagg ctgtggtgtt ccaagacagc gtggtcttcc    900
```

```
gcgtggcgcc ctggatcatg acccccaaca cccagccccc gcaggaggtg tacgcgtgca    960

gtatttttga aaatgaggac ttcctgaagt cagtgactac tctggccatg aaagccaagt   1020

gcaagctgac catctgccct gaggaggaga acatggatga ccagtggatg caggatgaaa   1080

tggagatcgg ctacatccaa gccccacaca aaacgctgcc cgtggtcttc gactctccaa   1140

ggaacagagg cctgaaggag tttcccatca aacgagtgat gggtccagat tttggctatg   1200

taactcgagg gccccaaaca gggggtatca gtggactgga ctcctttggg aacctggaag   1260

tgagcccccc agtcacagtc aggggcaagg aatacccgct gggcaggatt ctcttcgggg   1320

acagctgtta tcccagcaat gacagccggc agatgcacca ggccctgcag gacttcctca   1380

gtgcccagca ggtgcaggcc cctgtgaagc tctattctga ctggctgtcc gtgggccacg   1440

tggacgagtt cctgagcttt gtgccagcac ccgacaggaa gggcttccgg ctgctcctgg   1500

ccagccccag gtcctgctac aaactgttcc aggagcagca gaatgagggc cacgggggagg   1560

ccctgctgtt cgaagggatc aagaaaaaaa aacagcagaa aataaagaac attctgtcaa   1620

acaagacatt gagagaacat aattcatttg tggagagatg catcgactgg aaccgcgagc   1680

tgctgaagcg ggagctgggc ctggccgaga gtgacatcat tgacatcccg cagctcttca   1740

agctcaaaga gttctctaag gcggaagctt ttttccccaa catggtgaac atgctggtgc   1800

tagggaagca cctgggcatc cccaagccct tcgggcccgt catcaacggc cgctgctgcc   1860

tggaggagaa ggtgtgttcc ctgctggagc cactgggcct ccagtgcacc ttcatcaacg   1920

acttcttcac ctaccacatc aggcatgggg aggtgcactg cggcaccaac gtgcgcagaa   1980

agcccttctc cttcaagtgg tggaacatgg tgccctgagc ccatcttccc tggcgtcctc   2040

tccctcctgg ccagatgtcg ctgggtcctc tgcagtgtgg caagcaagag ctcttgtgaa   2100

tattgtggct ccctgggggc ggccagccct cccagcagtg gcttgctttc ttctcctgtg   2160

atgtcccagt ttcccactct gaagatccca acatggtcct agcactgcac actcagttct   2220

gctctaagaa gctgcaataa agttttttta agtcactttg tac                     2263
```

```
<210> SEQ ID NO 52
<211> LENGTH: 1440
<212> TYPE: DNA
<213> ORGANISM: Homo sapiens
<300> PUBLICATION INFORMATION:
<308> DATABASE ACCESSION NUMBER: NM_007115
<309> DATABASE ENTRY DATE: 2006-09-24
<313> RELEVANT RESIDUES IN SEQ ID NO: (1)..(1440)

<400> SEQUENCE: 52

cagtcacatt tcagccactg ctctgagaat ttgtgagcag cccctaacag gctgttactt     60

cactacaact gacgatatga tcatcttaat ttacttattt ctcttgctat gggaagacac    120

tcaaggatgg ggattcaagg atggaatttt tcataactcc atatggcttg aacgagcagc    180

cggtgtgtac cacagagaag cacggtctgg caaatacaag ctcacctacg cagaagctaa    240

ggcggtgtgt gaatttgaag gcggccatct cgcaacttac aagcagctag aggcagccag    300

aaaaattgga tttcatgtct gtgctgctgg atggatggct aagggcagag ttggataccc    360

cattgtgaag ccagggccca actgtggatt tggaaaaact ggcattattg attatggaat    420

ccgtctcaat aggagtgaaa gatgggatgc ctattgctac aacccacacg caaaggagtg    480

tggtggcgtc tttacagatc caaagcaaat ttttaaatct ccaggcttcc caaatgagta    540

cgaagataac caaatctgct actggcacat tagactcaag tatggtcagc gtattcacct    600

gagtttttta gattttgacc ttgaagatga cccaggttgc ttggctgatt atgttgaaat    660
```

atatgacagt tacgatgatg tccatggctt tgtgggaaga tactgtggag atgagcttcc 720
agatgacatc atcagtacag gaaatgtcat gaccttgaag tttctaagtg atgcttcagt 780
gacagctgga ggtttccaaa tcaaatatgt tgcaatggat cctgtatcca aatccagtca 840
aggaaaaaat acaagtacta cttctactgg aaataaaaac tttttagctg gaagatttag 900
ccacttataa aaaaaaaaaa aaggatgatc aaaacacaca gtgtttatgt tggaatcttt 960
tggaactcct ttgatctcac tgttattatt aacatttatt tattattttt ctaaatgtga 1020
aagcaataca taatttaggg aaaattggaa aatataggaa actttaaacg agaaaatgaa 1080
acctctcata atcccactgc atagaaataa caagcgttaa cattttcata tttttttctt 1140
tcagtcattt ttctatttgt ggtatatgta tatatgtacc tatatgtatt tgcatttgaa 1200
attttggaat cctgctctat gtacagtttt gtattatact ttttaaatct tgaactttat 1260
aaacattttc tgaaatcatt gattattcta caaaaacatg attttaaaca gctgtaaaat 1320
attctatgat atgaatgttt tatgcattat ttaagcctgt ctctattgtt ggaatttcag 1380
gtcattttca taaatattgt tgcaataaat atccttgaac acaaaaaaaa aaaaaaaaaa 1440

<210> SEQ ID NO 53
<211> LENGTH: 2377
<212> TYPE: DNA
<213> ORGANISM: Homo sapiens
<300> PUBLICATION INFORMATION:
<308> DATABASE ACCESSION NUMBER: NM_002467
<309> DATABASE ENTRY DATE: 2006-10-15
<313> RELEVANT RESIDUES IN SEQ ID NO: (1)..(2377)

<400> SEQUENCE: 53
acccccgagc tgtgctgctc gcggccgcca ccgccgggcc ccggccgtcc ctggctcccc 60
tcctgcctcg agaagggcag ggcttctcag aggcttggcg ggaaaaagaa cggagggagg 120
gatcgcgctg agtataaaag ccggttttcg gggctttatc taactcgctg tagtaattcc 180
agcgagaggc agagggagcg agcgggcggc cggctagggt ggaagagccg ggcgagcaga 240
gctgcgctgc gggcgtcctg ggaagggaga tccggagcga atagggggct tcgcctctgg 300
cccagccctc ccgctgatcc cccagccagc ggtccgcaac ccttgccgca tccacgaaac 360
tttgcccata gcagcgggcg ggcactttgc actggaactt acaacacccg agcaaggacg 420
cgactctccc gacgcgggga ggctattctg cccatttggg gacacttccc cgccgctgcc 480
aggacccgct tctctgaaag gctctccttg cagctgctta gacgctggat ttttttcggg 540
tagtggaaaa ccagcagcct cccgcgacga tgcccctcaa cgttagcttc accaacagga 600
actatgacct cgactacgac tcggtgcagc cgtatttcta ctgcgacgag gaggagaact 660
tctaccagca gcagcagcag agcgagctgc agcccccggc gcccagcgag gatatctgga 720
agaaattcga gctgctgccc accccgcccc tgtcccctag ccgccgctcc gggctctgct 780
cgccctccta cgttgcggtc acacccttct cccttcgggg agacaacgac ggcggtggcg 840
ggagcttctc cacggccgac cagctggaga tggtgaccga gctgctggga ggagacatgg 900
tgaaccagag tttcatctgc gacccggacg acgagacctt catcaaaaac atcatcatcc 960
aggactgtat gtggagcggc ttctcggccg ccgccaagct cgtctcagag aagctggcct 1020
cctaccaggc tgcgcgcaaa gacagcggca gcccgaaccc cgcccgcggc cacagcgtct 1080
gctccacctc cagcttgtac ctgcaggatc tgagcgccgc cgcctcagag tgcatcgacc 1140
cctcggtggt cttcccctac cctctcaacg acagcagctc gcccaagtcc tgcgcctcgc 1200
aagactccag cgccttctct ccgtcctcgg attctctgct ctcctcgacg gagtcctccc 1260

```
cgcagggcag ccccgagccc ctggtgctcc atgaggagac accgcccacc accagcagcg   1320

actctgagga ggaacaagaa gatgaggaag aaatcgatgt tgtttctgtg gaaaagaggc   1380

aggctcctgg caaaaggtca gagtctggat caccttctgc tggaggccac agcaaacctc   1440

ctcacagccc actggtcctc aagaggtgcc acgtctccac acatcagcac aactacgcag   1500

cgcctccctc cactcggaag gactatcctg ctgccaagag ggtcaagttg gacagtgtca   1560

gagtcctgag acagatcagc aacaaccgaa aatgcaccag ccccaggtcc tcggacaccg   1620

aggagaatgt caagaggcga acacacaacg tcttggagcg ccagaggagg aacgagctaa   1680

aacggagctt ttttgccctg cgtgaccaga tcccggagtt ggaaaacaat gaaaaggccc   1740

ccaaggtagt tatccttaaa aaagccacag catacatcct gtccgtccaa gcagaggagc   1800

aaaagctcat ttctgaagag gacttgttgc ggaaacgacg agaacagttg aaacacaaac   1860

ttgaacagct acggaactct tgtgcgtaag gaaaagtaag gaaaacgatt ccttctaaca   1920

gaaatgtcct gagcaatcac ctatgaactt gtttcaaatg catgatcaaa tgcaacctca   1980

caaccttggc tgagtcttga gactgaaaga tttagccata atgtaaactg cctcaaattg   2040

gactttgggc ataaaagaac tttttttatgc ttaccatctt tttttttct ttaacagatt   2100

tgtatttaag aattgttttt aaaaaatttt aagatttaca caatgtttct ctgtaaatat   2160

tgccattaaa tgtaaataac tttaataaaa cgtttatagc agttacacag aatttcaatc   2220

ctagtatata gtacctagta ttataggtac tataaaccct aatttttttt atttaagtac   2280

attttgcttt ttaaagttga tttttttcta ttgtttttag aaaaaataaa ataactggca   2340

aatatatcat tgagccaaaa aaaaaaaaaa aaaaaaa                            2377
```

<210> SEQ ID NO 54
<211> LENGTH: 20
<212> TYPE: DNA
<213> ORGANISM: Homo sapiens

<400> SEQUENCE: 54

```
gccctgtatt atgtggacct                                                 20
```

<210> SEQ ID NO 55
<211> LENGTH: 20
<212> TYPE: DNA
<213> ORGANISM: Homo sapiens

<400> SEQUENCE: 55

```
agatgggtac tgcaggtaga                                                 20
```

<210> SEQ ID NO 56
<211> LENGTH: 20
<212> TYPE: DNA
<213> ORGANISM: Homo sapiens

<400> SEQUENCE: 56

```
ccggctgagc ccagaccaat                                                 20
```

<210> SEQ ID NO 57
<211> LENGTH: 20
<212> TYPE: DNA
<213> ORGANISM: Homo sapiens

<400> SEQUENCE: 57

```
cactcggaga cacacttgtt                                                 20
```

<210> SEQ ID NO 58
<211> LENGTH: 19
<212> TYPE: DNA
<213> ORGANISM: Homo sapiens

<400> SEQUENCE: 58
cttggtctgg cttcttcag 19

<210> SEQ ID NO 59
<211> LENGTH: 21
<212> TYPE: DNA
<213> ORGANISM: Homo sapiens

<400> SEQUENCE: 59
catcgctggc actgacgtcc a 21

<210> SEQ ID NO 60
<211> LENGTH: 20
<212> TYPE: DNA
<213> ORGANISM: Homo sapiens

<400> SEQUENCE: 60
actcggagac acacttgttg 20

<210> SEQ ID NO 61
<211> LENGTH: 19
<212> TYPE: DNA
<213> ORGANISM: Homo sapiens

<400> SEQUENCE: 61
cttggtctgg cttcttcag 19

<210> SEQ ID NO 62
<211> LENGTH: 21
<212> TYPE: DNA
<213> ORGANISM: Homo sapiens

<400> SEQUENCE: 62
catcgctggc actgacgtcc a 21

<210> SEQ ID NO 63
<211> LENGTH: 20
<212> TYPE: DNA
<213> ORGANISM: Homo sapiens

<400> SEQUENCE: 63
agtggtggta gatgttgtgc 20

<210> SEQ ID NO 64
<211> LENGTH: 19
<212> TYPE: DNA
<213> ORGANISM: Homo sapiens

<400> SEQUENCE: 64
agaccactct ctggctgtc 19

<210> SEQ ID NO 65
<211> LENGTH: 21
<212> TYPE: DNA
<213> ORGANISM: Homo sapiens

<400> SEQUENCE: 65
tgcagccttc tgcctttggg a 21

<210> SEQ ID NO 66
<211> LENGTH: 20
<212> TYPE: DNA
<213> ORGANISM: Homo sapiens

<400> SEQUENCE: 66
cacttgttgt atgtggcaga 20

<210> SEQ ID NO 67
<211> LENGTH: 19
<212> TYPE: DNA
<213> ORGANISM: Homo sapiens

<400> SEQUENCE: 67
gcctggctat ctcatcatc 19

<210> SEQ ID NO 68
<211> LENGTH: 20
<212> TYPE: DNA
<213> ORGANISM: Homo sapiens

<400> SEQUENCE: 68
tagggaggag aaacagaagc 20

<210> SEQ ID NO 69
<211> LENGTH: 20
<212> TYPE: DNA
<213> ORGANISM: Homo sapiens

<400> SEQUENCE: 69
ggcctctaac tcgacctcta 20

<210> SEQ ID NO 70
<211> LENGTH: 25
<212> TYPE: DNA
<213> ORGANISM: Homo sapiens

<400> SEQUENCE: 70
tggaacatgc ttaccctgct gatga 25

<210> SEQ ID NO 71
<211> LENGTH: 20
<212> TYPE: DNA
<213> ORGANISM: Homo sapiens

<400> SEQUENCE: 71
tgtggtggat aagagctgtc 20

<210> SEQ ID NO 72
<211> LENGTH: 20
<212> TYPE: DNA
<213> ORGANISM: Homo sapiens

<400> SEQUENCE: 72
cccatcttct tcaggatttc 20

<210> SEQ ID NO 73
<211> LENGTH: 24
<212> TYPE: DNA
<213> ORGANISM: Homo sapiens

<400> SEQUENCE: 73
tggccatgaa atctctggct ctca 24

<210> SEQ ID NO 74
<211> LENGTH: 20
<212> TYPE: DNA
<213> ORGANISM: Homo sapiens

<400> SEQUENCE: 74
gaggagagtt tcaggagtgg 20

<210> SEQ ID NO 75
<211> LENGTH: 20
<212> TYPE: DNA
<213> ORGANISM: Homo sapiens

<400> SEQUENCE: 75
ctcccatctt tgaggtgaat 20

<210> SEQ ID NO 76
<211> LENGTH: 24
<212> TYPE: DNA
<213> ORGANISM: Homo sapiens

<400> SEQUENCE: 76
tggccatgaa atctctggct ctca 24

<210> SEQ ID NO 77
<211> LENGTH: 20
<212> TYPE: DNA
<213> ORGANISM: Homo sapiens

<400> SEQUENCE: 77
ttgcttggag atgacagttt 20

<210> SEQ ID NO 78
<211> LENGTH: 20
<212> TYPE: DNA
<213> ORGANISM: Homo sapiens

<400> SEQUENCE: 78
agcattggtt tgtggatatg 20

<210> SEQ ID NO 79
<211> LENGTH: 20
<212> TYPE: DNA
<213> ORGANISM: Homo sapiens

<400> SEQUENCE: 79
ggcacatctt ctgtcttctg 20

<210> SEQ ID NO 80
<211> LENGTH: 20
<212> TYPE: DNA
<213> ORGANISM: Homo sapiens

<400> SEQUENCE: 80
ctgtgaagag ctacgggaat 20

<210> SEQ ID NO 81
<211> LENGTH: 22
<212> TYPE: DNA
<213> ORGANISM: Homo sapiens

<400> SEQUENCE: 81
tggaatccct ttggctgttc cc 22

<210> SEQ ID NO 82
<211> LENGTH: 20
<212> TYPE: DNA
<213> ORGANISM: Homo sapiens

<400> SEQUENCE: 82
tggcacatct tctgtcttct 20

<210> SEQ ID NO 83
<211> LENGTH: 20
<212> TYPE: DNA
<213> ORGANISM: Homo sapiens

<400> SEQUENCE: 83
ctgtgaagag ctacgggaat 20

<210> SEQ ID NO 84
<211> LENGTH: 22
<212> TYPE: DNA
<213> ORGANISM: Homo sapiens

<400> SEQUENCE: 84
tggaatccct ttggctgttc cc 22

<210> SEQ ID NO 85
<211> LENGTH: 20
<212> TYPE: DNA
<213> ORGANISM: Homo sapiens

<400> SEQUENCE: 85
ccctactacc tggagaacga 20

<210> SEQ ID NO 86
<211> LENGTH: 20
<212> TYPE: DNA
<213> ORGANISM: Homo sapiens

<400> SEQUENCE: 86
attggtactg gccaatcttt 20

<210> SEQ ID NO 87
<211> LENGTH: 20
<212> TYPE: DNA
<213> ORGANISM: Homo sapiens

<400> SEQUENCE: 87
ctgccaccct ggcgtcgatt 20

<210> SEQ ID NO 88
<211> LENGTH: 20
<212> TYPE: DNA
<213> ORGANISM: Homo sapiens

<400> SEQUENCE: 88
caccattccc aagttaatcc 20

<210> SEQ ID NO 89
<211> LENGTH: 20
<212> TYPE: DNA
<213> ORGANISM: Homo sapiens

<400> SEQUENCE: 89
gaaatgcagt tggaaacaga 20

<210> SEQ ID NO 90
<211> LENGTH: 24
<212> TYPE: DNA
<213> ORGANISM: Homo sapiens

<400> SEQUENCE: 90
tgggaccaaa gttcatttgc tcca 24

<210> SEQ ID NO 91
<211> LENGTH: 20
<212> TYPE: DNA
<213> ORGANISM: Homo sapiens

<400> SEQUENCE: 91
tgccctacta cctggagaac 20

<210> SEQ ID NO 92
<211> LENGTH: 20
<212> TYPE: DNA
<213> ORGANISM: Homo sapiens

<400> SEQUENCE: 92
attggtactg gccaatcttt 20

<210> SEQ ID NO 93
<211> LENGTH: 20
<212> TYPE: DNA
<213> ORGANISM: Homo sapiens

<400> SEQUENCE: 93
agcccagcgg ctacacggtg 20

<210> SEQ ID NO 94
<211> LENGTH: 20
<212> TYPE: DNA
<213> ORGANISM: Homo sapiens

<400> SEQUENCE: 94
gtgccctact acctggagaa 20

<210> SEQ ID NO 95
<211> LENGTH: 20
<212> TYPE: DNA
<213> ORGANISM: Homo sapiens

<400> SEQUENCE: 95
attggtactg gccaatcttt 20

<210> SEQ ID NO 96
<211> LENGTH: 20
<212> TYPE: DNA
<213> ORGANISM: Homo sapiens

<400> SEQUENCE: 96
agcccagcgg ctacacggtg 20

<210> SEQ ID NO 97
<211> LENGTH: 20
<212> TYPE: DNA
<213> ORGANISM: Homo sapiens

<400> SEQUENCE: 97
tgtgcaatga ctatgcttca 20

<210> SEQ ID NO 98
<211> LENGTH: 20
<212> TYPE: DNA
<213> ORGANISM: Homo sapiens

<400> SEQUENCE: 98
ttatcaatgg tgcactggtt 20

<210> SEQ ID NO 99
<211> LENGTH: 20
<212> TYPE: DNA
<213> ORGANISM: Homo sapiens

<400> SEQUENCE: 99
tgtgcaatga ctatgcttca 20

<210> SEQ ID NO 100
<211> LENGTH: 20
<212> TYPE: DNA
<213> ORGANISM: Homo sapiens

<400> SEQUENCE: 100
tttatcaatg gtgcactggt 20

<210> SEQ ID NO 101
<211> LENGTH: 20
<212> TYPE: DNA
<213> ORGANISM: Homo sapiens

<400> SEQUENCE: 101
tgggtggttt atacactgga 20

<210> SEQ ID NO 102
<211> LENGTH: 20
<212> TYPE: DNA
<213> ORGANISM: Homo sapiens

<400> SEQUENCE: 102
ataagggttt cacccagcta 20

<210> SEQ ID NO 103
<211> LENGTH: 24
<212> TYPE: DNA
<213> ORGANISM: Homo sapiens

<400> SEQUENCE: 103
ccagatttgc ccatccttcc tctg 24

<210> SEQ ID NO 104
<211> LENGTH: 20
<212> TYPE: DNA
<213> ORGANISM: Homo sapiens

<400> SEQUENCE: 104
gagctcctct ccctcaagta 20

<210> SEQ ID NO 105
<211> LENGTH: 20
<212> TYPE: DNA
<213> ORGANISM: Homo sapiens

<400> SEQUENCE: 105
ggtgacgact tcttgtttga 20

<210> SEQ ID NO 106
<211> LENGTH: 22
<212> TYPE: DNA
<213> ORGANISM: Homo sapiens

<400> SEQUENCE: 106
cctcggtcat tctccgagac cc 22

<210> SEQ ID NO 107
<211> LENGTH: 20
<212> TYPE: DNA
<213> ORGANISM: Homo sapiens

<400> SEQUENCE: 107
ggatgtcagg tgagactgtg 20

<210> SEQ ID NO 108
<211> LENGTH: 20
<212> TYPE: DNA
<213> ORGANISM: Homo sapiens

<400> SEQUENCE: 108
gccttcaagt cattcctctc 20

<210> SEQ ID NO 109
<211> LENGTH: 20
<212> TYPE: DNA
<213> ORGANISM: Homo sapiens

<400> SEQUENCE: 109
ccctggcatc acctgtgcca 20

<210> SEQ ID NO 110
<211> LENGTH: 20
<212> TYPE: DNA
<213> ORGANISM: Homo sapiens

<400> SEQUENCE: 110
tcaaacaaga agtcgtcacc 20

<210> SEQ ID NO 111
<211> LENGTH: 20
<212> TYPE: DNA
<213> ORGANISM: Homo sapiens

<400> SEQUENCE: 111
gcgatcacaa ctatcgtagc 20

<210> SEQ ID NO 112
<211> LENGTH: 25
<212> TYPE: DNA
<213> ORGANISM: Homo sapiens

<400> SEQUENCE: 112
cccgagttta ccacgactgg tcctc 25

<210> SEQ ID NO 113
<211> LENGTH: 20
<212> TYPE: DNA
<213> ORGANISM: Homo sapiens

<400> SEQUENCE: 113
ccgctatacc tcggattact 20

<210> SEQ ID NO 114
<211> LENGTH: 20
<212> TYPE: DNA
<213> ORGANISM: Homo sapiens

<400> SEQUENCE: 114
gcgtctgata ggactctgtg 20

<210> SEQ ID NO 115
<211> LENGTH: 22
<212> TYPE: DNA
<213> ORGANISM: Homo sapiens

<400> SEQUENCE: 115
cccagtgtgt tccaccatcg ga 22

<210> SEQ ID NO 116
<211> LENGTH: 20
<212> TYPE: DNA
<213> ORGANISM: Homo sapiens

<400> SEQUENCE: 116
acagctgcca tcagaaacta 20

<210> SEQ ID NO 117
<211> LENGTH: 20
<212> TYPE: DNA
<213> ORGANISM: Homo sapiens

<400> SEQUENCE: 117
gcttcctgta gctcattcct 20

<210> SEQ ID NO 118
<211> LENGTH: 27
<212> TYPE: DNA
<213> ORGANISM: Homo sapiens

<400> SEQUENCE: 118
ccgggaagct gtaagattaa atcccaa 27

<210> SEQ ID NO 119
<211> LENGTH: 20
<212> TYPE: DNA
<213> ORGANISM: Homo sapiens

<400> SEQUENCE: 119
tgataaaggc aaccagacag 20

<210> SEQ ID NO 120
<211> LENGTH: 20
<212> TYPE: DNA
<213> ORGANISM: Homo sapiens

<400> SEQUENCE: 120
agcttcctgt agctcattcc 20

<210> SEQ ID NO 121
<211> LENGTH: 24
<212> TYPE: DNA
<213> ORGANISM: Homo sapiens

<400> SEQUENCE: 121
tgccatcaga aactaccggg aagc 24

<210> SEQ ID NO 122
<211> LENGTH: 20
<212> TYPE: DNA
<213> ORGANISM: Homo sapiens

<400> SEQUENCE: 122
ggatttctcg ttatcccatt 20

<210> SEQ ID NO 123
<211> LENGTH: 20
<212> TYPE: DNA
<213> ORGANISM: Homo sapiens

<400> SEQUENCE: 123
tcttggtatg tttgctcagg 20

<210> SEQ ID NO 124
<211> LENGTH: 20
<212> TYPE: DNA
<213> ORGANISM: Homo sapiens

<400> SEQUENCE: 124
aggacacgct ccgcgaccac 20

<210> SEQ ID NO 125
<211> LENGTH: 20
<212> TYPE: DNA
<213> ORGANISM: Homo sapiens

<400> SEQUENCE: 125
caaatacagc cagactttgc 20

<210> SEQ ID NO 126
<211> LENGTH: 20
<212> TYPE: DNA
<213> ORGANISM: Homo sapiens

<400> SEQUENCE: 126
tttaattgct gtccggtaac 20

<210> SEQ ID NO 127
<211> LENGTH: 23
<212> TYPE: DNA
<213> ORGANISM: Homo sapiens

<400> SEQUENCE: 127
tgctgcttca aaccgtttca ggc 23

<210> SEQ ID NO 128
<211> LENGTH: 20
<212> TYPE: DNA
<213> ORGANISM: Homo sapiens

<400> SEQUENCE: 128
caaatacagc cagactttgc 20

<210> SEQ ID NO 129
<211> LENGTH: 20
<212> TYPE: DNA
<213> ORGANISM: Homo sapiens

<400> SEQUENCE: 129
gtttaattgc tgtccggtaa 20

<210> SEQ ID NO 130
<211> LENGTH: 23
<212> TYPE: DNA
<213> ORGANISM: Homo sapiens

<400> SEQUENCE: 130
tgctgcttca aaccgtttca ggc 23

<210> SEQ ID NO 131
<211> LENGTH: 20
<212> TYPE: DNA
<213> ORGANISM: Homo sapiens

<400> SEQUENCE: 131
cttggtgata ggcaaattca 20

<210> SEQ ID NO 132
<211> LENGTH: 20
<212> TYPE: DNA
<213> ORGANISM: Homo sapiens

<400> SEQUENCE: 132
agcagggtca ttctgaagag 20

<210> SEQ ID NO 133
<211> LENGTH: 20
<212> TYPE: DNA
<213> ORGANISM: Homo sapiens

<400> SEQUENCE: 133
cccgttcctg agcatgccga 20

<210> SEQ ID NO 134
<211> LENGTH: 20
<212> TYPE: DNA
<213> ORGANISM: Homo sapiens

<400> SEQUENCE: 134
tttggctgtg ctttatcatc 20

<210> SEQ ID NO 135
<211> LENGTH: 20
<212> TYPE: DNA
<213> ORGANISM: Homo sapiens

<400> SEQUENCE: 135
cagcagaccg taattctcct 20

<210> SEQ ID NO 136
<211> LENGTH: 27
<212> TYPE: DNA
<213> ORGANISM: Homo sapiens

<400> SEQUENCE: 136
tgtttcttgg ccaagtctag atgtccc 27

<210> SEQ ID NO 137
<211> LENGTH: 20
<212> TYPE: DNA
<213> ORGANISM: Homo sapiens

<400> SEQUENCE: 137
attggaggac aagagcagat 20

<210> SEQ ID NO 138
<211> LENGTH: 19
<212> TYPE: DNA
<213> ORGANISM: Homo sapiens

<400> SEQUENCE: 138
ccatcgctct ctagattgg 19

<210> SEQ ID NO 139
<211> LENGTH: 21
<212> TYPE: DNA
<213> ORGANISM: Homo sapiens

<400> SEQUENCE: 139
ttcttaggtg ccgcagtgcc c 21

<210> SEQ ID NO 140
<211> LENGTH: 20
<212> TYPE: DNA
<213> ORGANISM: Homo sapiens

<400> SEQUENCE: 140
ccttcaggaa gactttccac 20

<210> SEQ ID NO 141
<211> LENGTH: 20
<212> TYPE: DNA
<213> ORGANISM: Homo sapiens

<400> SEQUENCE: 141
ctcaagttca ttcagccatc 20

<210> SEQ ID NO 142
<211> LENGTH: 20
<212> TYPE: DNA
<213> ORGANISM: Homo sapiens

<400> SEQUENCE: 142
acgggcggat ccacagcaac 20

<210> SEQ ID NO 143
<211> LENGTH: 20
<212> TYPE: DNA
<213> ORGANISM: Homo sapiens

<400> SEQUENCE: 143
tgatcagcaa gtgaacacac 20

<210> SEQ ID NO 144
<211> LENGTH: 20
<212> TYPE: DNA
<213> ORGANISM: Homo sapiens

<400> SEQUENCE: 144
ctcggtgata gcaaatcaga 20

<210> SEQ ID NO 145
<211> LENGTH: 23
<212> TYPE: DNA
<213> ORGANISM: Homo sapiens

<400> SEQUENCE: 145
tgcatccttg atggcaagct tca 23

<210> SEQ ID NO 146
<211> LENGTH: 20
<212> TYPE: DNA
<213> ORGANISM: Homo sapiens

<400> SEQUENCE: 146
gtgatcagca agtgaacaca 20

<210> SEQ ID NO 147
<211> LENGTH: 20
<212> TYPE: DNA
<213> ORGANISM: Homo sapiens

<400> SEQUENCE: 147
ctcggtgata gcaaatcaga 20

<210> SEQ ID NO 148
<211> LENGTH: 23
<212> TYPE: DNA
<213> ORGANISM: Homo sapiens

<400> SEQUENCE: 148
tgcatccttg atggcaagct tca 23

<210> SEQ ID NO 149
<211> LENGTH: 20
<212> TYPE: DNA
<213> ORGANISM: Homo sapiens

<400> SEQUENCE: 149
ttaatggtcc tgtctgatgc 20

<210> SEQ ID NO 150
<211> LENGTH: 20
<212> TYPE: DNA
<213> ORGANISM: Homo sapiens

<400> SEQUENCE: 150
gggtctctag acaagccaag 20

<210> SEQ ID NO 151
<211> LENGTH: 20
<212> TYPE: DNA
<213> ORGANISM: Homo sapiens

<400> SEQUENCE: 151
agatttgcag acacagaagc 20

<210> SEQ ID NO 152
<211> LENGTH: 20
<212> TYPE: DNA
<213> ORGANISM: Homo sapiens

<400> SEQUENCE: 152
ttctaacatc aggtggttgc 20

<210> SEQ ID NO 153
<211> LENGTH: 21
<212> TYPE: DNA
<213> ORGANISM: Homo sapiens

<400> SEQUENCE: 153
tacaactcac gaatcccttc t 21

<210> SEQ ID NO 154
<211> LENGTH: 20
<212> TYPE: DNA
<213> ORGANISM: Homo sapiens

<400> SEQUENCE: 154
acaggaagta gaggcagagg 20

<210> SEQ ID NO 155
<211> LENGTH: 21
<212> TYPE: DNA
<213> ORGANISM: Homo sapiens

<400> SEQUENCE: 155
caactcacga atcccttcta c 21

<210> SEQ ID NO 156
<211> LENGTH: 20
<212> TYPE: DNA
<213> ORGANISM: Homo sapiens

<400> SEQUENCE: 156
acaggaagta gaggcagagg 20

<210> SEQ ID NO 157
<211> LENGTH: 21
<212> TYPE: DNA
<213> ORGANISM: Homo sapiens

<400> SEQUENCE: 157
acaactcacg aatcccttct a 21

<210> SEQ ID NO 158
<211> LENGTH: 20
<212> TYPE: DNA
<213> ORGANISM: Homo sapiens

<400> SEQUENCE: 158
acaggaagta gaggcagagg 20

<210> SEQ ID NO 159
<211> LENGTH: 21
<212> TYPE: DNA
<213> ORGANISM: Homo sapiens

<400> SEQUENCE: 159
aactcacgaa tcccttctac a 21

<210> SEQ ID NO 160
<211> LENGTH: 20
<212> TYPE: DNA
<213> ORGANISM: Homo sapiens

<400> SEQUENCE: 160
acaggaagta gaggcagagg 20

<210> SEQ ID NO 161
<211> LENGTH: 20
<212> TYPE: DNA
<213> ORGANISM: Homo sapiens

<400> SEQUENCE: 161
gggatttcca tgacctttat 20

<210> SEQ ID NO 162
<211> LENGTH: 20
<212> TYPE: DNA
<213> ORGANISM: Homo sapiens

<400> SEQUENCE: 162
atccagaagg acagaagcat 20

<210> SEQ ID NO 163
<211> LENGTH: 20
<212> TYPE: DNA
<213> ORGANISM: Homo sapiens

<400> SEQUENCE: 163
tgccctgtcg gatgtcacca 20

<210> SEQ ID NO 164
<211> LENGTH: 20
<212> TYPE: DNA
<213> ORGANISM: Homo sapiens

<400> SEQUENCE: 164
attgaagagg caattccaag 20

<210> SEQ ID NO 165
<211> LENGTH: 20
<212> TYPE: DNA
<213> ORGANISM: Homo sapiens

<400> SEQUENCE: 165
tttagcttga aggcaatgtc 20

<210> SEQ ID NO 166
<211> LENGTH: 26
<212> TYPE: DNA
<213> ORGANISM: Homo sapiens

<400> SEQUENCE: 166
ccacatggag atgagtcctt ggttcc 26

<210> SEQ ID NO 167
<211> LENGTH: 20
<212> TYPE: DNA
<213> ORGANISM: Homo sapiens

<400> SEQUENCE: 167
catgtgtaat gctggatgtg 20

<210> SEQ ID NO 168
<211> LENGTH: 20
<212> TYPE: DNA
<213> ORGANISM: Homo sapiens

<400> SEQUENCE: 168
aaacaactca gggaacacct 20

<210> SEQ ID NO 169
<211> LENGTH: 23
<212> TYPE: DNA
<213> ORGANISM: Homo sapiens

<400> SEQUENCE: 169
tggacaacct gactggcttt gca 23

<210> SEQ ID NO 170
<211> LENGTH: 20
<212> TYPE: DNA
<213> ORGANISM: Homo sapiens

<400> SEQUENCE: 170
caggcctctg gtatttcttt 20

<210> SEQ ID NO 171
<211> LENGTH: 20
<212> TYPE: DNA
<213> ORGANISM: Homo sapiens

<400> SEQUENCE: 171
atttgtacac ctccgttgtg 20

<210> SEQ ID NO 172
<211> LENGTH: 27
<212> TYPE: DNA
<213> ORGANISM: Homo sapiens

<400> SEQUENCE: 172
ttggcagaac cattgatttc tcctgtt 27

<210> SEQ ID NO 173
<211> LENGTH: 20
<212> TYPE: DNA
<213> ORGANISM: Homo sapiens

<400> SEQUENCE: 173
aaacatgaag tcaggcctct 20

<210> SEQ ID NO 174
<211> LENGTH: 20
<212> TYPE: DNA
<213> ORGANISM: Homo sapiens

<400> SEQUENCE: 174
gtacacctcc gttgtgaaat 20

<210> SEQ ID NO 175
<211> LENGTH: 27
<212> TYPE: DNA
<213> ORGANISM: Homo sapiens

<400> SEQUENCE: 175
ttggcagaac cattgatttc tcctgtt 27

<210> SEQ ID NO 176
<211> LENGTH: 20
<212> TYPE: DNA
<213> ORGANISM: Homo sapiens

<400> SEQUENCE: 176
gtcaggcctc tggtatttct 20

<210> SEQ ID NO 177
<211> LENGTH: 20
<212> TYPE: DNA
<213> ORGANISM: Homo sapiens

<400> SEQUENCE: 177
atttgtacac ctccgttgtg 20

<210> SEQ ID NO 178
<211> LENGTH: 27
<212> TYPE: DNA
<213> ORGANISM: Homo sapiens

<400> SEQUENCE: 178
ttggcagaac cattgatttc tcctgtt 27

<210> SEQ ID NO 179
<211> LENGTH: 20
<212> TYPE: DNA
<213> ORGANISM: Homo sapiens

<400> SEQUENCE: 179
gaagtcaggc ctctggtatt 20

<210> SEQ ID NO 180
<211> LENGTH: 20
<212> TYPE: DNA
<213> ORGANISM: Homo sapiens

<400> SEQUENCE: 180
atttgtacac ctccgttgtg 20

<210> SEQ ID NO 181
<211> LENGTH: 27
<212> TYPE: DNA
<213> ORGANISM: Homo sapiens

<400> SEQUENCE: 181
ttggcagaac cattgatttc tcctgtt 27

<210> SEQ ID NO 182
<211> LENGTH: 20
<212> TYPE: DNA
<213> ORGANISM: Homo sapiens

<400> SEQUENCE: 182
cagatccaag gatgaaacaa 20

<210> SEQ ID NO 183
<211> LENGTH: 20
<212> TYPE: DNA
<213> ORGANISM: Homo sapiens

<400> SEQUENCE: 183
accaccattt gagagtgatg 20

<210> SEQ ID NO 184
<211> LENGTH: 23
<212> TYPE: DNA
<213> ORGANISM: Homo sapiens

<400> SEQUENCE: 184
caccagctcc tgcatcttca ggg 23

<210> SEQ ID NO 185
<211> LENGTH: 20
<212> TYPE: DNA
<213> ORGANISM: Homo sapiens

<400> SEQUENCE: 185
tcaatccaga tcacctgaaa 20

<210> SEQ ID NO 186
<211> LENGTH: 20
<212> TYPE: DNA
<213> ORGANISM: Homo sapiens

<400> SEQUENCE: 186
aatccttgag tccaactggt 20

<210> SEQ ID NO 187
<211> LENGTH: 21
<212> TYPE: DNA
<213> ORGANISM: Homo sapiens

<400> SEQUENCE: 187
cccatggaac agagccatgg c 21

<210> SEQ ID NO 188
<211> LENGTH: 20
<212> TYPE: DNA
<213> ORGANISM: Homo sapiens

<400> SEQUENCE: 188
aagctgttgt ttgccataga 20

<210> SEQ ID NO 189
<211> LENGTH: 20
<212> TYPE: DNA
<213> ORGANISM: Homo sapiens

<400> SEQUENCE: 189
cagagaagga caaacattgc 20

<210> SEQ ID NO 190
<211> LENGTH: 24
<212> TYPE: DNA
<213> ORGANISM: Homo sapiens

<400> SEQUENCE: 190
tgcccattca tggtgcaagt tctc 24

<210> SEQ ID NO 191
<211> LENGTH: 20
<212> TYPE: DNA
<213> ORGANISM: Homo sapiens

<400> SEQUENCE: 191
aagctgttgt ttgccataga 20

<210> SEQ ID NO 192
<211> LENGTH: 20
<212> TYPE: DNA
<213> ORGANISM: Homo sapiens

<400> SEQUENCE: 192
gcagagaagg acaaacattg 20

<210> SEQ ID NO 193
<211> LENGTH: 24
<212> TYPE: DNA
<213> ORGANISM: Homo sapiens

<400> SEQUENCE: 193
tgcccattca tggtgcaagt tctc 24

<210> SEQ ID NO 194
<211> LENGTH: 20
<212> TYPE: DNA
<213> ORGANISM: Homo sapiens

<400> SEQUENCE: 194
gctgttgttt gccatagaag 20

<210> SEQ ID NO 195
<211> LENGTH: 20
<212> TYPE: DNA
<213> ORGANISM: Homo sapiens

<400> SEQUENCE: 195
cagagaagga caaacattgc 20

<210> SEQ ID NO 196
<211> LENGTH: 24
<212> TYPE: DNA
<213> ORGANISM: Homo sapiens

<400> SEQUENCE: 196
tgcccattca tggtgcaagt tctc 24

<210> SEQ ID NO 197
<211> LENGTH: 20
<212> TYPE: DNA
<213> ORGANISM: Homo sapiens

<400> SEQUENCE: 197
gctgttgttt gccatagaag 20

<210> SEQ ID NO 198
<211> LENGTH: 20
<212> TYPE: DNA
<213> ORGANISM: Homo sapiens

<400> SEQUENCE: 198
gcagagaagg acaaacattg 20

<210> SEQ ID NO 199
<211> LENGTH: 24
<212> TYPE: DNA
<213> ORGANISM: Homo sapiens

<400> SEQUENCE: 199
tgcccattca tggtgcaagt tctc 24

<210> SEQ ID NO 200
<211> LENGTH: 20
<212> TYPE: DNA
<213> ORGANISM: Homo sapiens

<400> SEQUENCE: 200
caatgacgga cctctttatg 20

<210> SEQ ID NO 201
<211> LENGTH: 20
<212> TYPE: DNA
<213> ORGANISM: Homo sapiens

<400> SEQUENCE: 201
ggtagctccc aggtagtcat 20

<210> SEQ ID NO 202
<211> LENGTH: 23
<212> TYPE: DNA
<213> ORGANISM: Homo sapiens

<400> SEQUENCE: 202
tgccgcctac tccaatcaca tcc 23

<210> SEQ ID NO 203
<211> LENGTH: 20
<212> TYPE: DNA
<213> ORGANISM: Homo sapiens

<400> SEQUENCE: 203
tctgtgggaa gaaacatctg 20

<210> SEQ ID NO 204
<211> LENGTH: 20
<212> TYPE: DNA
<213> ORGANISM: Homo sapiens

<400> SEQUENCE: 204
tgatgagaat tccaccttca 20

<210> SEQ ID NO 205
<211> LENGTH: 20
<212> TYPE: DNA
<213> ORGANISM: Homo sapiens

<400> SEQUENCE: 205
aatccatcca gtgactaccc 20

<210> SEQ ID NO 206
<211> LENGTH: 20
<212> TYPE: DNA
<213> ORGANISM: Homo sapiens

<400> SEQUENCE: 206
acttgaggga acgaaagact 20

<210> SEQ ID NO 207
<211> LENGTH: 21
<212> TYPE: DNA
<213> ORGANISM: Homo sapiens

<400> SEQUENCE: 207
aacatcaaac gggtcacgcc c 21

<210> SEQ ID NO 208
<211> LENGTH: 20
<212> TYPE: DNA
<213> ORGANISM: Homo sapiens

<400> SEQUENCE: 208
cagccaaagc tagaaattca 20

<210> SEQ ID NO 209
<211> LENGTH: 20
<212> TYPE: DNA
<213> ORGANISM: Homo sapiens

<400> SEQUENCE: 209
tagggtagtc actggatgga 20

<210> SEQ ID NO 210
<211> LENGTH: 25
<212> TYPE: DNA
<213> ORGANISM: Homo sapiens

<400> SEQUENCE: 210
ttcactgctc ttcagggcac ttgaa 25

<210> SEQ ID NO 211
<211> LENGTH: 20
<212> TYPE: DNA
<213> ORGANISM: Homo sapiens

<400> SEQUENCE: 211
gcaatgacgg acctctttat 20

<210> SEQ ID NO 212
<211> LENGTH: 20
<212> TYPE: DNA
<213> ORGANISM: Homo sapiens

<400> SEQUENCE: 212
ggtagctccc aggtagtcat 20

<210> SEQ ID NO 213
<211> LENGTH: 23
<212> TYPE: DNA
<213> ORGANISM: Homo sapiens

<400> SEQUENCE: 213
tgccgcctac tccaatcaca tcc 23

<210> SEQ ID NO 214
<211> LENGTH: 20
<212> TYPE: DNA
<213> ORGANISM: Homo sapiens

<400> SEQUENCE: 214
agaatcagca tcatgtttgg 20

<210> SEQ ID NO 215
<211> LENGTH: 20
<212> TYPE: DNA
<213> ORGANISM: Homo sapiens

<400> SEQUENCE: 215
ataaccttct cttgggctga 20

<210> SEQ ID NO 216
<211> LENGTH: 20
<212> TYPE: DNA
<213> ORGANISM: Homo sapiens

<400> SEQUENCE: 216
cctcatggca ggctcctggc 20

<210> SEQ ID NO 217
<211> LENGTH: 20
<212> TYPE: DNA
<213> ORGANISM: Homo sapiens

<400> SEQUENCE: 217
tcagcccaag agaaggttat 20

<210> SEQ ID NO 218
<211> LENGTH: 20
<212> TYPE: DNA
<213> ORGANISM: Homo sapiens

<400> SEQUENCE: 218
tgagcatgtc ctctgataca 20

<210> SEQ ID NO 219
<211> LENGTH: 22
<212> TYPE: DNA
<213> ORGANISM: Homo sapiens

<400> SEQUENCE: 219
tcccaaggac cagtagctgc ca 22

<210> SEQ ID NO 220
<211> LENGTH: 20
<212> TYPE: DNA
<213> ORGANISM: Homo sapiens

<400> SEQUENCE: 220
gactacagct cacagcacac 20

<210> SEQ ID NO 221
<211> LENGTH: 19
<212> TYPE: DNA
<213> ORGANISM: Homo sapiens

<400> SEQUENCE: 221
aaagctacaa cttggcctt 19

<210> SEQ ID NO 222
<211> LENGTH: 20
<212> TYPE: DNA
<213> ORGANISM: Homo sapiens

<400> SEQUENCE: 222
tgcccaggct ggtctcaggc 20

<210> SEQ ID NO 223
<211> LENGTH: 20
<212> TYPE: DNA
<213> ORGANISM: Homo sapiens

<400> SEQUENCE: 223
tcagcccaag agaaggttat 20

<210> SEQ ID NO 224
<211> LENGTH: 20
<212> TYPE: DNA
<213> ORGANISM: Homo sapiens

<400> SEQUENCE: 224
aggcaagcat gtttctacac 20

<210> SEQ ID NO 225
<211> LENGTH: 22
<212> TYPE: DNA
<213> ORGANISM: Homo sapiens

<400> SEQUENCE: 225
tcccaaggac cagtagctgc ca 22

<210> SEQ ID NO 226
<211> LENGTH: 20
<212> TYPE: DNA
<213> ORGANISM: Homo sapiens

<400> SEQUENCE: 226
actacagctc acagcacacc 20

<210> SEQ ID NO 227
<211> LENGTH: 20
<212> TYPE: DNA
<213> ORGANISM: Homo sapiens

<400> SEQUENCE: 227
aaagctacaa cttggcctgt 20

<210> SEQ ID NO 228
<211> LENGTH: 20
<212> TYPE: DNA
<213> ORGANISM: Homo sapiens

<400> SEQUENCE: 228
tgcccaggct ggtctcaggc 20

<210> SEQ ID NO 229
<211> LENGTH: 20
<212> TYPE: DNA
<213> ORGANISM: Homo sapiens

<400> SEQUENCE: 229
tcagcccaag agaaggttat 20

<210> SEQ ID NO 230
<211> LENGTH: 20
<212> TYPE: DNA
<213> ORGANISM: Homo sapiens

<400> SEQUENCE: 230
cataaggcaa gcatgtttct 20

<210> SEQ ID NO 231
<211> LENGTH: 22
<212> TYPE: DNA
<213> ORGANISM: Homo sapiens

<400> SEQUENCE: 231
tcccaaggac cagtagctgc ca 22

<210> SEQ ID NO 232
<211> LENGTH: 20
<212> TYPE: DNA
<213> ORGANISM: Homo sapiens

<400> SEQUENCE: 232
aggctcatgg atcactcttt 20

<210> SEQ ID NO 233
<211> LENGTH: 20
<212> TYPE: DNA
<213> ORGANISM: Homo sapiens

<400> SEQUENCE: 233
ggtacgcaat ccagttctct 20

<210> SEQ ID NO 234
<211> LENGTH: 20
<212> TYPE: DNA
<213> ORGANISM: Homo sapiens

<400> SEQUENCE: 234
ccggccttcg cagactccag 20

<210> SEQ ID NO 235
<211> LENGTH: 20
<212> TYPE: DNA
<213> ORGANISM: Homo sapiens

<400> SEQUENCE: 235
gacctctctg atgaatgctg 20

<210> SEQ ID NO 236
<211> LENGTH: 20
<212> TYPE: DNA
<213> ORGANISM: Homo sapiens

<400> SEQUENCE: 236
aatgacgtga agggtaaggt 20

<210> SEQ ID NO 237
<211> LENGTH: 20
<212> TYPE: DNA
<213> ORGANISM: Homo sapiens

<400> SEQUENCE: 237
accggctctc ccgctgtcct 20

<210> SEQ ID NO 238
<211> LENGTH: 20
<212> TYPE: DNA
<213> ORGANISM: Homo sapiens

<400> SEQUENCE: 238
gacctctctg atgaatgctg 20

<210> SEQ ID NO 239
<211> LENGTH: 20
<212> TYPE: DNA
<213> ORGANISM: Homo sapiens

<400> SEQUENCE: 239
gaatgacgtg aagggtaagg 20

<210> SEQ ID NO 240
<211> LENGTH: 20
<212> TYPE: DNA
<213> ORGANISM: Homo sapiens

<400> SEQUENCE: 240
accggctctc ccgctgtcct 20

<210> SEQ ID NO 241
<211> LENGTH: 20
<212> TYPE: DNA
<213> ORGANISM: Homo sapiens

<400> SEQUENCE: 241
gacctctctg atgaatgctg 20

<210> SEQ ID NO 242
<211> LENGTH: 21
<212> TYPE: DNA
<213> ORGANISM: Homo sapiens

<400> SEQUENCE: 242
gaatgacgtg aagggtaagg t 21

<210> SEQ ID NO 243
<211> LENGTH: 20
<212> TYPE: DNA
<213> ORGANISM: Homo sapiens

<400> SEQUENCE: 243
accggctctc ccgctgtcct 20

<210> SEQ ID NO 244
<211> LENGTH: 20
<212> TYPE: DNA
<213> ORGANISM: Homo sapiens

<400> SEQUENCE: 244
gacctctctg atgaatgctg 20

<210> SEQ ID NO 245
<211> LENGTH: 20
<212> TYPE: DNA
<213> ORGANISM: Homo sapiens

<400> SEQUENCE: 245
ggaatgacgt gaagggtaag 20

<210> SEQ ID NO 246
<211> LENGTH: 20
<212> TYPE: DNA
<213> ORGANISM: Homo sapiens

<400> SEQUENCE: 246
accggctctc ccgctgtcct 20

<210> SEQ ID NO 247
<211> LENGTH: 20
<212> TYPE: DNA
<213> ORGANISM: Homo sapiens

<400> SEQUENCE: 247
cctctctgat gaatgctgac 20

<210> SEQ ID NO 248
<211> LENGTH: 20
<212> TYPE: DNA
<213> ORGANISM: Homo sapiens

<400> SEQUENCE: 248
gaatgacgtg aagggtaagg 20

<210> SEQ ID NO 249
<211> LENGTH: 20
<212> TYPE: DNA
<213> ORGANISM: Homo sapiens

<400> SEQUENCE: 249
accggctctc ccgctgtcct 20

<210> SEQ ID NO 250
<211> LENGTH: 20
<212> TYPE: DNA
<213> ORGANISM: Homo sapiens

<400> SEQUENCE: 250
acctctctga tgaatgctga 20

<210> SEQ ID NO 251
<211> LENGTH: 20
<212> TYPE: DNA
<213> ORGANISM: Homo sapiens

<400> SEQUENCE: 251
gaatgacgtg aagggtaagg 20

<210> SEQ ID NO 252
<211> LENGTH: 20
<212> TYPE: DNA
<213> ORGANISM: Homo sapiens

<400> SEQUENCE: 252
accggctctc ccgctgtcct 20

<210> SEQ ID NO 253
<211> LENGTH: 20
<212> TYPE: DNA
<213> ORGANISM: Homo sapiens

<400> SEQUENCE: 253
ccagtgaacc acaattcagt 20

<210> SEQ ID NO 254
<211> LENGTH: 20
<212> TYPE: DNA
<213> ORGANISM: Homo sapiens

<400> SEQUENCE: 254
atgcagtgtc ctattcgaga 20

<210> SEQ ID NO 255
<211> LENGTH: 21
<212> TYPE: DNA
<213> ORGANISM: Homo sapiens

<400> SEQUENCE: 255
tggatgtcct caggcccagc a 21

<210> SEQ ID NO 256
<211> LENGTH: 20
<212> TYPE: DNA
<213> ORGANISM: Homo sapiens

<400> SEQUENCE: 256
ggatcacacc tatgctcaaa 20

<210> SEQ ID NO 257
<211> LENGTH: 20
<212> TYPE: DNA
<213> ORGANISM: Homo sapiens

<400> SEQUENCE: 257
ccatttctgt gtccagtgac 20

<210> SEQ ID NO 258
<211> LENGTH: 26
<212> TYPE: DNA
<213> ORGANISM: Homo sapiens

<400> SEQUENCE: 258
tgacagcatg actcctccta aaggca 26

<210> SEQ ID NO 259
<211> LENGTH: 20
<212> TYPE: DNA
<213> ORGANISM: Homo sapiens

<400> SEQUENCE: 259
atttgagaga ggaggctgag 20

<210> SEQ ID NO 260
<211> LENGTH: 20
<212> TYPE: DNA
<213> ORGANISM: Homo sapiens

<400> SEQUENCE: 260
aatgaaatgc ctgtcagttg 20

<210> SEQ ID NO 261
<211> LENGTH: 27
<212> TYPE: DNA
<213> ORGANISM: Homo sapiens

<400> SEQUENCE: 261
ccactggaca accacaaacc atttctc 27

<210> SEQ ID NO 262
<211> LENGTH: 20
<212> TYPE: DNA
<213> ORGANISM: Homo sapiens

<400> SEQUENCE: 262
gacttgtaat ggcagcgtag 20

<210> SEQ ID NO 263
<211> LENGTH: 20
<212> TYPE: DNA
<213> ORGANISM: Homo sapiens

<400> SEQUENCE: 263
ctcgaagaag tttccaggtt 20

<210> SEQ ID NO 264
<211> LENGTH: 24
<212> TYPE: DNA
<213> ORGANISM: Homo sapiens

<400> SEQUENCE: 264
tgacagcaga gccagtgaac caca 24

<210> SEQ ID NO 265
<211> LENGTH: 20
<212> TYPE: DNA
<213> ORGANISM: Homo sapiens

<400> SEQUENCE: 265
acttgtaatg gcagcgtaga 20

<210> SEQ ID NO 266
<211> LENGTH: 20
<212> TYPE: DNA
<213> ORGANISM: Homo sapiens

<400> SEQUENCE: 266
ctcgaagaag tttccaggtt 20

<210> SEQ ID NO 267
<211> LENGTH: 24
<212> TYPE: DNA
<213> ORGANISM: Homo sapiens

<400> SEQUENCE: 267
tgacagcaga gccagtgaac caca 24

<210> SEQ ID NO 268
<211> LENGTH: 21
<212> TYPE: DNA
<213> ORGANISM: Homo sapiens

<400> SEQUENCE: 268
actttgacag cgacaagaag t 21

<210> SEQ ID NO 269
<211> LENGTH: 20
<212> TYPE: DNA
<213> ORGANISM: Homo sapiens

<400> SEQUENCE: 269
gcggtacata gggtacatga 20

<210> SEQ ID NO 270
<211> LENGTH: 20
<212> TYPE: DNA
<213> ORGANISM: Homo sapiens

<400> SEQUENCE: 270
cgccgccacg aggaacaaac 20

<210> SEQ ID NO 271
<211> LENGTH: 20
<212> TYPE: DNA
<213> ORGANISM: Homo sapiens

<400> SEQUENCE: 271
aactttgaca gcgacaagaa 20

<210> SEQ ID NO 272
<211> LENGTH: 21
<212> TYPE: DNA
<213> ORGANISM: Homo sapiens

<400> SEQUENCE: 272
gaagcggtac atagggtaca t 21

<210> SEQ ID NO 273
<211> LENGTH: 20
<212> TYPE: DNA
<213> ORGANISM: Homo sapiens

<400> SEQUENCE: 273
cgccgccacg aggaacaaac 20

<210> SEQ ID NO 274
<211> LENGTH: 19
<212> TYPE: DNA
<213> ORGANISM: Homo sapiens

<400> SEQUENCE: 274
cagtaccacg gccaactac 19

<210> SEQ ID NO 275
<211> LENGTH: 20
<212> TYPE: DNA
<213> ORGANISM: Homo sapiens

<400> SEQUENCE: 275
tggaagatga atggaaactg 20

<210> SEQ ID NO 276
<211> LENGTH: 20
<212> TYPE: DNA
<213> ORGANISM: Homo sapiens

<400> SEQUENCE: 276
cccatcagca ttgccgtccc 20

<210> SEQ ID NO 277
<211> LENGTH: 20
<212> TYPE: DNA
<213> ORGANISM: Homo sapiens

<400> SEQUENCE: 277
ccactactgt gcctttgagt 20

<210> SEQ ID NO 278
<211> LENGTH: 20
<212> TYPE: DNA
<213> ORGANISM: Homo sapiens

<400> SEQUENCE: 278
gtacttccca tccttgaaca 20

<210> SEQ ID NO 279
<211> LENGTH: 20
<212> TYPE: DNA
<213> ORGANISM: Homo sapiens

<400> SEQUENCE: 279
ttcccaatct ccgcgatggc 20

<210> SEQ ID NO 280
<211> LENGTH: 20
<212> TYPE: DNA
<213> ORGANISM: Homo sapiens

<400> SEQUENCE: 280
ccactactgt gcctttgagt 20

<210> SEQ ID NO 281
<211> LENGTH: 19
<212> TYPE: DNA
<213> ORGANISM: Homo sapiens

<400> SEQUENCE: 281
cttcccatcc ttgaacaaa 19

<210> SEQ ID NO 282
<211> LENGTH: 20
<212> TYPE: DNA
<213> ORGANISM: Homo sapiens

<400> SEQUENCE: 282
ttcccaatct ccgcgatggc 20

<210> SEQ ID NO 283
<211> LENGTH: 20
<212> TYPE: DNA
<213> ORGANISM: Homo sapiens

<400> SEQUENCE: 283
cacgaatagc agaagaggtg 20

<210> SEQ ID NO 284
<211> LENGTH: 20
<212> TYPE: DNA
<213> ORGANISM: Homo sapiens

<400> SEQUENCE: 284
gtatgtcacc ttctgggtca 20

<210> SEQ ID NO 285
<211> LENGTH: 25
<212> TYPE: DNA
<213> ORGANISM: Homo sapiens

<400> SEQUENCE: 285
cagcttgtcc atagcctcaa ccagg 25

<210> SEQ ID NO 286
<211> LENGTH: 20
<212> TYPE: DNA
<213> ORGANISM: Homo sapiens

<400> SEQUENCE: 286
cccatccttc aagttacaca 20

<210> SEQ ID NO 287
<211> LENGTH: 20
<212> TYPE: DNA
<213> ORGANISM: Homo sapiens

<400> SEQUENCE: 287
attagctgaa ttgccagaca 20

<210> SEQ ID NO 288
<211> LENGTH: 23
<212> TYPE: DNA
<213> ORGANISM: Homo sapiens

<400> SEQUENCE: 288
tccacagatg caacaagcat cgg 23

<210> SEQ ID NO 289
<211> LENGTH: 20
<212> TYPE: DNA
<213> ORGANISM: Homo sapiens

<400> SEQUENCE: 289
gggattgcta gtctcacaga 20

<210> SEQ ID NO 290
<211> LENGTH: 20
<212> TYPE: DNA
<213> ORGANISM: Homo sapiens

<400> SEQUENCE: 290
tcttctgcta ttcgtgcatt 20

<210> SEQ ID NO 291
<211> LENGTH: 23
<212> TYPE: DNA
<213> ORGANISM: Homo sapiens

<400> SEQUENCE: 291
tcctgaacca gctgcctctt cca 23

<210> SEQ ID NO 292
<211> LENGTH: 20
<212> TYPE: DNA
<213> ORGANISM: Homo sapiens

<400> SEQUENCE: 292
cccatccttc aagttacaca 20

<210> SEQ ID NO 293
<211> LENGTH: 20
<212> TYPE: DNA
<213> ORGANISM: Homo sapiens

<400> SEQUENCE: 293
agacaacgga ccagaaactt 20

<210> SEQ ID NO 294
<211> LENGTH: 23
<212> TYPE: DNA
<213> ORGANISM: Homo sapiens

<400> SEQUENCE: 294
tccacagatg caacaagcat cgg 23

<210> SEQ ID NO 295
<211> LENGTH: 20
<212> TYPE: DNA
<213> ORGANISM: Homo sapiens

<400> SEQUENCE: 295
gcacaggcta agtagtgacg 20

<210> SEQ ID NO 296
<211> LENGTH: 20
<212> TYPE: DNA
<213> ORGANISM: Homo sapiens

<400> SEQUENCE: 296
aggtggtctt gagcctttag 20

<210> SEQ ID NO 297
<211> LENGTH: 24
<212> TYPE: DNA
<213> ORGANISM: Homo sapiens

<400> SEQUENCE: 297
tttcccttga gatctccaca gcca 24

<210> SEQ ID NO 298
<211> LENGTH: 20
<212> TYPE: DNA
<213> ORGANISM: Homo sapiens

<400> SEQUENCE: 298
cacgaatagc agaagaggtg 20

<210> SEQ ID NO 299
<211> LENGTH: 20
<212> TYPE: DNA
<213> ORGANISM: Homo sapiens

<400> SEQUENCE: 299
gtatgtcacc ttctgggtca 20

<210> SEQ ID NO 300
<211> LENGTH: 25
<212> TYPE: DNA
<213> ORGANISM: Homo sapiens

<400> SEQUENCE: 300
cagcttgtcc atagcctcaa ccagg 25

<210> SEQ ID NO 301
<211> LENGTH: 20
<212> TYPE: DNA
<213> ORGANISM: Homo sapiens

<400> SEQUENCE: 301
cccatccttc aagttacaca 20

<210> SEQ ID NO 302
<211> LENGTH: 20
<212> TYPE: DNA
<213> ORGANISM: Homo sapiens

<400> SEQUENCE: 302
attagctgaa ttgccagaca 20

<210> SEQ ID NO 303
<211> LENGTH: 23
<212> TYPE: DNA
<213> ORGANISM: Homo sapiens

<400> SEQUENCE: 303
tccacagatg caacaagcat cgg 23

<210> SEQ ID NO 304
<211> LENGTH: 20
<212> TYPE: DNA
<213> ORGANISM: Homo sapiens

<400> SEQUENCE: 304
gggattgcta gtctcacaga 20

<210> SEQ ID NO 305
<211> LENGTH: 20
<212> TYPE: DNA
<213> ORGANISM: Homo sapiens

<400> SEQUENCE: 305
tcttctgcta ttcgtgcatt 20

<210> SEQ ID NO 306
<211> LENGTH: 23
<212> TYPE: DNA
<213> ORGANISM: Homo sapiens

<400> SEQUENCE: 306
tcctgaacca gctgcctctt cca 23

<210> SEQ ID NO 307
<211> LENGTH: 20
<212> TYPE: DNA
<213> ORGANISM: Homo sapiens

<400> SEQUENCE: 307
cccatccttc aagttacaca 20

<210> SEQ ID NO 308
<211> LENGTH: 20
<212> TYPE: DNA
<213> ORGANISM: Homo sapiens

<400> SEQUENCE: 308
agacaacgga ccagaaactt 20

<210> SEQ ID NO 309
<211> LENGTH: 23
<212> TYPE: DNA
<213> ORGANISM: Homo sapiens

<400> SEQUENCE: 309
tccacagatg caacaagcat cgg 23

<210> SEQ ID NO 310
<211> LENGTH: 20
<212> TYPE: DNA
<213> ORGANISM: Homo sapiens

<400> SEQUENCE: 310
gcacaggcta agtagtgacg 20

<210> SEQ ID NO 311
<211> LENGTH: 20
<212> TYPE: DNA
<213> ORGANISM: Homo sapiens

<400> SEQUENCE: 311
aggtggtctt gagcctttag 20

<210> SEQ ID NO 312
<211> LENGTH: 24
<212> TYPE: DNA
<213> ORGANISM: Homo sapiens

<400> SEQUENCE: 312
tttcccttga gatctccaca gcca 24

<210> SEQ ID NO 313
<211> LENGTH: 20
<212> TYPE: DNA
<213> ORGANISM: Homo sapiens

<400> SEQUENCE: 313
caccgtaact atccgcacta 20

<210> SEQ ID NO 314
<211> LENGTH: 20
<212> TYPE: DNA
<213> ORGANISM: Homo sapiens

<400> SEQUENCE: 314
cggtgtggtc ttgtacattt 20

<210> SEQ ID NO 315
<211> LENGTH: 20
<212> TYPE: DNA
<213> ORGANISM: Homo sapiens

<400> SEQUENCE: 315
aggcactgtc gccttcccgg 20

<210> SEQ ID NO 316
<211> LENGTH: 20
<212> TYPE: DNA
<213> ORGANISM: Homo sapiens

<400> SEQUENCE: 316
aagaaagcaa cgaaaggaac 20

<210> SEQ ID NO 317
<211> LENGTH: 20
<212> TYPE: DNA
<213> ORGANISM: Homo sapiens

<400> SEQUENCE: 317
tcattgcagc acctttactc 20

<210> SEQ ID NO 318
<211> LENGTH: 20
<212> TYPE: DNA
<213> ORGANISM: Homo sapiens

<400> SEQUENCE: 318
tgccagcacc aacattggcc 20

<210> SEQ ID NO 319
<211> LENGTH: 20
<212> TYPE: DNA
<213> ORGANISM: Homo sapiens

<400> SEQUENCE: 319
agacatggcc tgtatgagaa 20

<210> SEQ ID NO 320
<211> LENGTH: 20
<212> TYPE: DNA
<213> ORGANISM: Homo sapiens

<400> SEQUENCE: 320
atccaatctc cagctcactt 20

<210> SEQ ID NO 321
<211> LENGTH: 20
<212> TYPE: DNA
<213> ORGANISM: Homo sapiens

<400> SEQUENCE: 321
tgccagcacc aacattggcc 20

<210> SEQ ID NO 322
<211> LENGTH: 20
<212> TYPE: DNA
<213> ORGANISM: Homo sapiens

<400> SEQUENCE: 322
aagacatggc ctgtatgaga 20

<210> SEQ ID NO 323
<211> LENGTH: 20
<212> TYPE: DNA
<213> ORGANISM: Homo sapiens

<400> SEQUENCE: 323
atccaatctc cagctcactt 20

<210> SEQ ID NO 324
<211> LENGTH: 20
<212> TYPE: DNA
<213> ORGANISM: Homo sapiens

<400> SEQUENCE: 324
tgccagcacc aacattggcc 20

<210> SEQ ID NO 325
<211> LENGTH: 20
<212> TYPE: DNA
<213> ORGANISM: Homo sapiens

<400> SEQUENCE: 325
gacatggcct gtatgagaag 20

<210> SEQ ID NO 326
<211> LENGTH: 20
<212> TYPE: DNA
<213> ORGANISM: Homo sapiens

<400> SEQUENCE: 326
atccaatctc cagctcactt 20

<210> SEQ ID NO 327
<211> LENGTH: 20
<212> TYPE: DNA
<213> ORGANISM: Homo sapiens

<400> SEQUENCE: 327
tgccagcacc aacattggcc 20

<210> SEQ ID NO 328
<211> LENGTH: 20
<212> TYPE: DNA
<213> ORGANISM: Homo sapiens

<400> SEQUENCE: 328
aaggaacgca agaacagaat 20

<210> SEQ ID NO 329
<211> LENGTH: 20
<212> TYPE: DNA
<213> ORGANISM: Homo sapiens

<400> SEQUENCE: 329
attgcagcac ctttactcct 20

<210> SEQ ID NO 330
<211> LENGTH: 20
<212> TYPE: DNA
<213> ORGANISM: Homo sapiens

<400> SEQUENCE: 330
tgccagcacc aacattggcc 20

<210> SEQ ID NO 331
<211> LENGTH: 20
<212> TYPE: DNA
<213> ORGANISM: Homo sapiens

<400> SEQUENCE: 331
tacctggtca ttgatgaagc 20

<210> SEQ ID NO 332
<211> LENGTH: 20
<212> TYPE: DNA
<213> ORGANISM: Homo sapiens

<400> SEQUENCE: 332
caaaggtgtt ccagttagga 20

<210> SEQ ID NO 333
<211> LENGTH: 27
<212> TYPE: DNA
<213> ORGANISM: Homo sapiens

<400> SEQUENCE: 333
cgtgagttca agtcgactaa ccgcttg 27

<210> SEQ ID NO 334
<211> LENGTH: 20
<212> TYPE: DNA
<213> ORGANISM: Homo sapiens

<400> SEQUENCE: 334
tacctggtca ttgatgaagc 20

<210> SEQ ID NO 335
<211> LENGTH: 20
<212> TYPE: DNA
<213> ORGANISM: Homo sapiens

<400> SEQUENCE: 335
ttattctgca aaggtgttcc 20

<210> SEQ ID NO 336
<211> LENGTH: 25
<212> TYPE: DNA
<213> ORGANISM: Homo sapiens

<400> SEQUENCE: 336
ttcaagtcga ctaaccgctt gctcc 25

<210> SEQ ID NO 337
<211> LENGTH: 20
<212> TYPE: DNA
<213> ORGANISM: Homo sapiens

<400> SEQUENCE: 337
tggacccaga atatgaagag 20

<210> SEQ ID NO 338
<211> LENGTH: 20
<212> TYPE: DNA
<213> ORGANISM: Homo sapiens

<400> SEQUENCE: 338
atgttcagtg gagatgttgg 20

<210> SEQ ID NO 339
<211> LENGTH: 23
<212> TYPE: DNA
<213> ORGANISM: Homo sapiens

<400> SEQUENCE: 339
tctctttgct cggtcggctt tca 23

<210> SEQ ID NO 340
<211> LENGTH: 20
<212> TYPE: DNA
<213> ORGANISM: Homo sapiens

<400> SEQUENCE: 340
ctttgcttgg ttacctgaaa 20

<210> SEQ ID NO 341
<211> LENGTH: 20
<212> TYPE: DNA
<213> ORGANISM: Homo sapiens

<400> SEQUENCE: 341
aaacaaatga cacggagaga 20

<210> SEQ ID NO 342
<211> LENGTH: 26
<212> TYPE: DNA
<213> ORGANISM: Homo sapiens

<400> SEQUENCE: 342
ccgaaatatt cctggacctc acatgg 26

<210> SEQ ID NO 343
<211> LENGTH: 20
<212> TYPE: DNA
<213> ORGANISM: Homo sapiens

<400> SEQUENCE: 343
ggaaatggac ccagaatatg 20

<210> SEQ ID NO 344
<211> LENGTH: 20
<212> TYPE: DNA
<213> ORGANISM: Homo sapiens

<400> SEQUENCE: 344
gttggagatt tctgtgctga 20

<210> SEQ ID NO 345
<211> LENGTH: 23
<212> TYPE: DNA
<213> ORGANISM: Homo sapiens

<400> SEQUENCE: 345
tctctttgct cggtcggctt tca 23

```
<210> SEQ ID NO 346
<211> LENGTH: 20
<212> TYPE: DNA
<213> ORGANISM: Homo sapiens

<400> SEQUENCE: 346

aaggaaatgg acccagaata                                                20


<210> SEQ ID NO 347
<211> LENGTH: 20
<212> TYPE: DNA
<213> ORGANISM: Homo sapiens

<400> SEQUENCE: 347

ctgaaggctg aatgaaatgt                                                20


<210> SEQ ID NO 348
<211> LENGTH: 23
<212> TYPE: DNA
<213> ORGANISM: Homo sapiens

<400> SEQUENCE: 348

tctctttgct cggtcggctt tca                                            23


<210> SEQ ID NO 349
<211> LENGTH: 20
<212> TYPE: DNA
<213> ORGANISM: Homo sapiens

<400> SEQUENCE: 349

agtgggatgt ttgcgttact                                                20


<210> SEQ ID NO 350
<211> LENGTH: 20
<212> TYPE: DNA
<213> ORGANISM: Homo sapiens

<400> SEQUENCE: 350

cacgaacaat ctctgaaagc                                                20


<210> SEQ ID NO 351
<211> LENGTH: 26
<212> TYPE: DNA
<213> ORGANISM: Homo sapiens

<400> SEQUENCE: 351

tcatcaatga ccaggtatcg ccagtg                                         26
```

METHOD, COMPUTER READABLE MEDIUM, AND SYSTEM FOR DETERMINING A PROBABILITY OF COLORECTAL CANCER IN A TEST SUBJECT

PRIORITY CLAIM

This application claims the benefit of priority under 35 U.S.C. §119(e) to U.S. provisional application Ser. No. 60/729,055, filed Oct. 21, 2005, and to U.S. provisional application Ser. No. 60/758,418, filed Jan. 12, 2006, both of which are incorporated herein by reference in their entirety.

TECHNICAL FIELD

The disclosure relates to, apparatus and kits and computer based methods for correlating data corresponding to levels of biomarker products with a disease state in a subject.

BACKGROUND

Colorectal cancer is the second-leading cause of cancer-related deaths in the United States (11). Each year, approximately 150,000 people are diagnosed with colorectal cancer and almost 60,000 people die from the disease. Of those diagnosed, nearly half are expected to die within five years, since most cancers are detected when the cancer is less treatable. For those whose cancer is detected at an earlier stage, the five-year survival rate can be greater than 90%. The American Cancer Society recommends that all Americans age 50 and older be screened regularly for colorectal cancer. Unfortunately, only a fraction of this population is screened for the disease, as currently available screening technologies are considered as either too costly, and/or too invasive or in some cases insufficiently accurate.

Most colorectal cancers begin as small, noncancerous (benign) clumps of cells called polyps. Over time some of these polyps become cancerous. Incidence of polyps increase as individuals get older. It is estimated that 50% of the people over the age of 60 will have at least one polyp.

The significance of identifying one or more colorectal pathologies including polyps is that certain types of polyps are cancerous or indicative of an increased risk to develop cancer. It has been shown that the removal of certain subtypes of polyps reduces the risk of getting colorectal cancer significantly. Therefore, a test to screen for one or more colorectal pathologies including polyps and/or certain subtypes of polyps so as to allow early removal or to prevent unnecessary procedures should markedly reduce the incidence of colorectal cancer (12) and decrease the current costs to the medical system.

Currently utilized screening technologies to identify polyps include 1) a fecal occult blood test (FOBT); 2) a flexible sigmoidoscopy; 3) double contrast barium enema (DCBE); and 4) colonoscopy. Sometimes two or more of these tests are used in combination. The current recommended standards for screening for colorectal cancer in men over the age of 50 and who are considered part of an average risk population include: an FOBT yearly, a sigmoidoscopy every five years, a colonoscopy every ten years and a DCBE every five years. For a high risk population where one or more family members have had colorectal cancer, a colonoscopy is recommended every two years as a follow up to FOBT or sigmoidoscopy.

Each of these tests suffers significant disadvantages. FOBT testing, although a non-invasive procedure, requires significant dietary and other restrictions prior to testing and suffers from a low sensitivity. Sigmoidoscopy and colonoscopy are more sensitive since they involve direct visualization of the lumen, however, sigmoidoscopy only allows partial visualization, and the colonoscopy is known to miss about 12% of advanced adenomas. Both sigmoidoscopy and colonoscopy are highly invasive procedures which cause high levels of discomfort causing many individuals to opt not to undergo these recommended screening procedures. Also sigmoidoscopy and colonoscopy are costly, and may have complications which arise as a result of undergoing the procedure.

Thus, there is a need for an improved test which is minimally invasive so as to permit more widespread testing of the population to indicate the presence of one or more colorectal pathologies, and ensure greater adherence to recommended protocols. To date, despite this need, there have been very few advancements in identifying useful molecular biomarkers to test for colorectal pathology. Recent efforts have focused on DNA based biomarker methods (see for example Shuber et al. U.S. Patent Application Publication No. 2005-0260638A1; or Lofton-Day et al. WO2005/001142).

Identification of biomarkers for use in a non-invasive test for colorectal pathology thus fulfills a longstanding need in the art.

SUMMARY

In contrast to technologies available in the art, the inventions described herein identify biomarkers not previously associated with colorectal pathology whose gene expression levels, measured alone or in combination, and optionally applied to formulas to convert the levels to a measure, give an indication of a likelihood of colorectal pathology.

The present invention discloses novel colorectal pathology-specific biomarkers, such as blood-specific biomarkers, and methods, compositions and kits for use in testing for colorectal pathologies, such as pre-cancerous and cancerous pathologies. This use can be effected in a variety of ways as further described and exemplified herein.

According to one aspect of the present invention there is provided a method of testing for one or more colorectal pathologies in a test subject, the method comprising: (a) providing data representative of a level of one or more products of each of one or more biomarkers in a sample from the test subject; and (b) ascertaining whether the data characterizes either: (i) subjects having the one or more colorectal pathologies, or (ii) subjects not having the one or more colorectal pathologies; thus providing an indication of a probability that the test subject has the one or more colorectal pathologies.

According to another aspect of the present invention there is provided a computer-based method for testing for one or more colorectal pathologies in a test subject, the method comprising: inputting, to a computer, data representing a level of products of each of one or more biomarkers in a sample isolated and/or derived from a test subject, wherein the biomarkers are genes selected from the group consisting of BCNP1, CD163, CDA, MS4A1, BANK1 and MGC20553; and causing the computer to ascertain whether the data characterizes either: (i) subjects having the one or more colorectal pathologies, or (ii) subjects not having the one or more colorectal pathologies, thus providing an indication of a probability that the test subject has the one or more colorectal pathologies.

According to still another aspect of the present invention there is provided a computer-readable medium comprising instructions for ascertaining whether data characterizes either: (i) subjects having one or more colorectal pathologies, or (ii) subjects not having one or more colorectal pathologies, the data representing a level of one or more products of each of one or more biomarkers in a sample isolated and/or derived from a test subject, wherein the biomarkers are genes selected from the group consisting of BCNP1, CD163, CDA, MS4A1, BANK1, and MGC20553, thus providing an indication of a probability that the test subject has the one or more colorectal pathologies.

According to a yet another aspect of the present invention there is provided a computer system for providing an indication of a probability that a test subject has one or more colorectal pathologies, the computer system comprising a processor; and a memory configured with instructions that cause the processor to provide a user with the indication, wherein the instructions comprise ascertaining whether data characterizes either: (i) subjects having one or more colorectal pathologies, or (ii) subjects not having one or more colorectal pathologies, the data representing a level of one or more products of each of one or more biomarkers in a sample isolated or derived from the test subject, wherein the biomarkers are genes selected from the group consisting of BCNP1, CD163, CDA, MS4A1, BANK1, and MGC20553; thus providing the indication of a probability that the test subject has the one or more colorectal pathologies.

According to further features in preferred embodiments of the invention described below, the products in the sample are RNA.

According to still further features in the described preferred embodiments, the products in the sample are RNA, whereas the data represent a level of cDNA, EST and/or PCR product derived from the RNA.

According to still another aspect of the present invention there is provided a kit comprising packaging and containing one or more primer sets, wherein each set of which is able to generate an amplification product by selective amplification of at least a portion of a polynucleotide complementary to one or more RNA products of a biomarker, wherein the biomarker is a gene selected from the group consisting of: BCNP1, CD163, CDA, MS4A1, BANK1, and MGC20553; and wherein each set of the primer sets is selective for a different biomarker.

According to further features in preferred embodiments of the invention described below, the complementary polynucleotide is selected from the group consisting of total RNA, mRNA, DNA, cDNA and EST.

According to still further features in the described preferred embodiments, the one or more biomarkers are at least two biomarkers.

According to still further features in the described preferred embodiments, each of the probes is capable of selectively hybridizing to either a sense or an antisense strand of the amplification product.

According to still further features in the described preferred embodiments, the kit further comprises two or more components selected from the group consisting of: a thermostable polymerase, a reverse transcriptase, deoxynucleotide triphosphates, nucleotide triphosphates and enzyme buffer.

According to still further features in the described preferred embodiments, the kit further comprises a computer-readable medium encoded with instructions for ascertaining whether data characterizes either: (i) subjects having one or more colorectal pathologies, or (ii) subjects not having one or more colorectal pathologies, the data representing levels of the amplification product in a sample isolated and/or derived from a test subject, thus providing an indication of a probability that the test subject has the one or more colorectal pathologies.

According to still further features in the described preferred embodiments, ascertaining whether the data characterizes either: (i) subjects having the one or more colorectal pathologies, or (ii) subjects not having the one or more colorectal pathologies, comprises applying to the data a formula based on (i) a dataset representing levels of one or more products of each of the biomarkers in each subject of a reference population having the one or more pathologies, and (ii) a dataset representing levels of one or more products of each of the biomarkers in each subject of a reference population not having the one or more pathologies.

According to still further features in the described preferred embodiments, ascertaining whether the data characterizes either: (i) subjects having the one or more colorectal pathologies, or (ii) subjects not having the one or more colorectal pathologies, comprises ascertaining whether the data correlates more closely with (i) a dataset representing levels of one or more products of each of the biomarkers in each subject of a reference population of subjects who have the one or more colorectal pathologies, or (ii) a dataset representing levels of one or more products of each of the biomarkers in each subject of a reference population of subjects who do not have the colorectal pathology.

According to still further features in the described preferred embodiments, the formula has a form: $V=C+\Sigma\beta_i X_i$, wherein V is a value indicating a probability that the test subject has the colorectal pathology, $X_i$ is a level of products of an ith biomarker of the biomarkers in the sample, $\beta_i$ is a coefficient, and C is a constant.

According to still further features in the described preferred embodiments, the formula has a form: $V=C+\Sigma\beta_{ij}(X_i/X_j)$, wherein V is a value indicating a probability that the test subject has the colorectal pathology, $X_i$ is a level of products of an ith biomarker of the biomarkers, and $X_j$ is a level of products of a jth biomarker of the biomarkers in the sample, where the ith biomarker is not the jth biomarker, $\beta_{ij}$ is a coefficient, and C is a constant.

According to still further features in the described preferred embodiments, the formula is derived by a method selected from the group consisting of logistic regression, linear regression, neural networks, and principle component analysis.

According to still further features in the described preferred embodiments, the sample is selected from the group consisting of blood, lymph and lymphoid tissue.

According to still further features in the described preferred embodiments, the sample is selected from the group consisting of a sample of serum-reduced blood, a sample of erythrocyte-reduced blood, a sample of serum-reduced and erythrocyte-reduced blood, a sample of unfractionated cells of lysed blood, and a sample of fractionated blood.

According to a further aspect of the present invention there is provided a composition comprising a collection of two or more isolated polynucleotides, wherein each isolated polynucleotide selectively hybridizes to a biomarker selected from the biomarkers set out in Table 2 and wherein the composition is used to measure the level of expression of at least two of the biomarkers.

According to further features in preferred embodiments of the invention described below, each isolated polynucleotide selectively hybridizes a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); and wherein the composition is used to measure the level of expression of at least two of the biomarkers.

According to yet a further aspect of the present invention there is provided a composition comprising a collection of two or more isolated polynucleotides, wherein each isolated polynucleotide selectively hybridizes to (a) an RNA product of a biomarker selected from the biomarkers set out in Table 2, and/or (b) a polynucleotide sequence complementary to (a), wherein the composition is used to measure the level of RNA expression of at least two of the biomarkers.

According to further features in preferred embodiments of the invention described below, each isolated polynucleotide selectively hybridizes to (a) an RNA product of a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1%); and/or (b) a polynucleotide sequence complementary to (a), wherein the composition is used to measure the level of RNA expression of at least two of the biomarkers.

According to still a further aspect of the present invention there is provided a composition comprising a collection of two or more isolated polynucleotides, wherein each isolated polynucleotide selectively hybridizes to (a) an RNA sequences set out in Table 3; and/or (b) a polynucleotide sequences complementary to (a).

According to an additional aspect of the present invention there is provided a composition comprising a collection of two or more sets of biomarker specific primers as set out in Table 4 and/or Table 6.

According to yet an additional aspect of the present invention there is provided a composition comprising two or more polynucleotide probes as set out in Table 4.

According to further features in preferred embodiments of the invention described below, the polynucleotides are useful in quantitative RT-PCR (QRT-PCR).

According to still further features in the described preferred embodiments, the isolated polynucleotides comprise single or double stranded RNA.

According to still further features in the described preferred embodiments, the isolated polynucleotides comprise single or double stranded DNA.

According to still an additional aspect of the present invention there is provided a composition comprising a collection of two or more isolated proteins, wherein each isolated protein binds selectively to a protein product of a biomarker selected from the biomarkers set out in Table 2 and wherein the composition is used to measure the level of expression of at least two of the biomarkers.

According to further features in preferred embodiments of the invention described below, each isolated protein binds selectively to a protein product of a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); and wherein the composition is used to measure the level of expression of at least two of the biomarkers.

According to still further features in the described preferred embodiments, the isolated proteins are selected from the proteins set out in Table 5.

According to still further features in the described preferred embodiments, the isolated proteins are ligands.

According to still further features in the described preferred embodiments, the ligands are antibodies or fragments thereof.

According to still further features in the described preferred embodiments, the antibodies are monoclonal antibodies.

According to yet still an additional aspect of the present invention there is provided a method of diagnosing or detecting one or more colon pathologies in an individual comprising: (a) determining the level of RNA product of one or more biomarker selected from the group consisting of the biomarkers set out in Table 2 in a sample of an individual; and (b) comparing the level of RNA products in the sample with a control, wherein detecting differential expression of the RNA products between the individual and the control is indicative of a one or more colon pathologies in the individual.

According to further features in preferred embodiments of the invention described below, the method of diagnosing or detecting one or more colon pathologiess in an individual comprising: (a) determining the level of RNA product of one or more biomarker selected from the group consisting of the biomarkers set out in Table 2 in a sample of an individual; and (b) comparing the level of RNA products in the sample with a control further comprises (a) determining the level of RNA product of one or more biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); in a sample from an individual; and (b) comparing the level of RNA products in the sample with a control, wherein detecting differential expression of the RNA products between the individual and the control is indicative of a one or more colon pathologies in the individual.

According to still further features in the described preferred embodiments, the sample comprises whole blood.

According to still further features in the described preferred embodiments, the sample comprises a drop of whole blood.

According to still further features in the described preferred embodiments, the sample comprises blood that has been lysed.

According to still further features in the described preferred embodiments, prior to the determining step, the method comprises isolating RNA from the sample.

According to still further features in the described preferred embodiments, the step of determining the level of the RNA products comprises using quantitative RT-PCR (QRT-PCR).

According to still further features in the described preferred embodiments, the QRT-PCR comprises hybridizing primers which hybridize to the one or more RNA products or the complement thereof.

According to still further features in the described preferred embodiments, the primers are 15-25 nucleotides in length.

According to still further features in the described preferred embodiments, the step of determining the level of each of the one or more RNA products comprises hybridizing a first plurality of isolated polynucleotides that correspond to the one or more transcripts, to an array comprising a second plurality of isolated polynucleotides.

According to still further features in the described preferred embodiments, the first plurality of isolated polynucleotides comprises RNA, DNA, cDNA, PCR products or ESTs.

According to still further features in the described preferred embodiments, the array comprises a plurality of isolated polynucleotides comprising RNA, DNA, cDNA, PCR products or ESTs.

According to still further features in the described preferred embodiments, the second plurality of isolated polynucleotides on the array comprises polynucleotides corresponding to one or more of the biomarkers of Table 2.

According to still further features in the described preferred embodiments, the control is derived from an individual that does not have one or more colon pathologies.

According to another aspect of the present invention there is provided a kit for diagnosing or detecting one or more colon pathologies comprising any one of the compositions and instructions for use.

According to yet another aspect of the present invention there is provided a kit for diagnosing or detecting one or more colon pathologies comprising: (a) at least two sets of biomarker specific primers wherein each set of biomarker specific primers produces double stranded DNA complementary to a unique biomarker selected from Table 2; wherein each first primers of the sets contains a sequence which can selectively hybridize to RNA, cDNA or an EST complementary to one of the biomarkers to create an extension product and each the second primers of the sets is capable of selectively hybridizing to the extension product; (b) an enzyme with reverse transcriptase activity; (c) an enzyme with thermostable DNA polymerase activity, and (d) a labeling means; wherein each of the primer sets is used to detect the quantitative expression levels of the biomarker in a test subject.

According to further features in preferred embodiments of the invention described below, the kit for diagnosing or detecting one or more colon pathologies comprising: (a) at least two sets of biomarker specific primers wherein each set of biomarker specific primers produces double stranded DNA complementary to a unique biomarker selected from Table 2; and an enzyme further comprises (a) at least two sets of biomarker specific primers wherein each set of biomarker specific primers produces double stranded DNA complementary to a unique biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); wherein each first primers of the sets contains a sequence which can selectively hybridize to RNA, cDNA or an EST complementary to one of the biomarkers to create an extension product and each the second primers of the sets is capable of selectively hybridizing to the extension product; (b) an enzyme with reverse transcriptase activity; (c) an enzyme with thermostable DNA polymerase activity, and (d) a labeling means; wherein each of the primer sets is used to detect the quantitative expression levels of the biomarker in a test subject.

According to still another aspect of the present invention there is provided a method for diagnosing or detecting one or more colon pathologies in an individual comprising: (a) determining the level of protein product of one or more biomarker selected from the group consisting of the biomarkers set out in Table 2 in a sample from an individual; and (b) comparing the level of protein products in the sample with a control, wherein detecting differential expression of the protein products between the individual and the control is indicative of a one or more colon pathologies in the individual.

According to further features in preferred embodiments of the invention described below, the method for diagnosing or detecting one or more colon pathologies in an individual comprising determining the level of protein product of one or more biomarker selected from the group consisting of the biomarkers set out in Table 2 in a sample from an individual further comprises determining the level of protein product of one or more biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); in a sample from an individual; and (b) comparing the level of protein products in the sample with a control, wherein detecting differential expression of the protein products between the individual and the control is indicative of a one or more colon pathologies in the individual.

According to still further features in the described preferred embodiments, the level of protein product is determined using antibodies or fragments thereof.

According to still further features in the described preferred embodiments, the antibodies are selected from the group of antibodies set out in Table 5.

According to still further features in the described preferred embodiments, the antibodies are monoclonal antibodies.

According to a further aspect of the present invention there is provided a composition comprising a collection of two or more isolated polynucleotides, wherein each isolated polynucleotide selectively hybridizes to a biomarker selected from the biomarkers set out in Table 12 and wherein the composition is used to measure the level of expression in blood of at least two of the biomarkers.

According to yet a further aspect of the present invention there is provided a kit for diagnosing or detecting one or more colon pathologies comprising any one of the compositions comprising a collection of two or more isolated proteins and instructions for use.

The present invention successfully addresses the shortcomings of the presently known configurations, in particular by providing an effective and non-invasive method of testing for colorectal pathologies, such as pre-cancerous and cancerous pathologies, via biomarker analysis in surrogate tissues such as blood.

Other features and advantages of the invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

Figure 2:
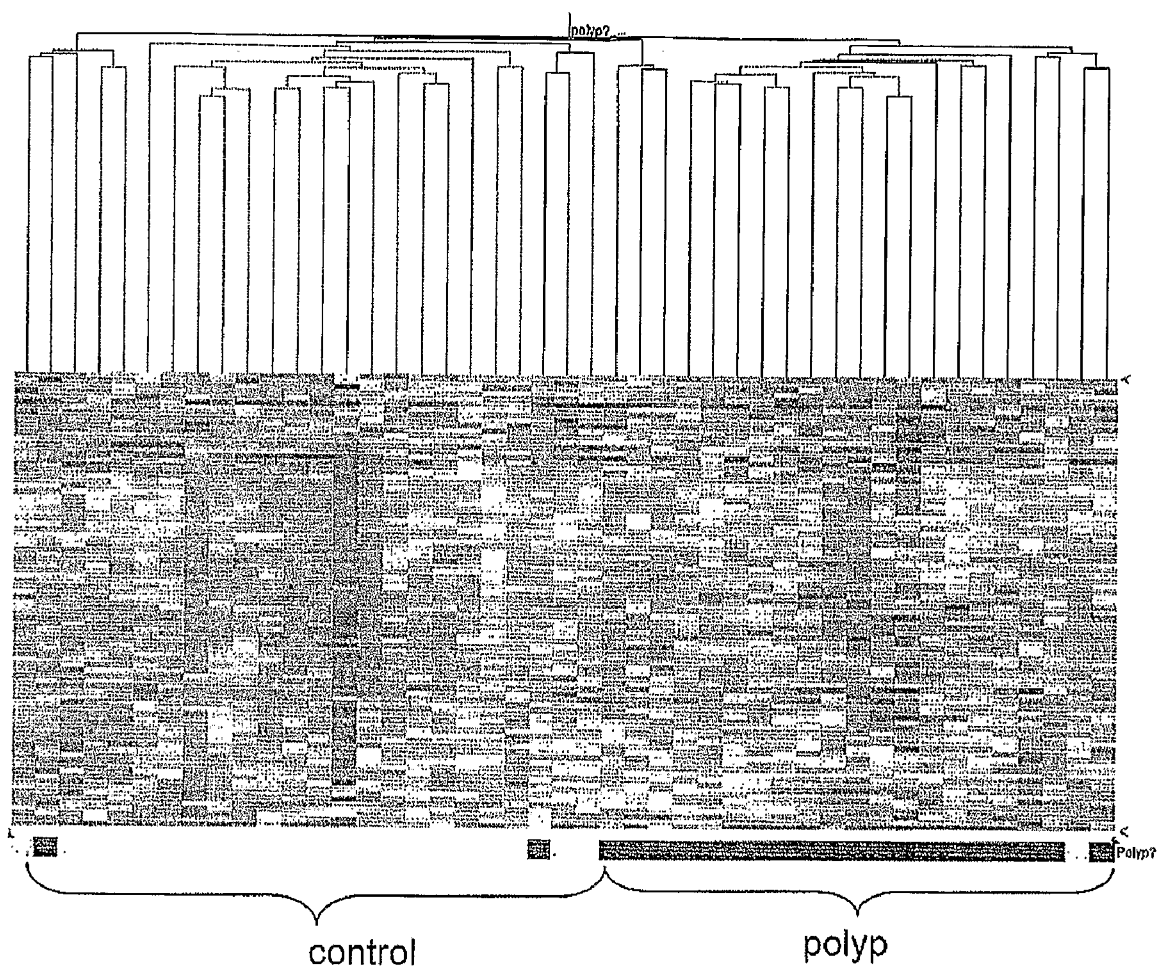
FIG. 2 is a comparison of gene expression profiles obtained from hybridization of RNA isolated from serum-reduced, erythrocyte-reduced blood from 23 controls having no identified colorectal polyps and 22 subjects with colorectal polyps as described in Example 2. Patients with colorectal polyps could have one or more of the subtypes of polyps including Hyperplastic; Tubular Adenoma; Villous Adenoma; Tubulovillous Adenoma; Hyperplasia; High Grade Dysplasia and Colorectal cancer; Gene expression profiles were clustered according to the expression of 86 significantly ($P<0.001$)

differentially expressed genes. As noted in grayscale, some of the individuals were misclassified (ie are shown in different grey scale under the appropriate bracket) and are considered outliers. Each column indicates a gene expression profile for a single sample and each row represents the expression level of a single gene in each of the samples. The color of each band within a row indicates the relative level of gene expression (grayscale represents level of expression, from low to high in expression). The resulting gene list from FIG. 2 is shown in Table 1.

Figure 3:
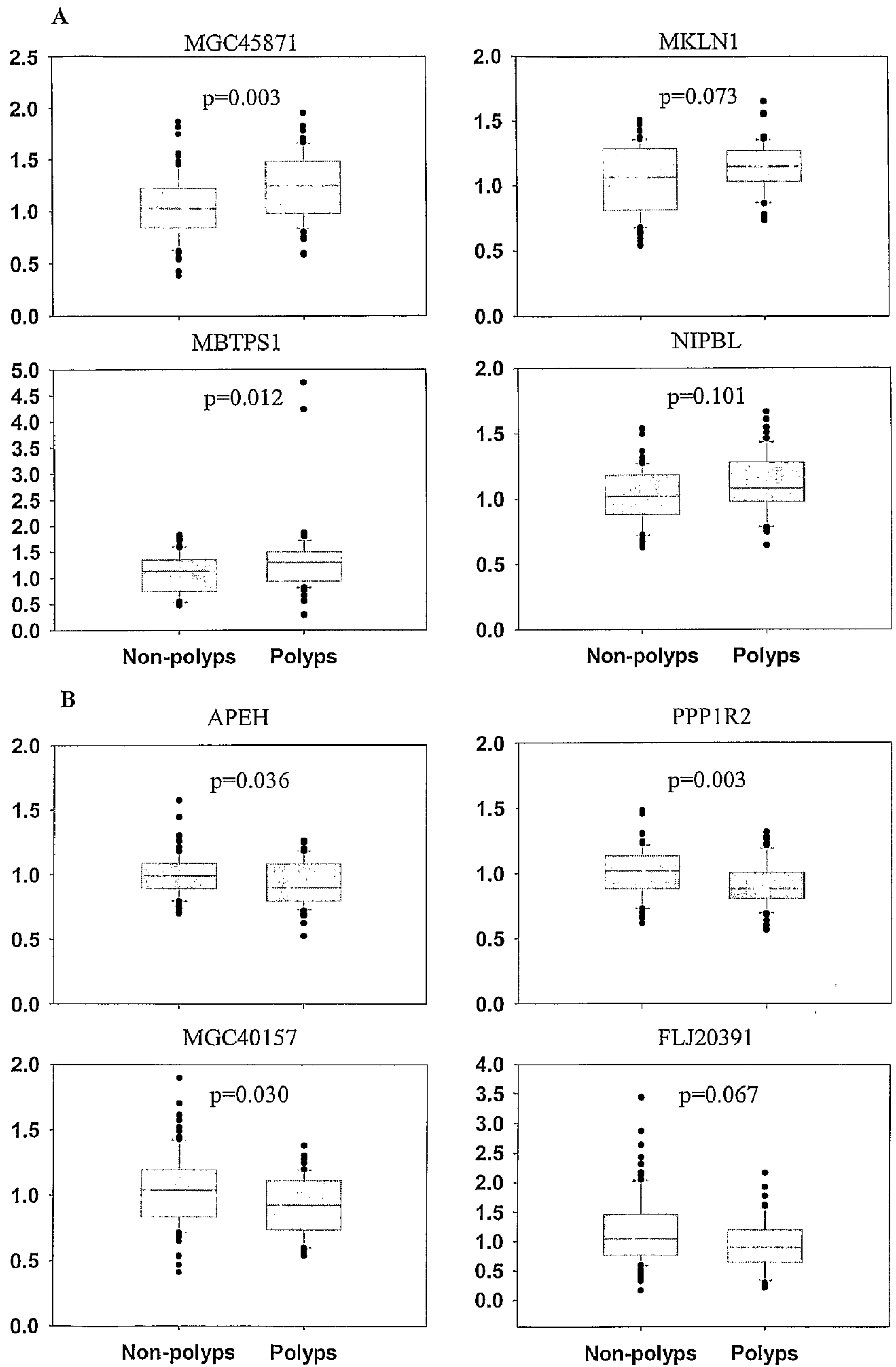

FIG. 3 shows blood mRNA levels as tested by QRT-PCR for four upregulated genes (A) and four downregulated genes (B) selected from the genes demonstrating statistically significant differentially expression using microarray analysis as described in Example 5. QRT-PCR results were tested as between 50 patients diagnosed as having colorectal pathology (ie one or more subtypes of colorectal polyps) (n=50) as compared with 78 control individuals where the control individuals were diagnosed as not having colorectal pathology (n=78). Comparative (Ct) method based fold change was used. Mann-Whitney test was used for statistical analysis between two groups. Results which demonstrated a f value of less than 0.05 were considered statistically significant suggesting that the gene corresponding to the mRNA level tested is differentially expressed as between the two patient populations (patients with colorectal pathology and patients without colorectal pathology). The lines inside the boxes denote the medians. The boxes mark the interval between the $25^{th}$ and $75^{th}$ percentiles. The whiskers denote the interval between the $10^{th}$ and $90^{th}$ percentiles.•indicates data points outside the $10^{th}$ and $90^{th}$ percentiles.

Figure 4:
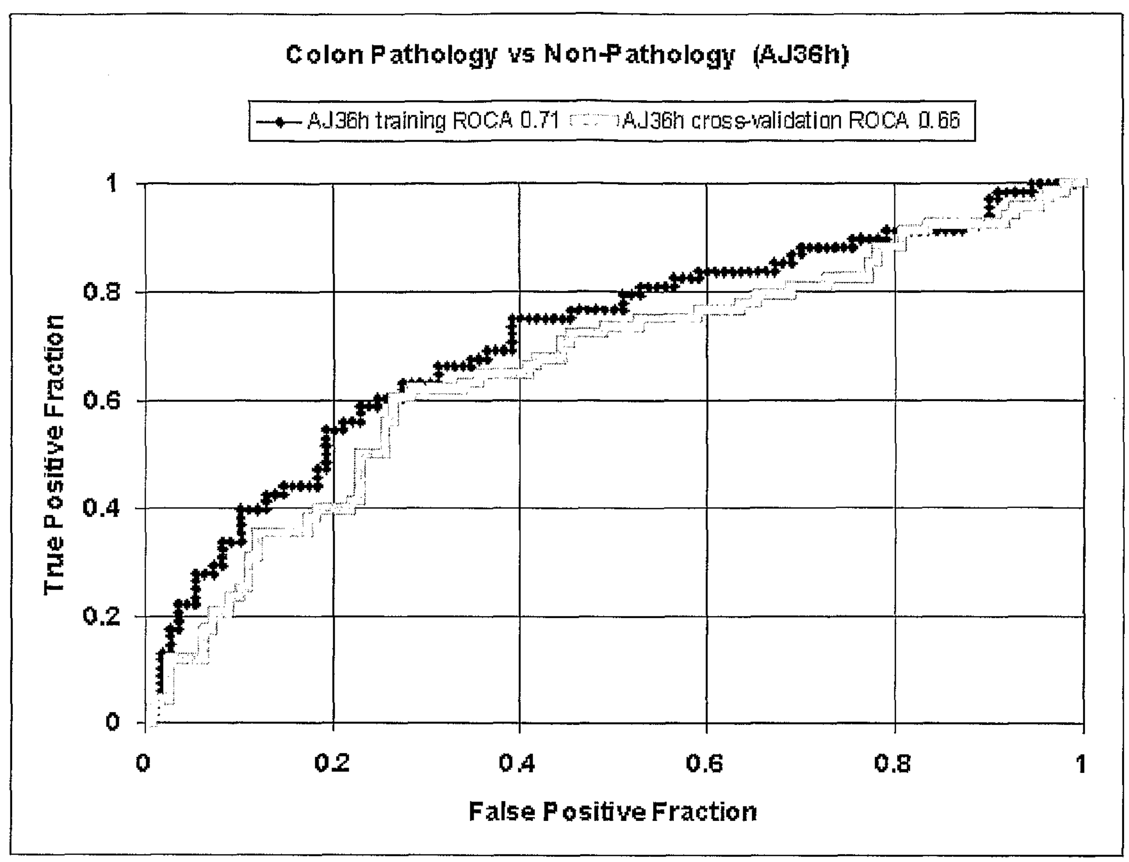

FIG. 4 depicts an ROC curve for a selected biomarker combination from combinations of pairs of the eight biomarkers tested and shown in FIG. 3. Experimental details are as described in Example 5. Combinations of a selection of the biomarkers identified in Table 1 were tested to determine the ability of the combinations to screen test subjects for one or more colorectal pathologies more effectively than can be achieved using the biomarkers of Table 1 individually. QRT-PCR as described in Example 3 was performed to measure the level of the RNA products of a select group of individual biomarkers from Table 1. Selected combinations of biomarkers were tested by applying logistic regression analysis to the QRT-PCR results of the selected combination and the ROC curve for the resulting logistic regression equation (logit function) determined. Panel (A)–ROC curve (ROC Area 0.72) for logit function for one of the datasets tested (AJ36h). This function returned by Simple Logistic operator in WEKA (ROC Area 0.66).

Figure 5:
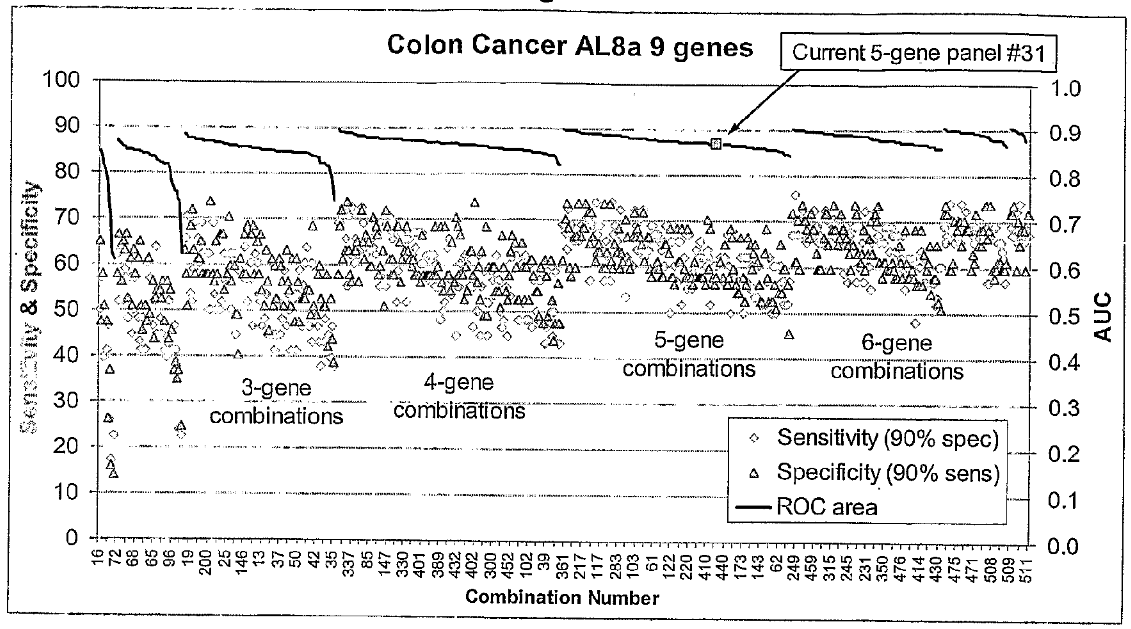

FIG. 5 depicts the graphical output results of the analysis of all possible combinations of 9 genes selected from the genes depicted in Table 12 and further described in Example 8. Shown is a graphical depiction of ROC area, sensitivity (specificity is set at the 90% threshold) and specificity (sensitivity is set at the 90% threshold) for each possible combination of 1, 2, 3, 4, 5, 6, 7, 8 or all 9 genes. Further details are described in Example 8.

Figure 6:
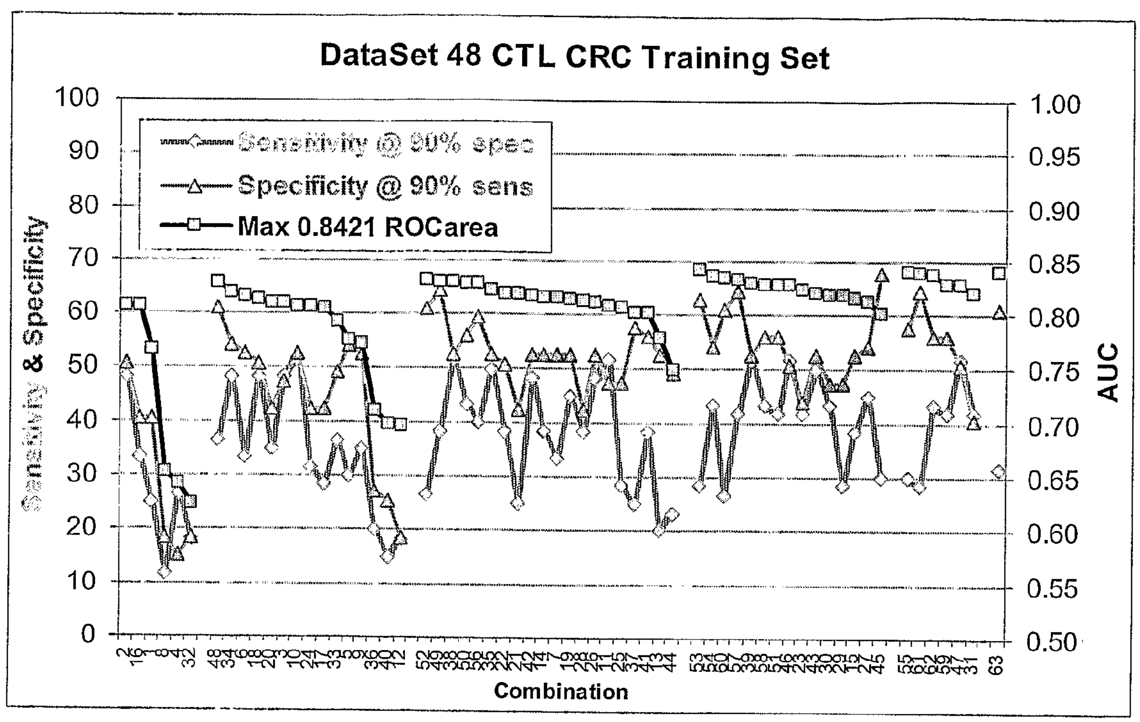

FIG. 6 depicts the graphical output results of the analysis of all possible combinations of 6 genes as further described in Example 11. Shown is a graphical depiction of the ROC area, sensitivity (specificity is set at the 90% threshold) and specificity (sensitivity is set at the 90% threshold) for each possible combination of 1, 2, 3, 4, 5 and all 6 of the genes noted in Example 11.

BRIEF DESCRIPTION OF THE TABLES

Table 1 (provided herewith on CD-R) shows genes identified as differentially expressed in samples from individuals having or not having one or more of any type of colorectal polyps where the polyps can include be one or more of the following subtypes of polyps: Hyperplastic; Tubular Adenoma; Villous Adenoma; Tubulovillous Adenoma; Hyperplasia; High Grade Dysplasia and Cancer. The table provides the Hugo Gene name (second column), symbol and locus link ID; the human RNA and protein accession number; the p value (which represents the statistical significance of the observed differential expression as determined by measuring RNA encoded by the biomarkers noted) and a measure of the fold change as between the average measured level of individuals having one or more types of colorectal pathology and the average measured level of individuals not having colorectal pathology. Column 1 is AffySpotID, column 2 is GeneSymbol, column 3 is GeneID, Column 4 is pvalue, column 5 is the HumanRNA Accession Number, column 6 is the Human Protein Accession Number, column 7 is the Fold Change, and column 8 is the Gene Description.

Table 2 is a selection of genes listed in Table 1. The table provides the gene symbol, locus link ID, and gene description. The table also includes the p value (which represents the statistical significance of the observed differential expression), the Mann-Whitney value (which is another measure to represent the statistical significance of differentiating samples with and without colorectal pathology), the measure of the fold change as between the average measured level of individuals having polyps and the average measured level of individuals not having polyps, and the direction of the differential expression between individuals having colorectal pathology and not having colorectal pathology.

Table 3 provides the human RNA accession number and human protein accession number of various species of the biomarkers identified as differentially expressed in samples from individuals having or not having colorectal polyps. The table provides the gene symbol and a description of the gene.

Table 4 provides a selection of examples of primers and TaqMan® probes useful in the invention for measuring the RNA products of the biomarkers disclosed in Table 2.

Table 5 provides reference to antibodies which are commercially available for protein products of the genes identified in Table 2.

Table 6 shows primer sequences utilized to perform RT-PCR to measure the differential expression of RNA products of the genes (biomarkers) from Table 2 as noted in Example 3 in samples from individuals having or not having one or more polyps. The table also provides the gene symbol and RNA accession number corresponding to the biomarkers tested.

Table 7 provides a summary of the phenotypic information of the patients used as noted in Example 5 to test selected biomarkers for the ability to test for the presence of colorectal polyps. Parameters including the sample size, gender, age and polyp subtype, (as determined by pathology reports), are listed.

Table 8 lists selected classifiers for use with data corresponding to the eight selected biomarkers MBTPS1, MGC45871, MKLN1, NIPBL APEH, MGC40157, PPP1, FLJ23091 which resulted in a ROC area of 0.72 so as to test for the presence of a colorectal polyps as described in Example 5. Results of QRT-PCR of the eight selected genes are shown in FIG. 3.

Table 9 provides the results of the blind test described in Example 5 when applying the formula comprised of classifiers noted in Table 8.

Table 10 is a list of reporter genes and the properties of the reporter gene products which may be used to identify compounds for use in preventing or treating one or more forms of colorectal pathology.

Table 11 (provided herewith on CD-R) shows genes identified as differentially expressed in samples from individuals having "high risk polyps" as compared with individuals not having high risk polyps (ie having low risk polyps or having no pathology at all) using microarray as described in Example 2. The table provides the gene name, gene ID; a representative human RNA accession number, and also provides the p value, the fold change (as between the average of individuals classified as having high risk polyps as compared with the average of individuals having low risk polyps), along with the coefficient of variation for both the high risk polyp individuals and the low risk polyp individuals (the standard deviation of the normalized intensity divided by the mean normalized intensity). Column 1 is AffySpotID, column 2 is Fold Change, column 3 is p value, Column 4 is CV (Coefficient of Variation) (High RiskPolyp), column 5 is CV(Low Risk Polyp), column 6 is Gene ID, column 7 is the HUGO Gene Symbol, column 8 is the Human RNA Accession Number and column 9 is the Gene Description.

Table 12 shows 48 biomarkers tested for differential expression by QRT-PCR in samples from individuals having colorectal cancer and individuals not having colorectal cancer The 48 biomarkers were tested using QRT-PCR. The table provides the gene symbol, locus link ID, and gene description for each biomarker. The table also includes the p value (which represents the statistical significance of the observed differential expression), the measure of the fold change as between the average measured level of individuals having colorectal cancer and the average measured level of individuals not having colorectal cancer and the direction of the differential expression between individuals having colorectal cancer and not having colorectal cancer.

Table 13 provides the human RNA accession number and human protein accession number of various species of the biomarkers identified as differentially expressed in samples from individuals having or not having colorectal cancer in Table 12. The table provides the gene symbol and a description of the gene.

Table 14 provides a selection of examples of primers and TaqMan® probes useful for measuring one or more RNA products of the biomarkers disclosed in Table 12 as described in Examples 6, 7, 8 or 9.

Table 15 provides reference to antibodies which are commercially available to measure protein products of the biomarkers identified in Table 12.

Table 16 shows a selection of primers which have been used for the genes described in Table 12 to quantify one or more RNA products of the biomarkers.

Table 17 shows primers and TaqMan® probes used in Example 11.

DETAILED DESCRIPTION

(A) Overview

In one aspect the invention discloses methods of generating formulas/classifiers which can be applied to data corresponding to levels of one or more products of selected biomarker combinations to classify test subjects as having one or more colorectal pathologies or one or more subtypes of colorectal pathologies. Also disclosed are biomarkers whose product levels are useful for testing subjects for one or more colorectal pathologies or one or more subtypes of colorectal pathologies. Also disclosed are computer-readable media comprising instructions for applying a formula to data representing a level of products of biomarkers so as to test subjects for one or more colorectal pathologies. Also disclosed is a computer system which is configured with instructions to provide the user with an indication of the probability of a test subject having one or more colorectal pathologies by applying a formula to biomarker product data.

The present invention provides biomarker product ligands capable of specific hybridization with RNA biomarker products so as to enable quantitation of the biomarker products. The biomarker product ligands may enable quantitation, either directly and/or indirectly in any one of various ways known to the skilled artisan. The biomarker product ligands capable of specifically hybridizing with biomarker RNA products or polynucleotides derived therefrom may have any one of various compositions. For example, specific ligands of biomarker products, such as biomarker RNA products, may be either polynucleotides (e.g. polynucleotides complementary to at least a portion of the RNA products or polynucleotides derived therefrom) or polypeptides (e.g. antibodies or affinity-selected polypeptides specific for at least a portion of the RNA products or polynucleotides derived therefrom). In one embodiment polynucleotide and/or polypeptide ligands are disclosed which are probes capable of specifically and/or selectively hybridizing with so as to quantitate biomarker RNA products and/or polynucleotides products. Such probes include those useful in techniques such as quantitative real-time PCR (QRT-PCR), and may be used, for example, with SYBR®Green, or using TaqMan® or Molecular Beacon techniques. In one embodiment, the polynucleotides useful as nucleic acid probes which can be spotted onto an array to measure levels of biomarker RNA products, or of polynucleotides derived therefrom, which are isolated or derived from test Subjects. In another embodiment, arrays for use in measuring the expression of the RNA products are contemplated.

In another embodiment, polynucleotide ligands are disclosed which are biomarker specific primer sets capable of specifically amplifying biomarker RNA products and/or polynucleotides corresponding to biomarker RNA products.

Further disclosed are methods of screening of products of the identified biomarkers to screen for therapeutic targets for treating or preventing one or more colorectal pathologies.

Kits of polynucleotides and/or polypeptide ligands which can be used to detect and monitor differential gene expression of the products of the identified biomarkers and biomarker combinations are also provided as are kits which include a computer readable medium to allow an indication of a probability that a test subject has one or more colorectal pathologies. Methods of generating the formulas for testing for one or more colorectal pathologies are also provided.

Further disclosed is the measurement/monitoring of biomarker product levels to screen for therapeutic targets for treating or preventing one or more colorectal pathologies. Methods of generating the formulas for testing a test subject for a one or more colorectal pathologies are also provided.

Also disclosed are methods of testing combinations of biomarkers by generating classifiers. Classifiers are generated by applying one or more mathematical models to data representative of the level of expression of the RNA and/or protein products of the biomarkers across a reference population encompassing subjects who have one or more colorectal pathologies, or one or more subtypes thereof, and subjects who do not have the one or more colorectal pathologies. Classifiers can be used alone or in combination to create a formula which is useful in testing a subject for the probability of having one or more colon pathologies subtypes. Also disclosed are methods of further selecting classifiers on the basis of area under the curve (AUC), sensitivity and/or specificity. One or more selected classifiers can be used to generate a formula and subsequently classifiers can be selected for inclusion into the formulas. Classifiers are generated by measuring levels of one or more RNA products and/or one or more protein products of the biomarkers in a sample and using the data resulting from said measurement for input into the mathematical model. Note that it is not necessary that the same method used to generate the data for creating the formulas is the method used to generate data from the test subject for inclusion within the formula for diagnostic purposes.

Other aspects of the invention are disclosed herein.

(B) Definitions

The practice of the present invention will employ, unless otherwise indicated, techniques of molecular biology, microbiology and recombinant DNA techniques, which are familiar to one of the skill in the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entireties.

The following definitions are provided for specific terms which are used in the following written description.

As used herein, the "5' end" refers to the end of an mRNA up to the first 1000 nucleotides or ⅓ of the mRNA (where the full length of the mRNA does not include the poly A tail) starting at the first nucleotide of the mRNA. The "5' region" of a gene refers to a polynucleotide (double-stranded or single-stranded) located within or at the 5' end of a gene, and includes, but is not limited to, the 5' untranslated region, if that is present, and the 5' protein coding region of a gene. The 5' region is not shorter than 8 nucleotides in length and not longer than 1000 nucleotides in length. Other possible lengths of the 5' region include but are not limited to 10, 20, 25, 50, 100, 200, 400, and 500 nucleotides.

As used herein, the "3' end" refers to the end of an mRNA up to the last 1000 nucleotides or ⅓ of the mRNA, where the 3' terminal nucleotide is that terminal nucleotide of the coding or untranslated region that adjoins the poly-A tail, if one is present. That is, the 3' end of an mRNA does not include the poly-A tail, if one is present. The "3' region" of a gene refers to a polynucleotide (double-stranded or single-stranded) located within or at the 3' end of a gene, and includes, but is not limited to, the 3' untranslated region, if that is present, and the 3' protein coding region of a gene. The 3' region is not shorter than 8 nucleotides in length and not longer than 1000 nucleotides in length. Other possible lengths of the 3' region include but are not limited to 10, 20, 25, 50, 100, 200, 400, and 500 nucleotides. As used herein, the "internal coding region" of a gene refers to a polynucleotide (double-stranded or single-stranded) located between the 5' region and the 3' region of a gene as defined herein. The "internal coding region" is not shorter than 8 nucleotides in length and not longer than 1000 nucleotides in length. Other possible lengths of the "internal coding region" include but are not limited to 10, 20, 25, 50, 100, 200, 400, and 500 nucleotides. The 5', 3' and internal regions are non-overlapping and may, but need not be contiguous, and may, but need not, add up to the full length of the corresponding gene.

As used herein, the "amino terminal" region of a polypeptide refers to the polypeptide sequences encoded by polynucleotide sequences (double-stranded or single-stranded) located within or at the 5' end of an mRNA molecule. As used herein, the "amino terminal" region refers to the amino terminal end of a polypeptide up to the first 300 amino acids or ⅓ of the polypeptide, starting at the first amino acid of the polypeptide. The "amino terminal" region of a polypeptide is not shorter than 3 amino acids in length and not longer than 350 amino acids in length. Other possible lengths of the "amino terminal" region of a polypeptide include but are not limited to 5, 10, 20, 25, 50, 100 and 200 amino acids.

As used herein, the "carboxy terminal" region of a polypeptide refers to the polypeptide sequences encoded by polynucleotide sequences (double-stranded or single-stranded) located within or at the 3' end of an mRNA molecule. As used herein, the "carboxy terminal" region refers to the carboxy terminal end of a polypeptide up to 300 amino acids or ⅓ of the polypeptide from the last amino acid of the polypeptide. The "3' end" does not include the polyA tail, if one is present. The "carboxy terminal" region of a polypeptide is not shorter than 3 amino acids in length and not longer than 350 amino acids in length. Other possible lengths of the "carboxy terminal" region of a polypeptide include, but are not limited to, 5, 10, 20, 25, 50, 100 and 200 amino acids.

As used herein, the "internal polypeptide region" of a polypeptide refers to the polypeptide sequences located between the amino terminal region and the carboxy terminal region of a polypeptide, as defined herein. The "internal polypeptide region" of a polypeptide is not shorter than 3 amino acids in length and not longer than 350 amino acids in length. Other possible lengths of the "internal polypeptide region" of a polypeptide include, but are not limited to, 5, 10, 20, 25, 50, 100 and 200 amino acids. The amino terminal, carboxy terminal and internal polypeptide regions of a polypeptide are non-overlapping and may, but need not be contiguous, and may, but need not, add up to the full length of the corresponding polypeptide.

As used herein, the term "amplified", when applied to a nucleic acid sequence, refers to a process whereby one or more copies of a particular nucleic acid sequence is generated from a template nucleic acid, in some embodiments by the method of polymerase chain reaction (Mullis and Faloona, 1987, Methods Enzymol., 155:335). "Polymerase chain reaction" or "PCR" refers to a method for amplifying a specific template nucleic acid sequence. In some embodiments, the PCR reaction involves a repetitive series of temperature cycles and is typically performed in a volume of 50-100 μl. The number of cycles performed in the PCR reaction can include 15, 20, 25, 30, 35, 40, 45, 50, 55 or 60 cycles. The reaction mix comprises dNTPs (each of the four deoxynucleotides DATP, dCTP, dGTP, and dTTP), primers, buffers, DNA polymerase, and nucleic acid template. The PCR reaction can comprise providing a set of polynucleotide primers wherein a first primer contains a sequence complementary to a region in one strand of the nucleic acid template sequence and primes the synthesis of a complementary strand, and a second primer contains a sequence complementary to a region in a second strand of the target nucleic acid sequence and primes the synthesis of a complementary strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" or "a set of primers" can comprise two, three, four or more primers. In some embodiments, nested PCR can occur using a primer set wherein a first subset of primers is utilized to amplify a single product and then a second subset of primers is utilized which hybridize to the product of the first subset of primers to amplify a smaller version of the. In one embodiment, an exo-Pfu DNA polymerase is used to amplify a nucleic acid template in PCR reaction. Other methods of amplification include, but are not limited to, ligase chain reaction (LCR), polynucleotide-specific based amplification (NSBA), or any other method known in the art.

In one aspect an "array" includes a specific set of probes, such as oligonucleotides and/or cDNA's (e.g. ESTs) corresponding in whole or in part, and/or continuously or discontinuously, to regions of expressed genomic DNA; wherein the probes are localized onto a support. In one embodiment, the probes can correspond to the 5' ends or 3' ends of the internal coding regions of a biomarker RNA product of the invention. Of course, mixtures of a 5' end of one gene may be used as a target or a probe in combination with a 3' end of another gene to achieve the same or similar biomarker RNA product level measurements.

As used herein, an "analog" of a reference proteinaceous agent includes any proteinaceous agent that possesses a similar or identical function as the reference proteinaceous agent but does not comprise a similar or identical amino acid sequence as reference proteinaceous agent, and/or possess a similar or identical structure as the reference proteinaceous agent. A proteinaceous agent that has a similar amino acid sequence as a second proteinaceous agent is at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of the second proteinaceous agent; (b) a proteinaceous agent encoded by a nucleotide sequence that hybridizes under stringent conditions to at least a segment of the nucleotide sequence encoding the second proteinaceous agent, where the segment has a length of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the second proteinaceous agent. A proteinaceous agent with similar structure to a second proteinaceous agent refers to a proteinaceous agent that has a similar secondary, tertiary or quaternary structure as the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous molecules refers to a second organic or inorganic molecule which possess a similar or identical function as a first organic or inorganic molecule and is structurally similar to the first organic or inorganic molecule. The term "analog" includes a molecule whose core structure is the same as, or closely resembles that of the first molecule, but which has a chemical or physical modification. The term "analog" includes copolymers of the first molecule that can be linked to other atoms or molecules. A "biologically active analog" and "analog" are used interchangeably herein to cover an organic or inorganic molecule that exhibits substantially the same agonist or antagonist effect of the first organic or inorganic molecule.

A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base.

The term "antibody" also encompasses antigen-binding fragments of an antibody. The term "antigen-binding fragment" of an antibody (or simply "antibody portion," or "fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody is in some embodiments monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

As used herein, the terms "attaching" and "spotting" in relation to an array can include a process of depositing or localizing a nucleic acid or proteinaceous agent onto a substrate to form a nucleic acid or protein array. In one embodiment, the substance spotted is attached or localized onto the array via covalent bonds, hydrogen bonds or ionic interactions.

As used herein, the term "biomarker" refers to a gene whose products can be measured and correlated with disease. A biomarker refers to a gene which encodes one or products (e.g. unspliced RNA, mRNA and/or polypeptide) present at measurably different levels in corresponding samples isolated and/or derived from subjects having the pathology and subjects not having the pathology. A biomarker may be a DNA molecule which is transcribed into RNA product. Alternately, the biomarker may be an RNA molecule which is translated into protein product, or reverse-transcribed into DNA product.

As used herein, a "blood nucleic acid sample" or "blood polynucleotide sample", refers to polynucleotides derived from blood and can include polynucleotides isolated and/or derived from whole blood, serum-reduced whole blood, lysed blood (erthyrocyte depleted blood), centrifuged lysed blood (serum-depleted, erythrocyte depleted blood), serum depleted whole blood or peripheral blood leukocytes (PBLs), globin reduced RNA from blood, or any possible fraction of blood as would be understood by a person skilled in the art. A blood polynucleotide sample can refer to RNA, mRNA or a nucleic acid corresponding to mRNA, for example, cDNA or EST derived from RNA isolated from said sample. A blood polynucleotide sample can also include a PCR product derived from RNA, mRNA or cDNA.

As used herein, the term "formula" includes one or more classifiers, or combination of classifiers where the term classifier is used to describe the output of a mathematical model.

As used herein the term "colorectal pathology" comprises any of one or more types or subtypes of pathology of the rectum and/or colon. "Colorectal pathologies" include precancerous polyps, cancerous polyps, polyps at risk of becoming cancerous, and polyps of unknown cancer-related status. As would be understood, in some cases a subject according to embodiments of the invention can have at any one time one or more colorectal pathologies, each of which being of the same or a different type or subtype of polyp. Colorectal pathologies may be classified in any one of various ways, for example as is known in the art. In one embodiment "Polyp" or "colorectal polyp" as would be understood in the art, includes an abnormal growth of cells and/or tissue, and/or a growth of cells and/or tissue that may project into the colon or rectum. A polyp can be further defined according to various factors including the morphology of the polyp; the risk of the polyp developing into a cancerous polyp and the like as would be understood by a person ordinarily skilled in the art. In one embodiment, polyps can be classified into various subtypes including: Hyperplastic; Tubular Adenoma; Villous Adenoma; Tubulovillous Adenoma; Hyperplasia; High Grade Dysplasia; and Cancer. For any one individual and or polyp, one or more polyp subtype description could apply. In another embodiment, (7) colorectal cancer can be subclassified into various categories as well. In yet another embodiment, one or more of the listed subtypes can be grouped together according to any one of various parameters in one category. Alternately, one or more of the listed subtypes can be further subclassified according to any one of various parameters. In yet another embodiment, one or more of the listed subtypes can be grouped together according to any one of various parameters in one category. Alternately, one or more of the listed subtypes can be further subclassified according to any one of various parameters. For example, in one embodiment, Tubular Adenoma polyps can be further classified in accordance with the diameter of the Adenoma polyp. For example Adenoma polyps with a diameter greater than 1 mm, 2 mm, 3 mm, 4 mm, 51 mm, 6 mm, 7 mm, 8 mm, 9 mm, 10 mm, 11 mm, 12 mm, 13 mm, 14 mm or 15 mm are possible. In yet another example, colorectal cancer can be further subclassified in accordance with disease progression as would be understood. For example, colorectal cancer can be subclassified using the Duke or Modified Duke Staging System. The Modified Duke Staging System groups colorectal cancer into four different stages A-D. Stage A indicates the tumor penetrating the mucosa of the colon and/or bowel but no further. Stage B1 indicates the tumor penetrating into, but not through the muscularis propria (the muscular layer) of the colon and/or bowel wall. Stage B2 indicates the tumor has penetrated into and through the muscularis propria of the colon and/or bowel wall. A Stage C1 tumor penetrates into, but not through the muscularis propria of the colon and/or bowel wall; there is pathologic evidence of colorectal cancer in the lymph nodes. Stage C2 tumors penetrates into and through the muscularis propria of the bowel wall; but there is pathologic evidence of colorectal cancer in the lymph nodes. Finally Stage D indicates the tumor has spread beyond the lymph nodes to other organs. In yet another embodiment, colorectal cancer can be subclassified using the TNM staging system. According to the TNM staging system there are four stages, stages I through IV, each reflecting status regarding Tumor, Node, and Metastasis. Tumor is subdivided as follows T1: Tumor invades submucosa, T2: Tumor invades muscularis propria, T3: Tumor invades through the muscularis propria into the subserosa, or into the pericolic or perirectal tissues and T4: Tumor directly invades other organs or structures, and/or perforates. Node is subdivided as follows: N0 indicates no regional lymph node metastasis. N1 indicates metastasis in 1 to 3 regional lymph nodes. N2 indicates metastasis in 4 or more regional lymph nodes. Metastasis is divided as follows: M0 indicates no distant metastasis and M1 indicates distant metastasis present. Thus for Stage I, in accordance with the TNM system, the tumor can either be categorized as T1N0M0 or T2N0M0; the cancer has begun to spread but is still in the inner lining. Stage II is T3N0M0 or T4 N0M0; the cancer has spread to other organs near the colon or rectum but has not yet reached the inner lining. Stage III includes all T's, N1-2 and M0; cancer has spread to lymph nodes but has not been carried to distant parts of the body. Stage IV includes any T, any N and M1; cancer is metastatic and has been carried to other organs, likely the lung or liver.

As used herein, the term "high risk polyps" indicates those subtypes of polyps which are considered at higher risk for developing into cancer or are already cancerous as would be understood by a person skilled in the art, and includes cancer-prone polyps or cancer-disposed polyps and cancerous polyps, whereas a "low risk polyp" includes all other types of polyps. For example, 70 to 90 percent of colorectal cancers arise from adenomatous polyps, and thus are considered high risk polyps. Adenomatous polyps can be further categorized into subtypes including: Tubular adenoma, which has been suggested to have approximately a 4% potential for malignancy; Tubulovillous adenoma, which has been suggested to have approximately a 16% potential for malignancy and Villous adenoma, which has been suggested to have approximately a 21% potential for malignancy. In addition, high grade dysplasia has increased malignant potential. In one embodiment, polyps which are "high risk polyps" are Tubulovillous Adenoma, Villous Adenoma, High Grade Dysplasia and Tubular Adenoma and also includes polyps which are cancerous including those which are cancerous and localized and those which have already led to dissemination in the peripheral blood. In this embodiment, a "low risk polyp" includes any other polyp morphology. In another embodiment, polyps which are "high risk polyps" are Tubulovillous Adenoma, Villous Adenoma, High Grade Dysplasia and Tubular Adenoma and does not include polyps which are already cancerous. The size of the polyp also correlates with the risk for developing into cancer. For example, polyps greater than 10 mm in diameter are considered large polyps and have a greater potential for malignancy. Polyps larger than 2 cm in diameter have a 50 percent chance of becoming malignant. See Zauber (2004) Gastroenterology; 126(5): 1474. In another embodiment "high risk polyps" comprise Tubulovillous Adenoma, Villous Adenoma, High Grade Dysplasia and Tubular Adenoma where the diameter of the Tubular Adenoma polyp is greater than 10 mm and the remaining polyp morphologies are considered "low risk polyps".

As used herein, the terms "compound" and "agent" are used interchangeably.

As used herein, the term "control" or "control sample" can include one or more samples isolated and/or derived from a subject or group of subjects who have been diagnosed as having one or more colorectal pathologies, including having one or more polyps or having one or more subtypes of polyps; not having colorectal pathologies; not having polyps; or not having one or more subtypes of polyps. The term control or control sample can also refer to the compilation of data derived from one or more samples of one or more subjects.

A "coding region" in reference to a DNA refers to DNA which encodes RNA.

A "coding region" in reference to RNA refers to RNA which encodes protein.

As used herein, the term "data" in relation to one or more biomarkers, or the term "biomarker data" generally refers to data reflective of the absolute and/or relative abundance (level) of a product of a biomarker in a sample. As used herein, the term "dataset" in relation to one or more biomarkers refers to a set of data representing levels of each of one or more biomarker products of a panel of biomarkers in a reference population of subjects. A dataset can be used to generate a formula/classifier of the invention. According to one embodiment the dataset need not comprise data for each biomarker product of the panel for each individual of the reference population. For example, the "dataset" when used in the context of a dataset to be applied to a formula can refer to data representing levels of products of each biomarker for each individual in one or more reference populations, but as would be understood can also refer to data representing levels of products of each biomarker for 99%, 95%, 90%, 85%, 80%, 75%, 70% or less of the individuals in each of said one or more reference populations and can still be useful for purposes of applying to a formula.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein the terms “testing”, “diagnosis” and “screening”, in relation to colorectal pathologies refer to a process of determining a likelihood (probability) of a test subject having one or more colorectal pathologies and includes both traditional medical diagnostic techniques as well as testing methods as encompassed by one or more aspects of the current invention. Traditional medical diagnostic techniques for testing for colorectal pathology includes physical exam and history, medical evaluation, and appropriate laboratory tests which can include FOBT, sigmoidoscopy and colonoscopy. In one embodiment, “diagnosis of colorectal pathology” refers to a determination as between two options: e.g., (i) that an individual has colorectal pathology or one or more subtypes of colorectal pathology, or one or more polyps and (ii) that an individual does not have the colorectal pathology or the one or more polyps or the one or more subtypes of polyps. In another embodiment diagnosis can include an option that it cannot be determined with sufficient degree of certainty as to whether an individual can be characterized as having colorectal pathology or not. In one context, a “sufficient degree of certainty” takes into account any limitations—such as limitations in the technology, equipment or measuring where as a result of the limitations, the result is within a range which suggests that the test is indeterminate. The range which suggests the test is indeterminate will depend upon the specific limitations of the equipment, reagents and technology used. In another context, “sufficient degree of certainty” depends upon the medical requirements for the sensitivity and/or specificity of the test. More particularly the sufficient degree of certainty includes greater than 50% sensitivity and/or specificity, greater than 60% sensitivity and/or specificity, greater than 70% sensitivity and/or specificity, greater than 80% sensitivity and/or specificity, greater than 90% sensitivity and/or specificity and 100% sensitivity and/or specificity.

As used herein, “normal” refers to an individual or group of individuals who do not have colorectal pathology. In some embodiments, the diagnosis of said individual or group of individuals not having colorectal pathology is determined using conventional diagnostic methods. In some embodiments said individual or group of individuals have not been diagnosed with any other disease. “Normal”, according to the invention, also refers to samples isolated from normal individuals and includes blood, total RNA or mRNA isolated from normal individuals. A sample taken from a normal individual can include a sample taken from an individual who does not have colorectal pathology at the time the sample is taken.

As used herein, the term “differential expression” refers to a difference in the level of expression of the products of one or more biomarkers. For instance, the term “differential expression” can refer to the difference in the level of RNA of one or more biomarkers between samples from subjects having and subjects not having one or more colorectal pathologies. Differences in biomarker RNA product levels can be determined by directly or indirectly measuring the amount or level of Differentially expressed” can also include different levels of protein encoded by the biomarker of the invention between samples or reference populations. “Differential expression can be determined as the ratio of the levels of one or more biomarker products between reference subjects/populations having or not having one or more colorectal pathologies, wherein the ratio is not equal to 1.0. Differential expression between populations can be determined to be statistically significant as a function of p-value. When using p-value to determine statistical significance, a biomarker, the p-value is preferably less than 0.2. In another embodiment the biomarker is identified as being differentially expressed when the p-value is less than 0.15, 0.1, 0.05, 0.01, 0.005, 0.0001 etc. When determining differential expression on the basis of the ratio, a biomarker product is differentially expressed if the ratio of the level of expression in a first sample as compared with a second sample is greater than or less than 1.0. For example, a ratio of greater than 1.0 for example includes a ratio of greater than 1.1, 1.2, 1.5, 1.7, 2, 3, 4, 10, 20 and the like. A ratio of less than 1.0, for example, includes a ratio of less than 0.9, 0.8, 0.6, 0.4, 0.2, 0.1, 0.05 and the like. In another embodiment of the invention a biomarker product is differentially expressed if the ratio of the mean of the level of expression of a first population as compared with the mean level of expression of the second population is greater than or less than 1.0. For example, a ratio of greater than 1.0 includes a ratio of greater than 1.1, 1.2, 1.5, 1.7, 2, 3, 4, 10, 20 and the like and a ratio less than 1.0, for example includes a ration of less than 0.9, 0.8, 0.6, 0.4, 0.2, 0.1, 0.05 and the like. In another embodiment of the invention a biomarker product is differentially expressed if the ratio of its level of expression in a first sample as compared with the mean of the second population is greater than or less than 1.0 and includes for example, a ratio of greater than 1.1, 1.2, 1.5, 1.7, 2, 3, 4, 10, 20, or a ratio less than 1, for example 0.9, 0.8, 0.6, 0.4, 0.2, 0.1, 0.05.

“Differentially increased expression” or “up regulation” refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold higher or more, than a control.

“Differentially decreased expression” or “down regulation” refers to biomarker product levels which are at least 10% or more, for example, 20%, 30%, 40%, or 50%, 60%, 70%, 80%, 90% lower or less, and/or 0.9 fold, 0.8 fold, 0.6 fold, 0.4 fold, 0.2 fold, 0.1 fold or less lower than a control.

For example, up regulated or down regulated genes include genes having an increased or decreased level, respectively, of expression of product (e.g. mRNA or protein) in blood isolated from individuals characterized as having one or more colorectal pathologies as compared with normal individuals. In another example, up regulated or down regulated genes include genes having an increased or decreased level, respectively, of expression of product (e.g. mRNA or protein) in blood isolated from individuals having one type of colorectal pathology or collection of colorectal pathologies as compared with individuals having a different type of colorectal pathology or collection of colorectal pathologies, respectively.

For example, up regulated genes include genes having an increased level of biomarker products in a test sample as compared with a control sample.

As used herein, the term “differential hybridization” refers to a difference in a quantitative level of hybridization of a nucleic acid or derivative thereof isolated and/or derived from a sample from a first individual or individuals with a trait to a complementary nucleic acid target as compared with the hybridization of a nucleic acid or derivative thereof isolated and/or derived from a second individual or individuals not having said trait to a complementary nucleic acid target. A “differential hybridization” means that the ratio of the level of hybridization of the first sample as compared with the second sample is not equal to 1.0. For example, the ratio of the level of hybridization of the first sample to the target as compared to the second sample is greater than 1.1, 1.2, 1.5, 1.7, 2, 3, 4, 10, 20, or less than 1, for example 0.9, 0.8, 0.6, 0.4, 0.2, 0.1, 0.05. A differential hybridization also exists if the hybridization is detectable in one sample but not another sample.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the alteration of gene expression and the gene expression pattern reflective of one or more colorectal pathologies as described herein. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

As used herein, the term "effective amount" refers to the amount of a compound which is sufficient to reduce or prevent the progression and/or severity of one or more colorectal pathologies; prevent the development, recurrence of onset of one or more colorectal pathologies; or enhance or improve the prophylactic or therapeutic effect(s) of another therapy.

As used herein, the term "fragment" in the context of a proteinaceous agent refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or a protein. In a specific embodiment, a fragment of a protein or polypeptide retains at least one function of the protein or polypeptide. In another embodiment, a fragment of a protein or polypeptide retains at least two, three, four, or five functions of the protein or polypeptide. In some embodiments, a fragment of an antibody retains the ability to immunospecifically bind to an antigen.

As used herein, the term "fusion protein" refers to a polypeptide that comprises an amino acid sequence of a first protein or polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used herein, a "gene" of the invention can include a gene expressed in blood, a gene expressed in blood and in a non-blood tissue, a gene differentially expressed in blood, a gene expressed in a non-blood cell, a gene expressed in a cell which is not of haematopoietic origin, a gene expressed in a specific subtype of cell found in blood including lymphocytes, granulocytes, leukocytes, basophils and the like. A gene can be an immune response gene or a gene not involved in an immune response. In particular an immune response gene is a gene in the major histocompatibility complex that controls a cells response to a foreign antigen. A gene of the invention can also include a gene which is differentially regulated in response to a foreign antigen introduced into peripheral blood.

As used herein, a "gene expression pattern" or "gene expression profile" indicates the pattern of the level of expression of two or more biomarkers of the invention including 2, 3, 4, 5, 6, 7, 8, 9, 10, 11, 12, 13, 14, 15, 16, 17, 18 or more or all of the biomarkers of the invention. A gene expression pattern or gene expression profile can be determined from the measurement of expression levels of the products of the biomarkers of the invention using any known technique. For example techniques to measure expression of the RNA products of the biomarkers of the invention include, PCR based methods (including reverse transcription-PCR, PCR, QRT-PCR) and non PCR based method, as well as microarray analysis. To measure levels of protein products of the biomarkers of the invention, techniques include densitometric western blotting and ELISA analysis.

As used herein, the term "hybridizing to" or "hybridization" refers to the sequence specific non-covalent binding interactions with a complementary nucleic acid, for example interactions between a target nucleic acid sequence and a nucleic acid member on an array.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, the term "in combination" when referring to therapeutic treatments refers to the use of more than one type of therapy (e.g., more than one prophylactic agent and/or therapeutic agent). The use of the term "in combination" does not restrict the order in which therapies (e.g., prophylactic and/or therapeutic agents) are administered to a subject. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject.

As used herein, "indicative of one or more colorectal pathologies" refers to a determination of a probability that a subject has or will have the one or more colorectal pathologies. In one aspect the application of a formula to data corresponding to biomarker products of a test subject can result in determination of the probability of whether the test subject has one or more colorectal pathologies as compared with not having said one or more colorectal pathologies. In another embodiment, an expression pattern can be indicative of one or more colorectal pathologies including one or more polyps or one or more subtypes of polyps if the expression pattern is found significantly more often in patients with said colorectal pathology than in patients without said colorectal pathology (as determined using routine statistical methods setting confidence levels at a minimum of 70%, 75%, 80%, 85%, 90%, 95% and the like). In some embodiments, an expression pattern which is indicative of disease is found in at least 70%, at least 75%, at least 80%, at least 85%, at least 90%, at least 95% or more in patients who have the disease and is found in less than 10%, less than 8%, less than 5%, less than 2.5%, or less than 1% of patients who do not have the disease. "Indicative of colorectal pathology" can also indicates an expression pattern which more properly categorizes with control expression patterns of individuals with the one or more colorectal pathologies as compared with control expression patterns of individuals without the one or more colorectal pathologies using statistical algorithms for class prediction as would be understood by a person skilled in the art and see for example commercially available programs such as those provided by Silicon Genetics (e.g. GeneSpring™).

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein, the terms "isolated" and "purified" in the context of a proteinaceous agent (e.g., a peptide, polypeptide, protein or antibody) refer to a proteinaceous agent which is substantially free of cellular material and in some embodiments, substantially free of heterologous proteinaceous agents (i.e., contaminating proteins) from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 40%, 30%, 20%, 10%, or 5% (by dry weight) of heterologous proteinaceous agent (e.g., protein, polypeptide, peptide, or antibody; also referred to as a "contaminating protein"). When the proteinaceous agent is recombinantly produced, it is also in some embodiments substantially free of culture medium, i.e., culture medium represents less than about 20%, 10%, or 5% of the volume of the protein preparation. When the proteinaceous agent is produced by chemical synthesis, it is in some embodiments substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In some embodiments, proteinaceous agents disclosed herein are isolated.

As used herein, a sample which is "isolated and/or derived" includes a sample which has been removed it from its natural environment in a subject and also includes samples which are further modified or altered. For example samples can include tissue, lymph, bodily fluid, blood, RNA, protein, mRNA, serum reduced blood, erythrocyte reduced blood, serum reduced and erythrocyte reduced blood, unfractionated cells of a lysed blood, globin reduced mRNA, cDNA, PCR products and the like.

As used herein, the term "level" or "level of expression" when referring to RNA refers to a measurable quantity (either absolute or relative quantity) of a given nucleic acid as determined by hybridization or measurements such as QRT-PCR and includes use of both SYBR® green and TaqMan® technology and which corresponds in direct proportion with the amount of product of the gene in a sample. Level of expression when referring to RNA can also refer to a measurable quantity of a given nucleic acid as determined by PCR wherein the number of cycles of PCR is limited to 10, 15, 20, 25, 30, 35, 40, 45, 50, 55, or 60 cycles. The level of expression when referring to RNA can also refer to a measurable quantity of a given nucleic acid as determined relative to the amount of total RNA, or cDNA used in QRT-PCR wherein the amount of total RNA used is 100 ng; 50 ng, 25 ng; 10 ng; 5 ng; 1.25 ng; 0.05 ng; 0.3 ng; 0.1 ng; 0.09 ng; 0.08 ng; 0.07 ng; 0.06 ng; or 0.05 ng. The level of expression of a nucleic acid can be determined by any methods known in the art. For microarray analysis, the level of expression is measured by hybridization analysis using nucleic acids corresponding to RNA isolated from one or more individuals according to methods well known in the art. The label can either be incorporated into the RNA or used in another manner as would be understood so as to monitor hybridization. The label used can be a luminescent label, an enzymatic label, a radioactive label, a chemical label or a physical label. In some embodiments, target and/or probe nucleic acids are labeled with a fluorescent molecule. Preferred fluorescent labels include, but are not limited to: fluorescein, amino coumarin acetic acid, tetramethylrhodamine isothiocyanate (TRITC), Texas Red, Cyanine 3 (Cy3) and Cyanine 5 (Cy5). The level of expression when referring to RNA can also refer to a measurable quantity of a given nucleic acid as determined relative to the amount of total RNA or cDNA used in microarray hybridizations wherein the amount of total RNA is 10 μg, 5 μg, 2.5 μg; 2 μg; 1 μg; 0.5 μg; 0.1 μg; 0.05 μg; 0.01 μg; 0.005 μg; 0.001 μg and the like.

As used herein, a "ligand" is a molecule that binds to another. "Polynucleotide Ligands" are those that specifically and/or selectively hybridize to products of the biomarkers and/or derivatives thereof. Polynucleotide ligands can specifically and/or selectively hybridize to RNA and/or protein products of the biomarkers, allowing measurement of the levels of the biomarker products. The polynucleotide ligands may be any of various types of molecule, including but not limited to, any of various combinations of oligonucleotides, cDNA, DNA, RNA, PCR products, synthetic DNA, synthetic RNA, and/or modified nucleotides.

A ligand of the invention can also include a "polypeptide ligand" that specifically or selectively binds to the biomarker products, for example, allowing detection or measurement of the level of biomarker products including either RNA products and/or protein products. A polypeptide ligand may include a scaffold peptide, a linear peptide, or a cyclic peptide. In a preferred embodiment, the polypeptide ligand is an antibody. The antibody can be a human antibody, a chimeric antibody, a recombinant antibody, a humanized antibody, a monoclonal antibody, or a polyclonal antibody. The antibody can be an intact immunoglobulin, e.g., an IgA, IgG, IgE, IgD, IgM or subtypes thereof. The antibody can be conjugated to a functional moiety (e.g., a compound which has a biological or chemical function (which may be a second different polypeptide, a therapeutic drug, a cytotoxic agent, a detectable moiety, or a support. A polypeptide ligand e.g. antibody of the invention interacts with a polypeptide, encoded by one of the genes of a biomarker, with high affinity and specificity. For example, the polypeptide ligand binds to a polypeptide, encoded by one of the genes of a biomarker, with an affinity constant of at least $10^7$ $M^{-1}$, preferably, at least $10^8$ $M^{-1}$, $10^9$ $M^{-1}$, or $10^{10}$ $M^{-1}$. The polynucleotide ligands and protein ligands may be used, according to standard art knowledge, to practice techniques such as Western blotting, immunoprecipitation, enzyme-linked immunosorbent assay (ELISA), protein microarray analysis and the like to measure the level of disclosed biomarker protein products.

An "mRNA" means an RNA complementary to a gene; an mRNA includes a protein coding region, and also may include 5' end and 3' untranslated regions (UTR).

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

Treatment of one or more colorectal pathologies or one or more subtypes of colorectal pathology is defined herein to provide medical aid to counteract the disease itself, the symptoms and/or the progression of the disease. Treatments also include removing the one or more colorectal pathologies and include palliative therapy to help relieve symptoms and improve quality of life. Treatments also include reducing or preventing polyp formation, reducing or preventing polyp differentiation or morphology changes, and can also include development, recurrence and onset.

As used herein, "mRNA integrity" refers to the quality of mRNA extracts from either tissue samples or samples. In one embodiment, mRNA extracts with good integrity do not appear to be degraded when examined by methods well known in the art, for example, by RNA agarose gel electrophoresis (e.g., Ausubel et al., John Wiley & Sons, Inc., 1997, *Current Protocols in Molecular Biology*). Preferably, the mRNA samples have good integrity (e.g., less than 10%, in some embodiments less than 5%, and more in some embodiments less than 1% of the mRNA is degraded) to truly represent the gene expression levels of sample from which they are extracted.

As used herein, "nucleic acid(s)" and "nucleic acid molecule(s)" are interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As defined herein, a "nucleic acid array" refers a plurality of nucleic acids (or "nucleic acid members") localized on a support where each of the nucleic acid members is localized to a unique pre-selected region of a support. In one embodiment, a nucleic acid member is attached to the surface of the support and the nucleic acid member is DNA. In another embodiment, the nucleic acid member is either cDNA or and oligonucleotide. In another embodiment, the nucleic acid member localized on the support is cDNA synthesized by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein "nucleic acid sample for hybridization to an array" is defined as a nucleic acid isolated and/or derived from a sample capable of binding to a nucleic acid bound to an array of complementary sequence through sets of non-covalent bonding interactions including complementary base pairing interactions. The nucleic acid sample for hybridization to an array can either be an isolated nucleic acid sequence corresponding to a gene or portion thereof, total RNA or mRNA isolated from a sample. In one embodiment, the nucleic acid sample for hybridization to an array is a blood nucleic acid sample (including whole blood, lysed blood, serum reduced, erythrocyte reduced blood, or peripheral blood leukocytes (PBLs)). In some embodiments, the nucleic acid sample is single- or double-stranded DNA, RNA, or DNA-RNA hybrids, from human blood and in some embodiments from RNA or mRNA extracts.

As used herein, a "nucleic acid member on an array" or a "nucleic acid member" includes nucleic acid immobilized on an array and capable of binding to a nucleic acid probes or samples of complementary sequence through sets of non-covalent bonding interactions, including complementary base pairing interactions. As used herein, a nucleic acid member or target may include natural (i.e., A, G, C, or T) or modified bases (7-deazaguanosine, inosine, etc.). In addition, the bases in nucleic acids may be joined by a linkage other than a phosphodiester bond, so long as it does not interfere with hybridization (i.e., the nucleic acid target still specifically binds to its complementary sequence under standard stringent or selective hybridization conditions). Thus, nucleic acid members may be peptide nucleic acids in which the constituent bases are joined by peptide bonds rather than phosphodiester linkages. In one embodiment, a conventional nucleic acid array of 'target' sequences bound to the array can be representative of the entire human genome, e.g. Affymetrix chip, and the biomarker or isolated biomarker consisting of or comprising one or more of the genes set out in Table 1, Table 2, or Table 11, or Table 12 or gene probes (e.g. Table 4) is applied to the conventional array. In another embodiment, sequences bound to the array can be the biomarker or isolated biomarker according to the invention and total cellular RNA is applied to the array.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oligonucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

As used herein, "patient" or "individual" or "subject" refers to a mammal and is in some embodiments human.

As used herein the term "peptide" refers to a polypeptide which is 50 amino acids in length or less.

As used herein, the phrase "pharmaceutically acceptable salt(s)" includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, "polynucleotide" encompasses single and double stranded polynucleotides, such as double-stranded DNA, single-stranded DNA, double-stranded RNA, single-stranded RNA or DNA-RNA double stranded hybrids, and the like, of more than 8 nucleotides in length. The term "polynucleotide" includes a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

As used herein a "polynucleotide ligand that specifically and/or selectively hybridizes to RNA products of the biomarkers" ("biomarker RNA products") and/or to polynucleotides corresponding to biomarker RNA products, allowing measurement of levels of the RNA products are disclosed.

The polynucleotide ligands may be any of various types of molecule, including but not limited to, any of various combinations of oligonucleotides, cDNA, DNA, RNA, PCR products, synthetic DNA, synthetic RNA, and/or modified nucleotides.

As used herein, the term "proteinaceous agent" refers to polypeptides, proteins, peptides, and the like.

As used herein, "polypeptide sequences encoded by or protein products of" refers to the amino acid sequences obtained after translation of the protein coding region of an mRNA transcribed from a gene. As would be understood, one or more mRNA nucleotide sequences for each of the genes (biomarkers) of the invention can be identified using public databases such as the NCBI database found at http://www.ncbi.nlm.nih.gov. For example, representative mRNA species of those biomarkers identified in Table 2 and Table 12 are provided by their Human Genbank Accession number (see Table 3 and Table 13 respectively) and the corresponding polypeptide sequence is identified by a Protein Accession number (see Table 3 and Table 13 respectively). These Genbank Accession numbers provide the sequence of products of the biomarkers. When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand. "Antigenic fragments" may be 5000, 1000, 500, 400, 300, 200, 100, 50 or 25 or 20 or 10 or 5 amino acids in length.

As used herein, the terms "prevent", "preventing" and "prevention" refer to the prevention of the development, recurrence or formation or growth or transformation of colorectal pathology including polyps or subtypes of polyps resulting from the administration of one or more compounds identified in accordance the methods of the invention or the administration of a combination of such a compound and another therapy.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used and also the specificity or selectivity of the desired priming (ie so as to act as a point of initiation of synthesis which is specific or selective for a given sequence of polynucleotide). For example, for testing applications, depending on the complexity of the target sequence, the oligonucleotide primer typically contains 15-25, but may contain additional nucleotides as well as fewer nucleotides. In addition, in some cases the primer can be selected so as to have a high GC content, can be selected so as to bind to regions which do not contain SNPs, can be selected so as to span an intron/exon junction of RNA and the like. Other factors involved in determining the appropriate length and/or features of a primer are readily known to one of ordinary skill in the art.

The term "biomarker specific set of primers" or "primer sets" as used herein refers to a set of polynucleotide primers wherein one primer primes the synthesis of a sense strand, and the second primer primes the synthesis of an antisense strand so as to produce double stranded DNA complementary to a portion of one or more RNA products of the biomarker of the invention. For example, the primers can include a first primer which is a sequence that can selectively hybridize to RNA, cDNA or EST complementary to a region of the biomarker of the invention to create an extension product and a second primer capable of selectively hybridizing to the extension product, which are used to produce double stranded DNA complementary to a region of the biomarker of the invention or products of the biomarker of the invention. The invention includes primers useful for measuring the level of RNA products of a biomarker. Table 4, Table 6, Table 14, Table 16 and Table 17 provide representative species of primers of the invention. A biomarker specific set of primers can be selected so that they will selectively amplify only portions of a polynucleotide complementary to one or more RNA products of a biomarker and do not amplify portions of polynucleotides complementary to other biomarkers.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length as long as it is less than the full length of the target gene. In some embodiments, probes can be used as target sequences bound on a microarray. In some embodiments, probes can be used for quantitative real-time PCR (QRT-PCR) and include modifications so as to incorporate a fluorophore, a quencher, a minor groove binding reagent or other substances which allow detection of the probe during PCR amplification. The probe can also be modified so as to have both a detectable tag and a quencher molecule, for example Taqman® and Molecular Beacon® probes. The invention includes probes useful for measuring the expression of RNA products of biomarkers of the invention. For example, Table 4, Table 6, and Table 14 and Table 17 provides some representative species of a probe of the invention useful for QRT-PCR.

The oligonucleotides and analogs thereof may be RNA or DNA, or analogs of RNA or DNA, commonly referred to as antisense oligomers or antisense oligonucleotides. Such RNA or DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)-Oligonucleotide Analogues with an Achiral Peptide Backbone, (1992)).

Probes may also be mixtures of any of the oligonucleotide analog types together or in combination with native DNA or RNA and may also include linker species. At the same time, the oligonucleotides and analogs thereof may be used alone or in combination with one or more additional oligonucleotides or analogs thereof.

As used herein, the term "products of the biomarker" or "biomarker products" refers to a species of RNA or a species of protein (wherein a species of RNA or protein can include multiple copies) isolated and/or derived from a sample including a tissue sample, a lymph sample, a lymph tissue sample, or a blood sample, or a fraction of a blood sample which corresponds to the biomarker (i.e., is transcribed from the gene or genetic element or is translated from RNA which is transcribed from the gene or genetic element). See Table 3 and Table 13. The RNA may be pre-mRNA, mRNA, spliced variants of mRNA and the like. The protein may be in its native state or post-translationally processed in any one of various ways.

As used herein, "a plurality of" or "a set of" refers to two or more, for example, 2 or more, 3 or more, 4 or more, 5 or more, 6 or more, 7 or more, 8 or more, 9 or more 10 or more etc.

As used herein, "pre-selected region", "predefined region", or "unique position" refers to a localized area on a substrate which is, was, or is intended to be used for the deposit of a nucleic acid and is otherwise referred to herein in the alternative as a "selected region" or simply a "region." The pre-selected region may have any convenient shape, e.g., circular, rectangular, elliptical, wedge-shaped, etc. In some embodiments, a pre-selected region is smaller than about 1 $cm^2$, more preferably less than 1 $mm^2$, still more preferably less than 0.5 $mm^2$, and in some embodiments less than 0.1 $mm^2$. A nucleic acid member at a "pre-selected region", "predefined region", or "unique position" is one whose identity (e.g., sequence) can be determined by virtue of its position at the region or unique position.

As used herein, the terms "prophylactic agent" and "prophylactic agents" refer to any compound(s) which can be used to prevent polyp formation, development, recurrence or onset. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression or transformation of one or more colorectal pathologies including one or more polyps or subtypes of polyps.

As used herein, the phrase "prophylactically effective amount" refers to the amount of a therapy (e.g., a prophylactic agent) which is sufficient to result in the prevention of the development, recurrence or onset or progression or transformation of one or more colorectal pathologies including one or more polyps or subtypes of polyps; the reduction or amelioration of the progression and/or severity of one or more colorectal pathologies including one or more polyps or subtypes of polyps; or the prevention of colorectal pathology including polyps or subtypes of polyps advancing to colorectal cancer.

As used herein, the terms "protein" and "polypeptide" are used interchangeably to refer to a chain of amino acids linked together by peptide bonds. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds.

A "protein coding region" refers to the portion of the mRNA encoding a polypeptide.

As used herein the "reference population" or "test population" refers to one or more populations of "control samples" used to develop one or more classifier. In one embodiment a single reference population can be divided into subpopulations. In another embodiment, two or more reference populations can be used. In some instances a classifier can be developed to differentiate between individuals with one or more colorectal pathologies or one or more polyps or one or more subtypes of polyps and individuals without the same colorectal pathology or one or more polyps or one or more subtypes of polyps. In some instances a first reference population would be comprised of individuals with the one or more colorectal pathologies and a second reference population would be comprised of individuals without the one or more colorectal pathologies. The "reference population" or "test population" can be comprised of control samples from a number of individuals diagnosed with one or more colorectal pathologies including one or more polyps or one or more subtypes of polyps and individuals not having the colorectal pathologies or not having the one or more polyps or not having the one or more subtypes of polyps as determined using conventional diagnostic techniques. Note that in some embodiments the population of individuals having one or more colorectal pathologies can be selected to include individuals having a single subtype of polyp or one or more subtypes of polyps. In other embodiments the individuals who do not have one or more colon pathologies can include individuals who have been diagnosed with other disease or diseases. In another embodiment the individuals who do not have one or more colon pathologies can include individuals who have been diagnosed with other cancers. In one embodiment the "reference population" or "test population" is comprised of a roughly equivalent number of "control samples" from each trait subgroup (e.g., in this instance wherein said trait is a determination of status with regards to the presence of colorectal pathology). In another embodiment, each trait subgroup (e.g. having or not having colorectal pathology) of the "reference population" has a similar distribution with regards to other traits e.g., age, sex, drug status, etc.

As used herein, the term "selectively binds" in the context of proteins encompassed by the invention refers to the specific interaction of any two of a peptide, a protein, a polypeptide an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein "selective hybridization" can refer to a hybridization which occurs as between a polynucleotide and an RNA or protein product of the biomarker of the invention wherein the hybridization is such that the polynucleotide binds to the RNA products of the biomarker of the invention preferentially to the RNA products of other genes in the genome in question. In a preferred embodiment a polynucleotide which "selectively hybridizes" is one which hybridizes with a selectivity of greater than 70%, greater than 80%, greater than 90% and most preferably on 100% (ie cross hybridization with other RNA species preferably occurs at less than 30%, less than 20%, less than 10%). As would be understood to a person skilled in the art, a polynucleotide which "selectively hybridizes" to the RNA products of a biomarker of the invention can be determined by taking into account the length and composition.

As used herein, "specifically hybridizes", "specific hybridization" can refer to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, Nucleic acids Res., 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature ($T_M$) than do shorter ones, and are less likely to be repeated within a given target sequence, thereby minimizing non-specific hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As used herein, "spotting" or "attaching" refers to a process of depositing a nucleic acid member onto a solid substrate to form a nucleic acid array such that the nucleic acid is stably bound to the solid substrate via covalent bonds, hydrogen bonds or ionic interactions.

As used herein, "stably associated" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" when referring to an array refers to a material capable of supporting or localizing an oligonucleotide or cDNA member. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, poly)tetrafluoroethylene, poly)vinylidenedifluoride, polystyrene, polycarbonate, a charged membrane, such as nylon 66 or nitrocellulose, or combinations thereof. In one embodiment, the support is glass. In some embodiments, at least one surface of the substrate will be substantially flat. In some embodiments, the support will contain reactive groups, including, but not limited to, carboxyl, amino, hydroxyl, thiol, and the like. In one embodiment, the support is optically transparent.

As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: Tm=81.5+16.6(log [Na+])+0.41 (fraction G+C)-(600/N) where N is the length of the oligonucleotide.

For example, the hybridization temperature may be decreased in increments of 5° C. from 68° C. to 42° C. in a hybridization buffer having a $Na^+$ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature may be calculated using the equation Tm=81.5+16.6(log [Na+])+0.41(fraction G+C)−(0.63% formamide)-(600/N), where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, *Nucl. Acids Res.,* 25:3389-3402; Schäffer, A. A. et al., 1999, *Bioinformatics* 15:1000-1011). As used herein, "significant match" encompasses non-contiguous or scattered identical nucleotides so long as the sequences exhibit at least 65%, and preferably, at least 70%, at least 75%, at least 80%, at least 85%, and preferably, at least 90% identity, when maximally aligned using alignment methods routine in the art.

As used herein, the term "synergistic" refers to a combination of a compound identified using one of the methods described herein, and another therapy (e.g., agent), which is more effective than the additive effects of the therapies. In some embodiments, such other therapy has been or is currently being to prevent, treat, or ameliorate one or more colorectal pathologies including one or more polyps or one or more subtypes of polyps. A synergistic effect of a combination of therapies (e.g., prophylactic or therapeutic agents) permits the use of lower dosages of one or more of the therapies and/or less frequent administration of said therapies to an individual with colorectal pathologies including polyps or subtypes of polyps. The ability to utilize lower dosages of a therapy (e.g., a prophylactic or therapeutic agent) and/or to administer said therapy less frequently reduces the toxicity associated with the administration of said agent to an individual without reducing the efficacy of said therapies in the prevention or treatment of colorectal pathology including polyps or subtypes of polyps. In addition, a synergistic effect can result in improved efficacy of therapies (e.g., agents) in the prevention or treatment of colorectal pathology including polyps or subtypes of polyps. Finally, a synergistic effect of a combination of therapies (e.g., prophylactic or therapeutic agents) may avoid or reduce adverse or unwanted side effects associated with the use of either therapy alone.

As used herein, a "therapeutic agent" or "agent" refers to a compound that increases or decreases the expression of a polynucleotide or polypeptide sequences that are differentially expressed in a sample from an individual having one or more colorectal pathologies including polyps or a subtype of polyps. The invention provides for a "therapeutic agent" that 1) prevents the formation of colorectal pathology 2) reduces, delays, or eliminates advancement or transformation of colorectal pathology and/or 3) restores one or more expression profiles of one or more colorectal pathology indicative nucleic acids or polypeptides of a patient to a profile more similar to that of a normal individual when administered to a patient. In addition, the terms "therapeutic agent" and "therapeutic agents" refer to any compound(s) which can be used in the treatment or prevention of colorectal pathology or polyps or a subtype of polyps. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to treat or prevent colorectal pathology or polyps or subtypes of polyps.

As used herein, the term "therapeutically effective amount" refers to that amount of a therapy (e.g., a therapeutic agent) sufficient to treat one or more colorectal pathologies including polyps or one or more subtypes of polyps; prevent one or more colorectal pathologies including polyps or one or more subtypes of polyps; prevent colorectal pathologies including polyps or one or more subtypes of polyps from transforming and/or advancing to colorectal cancer, cause regression of colorectal pathology, polyps or one or more subtypes of polyps, or to enhance or improve the therapeutic effect(s) of another therapy (e.g., therapeutic agent). In a specific embodiment, a therapeutically effective amount refers to the amount of a therapy (e.g., a therapeutic agent) that modulates gene expression of the products of the biomarkers of the inventions. In some embodiments, a therapeutically effective amount of a therapy (e.g., a therapeutic agent) modulates gene expression of the products of the biomarkers of the invention at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control therapeutic agent such as phosphate buffered saline ("PBS").

As used herein, the terms "treat", "treatment" and "treating" refer to the prevention of one or more colorectal pathologies including polyp formation or the formation of one or more subtypes of polyps, development, recurrence onset or transformation of one or more colorectal pathologies and, the reduction or amelioration of the progression and/or severity of one or more colorectal pathologies including polyps or subtypes thereof resulting from the administration of one or more compounds identified in accordance the methods of the invention, or a combination of one or more compounds identified in accordance with the invention and another therapy.

As used herein, a "tissue nucleic acid sample", refers to nucleic acids isolated and/or derived from tissue, for example polyp tissue, colon tissue, rectum tissue, lymphoid tissue, and the like. In some embodiments, a tissue nucleic acid sample is total RNA, mRNA or is a nucleic acid corresponding to RNA, for example, cDNA. A tissue nucleic acid sample can also include a PCR product derived from total RNA, mRNA or cDNA.

(C) Samples for Use in the Invention

Samples for use in the invention include refers to any one of various type of molecules, cells and/or tissues which can be isolated and/or derived from a test subject and/or control subject, and which contains one or more biomarker products. The sample can be isolated and/or derived from any fluid, cell or tissue. The sample can also be one which is isolated and/or derived from any fluid and/or tissue which predominantly comprises blood cells.

The sample which is isolated and/or derived from an individual can be assayed for gene expression products, particularly genes expression products differentially expressed in individuals with or without one or more colorectal pathologies. In one embodiment, the sample is a fluid sample, a lymph sample, a lymph tissue sample or a blood sample. In one embodiment the sample is isolated and/or derived from peripheral blood. Alternately, the sample may be isolated and/or derived from alternate sources, including from any one of various types of lymphoid tissue.

Examples of samples isolated and/or derived from blood include samples of whole blood, serum-reduced whole blood, serum-depleted blood, and serum-depleted and erythrocyte depleted blood.

Unless otherwise indicated herein, samples obtained from any individual may be used in accordance with the methods of the invention. Examples of individuals from which such a sample may be obtained and utilized in accordance with the methods of the invention include, but are not limited to, individuals suspected of having one or more colorectal pathologies, individuals diagnosed as having one or more colorectal pathologies; individuals that have not been diagnosed with having one or more colorectal pathologies; individuals who have been confirmed as not having one or more colorectal pathologies.

In a further embodiment, the individual from whom a sample may be obtained is a test subject wherein it is unknown whether the person has one or more colorectal pathologies or not. In another embodiment, the individual from whom a sample may be obtained is a test subject wherein it is unknown whether the person has one or more colorectal pathologies or not.

Blood

In one aspect of the invention, a sample of blood is obtained from an individual according to methods well known in the art. A sample of blood may be obtained from an individual, for example a subject having one or more colorectal pathologies, suspected of having one or more colorectal pathologies or not having one or more colorectal pathologies. In some embodiments, a drop of blood is collected from a simple pin prick made in the skin of an individual. Blood may be drawn from an individual from any part of the body (e.g., a finger, a hand, a wrist, an arm, a leg, a foot, an ankle, a stomach, and a neck) using techniques known to one of skill in the art, in particular methods of phlebotomy known in the art.

The amount of blood collected will vary depending upon the site of collection, the amount required for a method of the invention, and the comfort of the individual. However, an advantage of one embodiment of the present invention is that the amount of blood required to implement the methods of the present invention can be so small that more invasive procedures are not required to obtain the sample. For example, in some embodiments, all that is required is a drop of blood. This drop of blood can be obtained, for example, from a simple pinprick. In some embodiments, any amount of blood is collected that is sufficient to detect the expression of 1, 2, 3, 4, 5, 6, 7, 8, 9, 10, 11, 12, 13, 14, 15, 16, 17, 18 or all of the genes in Table 1 and Table 2 and Table 11 and Table 12. As such, in some embodiments, the amount of blood that is collected is 1 ml or less, 0.5 ml or less, 0.1 ml or less, or 0.01 ml or less. However, the present invention is not limited to such embodiments. In some embodiments more blood is available and in some embodiments, more blood can be used to effect the methods of the present invention.

As such, in various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In another embodiment, 0.001 ml to 15 ml, 0.01 ml to 10 ml, 0.1 ml to 10 ml, 0.1 ml to 5 ml, 1 to 5 ml of blood is collected from an individual. In a further embodiment, 0.001-100 ml, preferably 0.01-50 ml, more preferably 0.01-25 ml and most preferably 0.01-1 ml of blood is collected from an individual.

In some embodiments of the present invention, blood is stored within a K3/EDTA tube (e.g., from Becton Dickinson). In another embodiment, one can utilize tubes for storing blood which contain stabilizing agents such as disclosed in U.S. Pat. No. 6,617,170 (which is incorporated herein by reference). In another embodiment the PAXgene™ blood RNA system: provided by PreAnalytiX, a Qiagen/BD company, may be used to collect blood. In yet another embodiment, the Tempus™ blood RNA collection tubes, offered by Applied Biosystems may be used. Tempus™ collection tubes provide a closed evacuated plastic tube containing RNA stabilizing reagent for whole blood collection.

The blood collected is in some embodiments utilized immediately or within 1 hour, 2 hours, 3 hours, 4 hours, 5 hours or 6 hours or is optionally stored at temperatures such as 4° C., or at −20° C. prior to use in accordance with the methods of the invention. In some embodiments, a portion of the blood sample is used in accordance with the invention at a first instance of time whereas one or more remaining portions of the blood sample (or fractions thereof) are stored for a period of time for later use. For longer-term storage, storage methods well known in the art, such as storage at cryo temperatures (e.g. below −60° C.) can be used. In some embodiments, in addition to storage of the blood or instead of storage of the blood, plasma, serum, isolated nucleic acid or proteins are stored for a period of time for later use in accordance with methods known in the art.

In one aspect, whole blood is obtained from an individual according to the methods of phlebotomy well known in the art. Whole blood includes blood which can be used as is, and includes blood wherein the serum or plasma has been removed or reduced, and the RNA or mRNA from the remaining blood sample has been isolated in accordance with methods well known in the art (e.g., using, in some embodiments, gentle centrifugation at 300 to 800×g for 5 to 10 minutes). In a specific embodiment, whole blood (i.e., unfractionated blood) obtained from a subject is mixed with lysing buffer (e.g., Lysis Buffer (1 L): 0.6 g EDTA; 11.0 g $KHCO_2$, 8.2 g $NH_4Cl$ adjusted to pH 7.4 (using NaOH)), the sample is centrifuged and the cell pellet retained, and RNA or mRNA extracted in accordance with methods known in the art ("lysed blood") (see for example Sambrook et al.). In one embodiment, it is helpful to use unfractionated whole blood is preferred since it avoids the costly and time-consuming process to separate out the cell types within the blood (Kimoto, 1998, Mol. Gen. Genet. 258:233-239; Chelly J et al., 1989, Proc. Nat. Acad. Sci. USA 86:2617-2621; Chelly J et al., 1988, Nature 333:858-860).

In some embodiments of the present invention, whole blood collected from an individual is fractionated (i.e., separated into components) before isolated products of the biomarkers from the sample. In one embodiment, blood is serum depleted (or serum reduced). In another embodiment the blood is plasma depleted (or plasma reduced). In yet other embodiments blood is erythrocyte depleted or reduced. In some embodiments erythrocyte reduction is performed by preferentially lysing the red blood cells. In other embodiments, erythrocyte depletion or reduction is performed by lysing the red blood cells and further fractionating the remaining cells. In yet other embodiments erythrocyte depletion or reduction is performed but the remaining cells are not further fractionated. In other embodiments blood cells are separated from whole blood collected from an individual using other techniques known in the art. For example, blood collected from an individual can be subjected to Ficoll-Hypaque (Pharmacia) gradient centrifugation. Such centrifugation may separate various types of cells from a blood sample. In particular, Ficoll-Hypaque gradient centrifugation is useful to isolate peripheral blood leukocytes (PBLs) which can be used in accordance with the methods of the invention.

By way of example but not limitation, macrophages can be obtained as follows. Mononuclear cells are isolated from peripheral blood of a subject, by syringe removal of blood followed by Ficoll-Hypaque gradient centrifugation. Tissue culture dishes are pre-coated with the subject's own serum or with AB+ human serum and incubated at 37° C. for one hour. Non-adherent cells are removed by pipetting. Cold (4° C.) 1 mM EDTA in phosphate-buffered saline is added to the adherent cells left in the dish and the dishes are left at room temperature for fifteen minutes. The cells are harvested, washed with RPMI buffer and suspended in RPMI buffer. Increased numbers of macrophages can be obtained by incubating at 37° C. with macrophage-colony stimulating factor (M-CSF). Antibodies against macrophage specific surface markers, such as Mac-1, can be labeled by conjugation of an affinity compound to such molecules to facilitate detection and separation of macrophages. Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods, affinity chromatography, and panning.

Blood cells can be sorted using a using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150-165. Laser excitation of fluorescent moieties in the individual particles results in a small electrical charge allowing electromagnetic separation of positive and negative particles from a mixture. An antibody or ligand used to detect a blood cell antigenic determinant present on the cell surface of particular blood cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate blood cells in some embodiments of the present invention. For example, blood cells can be sorted using a using a magnetic activated cell sorting (MACS) technique, a method for separating particles based on their ability to bind magnetic beads (0.5-100 m diameter). A variety of useful modifications can be performed on the magnetic microspheres, including covalent addition of an antibody which specifically recognizes a cell-solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate blood cells by a method called panning. Separate dishes can be coated with antibody specific to particular blood cells. Cells can be added first to a dish coated with blood cell specific antibodies of interest. After thorough rinsing, the cells left bound to the dish will be cells that express the blood cell markers of interest. Examples of cell surface antigenic determinants or markers include, but are not limited to, CD2 for T lymphocytes and natural killer cells, CD3 for T lymphocytes, CD11a for leukocytes, CD28 for T lymphocytes, CD19 for B lymphocytes, CD20 for B lymphocytes, CD21 for B lymphocytes, CD22 for B lymphocytes, CD23 for B lymphocytes, CD29 for leukocytes, CD14 for monocytes, CD41 for platelets, CD61 for platelets, CD66 for granulocytes, CD67 for granulocytes and CD68 for monocytes and macrophages.

Whole blood can be separated into cell types such as leukocytes, platelets, erythrocytes, etc. and such cell types can be used in accordance with the methods of the invention. Leukocytes can be further separated into granulocytes and agranulocytes using standard techniques and such cells can be used in accordance with the methods of the invention. Granulocytes can be separated into cell types such as neutrophils, eosinophils, and basophils using standard techniques and such cells can be used in accordance with the methods of the invention. Agranulocytes can be separated into lymphocytes (e.g., T lymphocytes and B lymphocytes) and monocytes using standard techniques and such cells can be used in accordance with the methods of the invention. T lymphocytes can be separated from B lymphocytes and helper T cells separated from cytotoxic T cells using standard techniques and such cells can be used in accordance with the methods of the invention. Separated blood cells (e.g., leukocytes) can be frozen by standard techniques prior to use in the present methods.

(D) RNA Preparation

In one aspect of the invention, RNA is isolated from an individual in order to measure the RNA products of the biomarkers of the invention. RNA is isolated from a sample from individuals diagnosed as having one or more colorectal pathologies including one or more polyps or one or more subtype of polyps, individuals not having one or more colorectal pathologies, not having one or more polyps or not having a subtype of polyps, or test subjects.

In some embodiments, RNA is isolated from blood which is erythrocyte depleted by the following protocol. Lysis Buffer is added to blood sample in a ratio of 3 parts Lysis Buffer to 1 part blood (Lysis Buffer (1 L) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRizol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

In other aspects, RNA is prepared by first collecting blood into a PAXgene™ collection tube and then subsequently isolating the RNA using the PAXgene™ blood RNA isolated system provided by PreAnalytiX, a Qiagen/BD company. In another embodiment, RNA is prepared by first collecting blood into any known stabilizing solution (e.g. a PAXgene™ collection or a TEMPUS® collection tube and then isolating the RNA using any method known to a person skilled in the art.

In other aspects globin reduced or depleted RNA is prepared. In one embodiment RNA is isolated first and then is subsequently treated to remove globin mRNA using one of any technique known in the art. For example, one can hybridize DNA primers and/or probes specific for globin RNA and utilize RNAse H to selectively degrade globin mRNA. In other embodiments RNA is isolated in a manner which removes the globin RNA during the RNA isolation steps (for example reducing globin RNA by selectively removing globin RNA using globin primers and/or probes attached to paramagnetic particles).

In other aspects of the invention RNA is prepared using one or more known commercial kits for isolating RNA (including isolating total RNA or mRNA and the like) such as oligo dT based purification methods, Qiagen® RNA isolation methods, LeukoLOCKT Total RNA Isolation System, MagMAX-96 Blood Technology from Ambion, Promega® polyA mRNA isolation system and the like.

Purity and integrity of RNA can be assessed by absorbance at 260/280 nm and agarose gel electrophoresis followed by inspection under ultraviolet light. In some embodiments RNA integrity is assessed using more sensitive techniques such as the Agilent 2100 Bioanalyzer 6000 RNA Nano Chip.

(E) Biomarkers of the Invention

In one aspect, the invention provides biomarkers and biomarker combinations wherein the measure of the level of expression of the product or products of said biomarkers is indicative of the presence of one or more colorectal pathologies.

Table 1 is a list of biomarkers of one aspect of the invention. Each biomarker is differentially expressed in samples from individuals having or not having polyps using microarray assays. The table provides the Hugo Gene name, symbol and locus link ID; the RNA and protein accession number; and also includes both the p value (which represents the statistical significance of the observed differential expression) and a measure of the fold change as between the average measured level of individuals having polyps and the average measured level of individuals not having polyps.

Table 2 is a selection of those genes listed in Table 1 and lists the gene symbol and the associated locus link ID for the biomarkers of the invention. The table also provides the fold change and direction of differential gene expression in individuals having polyps as compared to individuals not having polyps. As described, differential expression of the genes between individuals having or not having polyps can be identified using a non-parametic Wilcoxan-Mann-Whitney test or a parametric t test. The results of the tests are also shown in Table 2.

Table 11 shows genes identified as differentially expressed in samples from individuals having "high risk polyps" as compared with individuals not having high risk polyps (ie having low risk polyps or having no pathology at all) using microarray as described in Example 2. The table provides the gene name, gene ID; a representative human RNA accession number, and also provides the p value, the fold change (as between the average of individuals classified as having high risk polyps as compared with the average of individuals having low risk polyps), along with the coefficient of variation for both the high risk polyp individuals and the low risk polyp individuals (the standard deviation of the normalized intensity divided by the mean normalized intensity). Column 1 is AffySpotID, column 2 is Fold Change, column 3 is p value, Column 4 is CV (Coefficient of Variation) (High RiskPolyp), column 5 is CV(Low Risk Polyp)., column 6 is Gene ID, column 7 is the HUGO Gene Symbol, column 8 is the Human RNA Accession Number and column 9 is the Gene Description.

Table 12 shows 48 biomarkers tested for differentially expression by QRT-PCR in samples from individuals having colorectal cancer and individuals not having colorectal cancer The 48 biomarkers were tested using QRT-PCR. The table provides the gene symbol, locus link ID, and gene description for each biomarker. The table also includes the p value (which represents the statistical significance of the observed differential expression), the measure of the fold change as between the average measured level of individuals having colorectal cancer and the average measured level of individuals not having colorectal cancer and the direction of the differential expression between individuals having colorectal cancer and not having colorectal cancer.

Other biomarkers of the invention are described within the specification. The invention thus encompasses the use of those methods known to a person skilled in the art to measure the expression of these biomarkers and combinations of biomarkers for each of the purposes outlined above.

As would be understood by a person skilled in the art, the locus link ID can be used to determine the sequence of all the RNA products and all the protein products of the biomarkers of the invention.

(F) Combinations of Biomarkers

In one embodiment, combinations of biomarkers of the present invention includes any combination of the biomarkers listed in Table 1, Table 2, Table 11, or Table 12. For instance, the number of possible combinations of a subset n of m genes in any of the tables above is described in Feller, *Intro to Probability Theory*, Third Edition, volume 1, 1968, ed. J. Wiley, using the general formula:

$$m!/(n)!(m-n)!$$

For example, where n is 2 and m is 8, the number of combinations of biomarkers is:

$$\frac{8!}{2!(8-2)!} = \frac{8\times7\times6\times5\times4\times3\times2\times1}{(2\times1)(6\times5\times4\times3\times2\times1)} = 40320/1440 = 28$$

unique two-gene combinations. The measurement of the gene expression of each of these two-gene combinations can independently be used to determine whether a patient has one or more colorectal pathologies. In another specific embodiment in which m is 8 and n is three, there are 8!/3!(8−3)! unique three-gene combinations. Each of these unique three-gene combinations can independently serve as a model for determining whether a patient has one or more colorectal pathologies.

(G) Testing Combinations of Biomarkers by Generating Formulas Resulting from One or More Classifiers The invention further provides a means of testing combinations of biomarkers from Table 1, Table 2, Table 11, or Table 12 or subsets thereof for their ability to test for one or more colorectal pathologies or one or more subtypes of colorectal pathology. Also provided are methods of evaluating the combinations tested for their ability to test an individual for the presence of one or more colorectal pathologies or one or more subtypes of colorectal pathology. In order to test combinations of biomarkers and generate classifiers, a mathematical model of the invention can be used. A mathematical model of the invention can be used to test each selected combination of biomarkers from all combinations of biomarkers or a selected subset thereof.

In some embodiments, it is useful to further select biomarkers to be tested as combinations in one embodiment, one can select individual biomarkers on the basis of the p value as a measure of the likelihood that the individual biomarker can distinguish as between the two phenotypic trait subgroups. Thus in one embodiment, biomarkers are chosen to test in combination by input into a model wherein the p value of each biomarker is less than 0.2, 0.1, 0.5; less than 0.1, less than 0.05, less than 0.01, less than 0.005, less than 0.001, less than 0.0005, less than 0.0001, less than 0.00005, less than 0.00001, less than 0.000005, less than 0.000001 etc. We have also surprisingly found that even biomarkers which demonstrate a p value of greater than 0.2 (and thus would normally not be considered to be a useful individual biomarker) do significantly increase the ability of a combination of biomarkers in which they are included to distinguish as between two phenotypic trait subgroups. In other embodiments, biomarkers for input into the model to test in combination are chosen on the basis of the fold change of differential expression of the product of the biomarker as between the two phenotypic trait subgroups. Note that in measuring differential fold change in blood, the fold change differences can be quite small, thus in some embodiments, selection of biomarker subsets for input into classifier is based on a differential fold change where the fold change is greater than 1.01, 1.02, 1.03, 1.04, 1.05, 1.06, 1.07, 1.08, 1.09, 1.1, 1.125, 1.15, 1.175, 1, 1.2, 1.225, 1.25, 1.275, 1.30, greater than 1.3, greater than 1.4, greater than 1.5, greater than 1.6, greater than 1.7, greater than 1.8, greater than 1.9, greater than 2.0, greater than 2.1, greater than 2.2, greater than 2.3, greater than 2.4, greater than 2.5, greater than 2.6, greater than 2.7, greater than 2.8, greater than 2.9, greater than 3.0, greater than 3.1, greater than 3.2. greater than 3.3, greater than 3.4 greater than 3.5, greater than 4.0 and the like. In yet other embodiments in order to select subsets of biomarkers to test in combination, one can also take into account the coefficient of variation as a variability of the data representing the level of expression of the product of the biomarker amongst individuals within a phenotypic trait subgroup. In some embodiments, it is helpful to select biomarkers on the basis of a combination of factors including p value, fold change, and coefficient of variation as would be understood by a person skilled in the art. In some embodiments, biomarkers are first selected as outlined above on the basis of the p value resulting from the biomarker data and then a subselection of said biomarkers is chosen on the basis of the differential fold change determined from the biomarker data. In other embodiments, biomarkers are first selected on the basis of differential fold change, and then subselection is made on the basis of p value. In some embodiments, the use of one or more of the selection criteria and subsequent ranking permits the selection of the top 2.5%, 5%, 7.5%, 10%, 12.5%, 15%, 17.5%, 20%, 30%, 40%, 50% or more of the ranked biomarkers for input into the model. In some embodiments, the desired number of selected biomarkers can be 4,000; 3,000; 2,000; 1,000; 900; 800; 700; 600; 500; 400; 300; 200; 190; 180; 170; 160; 150; 140; 130; 120; 110; 100; 90; 80; 70; 60; 50; 40; 30; 20; or 10. In other embodiments, the selection criteria noted above can be set on the basis of the desired number of selected biomarkers for use in the model. As would be understood, one can select therefore all of the individually identified biomarkers or subsets of the individually identified biomarkers and test all possible combinations of the selected biomarkers to identify useful combinations of biomarkers. In another embodiment, one can select a subset of biomarkers and then test all possible combinations of 2 biomarkers from that subset, 3 biomarkers from that subset, 4 biomarkers from that subset, 5 biomarkers from that subset, 6 biomarkers from that subset 7 biomarkers from that subset, 8 biomarkers from that subset 9 biomarkers from that subset or 10 biomarkers from that subset in order to identify useful combinations of biomarkers. A selection criteria to determine the number of selected individual biomarkers to test in combination, and to select the number of possible combinations of biomarkers will depend upon the resources available for obtaining the biomarker data and/or the computer resources available for calculating and evaluating classifiers resulting from the model.

The classifier generated by the mathematical model can be subsequently evaluated by determining the ability of the classifier to correctly call each individual for one of the two phenotypic traits of the population used to generate the classifier (ie having or not having one or more colorectal pathologies). In a preferred embodiment, the individuals of the training population used to derive the model are different from the individuals of the training population used to test the model. As would be understood by a person skilled in the art, this allows one to predict the ability of the combinations as to their ability to properly characterize an individual whose phenotypic trait characterization is unknown.

The data which is input into the mathematical model can be any data which is representative of the expression level of the product of the biomarkers being evaluated. Mathematical models useful in accordance with the invention include those using both supervised or unsupervised learning techniques. In a preferred embodiment of the invention, the mathematical model chosen uses supervised learning in conjunction with a "training population" to evaluate each of the possible combination of biomarkers of the invention. In one embodiment of the invention, the mathematical model used is selected from the following: a regression model, a logistic regression model, a neural network, a clustering model, principal component analysis, nearest neighbour classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, a projection pursuit, genetic programming and weighted voting. In a preferred embodiment, a logistic regression model is used. In another preferred embodiment, a neural network model is used.

The results of applying a mathematical model of the invention to the data will generate one or more classifiers using one or more biomarkers. In some embodiments, multiple classifiers are created which are satisfactory for the given purpose (e.g. all have sufficient AUC and/or sensitivity and/or specificity). In this instance, in some embodiments, a formula is generated which utilizes more than one classifier. For example, a formula can be generated which utilizes classifiers in series (e.g. first obtains results of classifier A, then classifier B e.g. Classifier A differentiates pathology from non pathology; classifier B then determines whether the pathology is colorectal cancer or not colorectal cancer). In another embodiment, a formula can be generated which results from weighting the results of more than one classifier. For example, the results of each classifier can be given a score of 1 and an indication of probability of a test subject having one or more colorectal pathologies is the result of the aggregate score of each of the selected classifiers of a given formula. Other possible combinations and weightings of classifiers would be understood and are encompassed herein.

Classifiers generated can be used to test an unknown or test subject. In one embodiment, the results from equations generated by logistic regression to answer the question does an individual have one or more colorectal pathologies or is an individual "normal". In yet another embodiment of the invention, the answer to the question above may be an answer of non-determinable.

In one embodiment of the invention, each classifier is evaluated for its ability to properly characterize each individual of the training population using those methods known to a person skilled in the art. For example one can evaluate the classifier using cross validation, Leave One out Cross Validation (LOOCV), n-fold cross validation, jackknife analysis using standard statistical methods as disclosed. In another embodiment of the invention, each classifier is evaluated for its ability to properly characterize those individuals of the training population which were not used to generate the classifier.

In one embodiment, the method used to evaluate the classifier for its ability to properly characterize each individual of the training population is a method which evaluates the classifier's sensitivity (TPF, true positive fraction) and 1-specificity (TNF, true negative fraction). In one embodiment, the method used to test the classifier is Receiver Operating Characteristic ("ROC") which provides several parameters to evaluate both the sensitivity and specificity of the result of the equation generated. In one embodiment using the Receiver Operating Characteristic ("ROC") the ROC area (area under the curve) is used to evaluate the equations. A ROC area greater than 0.5, 0.6, 0.7, 0.8, 0.9 is preferred. A perfect ROC area score of 1.0 indicates with both 100% sensitivity and 100% specificity. In some embodiments classifiers are selected on the basis of the score. For example, where the scoring system used is receiver operating characteristic (ROC) curve score determined by an area under the ROC curve, in some embodiments, those classifiers with scores of greater than 0.95, 0.9, 0.85, 0.8, 0.7, 0.65, 0.6, 0.55 0.5 or 0.45 are chosen. In other embodiments, where specificity is important to the use of the classifier, a sensitivity threshold can be set and classifiers ranked on the basis of the specificity chosen. For example classifiers with a cutoff for specificity of greater than 0.95, 0.9, 0.85, 0.8, 0.7, 0.65, 0.6, 0.55 0.5 or 0.45 can be chosen. Similarly, the specificity threshold can be set and classifiers ranked on the basis of sensitivity greater than 0.95, 0.9, 0.85, 0.8, 0.7, 0.65, 0.6, 0.55 0.5 or 0.45 can be chosen. Thus in some embodiments, only the top 10 ranking classifiers, the top 20 ranking classifiers, or the top 100 ranking classifiers are selected.

As would be understood by a person skilled in the art, the utility of the combinations and classifiers determined by a mathematical model will depend upon the phenotypes of the populations used to generate the data for input into the model. Examples of specific embodiments are described more thoroughly herein.

(H) Populations for Input into the Mathematical Models

Populations used for input should be chosen so as to result in statistically significant resulting classifier. In some embodiments, the reference or training population includes between 10 and 30 subjects. In another embodiment the reference population contains between 30-50 subjects. In still other embodiments, the reference population includes two or more populations each containing between 50 and 100, 100 and 500, between 500 and 1000, or more than 1000 subjects. The reference population includes two or more subpopulations. In a preferred embodiment, the phenotypic trait characteristics of the subpopulations are similar but for the diagnosis with respect to the presence of one or more colorectal pathologies, for example the distribution within the subpopulations are similar with regards to the age and sex of the subpopulations. It is also preferred that the subpopulations are of roughly equivalent numbers. It is to be understood that the methods herein do not require using data from every member of a population, but instead may rely on data from a subset of a population in question.

For example, for a reference or test population for input into a mathematical model to identify those biomarkers which are useful in identifying an individual as having any polyps or not having any polyps, the reference population is comprised of individuals having polyps (the first subpopulation), and individuals not having polyps (the second subpopulation). For purposes of characterizing the subpopulations as having or not having polyps, any verified method can be used including digital rectal examination, fecal occult blood testing, rigid sigmoidoscopy, flexible sigmoidoscopy, double-contrast barium enema, colonoscopy, and histological examination. Preferably only those individuals whose diagnoses are certain are utilized as part of the reference population.

In another embodiment, to identify those biomarkers which are useful in identifying an individual as having high risk polyps or not, the reference population is comprised of individuals having high risk polyps (the first subpopulation), and individuals not having high risk polyps (the second subpopulation) where high risk polyps are the following: Tubulovillous Adenoma, Villous Adenoma, Cancer High Grade Dysplasia and Tubular Adenoma where the Tubular Adenoma is greater than 10 mm. For purposes of characterizing the subpopulations as having or not having high risk polyps, any verified method can be used including digital rectal examination, fecal occult blood testing, rigid sigmoidoscopy, flexible sigmoidoscopy, double-contrast barium enema, colonoscopy, and histological examination.

In yet another embodiment, to test biomarkers which are useful in identifying an individual as having early stage of colorectal cancer or not, the reference population can, for example be comprised of individuals having localized colorectal cancer as compared with individuals with other types of colorectal cancer (e.g. late stage).

In another embodiment, to identify those biomarkers which are useful in identifying an individual as having high risk polyps or not, the reference population is comprised of individuals having high risk polyps (the first subpopulation), and individuals not having high risk polyps (the second subpopulation) where high risk polyps are the following: Tubulovillous Adenoma; Villous Adenoma; Cancer; High Grade Dysplasia; and Tubular Adenoma.

(I) Data for Input into the Mathematical Models to Identify Classifiers for Testing for Colorectal Pathology Data for input into the mathematical models is data representative of the level of the products of the biomarkers of the invention. As such the data is the measure of the level of expression of the products of the biomarkers of the invention including either mRNA and/or protein.

In one embodiment of the invention, the RNA products of the biomarkers of the invention which are measured are the population of RNA products including the mRNA, and all of the spliced variants of the mRNA. In another embodiment of the invention the products measured are all of the mRNA products expressed in blood. In yet another embodiment of the invention, the products measured include one or more specific spliced variants of the mRNA which are expressed in blood. In yet another embodiment of the invention, the products measured are the RNA products listed in Table 3 or Table 13.

Protein products of the biomarkers of the invention are also included within the scope of the invention. To practice the invention, measurement of the protein products of the biomarkers of the invention can be used for purposes of testing for one or more colorectal pathologies. More particularly, measurement of those populations of protein products of the biomarkers which are differentially expressed in individuals having or not having any polyps are useful for purposes of testing and are encompassed herein.

In one embodiment of the invention the protein products are those translated from the biomarkers listed in Table 1, Table 2, Table 11, or Table 12. In another embodiment, the protein products are those which are expressed in blood. In yet another embodiment of the invention, the protein products are those corresponding to the proteins listed in Table 3 or Table 13.

In yet another embodiment, data reflective of the level of expression of a combination of protein products and RNA products of the biomarkers are used. As would be understood by a person skilled in the art, other combinations of input data can be utilized to generate classifiers useful in accordance with the invention.

In other embodiments, as would be understood by one of ordinary skill in the art, data reflective of each biomarker in each member of the population is not necessary so long as there are data for sufficient members of each reference population to permit creation of a classifier. For example, data representative of biomarkers in 99%, 95%, 90%, 85%, 80%, or 75% of members of a population may suffice in given circumstances.

(J) Mathematical Models

Formulae for use with the methods described herein may generally have the form:

$$V=C+\tau\beta_i f(X_i)+\Sigma\beta_{ij} f(X_i,X_j)+\Sigma\beta_{ijk} f(X_i,X_j,X_k)+\ldots$$

Wherein V is a value indicating the probability that a test subject has one or more colorectal pathologies, $X_i$ is a level of one or more products of an ith biomarker in a sample from the test subject, βi is a coefficient for a term involving only the ith biomarker, $\beta_{ij}$ is a coefficient for a term that is a function of the ith and jth biomarkers, $\beta_{ijk}$ is a coefficient for a term that is a function of the ith, jth and kth biomarkers, and C is a constant. Still other terms may find themselves in this formula, such as terms depending on four or more biomarkers.

By 'indicates' is meant that V might be an actual probability (a number varying between 0 and 1), or V might be a quantity from which a probability can be readily derived.

There are various forms of functions $f X_i, X_j, \ldots)$ that depend on expression levels of the various biomarkers. For example, the functions may be polynomials in those expression levels, i.e., involve products of the various biomarkers raised to numeric powers. Examples include: $X_iX_j^2$, $X_iX_jX_k$, $(X_iX_j)^{1/2}$, $X_iX_j+X_iX_k$. The functions may additionally or alternatively involve logarithms, exponentials, or still other functions of the expression levels.

In certain embodiments, the $f(X_i, X_j, \ldots)$ depend on ratios of the biomarker expression levels, i.e., $f(X_i, X_j)=X_iX_j$.

Regression Models

In some embodiments the expression data for some or all of the biomarkers identified in the present invention are used in a regression model, such as but not limited to a logistic regression model or a linear regression model, so as to identify classifiers useful in diagnosing one or more colorectal pathologies. The regression model is used to test various combinations of two or more of the biomarkers identified in Table 1, Table 2, Table 11, or Table 12 to generate classifiers. In the case of regression models, the classifiers which result are in the form of equations which provide a dependent variable Y, which represents the presence or absence of a given phenotype where the data representing the expression of each of the biomarkers in the equation is multiplied by a weighted coefficient as generated by the regression model. The classifiers generated can be used to analyze expression data from a test subject and provide a result indicative of the probability of a test subject having one or more colorectal pathologies. In general, a multiple regression equation of interest can be written $$Y=\alpha+\beta_1X_1+\beta_2X_2+\ldots+\beta_kX_k+\epsilon$$

where Y, the dependent variable, indicates presence (when Y is positive) or absence (when Y is negative) of the biological feature (e.g., absence or presence of one or more colorectal pathologies) associated with the first subgroup. This model says that the dependent variable Y depends on k explanatory variables (the measured characteristic values for the k select genes (e.g., the biomarkers) from subjects in the first and second subgroups in the reference population), plus an error term that encompasses various unspecified omitted factors. In the above-identified model, the parameter $\beta_1$ gauges the effect of the first explanatory variable $X_1$ on the dependent variable Y (e.g., a weighting factor), holding the other explanatory variables constant. Similarly, $\beta_2$ gives the effect of the explanatory variable $X_2$ on Y, holding the remaining explanatory variables constant.

A logistic regression model is a non-linear transformation of the linear regression. The logistic regression model is often referred to as the "logit" model and can be expressed as $$\ln[p/(1-p)]=\alpha+\beta_1X_1+\beta_2X_2+\ldots+\beta_kX_k+\epsilon \text{ or}$$

$$[p/(1-p)]=\exp^{\alpha}\exp^{\beta_1X_1}\exp^{\beta_2X_2}\times\ldots\times\exp^{\beta_kX_k}\exp^{\epsilon}$$

where,

α and ϵ are constants ln is the natural logarithm, $\log_e$, where e=2.71828 . . . , p is the probability that the event Y occurs, p(Y=1), p/(1−p) is the "odds ratio", ln [p/(1−p)] is the log odds ratio, or "logit", and all other components of the model are the same as the general linear regression equation described above. It will be appreciated by those of skill in the art that the term for $\alpha$ and $\epsilon$ can be folded into a single constant. Indeed, in preferred embodiments, a single term is used to represent $\alpha$ and $\epsilon$. The "logistic" distribution is an S-shaped distribution function. The logit distribution constrains the estimated probabilities (p) to lie between 0 and 1.

In some embodiments of the present invention, the logistic regression model is fit by maximum likelihood estimation (MLE). In other words, the coefficients (e.g., $\alpha$, $\beta_1$, $\beta_2$, . . . ) are determined by maximum likelihood. A likelihood is a conditional probability (e.g., P(Y|X), the probability of Y given X). The likelihood function (L) measures the probability of observing the particular set of dependent variable values ($Y_1$, $Y_2$, . . . , $Y_n$) that occur in the sample data set. It is written as the probability of the product of the dependent variables:

$$L=\text{Prob}(Y_1*Y_2***Y_n)$$

The higher the likelihood function, the higher the probability of observing the Ys in the sample. MLE involves finding the coefficients ($\alpha$, $\beta_1$, $\beta_2$, . . . ) that makes the log of the likelihood function (LL<0) as large as possible or −2 times the log of the likelihood function (−2LL) as small as possible. In MLE, some initial estimates of the parameters $\alpha$, $\beta_1$, $\beta_2$, . . . are made. Then the likelihood of the data given these parameter estimates is computed. The parameter estimates are improved the likelihood of the data is recalculated. This process is repeated until the parameter estimates do not change much (for example, a change of less than 0.01 or 0.001 in the probability). Examples of logistic regression and fitting logistic logistic regression models are found in Hastie, *The Elements of Statistical Learning*, Springer, N.Y., 2001, pp. 95-100 which is incorporated herein in its entirety.

Neural Networks

In another embodiment, the expression measured for each of the biomarkers of the present invention can be used to train a neural network. A neural network is a two-stage regression or classification model. A neural network can be binary or non binary. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. As such a neural network can be applied to allow identification of biomarkers which differentiate as between more than two populations (ie more than two phenotypic traits). In one specific example, a neural network can be trained using expression data from the products of the biomarkers in Table 1, Table 2, Table 11, or Table 12 to identify those combinations of biomarkers which are specific for one or more colorectal pathologies. As a result, the trained neural network can be used to directly identify combinations of biomarkers useful to test for one or more colorectal pathologies. In some embodiments, the back-propagation neural network (see, for example Abdi, 1994, "A neural network primer", J. Biol System. 2, 247-283) containing a single hidden layer of ten neurons (ten hidden units) found in EasyNN-Plus version 4.0 g software package (Neural Planner Software Inc.) is used.

Neural networks are described in Duda et al., 2001, *Pattern Classification*, Second Edition, John Wiley & Sons, Inc., New York; and Hastie et al., 2001, *The Elements of Statistical Learning*, Springer-Verlag, New York which is incorporated herein in its entirety.

Singular Value Decomposition (SVD) and Principal Component Analysis (PCA)

Singular value decomposition (SVD) and Principal Component Analysis (PCA) are common techniques for analysis of multivariate data, and we have found that gene expression data is well suited to analysis using SVD/PCA. SVD or equivalently, in this case, PCA, is defined as follows:

Singular value decomposition (SVD) and Principal Component Analysis (PCA) are common techniques for analysis of multivariate data, and we have found gene expression data are well suited to analysis using SVD/PCA. SVD or equivalently, in this case, PCA, is defined as follows:

Let G be an m×n gene expression matrix with rank r, and m≧n, and therefore r≦n where m is a row and n is a column of data of the matrix. In the case of microarray data, gij is the level of one or more products of the ith biomarker in the jth assay. The elements of the ith row of G form the n-dimensional vector bi (where b is a biomarker), which we refer to as the transcriptional response of the ith biomarker. Alternatively, the elements of the jth column of G form the m-dimensional vector aj, which we refer to as the expression profile (or gene expression profile) of the jth assay.

The equation for singular value decomposition of G is the following:

$$G=USV^T$$

where U is an m×n matrix, S is an n×n diagonal matrix, and VT is also an n×n matrix. The columns of U are called the left singular vectors, {uk}, and form an orthonormal basis for the assay expression profiles, so that $u_i \cdot u_j=1$ for i=j, and $u_i \cdot u_j=0$ otherwise. The rows of $V^T$ contain the elements of the right singular vectors, $\{v_k\}$, and form an orthonormal basis for the gene transcriptional responses. The elements of S are only nonzero on the diagonal, and are called the singular values. Thus, $S=\text{diag}(s_1, \ldots, s_n)$. Furthermore, $s_k>0$ for $1 \leqq k \leqq r$, and $s_i=0$ for $(r+1) \leqq k \leqq n$. By convention, the ordering of the singular vectors is determined by high-to-low sorting of singular values, with the highest singular value in the upper left index of the S matrix. Note that for a square, symmetric matrix X, singular value decomposition is equivalent to diagonalization, or solution of the eigenvalue problem.

Other Mathematical Models

The pattern classification and statistical techniques described above are merely examples of the types of models that can be used to construct classifiers useful for diagnosing or detecting one or more colorectal pathologies, for example clustering as described on pages 211-256 of Duda and Hart, *Pattern Classification and Scene Analysis,* 1973, John Wiley & Sons, Inc., New York, incorporated herein by reference in its entirety; Principal component analysis, (see for Jolliffe, 1986, *Principal Component Analysis*, Springer, N.Y., incorporated herein by reference); nearest neighbour classifier analysis, (see for example Duda, *Pattern Classification*, Second Edition, 2001, John Wiley & Sons, Inc; and Hastie, 2001, *The Elements of Statistical Learning*, Springer, N.Y.); linear discriminant analysis, (see for example Duda, *Pattern Classification*, Second Edition, 2001, John Wiley & Sons, Inc; and Hastie, 2001, *The Elements of Statistical Learning*, Springer, N.Y.; Venables & Ripley, 1997, *Modern Applied Statistics with s-plus*, Springer, N.Y.); Support Vector Machines (see, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152;

Vapnik, 1998, *Statistical Learning Theory*, Wiley, New York, incorporated herein by reference.)

Computer Implementation

The methods described herein are preferably performed by a suitably programmed computer. The computer system for use with the methods described herein, as further described herein, is configured to accept and to process data and may be a single-processor or multi-processor computer system. Examples of suitable computer systems include, but are not limited to, any one of various combinations of mainframe computers, minicomputers, personal computers, laptop computers, notebook computers, hand-held computers, personal digital assistants, mobile phones, set-top boxes, microprocessor-based consumer electronics, programmable consumer electronics, and the like. Additionally, the methods of the invention may be practiced on networked computers, CPU-clusters, workstations, and so-called mainframe computers. The computer system may be a locally accessed computer, a remotely accessed computer system (e.g. server), or a combination of both. Depending on the application and purpose, the computer system may have access or be accessible to "the internet" [World Wide Web (WWW)]. It will be appreciated that the computer system may be a stand-alone system or a distributed system comprising multiple devices communicating with each other through a network. Depending on the application and purpose, the computer system may be a static or mobile computer system. One of ordinary skill in the art will possess the necessary knowledge and skills for selecting, obtaining and utilizing a suitable computer system for practicing any aspect of the invention.

It is therefore consistent with the description herein that various methods and formulae are implemented, in the form of computer program instructions, and executed on a computer as also described herein. Suitable programming languages for expressing the program instructions include, but are not limited to, one or more languages selected from the group consisting of: C, C++, an embodiment of FORTRAN such as FORTRAN77 or FORTRAN90, Java, Visual Basic, Perl, Tcl/Tk, JavaScript, and ADA. It is to be understood that various aspects of the methods may be written in different computing languages from one another, where such languages are preferred for particular applications, and the various aspects are caused to communicate with one another by appropriate system-level-tools available on a given computer.

The computer program instructions are stored in a computer memory during execution, and may additionally be stored on any of various forms of computer-readable media known in the art, such as, but not limited to, CD-Rom, CD-R, CD-RW, flash memory, memory cards, memory sticks, DVD-Rom, USB-sticks, optical discs, or high capacity network storage drives. It is thus consistent with ordinary practice of the present invention that the computer program instructions can be delivered to a user on a transferable medium such as a CD-Rom, and also delivered over a computer network, such as by downloading over the Internet through a web-interface.

Figure 1:
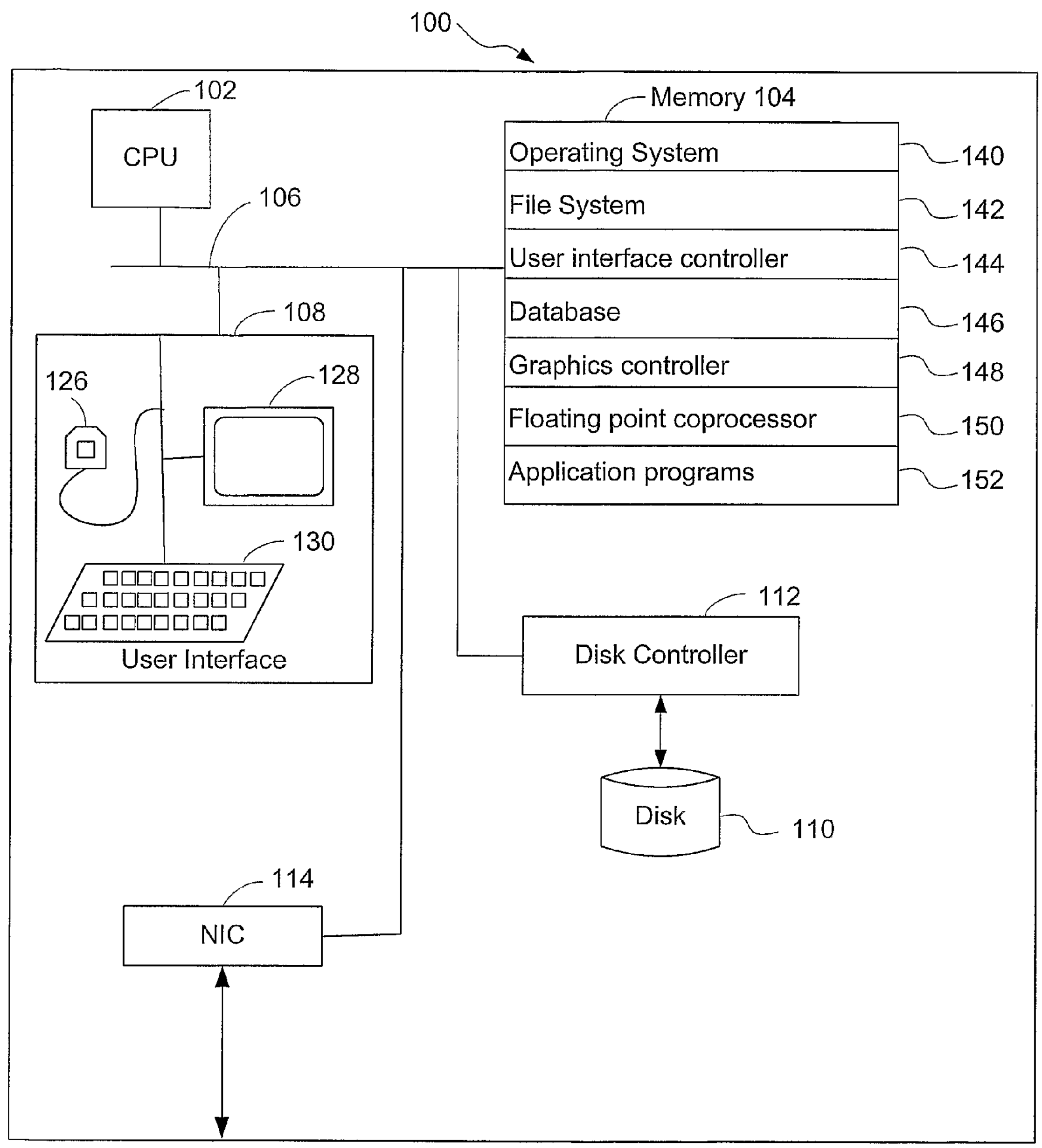
FIG. 1 shows an exemplary computer system for practicing certain of the methods described herein.

FIG. 1 shows a schematic of a general-purpose computer system 100 suitable for practicing the methods described herein. The computer system 100, shown as a self-contained unit but not necessarily so limited, comprises at least one data processing unit (CPU) 102, a memory 104, which will typically include both high speed random access memory as well as non-volatile memory (such as one or more magnetic disk drives) but may be simply flash memory, a user interface 108, optionally a disk 110 controlled by a disk controller 112, and at least one optional network or other communication interface card 114 for communicating with other computers as well as other devices. At least the CPU 102, memory 104, user interface 108, disk controller where present, and network interface card, communicate with one another via at least one communication bus 106.

Memory 104 stores procedures and data, typically including: an operating system 140 for providing basic system services; application programs 152 such as user level programs for viewing and manipulating data, evaluating formulae for the purpose of diagnosing a test subject; authoring tools for assisting with the writing of computer programs; a file system 142, a user interface controller 144 for handling communications with a user via user interface 108, and optionally one or more databases 146 for storing microarray data and other information, optionally a graphics controller 148 for controlling display of data, and optionally a floating point coprocessor 150 dedicated to carrying out mathematical operations. The methods of the present invention may also draw upon functions contained in one or more dynamically linked libraries, not shown in FIG. 1, but stored either in Memory 104, or on disk 110, or accessible via network interface connection 114.

User interface 108 may comprise a display 128, a mouse 126, and a keyboard 130. Although shown as separate components in FIG. 1, one or more of these user interface components can be integrated with one another in embodiments such as handheld computers. Display 128 may be a cathode ray tube (CRT), or flat-screen display such as an LCD based on active matrix or TFT embodiments, or may be an electroluminescent display, based on light emitting organic molecules such as conjugated small molecules or polymers. Other embodiments of a user interface not shown in FIG. 1 include, e.g., several buttons on a keypad, a card-reader, a touch-screen with or without a dedicated touching device, a trackpad, a trackball, or a microphone used in conjunction with voice-recognition software, or any combination thereof, or a security-device such as a fingerprint sensor or a retinal scanner that prohibits an unauthorized user from accessing data and programs stored in system 100. System 100 may also be connected to an output device such as a printer (not shown), either directly through a dedicated printer cable connected to a serial or USB port, or wirelessly, or via a network connection.

The database 146 may instead, optionally, be stored on disk 110 in circumstances where the amount of data in the database is too great to be efficiently stored in memory 104. The database may also instead, or in part, be stored on one or more remote computers that communicate with computer system 100 through network interface connection 114.

The network interface 134 may be a connection to the internet or to a local area network via a cable and modem, or ethernet, firewire, or USB connectivity, or a digital subscriber line. Preferably the computer network connection is wireless, e.g., utilizing CDMA, GSM, or GPRS, or bluetooth, or standards such as 802.11a, 802.11b, or 802.11g.

It would be understood that various embodiments and configurations and distributions of the components of system 10 across different devices and locations are consistent with practice of the methods described herein. For example, a user may use a handheld embodiment that accepts data from a test subject, and transmits that data across a network connection to another device or location wherein the data is analyzed according to a formulae described herein. A result of such an analysis can be stored at the other location and/or additionally transmitted back to the handheld embodiment. In such a configuration, the act of accepting data from a test subject can include the act of a user inputting the information. The network connection can include a web-based interface to a remote site at, for example, a healthcare provider. Alternatively, system 10 can be a device such as a handheld device that accepts data from the test subject, analyzes the data, such as by inputting the data into a formula as further described herein, and generating a result that is displayed to the user. The result can then be, optionally, transmitted back to a remote location via a network interface such as a wireless interface. System 100 may further be configured to permit a user to transmit by e-mail results of an analysis directly to some other party, such as a healthcare provider, or a diagnostic facility, or a patient.

(K) Use of the Biomarkers of the Invention for Testing, Screening or Diagnosing a Test Subject As would be understood by a person skilled in the art, the identification of one or more biomarkers can be used to allow for the testing, screening or diagnosis of one or more colorectal pathologies including polyps or one or more subtypes of polyps within a test subject by measuring the expression of the products of the biomarkers (gene) in the test subject (the "test subject").

In one embodiment, the results from the test subject are compared with the a control wherein the control can be results from one or more individuals having colorectal pathology, having polyps, having one or more subtypes of polyps and/or one or more individuals not having any colorectal pathology, not having any polyps or not having one or more specific subtypes of colorectal polyps.

In another embodiment, one can input data reflective of the expression of the products of the biomarkers of the test subject into a formula of the invention resulting in a determination of whether said test subject has one or more colorectal pathologies. It is not necessary to use the same formula used to test the biomarker combination for its ability to test for colorectal pathologies as to diagnose an individual using the biomarker combination identified. Data representative of the products of the biomarkers of the invention (including RNA and/or Protein) is input into a formula of the invention so as to determine a probability of a test subject having one or more colorectal pathologies. The data can be generated using any technique known to measure the level of expression of either the RNA and protein products of the biomarkers of the invention.

In one embodiment, use of the formula results in a determination of whether the test subject has polyps or does not have polyps. For example, using logistic regression as the model, Y is used as a predictor of polyps, where when $Y>0$a person is diagnosed as having polyps and where $Y<0$, a person is diagnosed as not having polyps. In yet another embodiment, one can also include a third category of prediction wherein diagnosis is indeterminable. For example, one can determine the standard deviation inherent within the methodology used to measure gene expression of the biomarkers ($\delta$). If $Y<\delta$ but $>0$ or $Y>-\delta$ but $<0$, then the test results are considered indeterminable.

(L) Polynucleotides Used to Measure the Products of the Biomarkers of the Invention Polynucleotides capable of specifically or selectively binding to the RNA products of the biomarkers of the invention are used to measure the level of expression of the biomarkers. For example: oligonucleotides, cDNA, DNA, RNA, PCR products, synthetic DNA, synthetic RNA, or other combinations of naturally occurring or modified nucleotides which specifically and/or selectively hybridize to one or more of the RNA products of the biomarker of the invention are useful in accordance with the invention.

In a preferred embodiment, the oligonucleotides, cDNA, DNA, RNA, PCR products, synthetic DNA, synthetic RNA, or other combinations of naturally occurring or modified nucleotides oligonucleotides which both specifically and selectively hybridize to one or more of the RNA products of the biomarker of the invention are used.

(M) Techniques to Measure the RNA Products of the Biomarkers of the Invention Array Hybridization In one embodiment of the invention, the polynucleotide used to measure the RNA products of the biomarkers of the invention can be used as nucleic acid members localized on a support to comprise an array according to one aspect of the invention. The length of a nucleic acid member can range from 8 to 1000 nucleotides in length and are chosen so as to be specific for the RNA products of the biomarkers of the invention. In one embodiment, these members are selective for the RNA products of the biomarkers of the invention. The nucleic acid members may be single or double stranded, and/or may be oligonucleotides or PCR fragments amplified from cDNA. In some embodiments oligonucleotides are approximately 20-30 nucleotides in length. ESTs are in some embodiments 100 to 600 nucleotides in length. It will be understood to a person skilled in the art that one can utilize portions of the expressed regions of the biomarkers of the invention as a probe on the array. More particularly oligonucleotides complementary to the genes of the invention and or cDNA or ESTs derived from the genes of the invention are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

As described, microarrays can be used to identify and select genes differentially expressed in individuals having or not having one or more colorectal pathologies, one or more polyps or one or more subtypes of polyps, and can be used to diagnose or detect polyps or one or more subtypes of polyps using the biomarkers of the invention. Genes identified as differentially expressed using microarrays can be seen in Table 1, and Table 11.

Construction of a Nucleic Acid Array

In the subject methods, an array of nucleic acid members stably associated with the surface of a substantially support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. In some embodiments, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/$cm^2$, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In a preferred embodiment, the nucleic acid attached to the surface of the support is cDNA or RNA. In another preferred embodiment, the nucleic acid attached to the surface of the support is cDNA synthesized by polymerase chain reaction (PCR). In some embodiments, a nucleic acid member in the array, according to the invention, is at least 10, 25 or 50 nucleotides in length. In one embodiment, a nucleic acid member is at least 150 nucleotides in length. In some embodiments, a nucleic acid member is less than 1000 nucleotides in length. More preferably, a nucleic acid member is less than 500 nucleotides in length.

In the arrays of the invention, the nucleic acid compositions are stably associated with the surface of a support. In one embodiment, the support may be a flexible or rigid support. By "stably associated" is meant that each nucleic acid member maintains a unique position relative to the support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of target nucleic acid sequences during the assay in which the array is employed. Generally, the amount of each nucleic acid member stably associated with the support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the support in a spot comprising an overall circular dimension, the diameter of the "spot" will generally range from about 10 to 5,000 μm, usually from about 20 to 2,000 μm and more usually from about 100 to 200 μm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Use of a Microarray

Nucleic acid arrays according to the invention can be used to assay nucleic acids in a sample comprising one or more target nucleic acid sequences (ie such as RNA products of the biomarkers of the invention). The arrays of the subject invention can be used for testing, screening, and/or diagnosis of one or more colorectal pathologies including polyps or one or more subtypes of polyps, or screening for therapeutic targets and the like.

The arrays are also useful in broad scale expression screening for drug discovery and research, such as the effect of a particular active agent on the expression pattern of biomarkers of the invention, where such information is used to reveal drug efficacy and toxicity, environmental monitoring, disease research and the like.

Arrays can be made using at least one, more preferably a combination of these sequences, as a means of diagnosing colon pathology or one or more subtypes of colon pathology.

The choice of a standard sample would be well understood by a person skilled in the art, and would include a sample complementary to RNA isolated from one or more normal individuals, wherein a normal individual is an individual not having polyps.

Preparation of Nucleic Acid Sample for Hybridization to an Array

The samples for hybridization with the arrays according to the invention are in some embodiments derived from total RNA from blood. In another embodiment, targets for the arrays are derived from mRNA from blood.

The nucleic acid sample is capable of binding to a nucleic acid member of complementary sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid samples used herein are in some embodiments derived from blood. Nucleic acids can be single- or double-stranded DNA, RNA, or DNA-RNA hybrids synthesized from human blood using methods known in the art, for example, reverse transcription or PCR.

In the simplest embodiment, such a nucleic acid sample comprises total mRNA or a nucleic acid sample corresponding to mRNA (e.g., cDNA) isolated from blood samples. In another embodiment, total mRNA is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratoy Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the nucleic acid sample prior to hybridization, for example, when only limited amounts of sample can be used (e.g. drop of blood). One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989, *Genomics*, 4:560; Landegren, et al., 1988, *Science*, 241:1077 and Barringer, et al., 1990, *Gene*, 89:117, transcription amplification (Kwoh, et al., 1989, *Proc. Natl. Acad. Sci. USA*, 86: 1173), and self-sustained sequence replication (Guatelli, et al., 1990, *Proc. Nat. Acad. Sci. USA*, 87: 1874).

In a particularly preferred embodiment, the nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, *Proc. Natl. Acad. Sci. USA*, 87: 1663-1667 who demonstrate that in vitro amplification according to this method preserves the relative frequencies of the various RNA transcripts. Moreover, Eberwine et al. *Proc. Natl. Acad. Sci. USA*, 89: 3010-3014 provide a protocol that uses two rounds of amplification via in vitro transcription to achieve greater than $10^6$ fold amplification of the original starting material thereby permitting expression monitoring even where biological samples are limited.

Labeling of Nucleic Acid Sample or Nucleic Acid Probe

Nucleic acid samples are labelled so as to allow detection of hybridization to an array of the invention. Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, 35S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The labels may be incorporated by any of a number of means well known to those of skill in the art. However, in one embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In another embodiment, the fluorescent modifications are by cyanine dyes e.g. Cy-3/Cy-5 dUTP, Cy-3/Cy-5 dCTP (Amersham Pharmacia) or alexa dyes (Khan, et al., 1998, *Cancer Res.* 58:5009-5013).

In one embodiment, the two Nucleic Acid Sample samples used for comparison are labeled with different fluorescent dyes which produce distinguishable detection signals, for example, nucleic acid samples made from normal intestinal cells are labeled with Cy5 and nucleic acid samples made from intestinal tissue cells are labeled with Cy3. The differently labeled target samples are hybridized to the same microarray simultaneously. In a preferred embodiment, the labeled nucleic acid samples are purified using methods known in the art, e.g., by ethanol purification or column purification.

In another embodiment, the nucleic acid samples will include one or more control molecules which hybridize to control probes on the microarray to normalize signals generated from the microarray. In one embodiment, labeled normalization nucleic acid samples are nucleic acid sequences that are perfectly complementary to control oligonucleotides that are spotted onto the microarray as described above. In another embodiment, labeled normalization nucleic acid samples are nucleic acid sequences that are 99%, 98%, 97%, 96%, 95%, 90%, 85%, 80% or 75% complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In one embodiment, signals (e.g., fluorescence intensity) read from all other probes in the array are divided by the signal (e.g., fluorescence intensity) from the control probes, thereby normalizing the measurements.

Preferred normalization nucleic acid samples are selected to reflect the average length of the other nucleic acid samples present in the sample, however, they are selected to cover a range of lengths. The normalization control(s) also can be selected to reflect the (average) base composition of the other probes in the array, however, in one embodiment, only one or a few normalization probes are used and they are selected such that they hybridize well (i.e., have no secondary structure and do not self hybridize) and do not match any nucleic acids on the array.

Normalization probes are localized at any position in the array or at multiple positions throughout the array to control for spatial variation in hybridization efficiency. In one embodiment, normalization controls are located at the corners or edges of the array as well as in the middle.

Hybridization Conditions

Nucleic acid hybridization involves providing a nucleic acid sample under conditions where the sample and the complementary nucleic acid member can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., *Laboratory Techniques in Biochemistry and Molecular Biology*, Vol. 24: *Hybridization With Nucleic acid Probes*, P. Tijssen, ed. Elsevier, N.Y., (1993)).

Following hybridization, non-hybridized labeled or unlabeled nucleic acid is removed from the support surface, conveniently by washing, thereby generating a pattern of hybridized target nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target nucleic acids to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two samples to be compared, where each sample is labeled with a different fluorescent dye.

Each element of the microarray is scanned for the first fluorescent color. The intensity of the fluorescence at each array element is proportional to the expression level of that gene in the sample. The scanning operation is repeated for the second fluorescent label. The ratio of the two fluorescent intensities provides a highly accurate and quantitative measurement of the relative gene expression level in the two samples.

In a preferred embodiment, fluorescence intensities of immobilized nucleic acid sequences were determined from images taken with a custom confocal microscope equipped with laser excitation sources and interference filters appropriate for the Cy3 and Cy5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each target are as described (Khan, et al., 1998, *Cancer Res.* 58:5009-5013. Chen, et al., 1997, *Biomed. Optics* 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A linear regression approach is used for normalization and assumes that a scatter plot of the measured Cy5 versus Cy3 intensities should have a slope of one. The average of the ratios is calculated and used to rescale the data and adjust the slope to one. A ratio of expression not equal to 1 is used as an indication of differential gene expression.

In a particular embodiment, where it is desired to quantify the transcription level (and thereby expression) of one or more nucleic acid sequences in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear and still provide meaningful results. Thus, for example, an assay where a 5 fold difference in concentration of the sample mRNA results in a 3- to 6-fold difference in hybridization intensity is sufficient for most purposes. Where more precise quantification is required, appropriate controls are run to correct for variations introduced in sample preparation and hybridization as described herein. In addition, serial dilutions of "standard" mRNA samples are used to prepare calibration curves according to methods well known to those of skill in the art. Of course, where simple detection of the presence or absence of a transcript is desired, no elaborate control or calibration is required.

For example, if a nucleic acid member on an array is not labeled after hybridization, this indicates that the gene comprising that nucleic acid member is not expressed in either sample. If a nucleic acid member is labeled with a single color, it indicates that a labeled gene was expressed only in one sample. The labeling of a nucleic acid member comprising an array with both colors indicates that the gene was expressed in both samples. Even genes expressed once per cell are detected (1 part in 100,000 sensitivity). A difference in expression intensity in the two samples being compared is indicative of differential expression, the ratio of the intensity in the two samples being not equal to 1.0, greater than 1.1, 1.2, 1.3, 1.4, 1.5, 1.6, 1.7, 1.8, 2.0, 3.0, 4.0 and the like or less than 0.9, 0.8, 0.7, 0.6, 0.5, 0.4, 0.3, 0.2 and the like.

PCR

In one aspect of the invention, the level of the expression of the RNA products of the biomarkers of the invention can be measured by amplifying the RNA products of the biomarkers from a sample by first using reverse transcription (RT). Either in combination, or as a second reaction step, the reverse transcribed product can then be amplified with the polymerase chain reaction (PCR). In accordance with one embodiment of the invention, the PCR can be QRT-PCR as would be understood to a person skilled in the art.

Total RNA, or mRNA from a sample is used as a template and a primer specific to the transcribed portion of a biomarker of the invention is used to initiate reverse transcription. Methods of reverse transcribing RNA into cDNA are well known and described in Sambrook et al., 1989, supra. Primer design can be accomplished utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, Methods Enzymol., 155: 335, which is incorporated herein by reference. PCR is performed using template DNA (at least lfg; more usefully, 1-1000 ng) and at least 25 pmol of oligonucleotide primers. A typical reaction mixture includes: 2 ml of DNA, 25 pmol of oligonucleotide primer, 2.5 ml of 10H PCR buffer 1 (Perkin-Elmer, Foster City, Calif.), 0.4 ml of 1.25 mM dNTP, 0.15 ml (or 2.5 units) of Taq DNA polymerase (Perkin Elmer, Foster City, Calif.) and deionized water to a total volume of 25 ml. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

QRT-PCR (Quantitative real time RT-PCR), can also be performed to provide a quantitative measure of gene expression levels. Similar to reverse transcription PCR, QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in 96 well plates, 384 well plates and the like so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercolating dye such as the commercially available QuantiTect SYBR Green PCR (Qiagen, Valencia Calif.). QRT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the flourescense increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880), isothermal amplification method (see, e.g., Walker et al. (1992) PNAS 89:382-396), strand displacement amplification (SDA), repair chain reaction, Asymmetric Quantitative PCR (see, e.g., U.S. Publication No. US20030134307A1) and the multiplex microsphere bead assay described in Fuja et al., 2004, Journal of Biotechnology 108:193-205.

The level of gene expression can be measured by amplifying RNA from a sample using transcription based amplification systems (TAS), including nucleic acid sequence amplification (NASBA) and 3SR. See, e.g., Kwoh et al (1989) PNAS USA 86:1173; International Publication No. WO 88/10315; and U.S. Pat. No. 6,329,179. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 1989. Several techniques for detecting PCR products quantitatively without electrophoresis may also be used according to the invention (see for example *PCR Protocols, A Guide to Methods and Applications*, Innis et al., Academic Press, Inc. N.Y., (1990)). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

Amplification products must be visualized in order to confirm amplification of the nucleic acid sequences of interest. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe in one embodiment is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 1989, supra. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

One embodiment of the invention includes the primers and probes in Table 4, 6, 16 or 17 can be used for use in measuring the expression of the biomarkers of the invention.

Nuclease Protection Assays

In another embodiment of the invention, Nuclease protection assays (including both ribonuclease protection assays and S1 nuclease assays) can be used to detect and quantitate the RNA products of the biomarkers of the invention. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Northern Blots

A standard Northern blot assay can also be used to ascertain an RNA transcript size, identify alternatively spliced RNA transcripts, and the relative amounts of RNA products of the biomarker of the invention, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

(N) Techniques to Measure the Protein Products of the Biomarkers of the Invention Antibody Based Methodologies Standard techniques can also be utilized for determining the amount of the protein or proteins of interest present in a sample. For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, in one embodiment an antibody with a detectable label.

For such detection methods, protein from the sample to be analyzed can easily be isolated using techniques which are well known to those of skill in the art. Protein isolation methods can, for example, be such as those described in Harlow and Lane (Harlow, E. and Lane, D., *Antibodies: A Laboratory Manual*, Cold Spring Harbor Laboratory Press, Cold Spring Harbor, N.Y. (1988)).

In some embodiments, methods for the detection of the protein or proteins of interest involve their detection via interaction with a protein-specific antibody. For example, antibodies directed a protein of interest can be utilized as described herein. Antibodies can be generated utilizing standard techniques well known to those of skill in the art. See, e.g., Section 15.13.2 of this application and Section 5.2 of U.S. Publication No. 20040018200 for a more detailed discussion of such antibody generation techniques, which is incorporated herein by reference. Briefly, such antibodies can be polyclonal, or monoclonal. An intact antibody, or an antibody fragment (e.g., Fab or $F(ab')_2$) can, for example, be used. In some embodiments, the antibody is a human or humanized antibody.

Table 5 and Table 15 are tables showing, in one embodiment of the invention, antibodies which are used to detect the proteins of the biomarkers of the invention.

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labeled antibody thereto that is directed to a protein. The antibody (or fragment) can be applied by overlaying the labeled antibody (or fragment) onto a biological sample. Through the use of such a procedure, it is possible to determine not only the presence of the protein of interest, but also its distribution, its presence in cells (e.g., intestinal cells and lymphocytes) within the sample. A wide variety of well-known histological methods (such as staining procedures) can be utilized in order to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

For example, the biological sample can be brought in contact with and immobilized onto a solid phase support or carrier such as nitrocellulose, or other support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on support can then be detected by conventional means.

By "solid phase support or carrier" in the context of proteinaceous agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme which is bound to the antibody will react with an appropriate substrate, in one embodiment a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}I$, $^{131}I$, $^{35}S$ or $^{3}H$) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}Eu$, or others of the lanthanide series. These metals can be attached to the antibody using such metal chelating groups as diethylenetriaminepentacetic acid (DTPA) or ethylenediamine-tetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Protein Arrays

Polypeptides which specifically and/or selectively bind to the protein products of the biomarkers of the invention can be immobilized on a protein array. The protein array can be used as a tool, e.g., to test individual samples (such as isolated cells, tissue, lymph, lymph tissue, blood, synovial fluid, sera, biopsies, and the like) for the presence of the polypeptides protein products of the biomarkers of the invention. The protein array can also include antibodies as well as other ligands, e.g., that bind to the polypeptides encoded by the biomarkers of the invention.

Methods of producing polypeptide arrays are described, e.g., in De Wildt et al., 2000, Nature Biotech. 18:989-994; Lueking et al., 1999, Anal. Biochem. 270:103-111; Ge, 2000, Nuc. Acids Res. 28:e3; MacBeath and Schreiber, 2000, Science 289:1760-1763; International Publication Nos. WO 01/40803 and WO 99/51773A1; and U.S. Pat. No. 6,406,921. Polypeptides for the array can be spotted at high speed, e.g., using commercially available robotic apparatus, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the polypeptide ligands can be grown on a filter in an arrayed format. Polypeptide production is induced, and the expressed antibodies are immobilized to the filter at the location of the cell. Information about the extent of binding at each address of the array can be stored as a profile, e.g., in a computer database.

In one embodiment the array is an array of protein products of the 1, 2, 3, 4, 5, 6, 7, 8, 9, 10, 11, 12, 13, 14, 15, 16, 17, 18 or all or any combination of the biomarkers of the invention. In one aspect, the invention provides for antibodies that are bound to an array which selectively bind to the protein products of the biomarkers of the invention.

(O) Protein Production

Standard recombinant nucleic acid methods can be used to express a polypeptide or antibody of the invention (e.g., a protein products of a biomarker of the invention). Generally, a nucleic acid sequence encoding the polypeptide is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Polypeptides comprising the 5' region, 3' region or internal coding region of a biomarker of the invention, are expressed from nucleic acid expression vectors containing only those nucleotide sequences corresponding to the 5' region, 3' region or internal coding region of a biomarker of the invention. Methods for producing antibodies directed to protein products of a biomarker of the invention, or polypeptides encoded by the 5' region, 3' region or internal coding regions of a biomarker of the invention.

The expression vector for expressing the polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK23-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual,* 3rd Edition, Cold Spring Harbor Laboratory, N.Y. (2001) and Ausubel et al., *Current Protocols in Molecular Biology* (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters. In specific embodiments, the promoter is an inducible promoter. In other embodiments, the promoter is a constitutive promoter. In yet other embodiments, the promoter is a tissue-specific promoter.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRPl genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and in some embodiments, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention provides host cells genetically engineered to contain the polynucleotides of the invention. For example, such host cells may contain nucleic acids of the invention introduced into the host cell using known transformation, transfection or infection methods. The present invention also provides host cells genetically engineered to express the polynucleotides of the invention, wherein such polynucleotides are in operative association with a regulatory sequence heterologous to the host cell which drives expression of the polynucleotides in the cell.

The present invention further provides host cells containing the vectors of the present invention, wherein the nucleic acid has been introduced into the host cell using known transformation, transfection or infection methods. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)). Cell-free translation systems can also be employed to produce such proteins using RNAs derived from the DNA constructs of the present invention.

Any host/vector system can be used to express one or more of the proteins products of the biomarkers of the invention including those listed in Table 3 and/or Table 13. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety. The most preferred host cells are those which do not normally express the particular polypeptide or which expresses the polypeptide at low natural level.

In a specific embodiment, the host cells are engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The host of the present invention may also be a yeast or other fingi. In yeast, a number of vectors containing constitutive or inducible promoters may be used. For a review see, Ausubel et al. (eds), *Current Protocols in Molecular Biology*, Vol. 2, Greene Publish. Assoc. & Wiley Interscience, Ch. 13 (1988); Grant et al., 1987, "Expression and Secretion Vectors for Yeast", Methods Enzymol. 153:516-544; Glover, *DNA Cloning*, Vol. II, IRL Press, Wash., D.C., Ch. 3 (1986); Bitter, 1987, "Heterologous Gene Expression in Yeast", Methods Enzymol. 152:673-684; and Strathern et al. (eds), *The Molecular Biology of the Yeast Saccharomyces*, Cold Spring Harbor Press, Vols. I and II (1982).

Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli*, enterobacteriaceae such as *Serratia marescans*, bacilli such as *Bacillus subtilis, Salmonella typhinmurium*, pseudomonads or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

Various mammalian cell culture systems can also be employed to express recombinant protein. Examples of mammalian expression systems include the monkey COS cells such as COS-7 lines of monkey kidney fibroblasts, described by Gluzman, 1981, Cell 23:175 (1981), Chinese Hamster Ovary (CHO) cells, human kidney 293 cells, human epidermal A431 cells, human Colo205 cells, 3T3 cells, CV-1 cells, normal diploid cells, cell strains derived from in vitro culture of primary tissue, primary explants, HeLa cells, mouse L cells, BHK, HL-60, U937, HaK, C127, 3T3, or Jurkat cells, and other cell lines capable of expressing a compatible vector. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

Microbial cells employed in expression of proteins can be disrupted by any convenient method, including freeze-thaw cycling, sonication, mechanical disruption, or use of cell lysing agents. Recombinant polypeptides produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine.

Recombinant proteins can be isolated using an technique well-known in the art. Scopes (*Protein Purification: Principles and Practice*, Springer-Verlag, New York (1994)), for example, provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography.

(P) Methods for Identifying Compounds for Use in the Prevention, Treatment, or Amelioration of One or More Colorectal Pathologies Methods to Identify Compounds that Modulate the Expression or Activity of a Biomarker The present invention provides methods of identifying compounds that bind to the products of the biomarkers of the invention. The present invention also provides methods for identifying compounds that modulate the expression and/or activity of the products of the biomarkers of the invention. The compounds identified via such methods are useful for the development of one or more animal models to study colorectal pathology including polyps or one or more subtypes of polyps. Further, the compounds identified via such methods are useful as lead compounds in the development of prophylactic and therapeutic compositions for prevention, treatment, and/or amelioration of one or more colorectal pathologies including one or more polyps or one or more subtypes of polyps. Such methods are particularly useful in that the effort and great expense involved in testing potential prophylactics and therapeutics in vivo is efficiently focused on those compounds identified via the in vitro and ex vivo methods described herein.

The present invention provides a method for identifying a compound to be tested for an ability to prevent, treat, or ameliorate one or more colorectal pathologies said method comprising: (a) contacting a cell expressing a protein products of one or more biomarkers of the invention or a fragment thereof, or RNA products of one or more biomarkers of the invention or a fragment thereof with a test compound; and (b) determining the ability of the test compound to bind to the protein products, protein fragment, RNA products, or RNA portion so that if a compound binds to the protein products, protein fragment, RNA products, RNA portions, a compound to be tested for an ability to prevent, treat, or ameliorate one or more colorectal pathologies is identified. The cell, for example, can be a prokaryotic cell, yeast cell, viral cell or a cell of mammalian origin. Determining the ability of the test compound to bind to the protein products, protein fragment, RNA products, or RNA portion can be accomplished, for example, by coupling the test compound with a radioisotope or enzymatic label such that binding of the test compound to the protein products, protein fragment, RNA products, or RNA portion can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a specific embodiment, the assay comprises contacting a cell which expresses a protein products of one or more biomarkers of the invention or a fragment thereof, or a RNA products of one or more biomarkers of the invention or a fragment thereof, with a known compound which binds the protein products, protein fragment, RNA products, or RNA portion to form an assay mixture, contacting the assay mixture with a test compound, and determining the ability of the test compound to interact with the protein products, protein fragment, RNA products, or RNA portion, wherein determining the ability of the test compound to interact with the protein products, protein fragment, RNA products, or RNA portion comprises determining the ability of the test compound to preferentially bind to the protein products, protein fragment, RNA products, or RNA portion as compared to the known compound.

Binding of the test compound to the protein products or protein fragment can be determined either directly or indirectly. In a specific embodiment, the assay includes contacting a protein products of one or more biomarkers of the invention or a fragment thereof, or one or more RNA products of one or more biomarkers of the invention or a portion thereof with a known compound which binds the protein products, protein fragment, RNA products, or RNA portion to form an assay mixture, contacting the assay mixture with a test compound, and determining the ability of the test compound to interact with the protein products, protein fragment, RNA products, or RNA portion, wherein determining the ability of the test compound to interact with the protein products, protein fragment, RNA products, or RNA portion comprises determining the ability of the test compound to preferentially bind to the protein products, protein fragment, RNA products, or RNA portion as compared to the known compound. Techniques well known in the art can be used to determine the binding between a test compound and a protein products of a biomarker of the invention or a fragment thereof, or a RNA products of a biomarker of the invention or a portion thereof.

In some embodiments of the above assay methods of the present invention, it may be desirable to immobilize a RNA products of a biomarker of the invention or a portion thereof, or its target molecule to facilitate separation of complexed from uncomplexed forms of the RNA products or RNA portion, the target molecule or both, as well as to accommodate automation of the assay. In more than one embodiment of the above assay methods of the present invention, it may be desirable to immobilize either a protein products of a biomarker of the invention or a fragment thereof, or its target molecule to facilitate separation of complexed from uncomplexed forms of one or both of the proteins, as well as to accommodate automation of the assay. Binding of a test compound to a protein products of a biomarker of the invention or a fragment thereof can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-5-transferase (GST) fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or a protein products of a biomarker of the invention or a fragment thereof, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding of a protein products of a biomarker of the invention or a fragment thereof can be determined using standard techniques.

Other techniques for immobilizing proteins on matrices can also be used in the screening assays of the invention. For example, either a protein products of a biomarker of the invention or a fragment thereof, or a target molecule can be immobilized utilizing conjugation of biotin and streptavidin. A biotinylated protein products of a biomarker of the invention or a target molecule can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a protein products of a biomarker of the invention or a fragment thereof can be derivatized to the wells of the plate, and protein trapped in the wells by antibody conjugation. Methods for detecting such complexes, in addition to those described above for the GST-immobilized complexes, include immunodetection of complexes using antibodies reactive with a protein products of a biomarker of the invention, as well as enzyme-linked assays which rely on detecting an enzymatic activity associated with a protein products of a biomarker of the invention or a fragment thereof, or target molecule.

The interaction or binding of a protein products of a biomarker of the invention or a fragment thereof to a test compound can also be determined using such proteins or protein fragments as "bait proteins" in a two-hybrid assay or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and International Publication No. WO 94/10300).

The present invention provides a method for identifying a compound to be tested for an ability to prevent, treat, or ameliorate one or more colorectal pathologies, said method comprising: (a) contacting a cell expressing a protein or RNA products of one or more biomarkers of the invention with a test compound; (b) determining the amount of the protein or RNA products present in (a); and (c) comparing the amount in (a) to that present in a corresponding control cell that has not been contacted with the test compound, so that if the amount of the protein or RNA products is altered relative to the amount in the control, a compound to be tested for an ability to prevent, treat, or ameliorate one or more colorectal pathologies is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control as determined by utilizing an assay described herein (e.g., a microarray or QRT-PCR) or an assay well known to one of skill in the art. In alternate embodiments, such a method comprises determining the amount of the protein or RNA products of at least 2, at least 3, at least 4, at least 5, at least 6, at least 7, at least 8, 1 to 3, 1 to 5, 1-8, all or any combination of the biomarkers of the invention present in the cell and comparing the amounts to those present in the control.

The cells utilized in the cell-based assays described herein can be engineered to express a biomarker of the invention utilizing techniques known in the art. See, e.g., Section III entitled "Recombinant Expression Vectors and Host Cells" of U.S. Pat. No. 6,245,527, which is incorporated herein by reference. Alternatively, cells that endogenously express a biomarker of the invention can be used. For example, intestinal cells may be used.

In a specific embodiment, intestinal cells are isolated from a "normal" individual, or an individual with one or more colorectal pathologies and are incubated in the presence and absence of a test compound for varying amounts of time (i.e., 30 min, 1 hr, 5 hr, 24 hr, 48 hr and 96 hrs). When screening for prophylactic or therapeutic agents, a clone of the full sequence of a biomarker of the invention or functional portion thereof is used to transfect the cells. The transfected cells are cultured for varying amounts of time (i.e., 1, 2, 3, 5, 7, 10, or 14 days) in the presence or absence of test compound. Following incubation, target nucleic acid samples are prepared from the cells and hybridized to a nucleic acid probe corresponding to a nucleic acid sequence which are differentially expressed in individuals with one or more colorectal pathologies. The nucleic acid probe is labeled, for example, with a radioactive label, according to methods well-known in the art and described herein. Hybridization is carried out by northern blot, for example as described in Ausubel et al., supra or Sambrook et al., supra). The differential hybridization, as defined herein, of the target to the samples on the array from normal relative to RNA from samples having one or more colorectal pathologies is indicative of the level of expression of RNA corresponding to a differentially expressed specific nucleic acid sequence. A change in the level of expression of the target sequence as a result of the incubation step in the presence of the test compound, is indicative of a compound that increases or decreases the expression of the corresponding polyp biomarker specific nucleic acid sequence.

The present invention also provides a method for identifying a compound to be tested for an ability to prevent, treat, or ameliorate one or more colorectal pathologies, said method comprises: (a) contacting a cell-free extract (e.g., an intestinal cell extract) with a nucleic acid sequence encoding a protein or RNA products of one or more biomarkers of the invention and a test compound; (b) determining the amount of the protein or RNA product present in (a); and (c) comparing the amount(s) in (a) to that present to a corresponding control that has not been contacted with the test compound, so that if the amount of the protein or RNA product is altered relative to the amount in the control, a compound to be tested for an ability to prevent, treat, or ameliorate one or more colorectal pathologies is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control sample determined by utilizing an assay described herein (e.g., a microarray or QRT-PCR) or an assay well known to one of skill in the art. In alternate embodiments, such a method comprises determining the amount of a protein or RNA product of at least 2, at least 3, at least 4, at least 5, at least 6, at least 7, at least 8, 1 to 3, 1 to 5, 1-8, all or any combination of the biomarkers of the invention present in the extract and comparing the amounts to those present in the control.

In certain embodiments, the amount of RNA product of a biomarker of the invention is determined, in other embodiments, the amount of protein products of a biomarker of the invention is determined, while in still other embodiments, the amount of RNA and protein products of a biomarker of the invention is determined. Standard methods and compositions for determining the amount of RNA or protein products of a biomarker of the invention can be utilized. Such methods and compositions are described in detail above.

Kits to Identify Compounds that Modulate the Expression or Activity of a Biomarker In specific embodiments, in a screening assay described herein, the amount of protein or RNA product of a biomarker of the invention is determined utilizing kits. Such kits comprise materials and reagents required for measuring the expression of at least 1, at least 2, at least 3, at least 4, at least 5, at least 6, at least 7, at least 8 protein or RNA products of at least 1, at least 2, at least 3, at least 4, at least 5, at least 6, at least 7, at least 8, all or any combination of the biomarkers of the invention. In specific embodiments, the kits may further comprise one or more additional reagents employed in the various methods, such as: (1) reagents for purifying RNA from blood; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA transcript (in some embodiments, mRNA) for use as a control.

In some embodiments, the kits are QRT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In a specific embodiment, kits for measuring a RNA product of a biomarker of the invention comprise materials and reagents that are necessary for measuring the expression of the RNA product. For example, a microarray or QRT-PCR kit may be used and contain only those reagents and materials necessary for measuring the levels of RNA products of at least 1, at least 2, at least 3, at least 4, at least 5, at least 6, at least 7, at least 8, all or any combination of the biomarkers of the invention. Alternatively, in some embodiments, the kits can comprise materials and reagents that are not limited to those required to measure the levels of RNA products of 1, 2, 3, 4, 5, 6, 7, 8 all or any combination of the biomarkers of the invention. For example, a microarray kit may contain reagents and materials necessary for measuring the levels of RNA products 1, 2, 3, 4, 5, 6, 7, 8, all or any combination of the biomarkers of the invention, in addition to reagents and materials necessary for measuring the levels of the RNA products of at least 1, at least 2, at least 3, at least 4, at least 5, at least 6, at least 7, at least 8, or more genes other than the biomarkers of the invention. In a specific embodiment, a microarray or QRT-PCR kit contains reagents and materials necessary for measuring the levels of RNA products of at least 1, at least 2, at least 3, at least 4, at least 5, at least 6, at least 7, at least 8, all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 or more genes that are not biomarkers of the invention.

For nucleic acid microarray kits, the kits generally comprise probes attached or localized to a support surface. The probes may be labeled with a detectable label. In a specific embodiment, the probes are specific for the 5' region, the 3' region, the internal coding region, an exon(s), an intron(s), an exon junction(s), or an exon-intron junction(s), of 1,2,3, 4, 5, 6, 7, 8, all or any combination of the biomarkers of the invention. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For QRT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, 8, all or any combination of the biomarkers of the invention. The QRT-PCR kits may also comprise enzymes suitable for reverse transcribing and/or amplifying nucleic acids (e.g., polymerases such as Taq, enzymes such as reverse transcriptase etc.), and deoxynucleotides and buffers needed for the reaction mixture for reverse transcription and amplification. The QRT-PCR kits may also comprise biomarker specific sets of primers specific for 1, 2, 3, 4, 5, 6, 7, 8, all or any combination of the biomarkers of the invention. The QRT-PCR kits may also comprise biomarker specific probes which are specific for the sequences amplified from 1, 2, 3, 4, 5, 6, 7, 8, all or any combination of the biomarkers of the invention using the biomarker specific sets of primers. The probes may or may not be labeled with a detectable label (e.g., a fluorescent label). In some embodiments, when contemplating multiplexing it is helpful if the probes are labeled with a different detectable label (e.g. FAM or HEX) Each component of the QRT-PCR kit is generally in its own suitable container. Thus, these kits generally comprise distinct containers suitable for each individual reagent, enzyme, primer and probe. Further, the QRT-PCR kits may comprise instructions for performing the assay and methods for interpreting and analyzing the data resulting from the performance of the assay.

For antibody based kits, the kit can comprise, for example: (1) a first antibody (which may or may not be attached to a support) which binds to protein of interest (e.g., a protein products of 1, 2, 3, 4, 5, 6, 7, 8, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

Reporter gene-based assays may also be conducted to identify a compound to be tested for an ability to prevent, treat, or ameliorate one or more colorectal pathologies. In a specific embodiment, the present invention provides a method for identifying a compound to be tested for an ability to prevent, treat, or ameliorate one or more colorectal pathologies, said method comprising: (a) contacting a compound with a cell expressing a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control cell that has not been contacted with the test compound, so that if the amount of expressed reporter gene is altered relative to the amount in the control cell, a compound to be tested for an ability to prevent, treat, or ameliorate one or more colorectal pathologies is identified. In accordance with this embodiment, the cell may naturally express the biomarker or be engineered to express the biomarker. In another embodiment, the present invention provides a method for identifying a compound to be tested for an ability to prevent, treat, or ameliorate one or more colorectal pathologies, said method comprising: (a) contacting a compound with a cell-free extract and a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control that has not been contacted with the test compound, so that if the amount of expressed reporter gene is altered relative to the amount in the control, a compound to be tested for an ability to prevent, treat, or ameliorate one or more colorectal pathologies is identified.

Any reporter gene well-known to one of skill in the art may be used in reporter gene constructs used in accordance with the methods of the invention. Reporter genes refer to a nucleotide sequence encoding a RNA transcript or protein that is readily detectable either by its presence (by, e.g., RT-PCR, Northern blot, Western Blot, ELISA, etc.) or activity. Non-limiting examples of reporter genes are listed in Table 10. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

In accordance with the invention, cells that naturally or normally express one or more, all or any combination of the biomarkers of the invention can be used in the methods described herein. Alternatively, cells can be engineered to express one or more, all or any combination of the biomarkers of the invention, or a reporter gene using techniques well-known in the art and used in the methods described herein. Examples of such techniques include, but are not to, calcium phosphate precipitation (see, e.g., Graham & Van der Eb, 1978, Virol. 52:546), dextran-mediated transfection, calcium phosphate mediated transfection, polybrene mediated transfection, protoplast fusion, electroporation, encapsulation of the nucleic acid in liposomes, and direct microinjection of the nucleic acid into nuclei.

In a specific embodiment, the cells used in the methods described herein are intestinal cells or cell lines, lymphocytes (T or B lymphocytes), monocytes, neutrophils, macrophages, eosinophils, basophils, erythrocytes or platelets. In a preferred embodiment, the cells used in the methods described herein are intestinal cells. In another preferred embodiment, the cells used in the methods described herein are lymphocytes. In another embodiment, the cells used in the methods described herein are immortalized cell lines derived from a source, e.g., a tissue.

Any cell-free extract that permits the translation, and optionally but preferably, the transcription, of a nucleic acid can be used in accordance with the methods described herein. The cell-free extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a specific embodiment, the human cells are HeLa cells, lymphocytes, or intestinal cells or cell lines.

In addition to the ability to modulate the expression levels of RNA and/or protein products a biomarker of the invention, it may be desirable, at least in certain instances, that compounds modulate the activity of a protein products of a biomarker of the invention. Thus, the present invention provides methods of identifying compounds to be tested for an ability to prevent, treat, or ameliorate one or more colorectal pathologies, comprising methods for identifying compounds that modulate the activity of a protein products of one or more biomarkers of the invention. Such methods can comprise: (a) contacting a cell expressing a protein products of one or more biomarkers of the invention with a test compound; (b) determining the activity level of the protein products; and (c) comparing the activity level to that in a corresponding control cell that has not been contacted with the test compound, so that if the level of activity in (a) is altered relative to the level of activity in the control cell, a compound to be tested for an ability to prevent, treat, or ameliorate one or more colorectal pathologies is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or QRT-PCR) or an assay well known to one of skill in the art. In alternate embodiments, such a method comprises determining the activity level of a protein products of at least 2, at least 3, at least 4, at least 5, at least 6, at least 7, at least 8, at least 9, at least 10, at least 12, at least 15, 1 to 5, 1-10, 5-10, 5-15, or 10-15, or more, or all or any combination of the biomarkers of the invention present in the cell and comparing the activity levels to those present in the control.

The present invention provides methods of identifying compounds to be tested for an ability to prevent, treat, or ameliorate one or more colorectal pathologies, comprising: (a) contacting a cell-free extract with a nucleic acid encoding a protein products of one or more biomarkers of the invention and a test compound; (b) determining the activity level of the protein products; and (c) comparing the activity level to that in a corresponding control that has not been contacted with the test compound, so that if the level of activity in (a) is altered relative to the level of activity in the control, a compound to be tested for an ability to prevent, treat, or ameliorate one or more colorectal pathologies is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or QRT-PCR) or an assay well known to one of skill in the art. In alternate embodiments, such a method comprises determining the activity level of a protein products of at least 2, at least 3, at least 4, at least 5, at least 6, at least 7, at least 8, 1 to 3, 1 to 5, 1-8 all or any combination of the biomarkers of the invention present in the sample and comparing the activity levels to those present in the control.

Standard techniques can be utilized to determine the level of activity of a protein products of a biomarker of the invention. Activities of protein products of biomarkers of the invention that can be determined using techniques well known in the art.

Method to Utilize the Biological Activity of the Compounds

Upon identification of compounds to be tested for an ability to prevent, treat, or ameliorate one or more colorectal pathologies (for convenience referred to herein as a "lead" compound), the compounds can be further investigated. For example, the compounds identified via the present methods can be further tested in vivo in accepted animal models of polyp formation. Further, the compounds identified via the methods can be analyzed with respect to their specificity. Techniques for such additional compound investigation are well known to one of skill in the art.

In one embodiment, the effect of a lead compound can be assayed by measuring the cell growth or viability of the target cell. Such assays can be carried out with representative cells of cell types involved in polyp formation (e.g., intestinal cells; cells isolated from different portions of the gastrointestinal system and the like). Alternatively, instead of culturing cells from a patient, a lead compound may be screened using cells of a cell line.

Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or ($^3$H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and RNA (e.g., mRNA) and activity can be determined by any method well known in the art. For example, protein can be quantitated by known immunological based methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

Animal Models

Compounds can be tested in suitable animal model systems prior to use in humans. Such animal model systems include but are not limited to rats, mice, chicken, cows, monkeys, pigs, dogs, rabbits, etc. Any animal system well-known in the art may be used. In certain embodiments, compounds are tested in a mouse model. Compounds can be administered repeatedly.

Accepted animal models can be utilized to determine the efficacy of the compounds identified via the methods described above for the prevention, treatment, and/or amelioration of one or more colorectal pathologies.

Toxicity

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to the proteins of interest (i.e., the protein products of a biomarker of the invention) using the above-described screens for biologic activity. Alternatively, lead compounds with little or no biologic activity, as ascertained in the screen, can also be used to design analogs and congeners of the compound that have biologic activity.

Compounds

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, L A 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272); Further any kind of natural products may be screened using the methods of the invention, including microbial, fungal, plant or animal extracts.

Compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Furthermore, diversity libraries of test compounds, including small molecule test compounds, may be utilized. Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (in some embodiments, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as $\alpha$-amino phosphoric acids and $\alpha$-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a specific embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available For example, libraries may be commercially obtained from, e.g., Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), Asinex (Moscow, Russia), ComGenex (Princeton, N.J.), Ru, Tripos, Inc. (St. Louis, Mo.), ChemStar, Ltd (Moscow, Russia), 3D Pharmaceuticals (Exton, Pa.), and Martek Biosciences (Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will in some embodiments be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264: 399; and Stevanovic et al., 1993, Bioorg. Med. Chem. Lett. 3:431).

Combinatorial compound libraries useful for the methods of the present invention can be synthesized on supports. In one embodiment, a split synthesis method, a protocol of separating and mixing supports during the synthesis, is used to synthesize a library of compounds on supports (see e.g. Lam et al., 1997, Chem. Rev. 97:41-448; Ohlmeyer et al., 1993, Proc. Natl. Acad. Sci. USA 90:10922-10926 and references cited therein). Each support in the final library has substantially one type of compound attached to its surface. Other methods for synthesizing combinatorial libraries on supports, wherein one product is attached to each support, will be known to those of skill in the art (see, e.g., Nefzi et al., 1997, Chem. Rev. 97:449-472).

In some embodiments of the present invention, compounds can be attached to supports via linkers. Linkers can be integral and part of the support, or they may be nonintegral that are either synthesized on the support or attached thereto after synthesis. Linkers are useful not only for providing points of compound attachment to the support, but also for allowing different groups of molecules to be cleaved from the support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the support prior to high throughput screening of the compounds.

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds. Examples of such techniques include, but are not limited to, mass spectrometry, NMR spectroscopy, X-ray crytallography and vibrational spectroscopy.

(Q) Use of Identified Compounds to Prevent, Treat, or Ameliorate One or more Colorectal Pathologies The present invention provides methods of preventing, treating, or ameliorating one or more colorectal pathologies, said methods comprising administering to a subject in need thereof one or more compounds identified in accordance with the methods of the invention. In a preferred embodiment, the individual is human.

In one embodiment, the invention provides a method of preventing, treating, or ameliorating one or more colorectal pathologies, said method comprising administering to an individual in need thereof a dose of a prophylactically or therapeutically effective amount of one or more compounds identified in accordance with the methods of the invention. In a specific embodiment, a compound identified in accordance with the methods of the invention is not administered to prevent, treat, or ameliorate one or more colorectal pathologies, if such compound has been used previously to prevent, treat, or ameliorate one or more colorectal pathologies. In another embodiment, a compound identified in accordance with the methods of the invention is not administered to prevent, treat, or ameliorate one or more colorectal pathologies, if such compound has suggested to be used to prevent, treat, or ameliorate one or more colorectal pathologies. In another embodiment, a compound identified in accordance with the methods of the invention specifically binds to and/or alters the expression and/or activity level of a protein or RNA products of only one biomarker of the invention. In another embodiment, a compound identified in accordance with the methods of the invention is not administered to prevent, treat, or ameliorate one or more colorectal pathologies, if such compound binds to and/or alters the expression and/or activity of a protein or RNA products of 1, 2, 3, 4, 5, 6, 7, 8, 9, 10, 11, 12, 13, 14, 15, 16, 17, 18, or more or all or any combination of the biomarkers of Tables 2 or 6. In yet another embodiment, a compound identified in accordance with the methods of the invention binds to and/or alters the expression and/or activity level of a protein or RNA products of at least 2, at least 3, at least 4, at least 5, at least 10, at least 15, or more biomarkers of the invention.

The invention also provides methods of preventing, treating, or ameliorating one or more colorectal pathologies, said methods comprising administering to a subject in need thereof one or more of the compounds identified utilizing the screening methods described herein, and one or more other therapies (e.g., prophylactic or therapeutic agents and surgery). In a specific embodiment, such therapies are currently being used, have been used or are known to be useful in the prevention, treatment, or amelioration of one or more colorectal pathologies (including, but not limited to the prophylactic or therapeutic agents listed herein). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in an assay described herein is administered to an individual, in some embodiments a human, to prevent, treat, or ameliorate one or more colorectal pathologies. In accordance with the invention, the pharmaceutical composition may also comprise one or more prophylactic or therapeutic agents. In some embodiments, such agents are currently being used, have been used or are known to be useful in the prevention, treatment, or amelioration of one or more colorectal pathologies.

(R) Compounds of the Invention

Representative, non-limiting examples of compounds that can be used in accordance with the methods of the invention to prevent, treat, and/or ameliorate one or more colorectal pathologies are described in detail below.

First, such compounds can include, for example, antisense, ribozyme, or triple helix compounds that can downregulate the expression or activity of a protein or RNA products of a biomarker of the invention. Such compounds are described in detail in the subsection below.

Second, such compounds can include, for example, antibody compositions that can modulate the expression of a protein or RNA products of a biomarker of the invention, or the activity of a protein products of a biomarker of the invention. In a specific embodiment, the antibody compositions downregulate the expression a protein or RNA products of a biomarker of the invention, or the activity of a protein products of a biomarker of the invention. Such compounds are described in detail in the subsection below.

Third, such compounds can include, for example, protein products of a biomarker of the invention. The invention encompasses the use of peptides or peptide mimetics selected to mimic a protein products of a biomarker of the invention to prevent, treat, or ameliorate one or more colorectal pathologies. Further, such compounds can include, for example, dominant-negative polypeptides that can modulate the expression a protein or RNA products of a biomarker of the invention, or the activity protein products of a biomarker of the invention.

The methods also encompass the use derivatives, analogs and fragments of protein products of a biomarker of the invention to prevent, treat, or ameliorate one or more colorectal pathologies. In particular, the invention encompasses the use of fragments of protein products of a biomarker of the invention comprising one or more domains of such a protein(s) to prevent, treat, or ameliorate one or more colorectal pathologies. In another specific embodiment, the invention encompasses the use of a protein products of a biomarker of the invention, or an analog, derivative or fragment of such a protein which is expressed as a fusion, or chimeric protein products (comprising the protein, fragment, analog, or derivative joined via a peptide bond to a heterologous protein sequence).

In specific embodiments, an antisense oligonucleotide of at least 1, at least 2, at least 3, at least 4, at least 5, at least 6, at least 7, at least 8, at least 9, at least 10, at least 15, or more of biomarkers of the invention are administered to prevent, treat, or ameliorate one or more colorectal pathologies. In other embodiments, one or more of protein products of a biomarker of the invention or a fragment, analog, or derivative thereof are administered to prevent, treat, or ameliorate one or more colorectal pathologies. In other embodiment, one or more antibodies that specifically bind to protein products of the invention are administered to prevent, treat, or ameliorate one or more colorectal pathologies. In other embodiments, one or more dominant-negative polypeptides are administered to prevent, treat, or ameliorate one or more colorectal pathologies.

Antisense, Ribozyme, Triple-Helix Compositions

Standard techniques can be utilized to produce antisense, triple helix, or ribozyme molecules reactive to one or more of the genes listed in Tables 2 or 6, and transcripts of the genes listed in Tables 2 or 6, for use as part of the methods described herein. First, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue, e.g., a joint (e.g., a knee, hip, elbow, and knuckle), site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or intestinal cell, surface, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an $\alpha$-anomeric nucleic acid molecule. An $\alpha$-anomeric nucleic acid molecule forms specific double-stranded hybrids with complementary RNA in which, contrary to the usual $\alpha$-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660:27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, sup7-a). The synthesis of PNA-DNA chimeras can be performed as described in Hyrup, 1996, supra, and Finn et al., 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Antibody Compositions

In one embodiment, antibodies that specifically bind to one or more protein products of one or more biomarkers of the invention are administered to an individual, in some embodiments a human, to prevent, treat, or ameliorate one or more colorectal pathologies. In another embodiment, any combination of antibodies that specifically bind to one or more protein products of one or more biomarkers of the invention are administered to a subject, in some embodiments a human, to prevent, treat, or ameliorate one or more colorectal pathologies. In a specific embodiment, one or more antibodies that specifically bind to one or more protein products of one or more biomarkers of the invention are administered to a subject, in some embodiments a human, in combination with other types of therapies to prevent, treat, or ameliorate one or more colorectal pathologies.

One or more antibodies that specifically bind to one or more protein products of one or more biomarkers of the invention can be administered to a subject, in some embodiments a human, using various delivery systems are known to those of skill in the art. For example, such antibodies can be administered by encapsulation in liposomes, microparticles or microcapsules. See, e.g., U.S. Pat. Nos. 5,762,904, 6,004,534, and International Publication No. WO 99/52563. In addition, such antibodies can be administered using recombinant cells capable of expressing the antibodies, or retroviral, other viral vectors or non-viral vectors capable of expressing the antibodies.

Antibodies that specifically bind one or more protein products of one or more biomarkers of the invention can be obtained from any known source. For example, Table 5 provides a list of commercially available antibodies specific for one or more of the protein products of the biomarkers of the invention. Alternatively, antibodies that specifically bind to one or more protein products of one or more biomarkers of the invention can be produced by any method known in the art for the synthesis of antibodies, in particular, by chemical synthesis or in some embodiments, by recombinant expression techniques.

Antibodies include, but are not limited to, polyclonal antibodies, monoclonal antibodies, bispecific antibodies, multispecific antibodies, human antibodies, humanized antibodies, camelised antibodies, chimeric antibodies, single-chain Fvs (scFv) (see e.g., Bird et al. (1988) *Science* 242:423-426; and Huston et al. (1988) *Proc. Natl. Acad. Sci. USA* 85:5879-5883), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. The term "antibody", as used herein, refers to immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$, and $IgA_2$) or subclass. Examples of immunologically active fragments of immunoglobulin molecules include F(ab) fragments (a monovalent fragment consisting of the VL, VH, CL and CH1 domains) and F(ab')2 fragments (a bivalent fragment comprising two Fab fragments linked by a disulfide bridge at the hinge region) which can be generated by treating the antibody with an enzyme such as pepsin or papain. Immunologically active fragments also include, but are not limited to, Fd fragments (consisting of the VH and CH1 domains), Fv fragments (consisting of the VL and VH domains of a single arm of an antibody), dAb fragments (consisting of a VH domain; Ward et al., (1989) *Nature* 341:544-546), and isolated complementarity determining regions (CDRs). Antibodies that specifically bind to an antigen can be produced by any method known in the art for the synthesis of antibodies, in particular, by chemical synthesis or in some embodiments, by recombinant expression techniques.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

The term "monospecific antibody" refers to an antibody that displays a single binding specificity and affinity for a particular target, e.g., epitope. This term includes monoclonal antibodies. Monoclonal antibodies can be prepared using a wide variety of techniques known in the art including the use of hybridoma, recombinant, and phage display technologies, or a combination thereof. See, e.g., U.S. Pat. Nos. RE 32,011, 4,902,614, 4,543,439, 4,411,993 and 4,196,265; Kennett et al (eds.), *Monoclonal Antibodies, Hybridomas: A New Dimension in Biological Analyses*, Plenum Press (1980); and Harlow and Lane (eds.), *Antibodies. A Laboratory Manual*, Cold Spring Harbor Laboratory Press (1988), which are incorporated herein by reference. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). Other techniques that enable the production of antibodies through recombinant techniques (e.g., techniques described by William D. Huse et al., 1989, Science, 246: 1275-1281; L. Sastry et al., 1989, Proc. Natl. Acad. Sci. USA, 86: 5728-5732; and Michelle Alting-Mees et al., Strategies in Molecular Biology, 3: 1-9 (1990) involving a commercial system available from Stratacyte, La Jolla, Calif.) may also be utilized to construct monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a protein products of a biomarker of the invention, and once an immune response is detected, e.g., antibodies specific for the protein are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997, Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, in some embodiments, the hybridoma is generated by fusing splenocytes isolated from a mouse immunized with a protein products of a biomarker of the invention, with mycloma cells and then screening the hybridomas resulting from the fusion for hybridoma clones that secrete an antibody able to bind to the protein or protein fragment.

Antibody fragments which recognize specific epitopes of a protein products of a biomarker of the invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. In some embodiments, the vectors for expressing the VH or VL domains comprise an EF-1a promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Antibodies can also be produced by a transgenic animal. In particular, human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

U.S. Pat. No. 5,849,992, for example, describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly. A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab').sub.2, Fabc, Fv) in which all or substantially all of the CDR regions correspond to those of a non-human immunoglobulin (i.e., donor antibody) and all or substantially all of the framework regions are those of a human immunoglobulin consensus sequence. In some embodiments, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most often greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., 2002, J. Immunol. 169:1119-25, Caldas et al., 2000, Protein Eng. 13(5):353-60, Morea et al., 2000, Methods 20(3):267-79, Baca et al., 1997, J. Biol. Chem. 272(16):10678-84, Roguska et al., 1996, Protein Eng. 9(10):895-904, Couto et al., 1995, Cancer Res. 55 (23 Supp): 5973s-5977s, Couto et al., 1995, Cancer Res. 55(8):1717-22, Sandhu J S, 1994, Gene 150(2):409-10, and Pedersen et al., 1994, J. Mol. Biol. 235(3):959-73. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to an antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8): 2429-2438). Such antibodies can be used, alone or in combination with other therapies, in the prevention, treatment, or amelioration of one or more colorectal pathologies.

The invention encompasses polynucleotides comprising a nucleotide sequence encoding an antibody or fragment thereof that specifically binds to an antigen. The invention also encompasses polynucleotides that hybridize under high stringency, intermediate or lower stringency hybridization conditions to polynucleotides that encode an antibody of the invention.

The polynucleotides may be obtained, and the nucleotide sequence of the polynucleotides determined, by any method known in the art. The nucleotide sequences encoding known antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, in some embodiments poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

Once a polynucleotide encoding an antibody molecule, heavy or light chain of an antibody, or fragment thereof (in some embodiments, but not necessarily, containing the heavy or light chain variable domain) of the invention has been obtained, the vector for the production of the antibody molecule may be produced by recombinant DNA technology using techniques well-known in the art.

In one preferred embodiment, monoclonal antibodies are produced in mammalian cells.

Preferred mammalian host cells for expressing the clone antibodies or antigen-binding fragments thereof include Chinese Hamster Ovary (CHO cells) (including dhfr− CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in $dhfr^-$ host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into $difr^-$ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Once an antibody molecule has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or fragments thereof may be fused to heterologous polypeptide sequences known in the art to facilitate purification.

Gene Therapy Techniques

Gene therapy refers to therapy performed by the administration to a subject of an expressed or expressible nucleic acid. Any of the methods for gene therapy available in the art can be used according to the present invention. Exemplary methods are described below.

In specific embodiments, one or more antisense oligonucleotides for one or more biomarkers of the invention are administered to prevent, treat, or ameliorate one or more colorectal pathologies, by way of gene therapy. In other embodiments, one or more nucleic acid molecules comprising nucleotides encoding one or more antibodies that specifically bind to one or more protein products of one or more biomarkers of the invention are administered to prevent, treat, or ameliorate one or more colorectal pathologies, by way of gene therapy. In other embodiments, one or more nucleic acid molecules comprising nucleotides encoding protein products of one or more biomarkers of the invention or analogs, derivatives or fragments thereof, are administered to prevent, treat, or ameliorate one or more colorectal pathologies, by way of gene therapy. In yet other embodiments, one or more nucleic acid molecules comprising nucleotides encoding one or more dominant-negative polypeptides of one or more protein products of one or more biomarker of the invention are administered to prevent, treat, or ameliorate one or more colorectal pathologies, by way of gene therapy.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition of the invention comprises nucleic acid sequences encoding one or more antibodies that specifically bind to one or more protein products of one or more biomarkers of the invention, said nucleic acid sequences being part of expression vectors that express one or more antibodies in a suitable host. In particular, such nucleic acid sequences have promoters operably linked to the antibodies, said promoter being inducible or constitutive, and, optionally, tissue-specific.

In another aspect, a composition of the invention comprises nucleic acid sequences encoding dominant-negative polypeptides of one or protein products of one or more biomarkers of the invention, said nucleic acid sequences being part of expression vectors that express dominant-negative polypeptides in a suitable host. In particular, such nucleic acid sequences have promoters operably linked to the dominant-negative polypeptides, said promoter being inducible or constitutive, and, optionally, tissue-specific. In another particular embodiment, nucleic acid molecules are used in which the dominant-negative coding sequences and any other desired sequences are flanked by regions that promote homologous recombination at a desired site in the genome, thus providing for intrachromosomal expression of the dominant-negative nucleic acids (Koller and Smithies, 1989, Proc. Natl. Acad. Sci. USA 86:8932-8935; Zijlstra et al., 1989, Nature 342: 435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequence is directly administered in vivo, where it is expressed to produce the encoded product. This can be accomplished by any of numerous methods known in the art, e.g., by constructing it as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

For example, a retroviral vector can be used. These retroviral vectors have been modified to delete retroviral sequences that are not necessary for packaging of the viral genome and integration into host cell DNA. The nucleic acid sequences encoding the antibodies of interest, or proteins of interest or fragments thereof to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) and/or intestinal cells are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, intestinal cells, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, nucleic acid sequences encoding antibodies of interest, or proteins of interest or fragments thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., International Publication No. WO 94108598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

Promoters that may be used to control the expression of nucleic acid sequences encoding antibodies of interest, proteins of interest or fragments thereof may be constitutive, inducible or tissue-specific. Non-limiting examples include the SV40 early promoter region (Bemoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus $^{35}$S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fingi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94;

myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

(S) Pharmaceutical Compositions

Biologically active compounds identified using the methods of the invention or a pharmaceutically acceptable salt thereof can be administered to a patient, in some embodiments a mammal, including a human, having one or more colorectal pathologies. In a specific embodiment, a compound or pharmaceutically acceptable salt thereof is administered to a patient, in some embodiments a mammal, including a human, having one or more colorectal pathologies. In another embodiment, a compound or a pharmaceutically acceptable salt thereof is administered to a patient, in some embodiments a mammal, including a human, as a preventative measure against one or more colorectal pathologies. In accordance with these embodiments, the patient may be a child, an adult or elderly, wherein a "child" is a subject between the ages of 24 months of age and 18 years of age, an "adult" is a subject 18 years of age or older, and "elderly" is a subject 65 years of age or older.

When administered to a patient, the compound or a pharmaceutically acceptable salt thereof is administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In a specific embodiment, a compound is administered locally to one or more sections of the gastrointestinal system.

In certain embodiments, it may be desirable to introduce the compound or a pharmaceutically acceptable salt thereof into the gastrointestinal system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

The compounds described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of interest. Such methods comprise formulating a pharmaceutically acceptable carrier with an agent that modulates expression or activity of a polypeptide or nucleic acid of interest. Such compositions can further include additional active agents. Thus, the invention further includes methods for preparing a pharmaceutical composition by formulating a pharmaceutically acceptable carrier with an agent that modulates expression or activity of a polypeptide or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Intravenous administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotopic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the individual to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (more preferably, 0.1 to 20 mg/kg, 0.1-10 mg/kg). Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the gastrointestinal system). A method for lipidation of antibodies is described by Cruikshank et al. (1997, J. Acquired Immune Deficiency Syndromes and Human Retrovirology 14:193).

In a specific embodiment, an effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 0.1 to 1.0 mg/kg, 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat an individual, including but not limited to the severity of the disease or disorder, previous treatments, the general health and/or age of the individual, and other diseases present. Moreover, treatment of a individual with a therapeutically effective amount of a protein, polypeptide, or antibody can include a single treatment or, preferably, can include a series of treatments.

In addition to those compounds described above, the present invention encompasses the use of small molecules that modulate expression or activity of a nucleic acid or polypeptide of interest. Non-limiting examples of small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the individual or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of individual or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an individual (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

(T) Kits

The present invention provides kits for measuring the expression of the protein and RNA products of at least 1, at least 2, at least 3, at least 4, at least 5, at least 6, at least 7, at least 8, at least 9, at least 10, at least 12, at least 15, or all or any combination of the biomarkers of the invention. Such kits comprise materials and reagents required for measuring the expression of such protein and RNA products. In specific embodiments, the kits may further comprise one or more additional reagents employed in the various methods, such as: (1) reagents for purifying RNA from blood; (2) biomarker specific primer sets for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization, washing and/or enzymatic buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA isolated from a sample (e.g., blood) or synthesized for use as a control. In some embodiments kits can include a computer-readable medium which has a formula which uses data representing a level of products of at least one biomarker and generating an indication of the probability that a test subject has one or more colorectal pathologies including one or more polyps or one or more subtypes of polyps. The formula of the computer-readable medium can be generated by using the methods outlined in section (G).

In some embodiments, the kits are PCR kits or Real time PCR kits and/or QRT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In one embodiment, the QRT-PCR kit includes the following: (a) two or more biomarker specific primer sets, each set used to amplify a biomarker within the combination of biomarkers of the invention; (b) buffers and enzymes including a reverse transcriptase; (c) one or more thermos table polymerases; and (d) Sybr® Green. In another embodiment, the kit of the invention can include (a) a reference control RNA and/or (b) a spiked control RNA. In another embodiment, the kit also includes a computer readable medium which has a formula which uses data representing a level of products of at least one biomarker and generating an indication of the probability that a test subject has one or more colorectal pathologies including one or more polyps or one or more subtypes of polyps. The formula of the computer-readable medium can be generated by using the methods outlined in section (G).

The invention provides kits that are useful for testing, detecting, screening, diagnosing, monitoring and prognosing one or more colorectal pathologies including one or more polyps or one or more subtypes of polyps. For example, in a particular embodiment of the invention a kit is comprised a forward and reverse primer wherein the forward and reverse primer are designed to quantitate expression of all of the species of mRNA corresponding to a single distinct biomarker, where each of the distinct biomarkers is selected from the group identified in Tables 1, 2, 11, or 12. In certain embodiments, at least one of the primers of a primer set is designed to span an exon junction of a species of mRNA.

The invention includes kits that are useful for testing, detecting, screening, diagnosing, monitoring and prognosing one or more colorectal pathologies including one or more types or subtypes of polyps based upon the expression levels of protein or RNA products of at least 1, at least 2, at least 3, at least 4, at least 5, at least 6, at least 7, at least 8, or all or any combination of the biomarkers of the invention in a sample.

The invention includes kits useful for monitoring the efficacy of one or more therapies that an individual is undergoing based upon the expression of a protein or RNA products of at least 1, at least 2, at least 3, at least 4, at least 5, at least 6, at least 7, at least 8, or all or any combination of the biomarkers of the invention in a sample.

The invention includes kits using for determining whether an individual will be responsive to a therapy based upon the expression of a protein or RNA products of at least 1, at least 2, at least 3, at least 4, at least 5, at least 6, at least 7, at least 8, or all or any combination of the biomarkers of the invention in a sample.

The invention includes kits for measuring the expression of a RNA products of at least 1, at least 2, at least 3, at least 4, at least 5, at least 6, at least 7, at least 8, or all or any combination of the biomarkers of the invention in a sample. In a specific embodiment, such kits comprise materials and reagents that are necessary for measuring the expression of a RNA products of a biomarker of the invention. For example, a microarray or QRT-PCR kit may be produced for detecting one or more colon pathologies including polyps or one or more subtypes of polyps and contain only those reagents and materials necessary for measuring the levels of RNA products of at least 1, at least 2, at least 3, at least 4, at least 5, at least 6, at least 7, at least 8, or all or any combination of the biomarkers of the invention. Alternatively, in some embodiments, the kits can comprise materials and reagents that are not limited to those required to measure the levels of RNA products of 1, 2, 3, 4, 5, 6, 7, 8 or all or any combination of the biomarkers of the invention. For example, a microarray kit may contain reagents and materials necessary for measuring the levels of RNA products not necessarily associated with or indicative of one or more colorectal pathologies, in addition to reagents and materials necessary for measuring the levels of the RNA products of at least 1, at least 2, at least 3, at least 4, at least 5, at least 6, at least 7, at least 8, or all or any combination of the biomarkers of the invention. In a specific embodiment, a microarray or QRT-PCR kit contains reagents and materials necessary for measuring the levels of RNA products of at least 1, at least 2, at least 3, at least 4, at least 5, at least 6, at least 7, at least 8, or all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes other than the biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, 500-1000 other genes than the biomarkers of the invention.

For nucleic acid micoarray kits, the kits generally comprise probes attached or localized to a support surface. The probes may be labeled with a detectable label. In a specific embodiment, the probes are specific for an exon(s), an intron(s), an exon junction(s), or an exon-intron junction(s)), of RNA products of 1, 2, 3, 4, 5, 6, 7, 8, all or any combination of the biomarkers of the invention. The microarray kits may comprise instructions for performing the assay and methods for interpreting and analyzing the data resulting from the performance of the assay. In a specific embodiment, the kits comprise instructions for detecting or diagnosing one or more colorectal pathologies including one or more polyps or one or more subtypes of polyps. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container. In another embodiment, the kit also includes a computer readable medium which has a formula which uses data representing a level of products of at least one biomarker and generating an indication of the probability that a test subject has one or more colorectal pathologies or a subtype of colorectal pathology including a polyp or one or more subtypes of polyps. The formula of the computer-readable medium can be generated by using the methods outlined in section (G).

For QRT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, 8, or all or any combination of the biomarkers of the invention. The QRT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The QRT-PCR kits may also comprise probes specific for RNA products of 1, 2, 3, 4, 5, 6, 7, 8, or all or any combination of the biomarkers of the invention. The probes may or may not be labeled with a detectable label (e.g., a fluorescent label). Each component of the QRT-PCR kit is generally in its own suitable container. In another embodiment, the kit also includes a computer readable medium which has a formula which uses data representing a level of products of at least one biomarker and generating an indication of the probability that a test subject has one or more colorectal pathologies or a subtype of colorectal pathology including a polyp or one or more subtypes of polyps. The formula of the computer-readable medium can be generated by using the methods outlined in section (G).

Thus, these kits generally comprise distinct containers suitable for each individual reagent, enzyme, primer and probe. Further, the QRT-PCR kits may comprise instructions for performing the assay and methods for interpreting and analyzing the data resulting from the performance of the assay. In a specific embodiment, the kits contain instructions for diagnosing or detecting one or more colorectal pathologies including one or more polyps or one or more subtypes of polyps.

In a specific embodiment, the kit is a QRT-PCR kit. Such a kit may comprise a 96 well plate and reagents and materials necessary for SYBR Green detection. The kit may comprise reagents and materials so that beta-actin can be used to normalize the results. The kit may also comprise controls such as water, phospate buffered saline, and phage MS2 RNA. Further, the kit may comprise instructions for performing the assay and methods for interpreting and analyzing the date resulting from the performance of the assay. In a specific embodiment, the instructions state that the level of a RNA products of 1, 2, 3, 4, 5, 6, 7, 8, all or any combination of the biomarkers of the invention should be examined at two concentrations that differ by, e.g., 5 fold to 10-fold.

For antibody based kits, the kit can comprise, for example: (1) a first antibody (which may or may not be attached to a support) which binds to protein of interest (e.g., a protein products of 1, 2, 3, 4, 5, 6, 7, 8, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for diagnosing or detecting one or more colorectal pathologies including one or more polyps or one or more subtypes of polyps. In another embodiment, the kit contains instructions for applying the data to a formula in the form of a computer readable medium which contains said instructions. Said computer readable medium can also contain instructions for interpreting the analyzing the data resulting from the performance of the assay.

(U) SNPs

A Single Nucleotide Polymorphism (SNP) is a single nucleotide variation at a specific location in the genome of different individuals. SNPs are found in both coding and non-coding regions of genomic DNA. In spite of the paucity of scorable phenotypes, SNPs are found in large numbers throughout the human genome (Cooper et al., Hum Genet. 69:201-205, 1985). SNPs are stable genetic variations frequently found in genes, and contribute to the wide range of phenotypic variations found in organisms. Single nucleotide polymorphisms (SNPs) can be of predictive value in identifying many genetic diseases, as well as phenotypic characteristics. It is known for example that certain SNPs result in disease-causing mutations such as the SNP correlated with heritable breast cancer (Cannon-Albright and Skolnick, Semin. Oncol. 23:1-5, 1996).

A SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization.

The instant invention offers a more focused and efficient method of screening SNPs to identify those SNPs which are specifically associated with one or more colorectal pathologies by having identified a selection of genes which are differentially expressed in blood from individuals having one or more colorectal pathologies as compared with individuals not having said one or more colorectal pathologies. In one aspect of the invention, a selection of SNPs to be screened are those SNPs found in the genes listed in Tables 2 and 6. In another aspect of the invention, novel SNPs can be identified in the disease-associated biomarkers using those methods listed above.

In particular, this invention focuses on methods for identifying those SNPs which are associated with one or more colorectal pathologies by screening only those SNPs in the biomarkers identified herein. Those SNPs which are identified using the methods disclosed herein will be convenient diagnostic markers.

More specifically a SNP is considered to be a polyp associated SNP, if those individuals having one or more colorectal pathologies have a different polymorphism at the SNP locus than those individuals not having the one or more colorectal pathologies. Further, a particular SNP is considered to be diagnostic for one or more colorectal pathologies if a particular polymorphism of the SNP is found to present at a statistically significant higher frequency in those individuals having one or more colorectal pathologies than in those individuals not having the one or more colorectal pathologies. Indices of statistical significance include $p<0.05$, $p<0.001$, $p<0.01$, and $p<0.10$. This invention includes methods of determining the diagnostic value of SNPs with respect to diagnosing or detecting one or more colorectal pathologies.

As would be understood, a preferred sample is blood, but these methods encompass any samples from which DNA can be obtained including epithelial cells, buccal cells, hair, saliva, tissue cells and the like. There are a variety of available methods for obtaining and storing tissue and/or blood samples. These alternatives allow tissue and blood samples to be stored and transported in a form suitable for the recovery of genomic DNA from the samples for genotype analysis. DNA samples can be collected and stored on a variety of solid mediums, including Whatmann paper, Guthrie cards, tubes, swabs, filter paper, slides, or other containers. When whole blood is collected on filter paper, for example, it can be dried and stored at room temperature.

The blood sample may be any one of various types of blood samples, including, for example, a sample of serum-depleted blood, a sample of erythrocyte-depleted blood, a sample of serum-depleted and erythrocyte-depleted blood, a sample of lysed blood, a blood sample which has not been fractionated into cell types and a sample of unfractionated cells of a lysed blood sample. Examples of blood samples are described in Example 1 of the Examples section below.

In another aspect of the invention, polyp associated SNPs can be identified from RNA transcripts of the polyp biomarker genes, listed in Tables 2 and 6, instead of from genomic DNA. In one embodiment, RNA is isolated from a sample such as blood, from individuals with and without the given disease or disorder, and transcripts encoded by these polyp biomarker genes are reversed transcribed into cDNA. The cDNA is amplified and analyzed to determine the presence of SNPs in the polyp biomarker genes. A polyp associated SNP, can be identified by then comparing the distribution of each of the SNPs identified in the polyp associated biomarker gene(s) differentially expressed in those individuals having one or more colorectal pathologies and individuals who do not have one or more colorectal pathologies. In a further variation of this embodiment, instead analyzing cDNA for the presence of SNPs, the RNA transcripts of the disease specific biomarker genes, or their amplified products, are analyzed for the presence of SNPs.

Analysis of genomic DNA comprising the polyp biomarker genes has the potential to identify SNPs in the coding region as well as in regulatory regions, the latter which may contribute to the change in expression levels of the gene. Analysis of cDNA encoded SNPs has the potential to identify only SNPs in the coding region of the polyp biomarker genes, which may be instrumental in deciphering protein based mechanisms of polyp formation. Methods of analyzing cDNA encoded SNPs can be carried out by analyzing the cDNA generated in the reverse transcription PCR reactions described herein that are used to identify the level of the biomarker in samples from patients and non patients.

A polyp associated SNP may be identified in the DNA of the polyp biomarker genes by a number of methods well known to those of skill in the art (see for example U.S. Pat. Nos. 6,221,592 and 5,679,524), including but not limited to identifying the SNP by PCR or DNA amplification, Oligonucleotide Ligation Assay (OLA) (Landegren et al., Science 241:1077, 1988), Doublecode OLA, mismatch hybridization, mass spectrometry, Single Base Extension Assay, (U.S. Pat. No. 6,638,722), RFLP detection based on allele-specific restriction-endonuclease cleavage (Kan and Dozy, Lancet ii: 910-912, 1978), hybridization with allele-specific oligonucleotide probes (Wallace et al., Nucl Acids Res 6:3543-3557, 1978), including immobilized oligonucleotides (Saiki et al., Proc Natl Acad Sci USA 86:6230-6234, 1989) or oligonucleotide arrays (Maskos and Southern, Nucl Acids Res 21:2269-2270, 1993), allele-specific PCR (Newton et al., Nucl Acids Res 17:2503-16, 1989), mismatch-repair detection (MRD) (Faham and Cox, Genome Res 5:474-482, 1995), binding of MutS protein (Wagner et al., Nucl Acids Res 23:3944-3948, 1995), single-strand-conformation-polymorphism detection (Orita et al., Genomics 5:874-879, 1983), RNAase cleavage at mismatched base-pairs (Myers et al., Science 230:1242, 1985), chemical (Cotton et al., Proc Natl Acad Sci USA 85:4397-4401, 1988) or enzymatic (Youil et al., Proc Natl Acad Sci USA 92:87-91, 1995) cleavage of heteroduplex DNA, methods based on allele specific primer extension (Syvanen et al., Genomics 8:684-692, 1990), genetic bit analysis (GBA) (Nikiforov et al., Nucl Acids Res 22:4167-4175, 1994), and radioactive and/or fluorescent DNA sequencing using standard procedures well known in the art.

The instant methods of screening a subset of SNPs to identify polyp associated SNPs in polyp biomarker genes also encompass non-PCR methods of DNA. These methods include ligase chain reaction ("LCR"), disclosed in European Patent Application No. 320,308, Qbeta Replicase, described in PCT Patent Application No. PCT/US87/00880, isothermal amplification methods, Walker et al. (Nucleic Acids Res 20(7):1691-6, 1992), Strand Displacement Amplification (SDA) described in U.S. Pat. Nos. 5,712,124, 5,648,211 and 5,455,166, Cyclic Probe Reaction, Transcription-Based Amplification, including nucleic acid sequence based amplification (NASBA) and 3SR, Kwoh et al., Proc Natl Acad Sci USA, 86:1173-77, 1989; PCT Patent Application WO 88/10315 et al., 1989, other amplification methods, as described in British Patent Application No. GB 2,202,328, and in PCT Patent Application No. PCT/US89/01025, Davey et al., European Patent Application No. 329,822, Miller et al., PCT Patent Application WO 89/06700, "race and "one-sided PCR™." described in Frohman, In: PCR Protocols: A Guide To Methods And Applications, Academic Press, N.Y., 1990, methods based on ligation of two (or more) oligonucleotides in the presence of nucleic acid having the sequence of the resulting "di-oligonucleotide, described in Wu et al., Genomics 4:560-569, 1989.

While it is generally contemplated that the polymerase employed will be thermostable, non-thermostable polymerases may also be employed in the context of the present disclosure. Exemplary polymerases and nucleic acid modifying enzymes that may be used in the context of the disclosure include the thermostable DNA Polymerases of OmniBase Sequencing Enzyme, Pfu DNA Polymerase, Taq DNA Polymerase, Taq DNA Polymerase, Sequencing Grade, TaqBead Hot Start Polymerase, AmpliTaq Gold, Vent DNA Polymerase, Tub DNA Polymerase, TaqPlus DNA Polymerase, Tfl DNA Polymerase, Tli DNA Polymerase, Tth DNA Polymerase; the DNA Polymerases of DNA Polymerase I, Klenow Fragment, Exonuclease Minus, DNA Polymerase I, DNA Polymerase I Large (Klenow) Fragment, Terminal Deoxynucleotidyl Transferase, T7 DNA Polymerase, T4 DNA Polymerase; the Reverse trancriptases of AMV Reverse Transcriptase and M-MLV Reverse Transcriptase; T4 DNA ligase and T4 polynucleotide kinase.

Recognition moieties incorporated into primers, incorporated into the amplified product during amplification, or attached to probes are useful in the identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure. Examples of affinity labels include but are not limited to the following: an antibody, an antibody fragment, a receptor protein, a hormone, biotin, DNP, or any polypeptide/protein molecule that binds to an affinity label and may be used for separation of the amplified gene. Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above. The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In the context of the present disclosure, it is specifically contemplated that the DNA amplification products of the disclosed methods may be analyzed using DNA chips or microarrays in order to detect SNPs. The amplified DNA products may then be passed over a DNA chip or microarray encompassing oligonucleotide or polynucleotide probes. The ability or inability of the amplified DNA to hybridize to the microarray or DNA chip will facilitate the characterization of the SNPs present in the biomarker genes encoding the transcripts present in the sample.

The following non-limiting examples are illustrative of the present invention:

EXAMPLES

Example 1

RNA Isolation from Unfractionated Whole Blood (a) Centrifuged Lysed Blood (Serum Reduced, Erythrocyte Reduced Blood Sample)

Ten ml of peripheral whole blood was collected in EDTA Vacutainer tubes (Becton Dickinson, Franklin Lakes, N.J.) and stored on ice until processing (within 6 hours). Upon centrifugation, blood samples separated into plasma (including the buffy coat) and red blood cell layers. The plasma was removed and a hypotonic buffer (1.6 mM EDTA, 10 mM KHCO3, 153 mM NH4Cl, pH 7.4) was added to lyse the red blood cells at a 3:1 volume ratio. The mixture was centrifuged to yield a cell pellet, which was dissolved and homogenized into 1.0 ml of TRIzol® Reagent (Invitrogen Corp., Carlsbad, Calif.) and 0.2 ml of chloroform according to the manufacture's instructions. After centrifugation, isopropanol was added to the aqueous phase at a 1:1 ratio and allowed to precipitate at −20° C. Subsequent centrifugation yielded an RNA pellet that was resuspended in water for experimental use. RNA quality was assessed on Agilent 2100 Bioanalyzer RNA 6000 Nano Chips as specified by the manufacturer, and RNA quantity was determined by absorbance at 260 nm in a Beckman-Coulter DU640 Spectrophotometer.

(b) Lysed Blood 10 ml whole blood is obtained in a Vacutainer or any smaller volume container desired. Lysis Buffer is added directly to the blood sample (where the blood sample does not have the serum removed) in a ratio of 3 parts Lysis Buffer to 1 part blood (Lysis Buffer (1 L) 0.6 g EDTA; 1.0 g KHCO2, 8.2 g NH4Cl adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

(c) From Serum Reduced Whole Blood 10 ml whole blood is obtained in a Vacutainer and spun at 2,000 rpm (800 g) for 5 min at 4° C. and the plasma layer removed. The remaining blood sample is homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

d) From Whole Blood 10 ml whole blood is obtained in a Vacutainer and the sample is homogenized using TRIzol (GIBCO/BRL) in a ratio of approximately 6 ml of TRIzol for every 10 ml of the blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

(e) From Whole Blood Using PAXgene™

2.5 ml whole blood is collected into PAXgene™ Blood RNA Tubes and processed in accordance with the instructions of the PAXgene™ Blood RNA Kit protocol. In brief after storing the blood in the PAXgene™ tube for at least 2 hours, the blood sample is centriguted and the supernatant discarded. To the remaining sample, 360 μl of the supplied Buffer BR1 is added and the sample is pipetted into the spin column and centrifuged an then washed with numerous wash steps and finally eluted and stored.

(f) From Whole Blood Using Paxgene™ and Subsequent Globin Reduction

RNA isolated from PAXGene™ as noted in (d) above is subsequently treated to selectively remove globin mRNA as is described in Affymetrix® technical note entitled "Globin Reduction Protocol". Oligonucleotides specific for the alpha 1, alpha 2 and beta globin species are incubated with an oligonucleotide hybridization buffer and RNAse H used to specifically target degredation of the globin mRNA and the cRNA clean up column from Affymetrix used to remove the globin mRNA.

Example 2

Target Nucleic Acid Preparation and Hybridization (a) Genes which are Differentially Expressed with the Presence of One or More Colorectal Pathologies Total RNA (5 μg) was labeled and hybridized onto Affymetrix U133Plus 2.0 GeneChips (Affymetrix; Santa Clara, Calif.) along with other similarly prepared samples from individuals having or not having polyps and hybridized according to the manufacturer's instructions. Briefly, the five μg total RNA was used for cDNA synthesis with GeneChip T7-Oligo (dT) primer provided in the promoter primer kit (Affymetrix, P/N 900375). cDNA was cleaned up with cDNA Cleanup Spin Column and then subjected to synthesis of Biotin-Labeled cRNA with Enzo®BioArray™ High Yield™ RNA Transcript Labeling Kit. The labeled cRNA was further purified using the IVT cTNA Cleanup Spin Column and quantified using spectrophotometer with absorbance at 260 nm. 20 μg cRNA was then added into the hybridization cocktail and the cocktail was applied to the probe array cartridge. After approximately 16 hours hybridization, the array was washed with Affymetrix fluidics station 400. The array was then scanned with Affymetrix®GeneChip®Scanner.

Hybridization signals were scaled in the Affymetrix GCOS software (version 1.1.1), using a scaling factor determined by adjusting the global trimmed mean signal intensity value to 500 for each array, and imported into GeneSpring version 7.2 (Silicon Genetics; Redwood City, Calif.). Signal intensities were then centered to the $50^{th}$ percentile of each chip, and for each individual gene, to the median intensity of the whole sample set. Only genes called present or marginal by the GCOS software in at least 80% of each group of samples were used for further analysis. Differentially expressed genes were identified using 1) the non-parametric Wilcoxon-Mann-Whitney non-parametric test ($P<0.05$), 2) parametric t test ($P<0.05$), and/or the 3) unsupervised analysis method (14). In the un-supervised analysis, the signal-intensity filtered genes were used to select genes with at least 2-fold change (up or down) in expression level, away from the mean, in at least 15% of the samples. Hierarchical cluster analysis was performed on each comparison to assess correlation analysis using Spearman correlation among samples for each identified gene set as the similarity measure with average centroid linkage in GeneSpring v6.0. Results from numerous experiments were analyzed and a compiled list of results provided in Table 1.

(b) Genes which are Differentially Expressed with the Presence of High Risk Polyps Total RNA was isolated from centrifuged lysed blood (ie serum reduced, erythrocyte reduced blood) as described in Example 1 from patients diagnosed with having high risk polyps. 1 μg of Oligo-dT primers were annealed to 10 μg of total RNA for each individual tested in a total volume of 10 μl, by heating to 70° C. for 10 min, and cooled on ice. Individuals were diagnosed as having one or more of the high risk polyp subtypes (colorectal pathology during a colonoscopy identified the polyp identified as one or more of the following types: Tubulovillous Adenoma; Villous Adenoma; Cancer; High Grade Dysplasia; and Tubular Adenoma wherein the diameter of the Tubular Adenoma is greater than 10 mm). Procedures were otherwise carried out as described in Example 2(a) above.

Results from numerous experiments were analyzed and a compiled list of results provided in Table 11.

Example 3

Quantitative Real Time PCR (QRT-PCR)

QRT-PCR was performed on a selection of the genes in Table 1 which are disclosed in Table 2. QRT-PCR was done using either the SYBR® Green Kit from Qiagen (Product Number 204143) and/or using Applied Biosystems PCR reagent kits (Cat 433-4973). Amplicons were detected in real time using a Prism 7500 instrument (Applied Biosystems).

Reverse transcription was first performed using the High-Capacity cDNA Archive Kit from Applied Biosystems (Product number 4322171) and following the protocol utilized therein.

More specifically purified RNA as described previously herein was incubated with reverse transcriptase buffer, dNTPs, random primers and reverse transcriptase and incubated for 25° C. for 10 minutes and subsequently for 37° C. for two hours and the resulting mixture utilized as the starting product for quantitative PCR.

cDNA resulting from reverse transcription was incubated with the QuantiTect SYBR® Green PCR Master Mix as provided and no adjustments were made for magnesium concentration. Uracil-N-Glycosylase was not added. 5 μM of both forward primer and reverse primer specific to the genes of the invention were added and the reaction was incubated and monitored in accordance with the standard protocol utilizing the ABI PRISM 7700/ABI GeneAmp 5700/iCycler/DNA Engine Opticon. Primers utilized are shown in Table 6. Other examples of primers which can be used are disclosed in Table 4. Forward and reverse primers for the candidate biomarkers were designed using "PrimerQuest". A tool which is available from Integrated DNA Technologies, Coralville, Iowa. Table 6 lists the primer sets for eight of the genes of Table 2, namely, MBTPS1 (membrane-bound transcription factor protease site 1), MGC45871, MKLN1 (muskelin 1), NIPBL (Nipped-B homolog (Drosophila)), APEH (acylpeptide hydrolase), FLJ23091, MGC40157, and PPP1R2 (protein phosphatase 1, regulatory (inhibitor) subunit 2). Serial dilution measurements for the target genes and a housekeeping gene (beta-actin, ACTB) were assayed, to ensure that the values were within linear range and the amplification efficiency was approximately equal for the target and ACTB. ACTB was selected as a housekeeping gene because no statistical significant differences were observed between control and disease group in this study (data not shown). The melting temperature [Tm] in thermal dissociation, and examination on agarose gels provided confirmation of specific PCR amplification and the lack of primer-dimer formation in each reaction well.

For individual target gene analysis, changes in Ct value between each gene and the ACTB house-keeping was calculated as ΔCt=Ct (target gene)−Ct (house-keeping gene).

Example 4

TaqMan® QRT PCR can also be performed using the QuantiTect™ Probe RT-PCR system from Qiagen (Product Number 204343) in conjunction with a TaqMan® dual labelled probe and primers corresponding to the gene of interest. The TaqMan® probe and primers can be ordered from Applied Biosystems Assays-On-Demand™.

The dual labelled probe contains both a fluorophore and a quencher molecule. The proximity of the fluorescent reporter with the quencher prevents the reporter from fluorescing, but during the PCR extension step, the 5'-3' exonuclease activity of the Taq DNA polymerase releases the fluorophore which allows it to fluoresce. As such, the amount of fluorescence correlates with the amount of PCR product generated. Examples of TaqMan® probes which can be utilized with the genes disclosed in Table 2 are shown in Table 6 and/or 4.

Example 5

Identification of Combinations of Biomarkers Using Logistic Regression

A selection of eight genes from Table 2 were chosen as follows: MBTPS1, MGC45871, MKLN1, NIPBL APEH, MGC40157, PPP1R2, FLJ23091. Combinations of pairs of the selected eight genes were tested to determine the ability of each combination of pairs to screen for one or more colorectal pathologies. Blood samples were drawn into into lavender-top BD Vacutainer tube prior to anaesthesia and prior to any surgery. RNA from whole blood was prepared by first removing the serum and subsequently treating the remaining sample with hypotonic Lysis Buffer (Lysis Buffer (1) 0.6 g EDTA; 11.0 g $KHCO_2$, 8.2 g $NH_4Cl$ adjusted to pH 7.4 (using NaOH)) in a ratio of 3 parts Lysis Buffer to 1 part blood so as to preferentially lyse the red blood cells. The samples were centrifuged and RNA extracted from the unfractionated cells of the sample.

Real-time quantitative PCR was conducted on 68 patients diagnosed as having colorectal pathology (ie one or more subtypes of polyps) (n=68) and 110 control individuals where the control individuals were diagnosed as not having one or more colorectal pathologies (n=110). QRT-PCR was performed using a two step procedure whereby cDNA was first prepared before performing PCR using ABI reagents. In this example, a matrix containing the ΔCt of "ratios" of the eight biomarkers was used to create a reference training data set (AJ36h). The ratios used to generate the matrix of ΔCts was further constrained by requiring each ratio to be comprised of one upregulated gene and a second downregulated gene where the ΔCt was generated by subtracting the Ct of the downregulated gene from the Ct of the upregulated gene. MBTPS1, MGC45871, MKLN1, NIPBL were identified as upregulated genes (ie when comparing polyps vs non polyp individuals) (FIG. 3). APEH, MGC40157, PPP1R2, FLJ23091 were identified as down regulated genes (FIG. 3). The advantages of gene-pair ratio method include a) reducing inter-individual variability, b) permitting analysis of individual samples without references so as to ensure technical differences between plates are minimized, c) can use any reliable method (microarray, real-time PCR, etc), d) independent of the platform utilized for data acquisition, e) no housekeeping gene required (relatively independent of the input of sample amount), f) translating the strengths of micorarray expression profiling into simple clinical tests, g) highly precise in disease discrimination.

A reference (training) data set (AJ36h) was constructed containing ΔCt values for each possible-ratio as described and constrained as noted above for the above eight genes assayed against a total of 178 subjects including 110 subject without pathology (Female/male: 55/54 with one missing information, age average 57 year ranging 23 to 83 years of age) and 68 subjects with diagnosed colorectal pathology (Female/male: 22/45 with one missing information, age average 57 ranging from 38 to 82 years). The types of pathology identified include 21 (31%) tubular adenomas, 18 (27%) hyperplastic and 7 (10%) high risk pathology (villous morphology) and 22 (32%) other minor polyp (see Table 7).

Logistic regression (15-18) was used to analyze the dependence of the binary variable Y (0=control (has no pathology), 1=disease (has pathology) on all possible combinations of the Act values from the reference data training set AJ36h. If P=probability that a patient sample is diagnosed as "diseased", then a function X=Logit (p) can be defined as follows:

$$X=\text{Logit}(P)=\ln(P/(1-P))b_0+b_1\Delta Ct_1+b_2\Delta Ct_2+\ldots+b_n\Delta Ct_n \quad \text{(Eq 1)}$$

If X≧threshold then Y=1 (diagnosis="diseased"), and if X<threshold then Y=0 (diagnosis="control"). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of each combination of ratios wherein all combinations of ratios as described above were tested (19-21). Each combinations of ratios resulted in an equation in the form of Equation 1. The top 10 best equations that gave an ROC=0.72 were used in a formula where each equation was given equal ranking to perform the subsequent blind test prediction.

Cross Validation

Cross-validation was performed on dataset AJ36h (the 178-sample training set) using WEKA (22). Two different cross-validation schemes were used. The WEKA MetaAnalysis function was used to construct 100 bootstrap replicates of dataset AJ36h. Each of the new datasets was analyzed with the SimpleLogistic classifier. Each of the resultant 100 logistic equations was then analyzed by 10-fold cross-validation. The results for all equations were averaged (bootstrap aggregating).

Prospective (Blind) Test

A blind set of 80 clinical samples were tested. The test set consisted of 40 controls and 40 subjects with one or more colorectal pathologies (having one or more polyps of any type). None of the test subjects used in the blind test were used to generate a classifier for each possible combination of the ratio of biomarkers "ratios" where each ratio is selected as a combination of an upregulated gene (when comparing colorectal pathology to no colorectal pathology) and a down regulated gene (when comparing colorectal pathology to no colorectal pathology). MBTPS1, MGC45871, MKLN1, NIPBL were identified as upregulated genes (ie when comparing polyps vs non polyp individuals (FIG. 3). APEH, MGC40157, PPP1R2, FLJ23091 were identified as down regulated genes (FIG. 3).

Medical information on subjects in this blind set, including age, gender, and pathologist's report, is summarized in Table 7. Samples were run on a single 96-well plate for Q RT-PCR with each of the eight genes measured in triplicate.

The measured values for each blind sample were evaluated using the following algorithm, which consists of an initial calculation, a binary logic gate, and a "committee machine" vote. Initial Calculation: The logit function $X_i$ is computed for each of the equations (I=1 to N) that gave ROC Area=0.72 against the reference data set AJ36h. Logic Gate: If $X_i$<threshold of j (where j stands for an equation number), then the blind sample is given score $S_i$=−1 for Eqn #j. If $X_i$≧threshold of j, then it is given score $S_i$=+1 for Eqn #j. Vote by Committee Machine (23): A vote is taken over the scores from the 10 logit equations used for diagnosis. By definition, Vote=$\Sigma S_i$. If Vote ≦0 then the sample is called "no pathology", while if Vote>0 then the sample is called "diseased or with pathology".

The best equation gives an ROC area 0.72 as shown in FIG. 4. Ten top equations that gave ROC=0.72 were used for the blind test prediction. Table 8 lists the parameters for the 10 equations.

Cross-validation was done with the SimpleLogistic function in WEKA. 100 bootstrap replicates of dataset AJ36h were constructed and analyzed each with the WEKA SimpleLogistic function. The resultant set of 100 logistic equations was subjected to 10-fold cross-validation. The results for all equations were then averaged which gave an ROC Area=0.66, overall accuracy 65%, sensitivity (TPF) 41%, specificity (TNF) 83%.

Prediction of Blind Samples

A blind test was conducted on an additional set of 80 samples (40 samples without pathology and 40 samples with colorectal pathology). A committee vote was taken over the ten (10) best logit equations from Reference Dataset AJ36h, to predict a state of either "colorectal pathology present" or "colorectal pathology absent (control)". For the set of blind samples the sensitivity (true positive fraction, TPF) is 43% (17/40), and the specificity (true negative fraction, TNF) is 80% (32/40), with an overall accuracy of 61% (49/80, Table 9).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Example 6

Testing of Combinations of Biomarkers Using Logistic Regression and Application of Said Combinations to Screen for One or More Types of Colorectal Pathology or One or More Pathologies A selection of seven genes were chosen including: LIM domain containing preferred translocation partner in lipoma (LPP) Gene ID 4026; cytidine deaminase (CDA) Gene ID 978; sarcoma antigen NY-SAR-48 (MGC20553) Gene ID 93323; serine (or cysteine) proteinase inhibitor, clade E (nexin, plasminogen activator inhibitor type 1), member 2(SERPINE 2) Gene ID 5270; B-cell novel protein 1 (BCNP1) Gene ID 199786; hypothetical protein MGC45871 (MGC45871) Gene ID 359845; membrane-bound transcription factor protease, site 1 (MBTPS1) Gene ID 8720. Genes were chosen from either Table 1 or other similar experiments.

Clinical Question—Polyp v. No Pathology

A reference (training) data set was constructed containing ΔCt values for the above seven genes assayed against a total of 185 subjects having any type of polyp and 239 subjects not having polyps.

Logistic regression was used to analyze the dependence of the binary variable Y (0=control, 1=disease) on the ΔCt values from the reference data set. If P=probability that a patient sample is identified as "diseased", then a function X Logit (p) can be defined as follows:

$$X=\text{Logit}(P)=\ln(P/(1-P))=b_0+b_1\Delta\text{Ct}_1+b_2\Delta\text{Ct}_2+\ldots+b_n\Delta\text{Ct}_n \quad \text{(Eq 1)}$$

If X≧threshold then Y=1 (diagnosis="has polyps"), and if X<threshold then Y=O (diagnosis=does not have polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (LPP; CDA; MBTPS1; SERPINE2; BCNP1) and shown as follows:

$$X=\text{Logit}(P)=\ln(P/(1-P))=-4.9104-0.4278\Delta\text{CtMGC20553}-0.6164\Delta\text{CtCDA}+0.8230\Delta\text{CtMBTPS1}+0.3961\Delta\text{CtSERPINE2}+0.1641\Delta\text{CtBCNP1}$$

gave an ROC=0.73 with a sensitivity of 80% and a specificity of 50%.

Clinical Question—High Risk Pathology v. Other

Using the same selection of seven biomarkers, but this time tested against a reference (training) data set with ΔCt values for the above seven genes assayed against a total of 129 subjects having "high risk" polyp and 295 subjects either having a polyp not classified as high risk or having no pathology, where subjects where classified as having "high risk polyps" if they had one of the following categories of polyps: Tubulovillous Adenoma; Villous Adenoma; High Grade Dysplasia and Tubular Adenoma where the diameter of the Tubular Adenoma polyp is greater than 10 mm and cancer Logistic regression was used to analyze the dependence of the binary variable Y (0=control, 1=disease) on the ΔCt values from the reference data set. If P=probability that a patient sample is identified as "diseased", then a function X=Logit (p) can be defined as follows:

$$X=\text{Logit}(P)=\ln(P/(1-P))=b_0+b_1\Delta\text{Ct}+b_2\Delta\text{Ct}_2+\ldots+b_n\Delta\text{Ct}_n \quad \text{(Eq 1)}$$

If X≧threshold then Y=1 (diagnosis="has high risk polyps"), and if X<threshold then Y=0 (diagnosis=does not have high risk polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (CDA; MGC20553; MBTPS1; SERPINE2; BCNP1;) and shown as follows:

$$X=\text{Logit}(P)=\ln(P/(1-P))-5.2981-0.5433\Delta\text{CtCDA}-0.4958\Delta\text{CtMGC20553}+0.8551\Delta\text{CtMBTPS1}+0.3554\Delta\text{CtBCNP1}+0.2438\Delta\text{CtSERPINE2}$$

gave an ROC=0.74 with a sensitivity of 83% and a specificity of 46%.

Clinical Question—Cancer v. Other

Finally the same seven genes were tested in combinations using a reference (training) data set containing ΔCt values for the above seven genes assayed against a total of 80 subjects having cancerous polyps and 344 subjects having other types of polyps or having no pathology.

Logistic regression was used to analyze the dependence of the binary variable Y (0=control, 1=disease) on the ΔCt values from the reference data set. If P=probability that a patient sample is identified as "diseased", then a function X=Logit (p) can be defined as follows:

$$X=\text{Logit}(P)=\ln(P/(1-P))=b_0+b_1\Delta\text{Ct}_1+b_2\Delta\text{Ct}_2+\ldots+b_n\Delta\text{Ct}_n \quad \text{(Eq 1)}$$

If X≧threshold then Y=1 (diagnosis="has cancerous polyps"), and if X<threshold then Y=0 (diagnosis=does not have cancerous polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (MGC20553, CDA, MBTPS1, SERPINE2, MGC45871; BCNP1) and shown as follows:

$$X=\text{Logit}(P)=\ln(P(1-P))=-12.9149-0.5378\Delta\text{CtCDA}-0.5398\Delta\text{CtMGC20553}+1.0386\Delta\text{CtMBTPS1}++0.7405\Delta\text{CtBCNP1}+0.4002\Delta\text{CtMGC45871}+0.2074\Delta\text{CtSERPINE2}$$

gave an ROC=0.83 with a sensitivity of 90% and a specificity of 55%.

Clinical Question—High Risk Pathology v. Other

A reference (training) data set was constructed containing ΔCt values for the above seven genes assayed against a total of 252 subjects having high risk polyps and 272 subjects having other types of polyps or having no pathology where by high risk polyps is meant Tubulovillous Adenoma, Villous Adenoma, High Grade Dysplasia and Tubular Adenoma—regardless of diameter of polyp.

Logistic regression was used to analyze the dependence of the binary variable Y (0=control, 1=disease) on the ΔCt values from the reference data set. If P=probability that a patient sample is identified as "diseased", then a function X Logit (p) can be defined as follows:

$$X=\text{Logit}(P)=\ln(P/(1-P))=b_0+b_1\Delta\text{Ct}_1+b_2\Delta\text{Ct}_2+\ldots+b_n\Delta\text{Ct}_n \quad \text{(Eq 1)}$$

If X≧threshold then Y=1 (diagnosis="has high risk polyps"), and if X<threshold then Y=0 (diagnosis=does not have high risk polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (MGC20553; CDA; MBTPS1; SERPINE2; BCNP1;) and shown as follows:

$$X=\text{Logit}(P)=\ln(P/(1-P))=-3.5819-0.7625\Delta\text{CtCDA}-0.6117\Delta\text{CtMGC20553}+1.15\Delta\text{CtMBTPS1}+0.2174\Delta\text{CtBCNP1}+0.2439\Delta\text{Ct SERPINE2}$$

gave an ROC=0.76 with a sensitivity of 82% and a specificity of 52%.

Example 7

Biomarkers to Screen for Presence of Colorectal Cancer. Deriving Classifiers to be Used with Combinations of Biomarkers and Application of Said Classifiers to Determine Presence of Colorectal Cancer QRT-PCR was performed on a selection of the genes identified from one or more microarray analyses (data not shown) as being able to differentiate as between individuals having colorectal cancer and individuals not having colorectal cancer. Some of genes selected for QRT-PCR were selected from microarray data performed on samples collected from three regions of China for over 593 samples including 61 samples from individuals having been diagnosed with colorectal cancer and 532 from individuals not having colorectal cancer (data not shown). Other genes were selected from other similar microarray experiments with individuals from North America and/or Asia. Among the individuals not having colorectal cancer was a mixture of individuals having breast cancer, kidney cancer, prostate cancer, bladder cancer, and individuals having other subtypes of colorectal pathology which were not colorectal cancer.

QRT-PCR was done on each individual gene across a population of individuals having colorectal cancer and a population of individuals not having colorectal cancer. QRT-PCR experiments were done using either the SYBR® Green Kit from Qiagen (Product Number 204143) and/or using Applied Biosystems PCR reagent kits (Cat 433-4973) and/or using TaqMan Assay using the QuantiTect® Probe PCR Kit (Qiagen, Cat. # 204345). TaqMan® probes were developed for each gene of interest and labelled with FAM and the Black Hole Quencher® from Biosearch Technologies. Beta-actin was used as a housekeeping gene in the duplexed assays and labelled using HEX and Black Hole Quencher®. Amplicons were detected in real time using a Prism 7500 instrument (Applied Biosystems). Results of the QRT-PCR for each gene across the population tested are shown in Table 12.

Rather than testing all possible combinations of the biomarkers noted in Table 12, in other embodiments, all possible combinations of biomarkers with a p value of less than 0.05 can be chosen and all or a portion of combinations of biomarkers tested. Discussed below is representative classifiers identified for selected combinations tested.

Classifiers were derived for all two gene combinations of the biomarkers identified in Table 12 using QRT-PCR for 28 of the genes identified in Table 12 across 58 individuals having colorectal cancer and 57 individuals not having colorectal cancer. The 28 genes utilized are represented by the following gene symbols and are described in more detail herein: OSBPL10, LOC283130, BANK1, COBLL1, MGC24039, C9orf85, BLNK, BCNP1, PDE3B, AKAP13, WDFY1, CDA, AGTRAP, ACTR2, UTS2, MS4A1, SPAP1, ANK3, KIAA1559, GBP5, MGC20553, CEACAM1, HIST1H4H, PRG1, BRD2, LTBP3, MAP4K3, and NIPA2 Primers utilized for the real time RT-PCR are further described in Table 16. Classifiers derived for selection combinations of two genes are shown as follows:

Table A: Table showing Resulting Classifiers for a Selection of Two Gene Combinations Wherein the Combinations are in the Form of Ratios and the Biomarkers Are Selected from the 28 Genes Selected from Table 12. Shown is the resulting ROC area of the Classifiers, the Sensitivity (at the noted cutoff Sens) and Specificity (at the noted cutoff Spec) are shown. The constant, and the coefficient for the selected two gene ratio are noted.

TABLE A

| | ROCarea | Sensitivity at 90% Specificity | Specificity at 90% Sensitivity | Constant | Coeffic for Ratio |
|---|---|---|---|---|---|
| BANK1/CDA | 0.8621 | 46.55 | 68.42 | −3.7808 | 1.256 |
| BCNP1/CDA | 0.8451 | 43.10 | 57.89 | −2.7251 | 1.2554 |
| CDA/MS4A | 0.8430 | 43.10 | 63.16 | −1.3171 | −1.0944 |
| C9orf85/CDA | 0.8382 | 44.83 | 52.63 | −16.482 | 2.2374 |
| CDA/OSBPL10 | 0.8367 | 56.90 | 47.37 | −5.9699 | −1.2875 |
| CDA/SPAP1 | 0.8364 | 48.28 | 59.65 | −3.3047 | −0.9384 |
| BLNK/CDA | 0.8361 | 50.00 | 68.42 | −4.8603 | 1.2367 |
| CDA/LOC283130 | 0.8339 | 67.24 | 52.63 | −3.9388 | −1.6368 |
| CDA/COBLL1 | 0.8321 | 53.45 | 56.14 | −6.9371 | −1.3126 |
| BANK1/PRG1 | 0.8306 | 55.17 | 54.39 | −8.6282 | 1.2825 |
| BANK1/CEACAM1 | 0.8291 | 56.9 | 56.14 | −1.7783 | 1.1225 |
| BCNP1/PRG1 | 0.8224 | 60.34 | 45.61 | −7.4478 | 1.2631 |
| BANK1/MGC20553 | 0.8197 | 44.83 | 59.65 | 2.2412 | 0.9436 |
| BANK1/NIPA2 | 0.8176 | 58.62 | 50.88 | −2.2946 | 1.6015 |
| ACTR2/BANK1 | 0.8155 | 41.38 | 54.39 | −9.1667 | −1.4596 |
| CDA/HIST1H4H | 0.8134 | 51.72 | 47.37 | 1.6688 | −1.5062 |
| AKAP13/GBP5 | 0.7012 | 22.41 | 22.81 | −0.7784 | 0.6743 |
| BCNP1/CEACAM1 | 0.8131 | 44.83 | 52.63 | −0.8916 | 1.1843 |
| CEACAM1/SPAP1 | 0.8128 | 34.48 | 56.14 | −1.8563 | −0.88 |
| CDA/MAP4K3 | 0.8128 | 39.66 | 45.61 | −9.7566 | −1.7304 |
| BCNP1/GBP5 | 0.8107 | 36.21 | 57.89 | −4.611 | 1.1411 |

As noted for each two gene combination the ROC area is provided in addition to the specificity (when sensitivity is set at 90%) and sensitivity (when specificity is set at 90%). The cutoff utilized to generate the sensitivity and specificity as noted are provided in the two righthand most columns. The classifier for each of the two gene combinations can be generically described as follows:

$$X(\text{having colorectal cancer})=\text{Logit}(P)=\ln(P/(1-P))=b_0+b_1(\Delta Ct_1-\Delta Ct_2)$$

Where $b_0$ is identified as the coefficient and $b_1$ is noted as the coefficient for the ratio.

Example 8

Classifiers were also derived for all possible combinations of a selection of nine of the biomarkers identified in Table 12. Data for use in generating the classifiers for the combinations were obtained using real time RT-PCR for each of the nine genes tested across the same 58 individuals having colorectal cancer and 57 individuals not having colorectal cancer described in Example 7. The 9 genes utilized are represented by the following gene symbols and are described in more detail herein: CDA, MGC20553, MS4A1, BCNP1, BANK1, GBP5, OSBPL10, SPAP1, LOC283130. Primers utilized for the real time RT-PCR are further described in Table 16. A selection of the resulting classifiers are described below in Table B below:

TABLE B

| # | ROC area | Constant | CDA | MGC20553 | MS4A1 | BCNP1 | BANK1 | GBP5 | OSBPL10 | SPAP1 | LOC283130 |
|---|---|---|---|---|---|---|---|---|---|---|---|
| 1 | 0.8364 | −14.48 | | | | 1.61 | | | | | |
| 1 | 0.8197 | −10.07 | | | 1.25 | | | | | | |
| 1 | 0.8091 | −10.56 | | | | | | | | 1.02 | |
| 2 | 0.8681 | −21.35 | | | | 1.39 | | | 0.77 | | |
| 2 | 0.8648 | −7.58 | −0.93 | | | | 1.41 | | | | |
| 2 | 0.8594 | −21.80 | | | | | 1.27 | | 0.81 | | |
| 3 | 0.8839 | −12.85 | −1.26 | | | 1.20 | | | 0.93 | | |
| 3 | 0.8811 | −13.04 | −1.25 | | | | 1.06 | | 0.97 | | |
| 3 | 0.8757 | −10.48 | −1.20 | | | 1.11 | | | | | 0.94 |
| 4 | 0.8963 | −9.09 | −1.47 | | | 1.34 | | −0.72 | 0.93 | | |
| 4 | 0.8917 | −7.25 | −1.29 | −0.51 | | 1.17 | | | 1.02 | | |
| 4 | 0.8902 | −5.32 | −1.59 | | | 1.11 | | −0.88 | | | 1.14 |
| 5 | 0.8987 | −10.60 | −1.42 | | | 0.99 | 0.43 | −0.71 | 0.92 | | |
| 5 | 0.8984 | −8.84 | −1.63 | | | 1.16 | | −0.80 | 0.75 | | 0.52 |
| 5 | 0.8969 | −9.34 | −1.65 | | | | 0.94 | −0.72 | 0.69 | | 0.75 |
| 6 | 0.9035 | −10.25 | −1.57 | | | 0.82 | 0.43 | −0.78 | 0.73 | | 0.52 |
| 6 | 0.9005 | −10.91 | −1.42 | | −0.32 | 1.13 | 0.62 | −0.72 | 0.91 | | |
| 6 | 0.9005 | −10.64 | −1.41 | | | 1.19 | 0.57 | −0.71 | 0.88 | −0.26 | |
| 7 | 0.9053 | −10.60 | −1.57 | | −0.31 | 0.96 | 0.61 | −0.79 | 0.73 | | 0.51 |
| 7 | 0.9020 | −10.31 | −1.55 | | | 0.98 | 0.53 | −0.77 | 0.71 | −0.20 | 0.49 |
| 7 | 0.9014 | −11.32 | −1.59 | 0.14 | | 0.82 | 0.46 | −0.87 | 0.71 | | 0.52 |
| 8 | 0.9056 | −10.57 | −1.57 | | −0.27 | 0.99 | 0.62 | −0.79 | 0.72 | −0.06 | 0.50 |
| 8 | 0.9044 | −11.30 | −1.59 | 0.09 | −0.29 | 0.95 | 0.62 | −0.85 | 0.71 | | 0.51 |
| 8 | 0.9026 | −11.17 | −1.57 | 0.11 | | 0.96 | 0.55 | −0.85 | 0.70 | −0.18 | 0.49 |
| 9 | 0.9041 | −11.26 | −1.58 | 0.09 | −0.25 | 0.98 | 0.63 | −0.85 | 0.71 | −0.06 | 0.50 |

The classifiers shown above can be generically described in the following equation.

$$X(\text{possibility of having colorectal cancer})=\text{Logit}(P)=\ln(P/(1-P))=b_0+b_1\Delta Ct_1+b_2\Delta Ct_2+\ldots+b_n\Delta Ct_n$$

Noted above are selected classifiers for combinations of 1, 2, 3, 4, 5, 6, 7, 8 or all 9 of the selected genes. The area under the curve is noted (ROC Area). Also provided is the constant $b_0$ and the coefficient for each biomarker (e.g. $b_n$) required for the selected classifier to be applied to the delta Ct of the noted gene for a test sample. As would be understood, where no coefficient is noted, that biomarker is not required for the classifier. Additional sensitivity and specificity determinations can be ma de for each classifier, and will vary depending upon the threshold set.

The results of all of the combinations of the 9 genes is graphically represented in FIG. 5.

Example 9

All possible combinations of biomarkers identified in Table 12 are tested by applying logistic regression to data corresponding to level of product of the biomarkers noted. QRT-PCR is conducted on each of the genes noted in Table 12 for a population of individuals who have been diagnosed as having colorectal cancer or not having colorectal cancer. A matrix containing the ΔCt for RNA corresponding to each gene for each individual of the two populations is created and classifiers derived for each possible combination of biomarkers of those listed in Table 12 (whether individually statistically significant or not) using techniques as described herein. For each classifier the ROC curve is plotted and the area under the curve determined. Classifiers are chosen depending on the specific sensitivity and specificity requirements of the specific intended use of the biomarkers (for example, if may be desirable to have a high sensitivity and fewer false negatives so as to miss less colorectal cancers); (alternatively high specificity resulting in lower false positives is also desirable as it can decrease costs of additional unnecessary medical interventions). A blind test is conducted on one or more of the resulting classifiers so as to demonstrate the utility of the classifier to test for colorectal cancer in a test individual. One or more the classifiers is applied to test an individual to determine the likelihood of said test subject having colorectal cancer.

Example 10

Blind Testing of One of the Combinations of the Genes in Table 12 Using the Derived Classifier A five gene combination encompassing B-cell scaffold protein with ankyrin repeats (BANK1), B-cell novel protein 1 (13CNP1), cytidine deaminase (CDA) membrane-spanning 4-domains, subfamily A, member 1 (MS4A1) and FERM domain containing 3 (MGC20553 aka FRMD3) was selected to pursue further blind sample testing.

The reference (training) data set was constructed containing ΔCt values for the above five genes assayed against a total of 57 subjects having colorectal cancer and 58 subjects not having colorectal cancer as described in more detail in Example 7.

Logistic regression was used to analyze the dependence of the binary variable Y (0=control, 1=disease) on the ΔCt values from the reference data set. If P=probability that a patient sample is identified as "having colorectal cancer), then a function X=Logit (p) can be defined as follows:

$$X = \text{Logit}(P) = \ln(P/(1-P)) = b_0 + b_1\Delta Ct_1 + b_2\Delta Ct_2 + \ldots + b_n\Delta Ct_n \quad \text{(Eq 1)}$$

If X≧threshold then Y=1 (diagnosis=has colorectal cancer), and if X<threshold then Y=0 (diagnosis=does not have colorectal cancer). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The classifier derived using the selected genes(BANK1, BCNP1, CDA, MS4A1, and MGC20553) and shown as follows:

$X = \text{Logit}(P) = \ln(P/(1-P)) = -5.1338 - 0.8399\ (\Delta Ct\ CDA) - 0.3314(\Delta Ct MGC20553) - 0.3245\ (\Delta Ct MS4A1) + 1.0903\ (\Delta Ct BCNP1) + 0.7842\ (\Delta Ct\text{-}BANK1)$ gave an area under the curve of 0.883±0.032. One can adjust the sensitivity or specificity by adjusting the testing cut off point as follows:

| Cut-off | Sens. (95% C.I.) | Spec. (95% C.I.) |
|---|---|---|
| −0.53 | 89.7 (78.8-96.1) | 78.9 (66.1-88.6) |
| −0.31 | 86.2 (74.6-93.8) | 80.7 (68.1-89.9) |
| −0.04 | 81.0 (68.6-90.1) | 82.5 (70.1-91.2) |
| 0.47 | 72.4 (59.1-83.3) | 87.7 (76.3-94.9) |
| 0.59 | 67.2 (53.7-79.0) | 89.5 (78.5-96.0) |
| 1.46 | 43.1 (30.2-56.8) | 94.7 (85.4-98.8) |

Using a cutoff of −1.1 gives a sensitivity of 98.3% and a specificity 50.9%.

A first blind test was performed using a scoring population comprised of 15 individuals not having colorectal cancer and 6 individuals having colorectal cancer. This blind test utilized individuals selected from a single site in Penang. The first blind test resulted in a sensitivity of 100% and a specificity of 43%. A second blind test was performed using a second scoring population (non overlapping with the first scoring population) of 31 non colorectal patients and 23 colorectal patients. Patient samples were collected from three different sites in Asia. The test resulted in a sensitivity of 100% (all samples with colorectal cancer properly identified) and a specificity of 47% (almost half of the samples without colorectal cancer properly identified). A final blind test was performed utilizing samples obtained from two clinics in North America including 15 colorectal cancer patients and 16 non colorectal cancer patients resulting in a sensitivity of 88% and a specificity of 33%.

Example 11

Selection of 6 Biomarkers (BCNP1, CD163, CDA, MS4A1, BANK1, MGC20553) to derive classifiers which are particularly useful in screening for the presence of colorectal cancer and application of the classifiers with the combinations selected to determine presence of colorectal cancer QRT-PCR was performed on the selection of genes BCNP1, CD163, CDA, MS4A1, BANK 1, MGC20553 identified from one or more microarray analyses (selected from Table 12 and Table 11). QRT-PCR data was most recently collected on RNA samples from centrifuged lysed blood from 109 samples, 60 individuals having colorectal cancer and 59 individuals not having colorectal cancer. QRT-PCR was performed using a duplexed TaqMan Assay using the QuantiTect® Probe PCR Kit (Qiagen, Cat. # 204345). TaqMane probes were developed for each gene of interest and labelled with FAM and the Black Hole Quencher® from Biosearch Technologies. Beta-actin was used as a housekeeping gene in the duplexed assays and labelled using HEX and Black Hole Quencher®. ΔCts (Ct gene of interest —Ct Beta-actin) were calculated.

Results of the average QRT-PCR results for each gene across the population tested are shown in Table C below. The average ΔCt (Ct gene-Ct Beta-actin) of each gene in both the control population and the population having colorectal cancer (CRC) are shown, as is the standard deviation (SD) as amongst the data from the population. The p value for each gene individually is shown. The change in ΔCt as between the ΔCt of the Control samples for each gene and the ΔCt for the CRC samples for each gene are shown as ΔCt and the standard deviation are shown. Also shown is the fold change for each individual marker.

TABLE C

| | | BANK1 | BCNP1 | CDA | MGC20553 | MS4A1 | CD163 |
|---|---|---|---|---|---|---|---|
| Control | Avg ΔCt of Control (non CRC) | 7.5998 | 6.5558 | 3.4814 | 9.7375 | 3.9940 | 5.2012 |
| | SD | 0.767 | 0.907 | 0.491 | 1.036 | 0.974 | 0.381 |
| Colorectal Cancer (CRC) | CRC Avg | 8.3398 | 7.6368 | 3.2070 | 9.3773 | 5.1298 | 5.3896 |
| | Standard Deviation | 0.708 | 0.893 | 0.539 | 0.867 | 1.041 | 0.482 |
| | p-value (CRC v. Control) | 2.6E−07 | 1.6E−09 | 4.4E−03 | 4.2E−02 | 1.1E−08 | 2.0E−02 |
| | ΔΔCt(ΔCtCont-ΔCtCRC) | −0.7400 | −1.0810 | 0.2743 | 0.3602 | −1.1359 | −0.1884 |
| | Standard Deviation | 1.044 | 1.273 | 0.729 | 1.351 | 1.425 | 0.614 |
| | Regulation (direction of regulation comparing CRC v. Control) | Down regulated | Down Regulated | Up regulated | Up regulated | Down regulated | Down regulated |
| | Fold change (CRC v. Control) | 1.67 | 2.12 | 1.21 | 1.28 | 2.20 | 1.14 |

TABLE C-continued

| | BANK1 | BCNP1 | CDA | MGC20553 | MS4A1 | CD163 |
|---|---|---|---|---|---|---|
| Standard Deviation (Fold change) | 2.06 | 2.42 | 1.66 | 2.55 | 2.69 | 1.53 |

A matrix of the individual QRT-PCR data corresponding to each of the six biomarkers across a population comprising 60 individuals having colorectal cancer and 59 individuals not having colorectal cancer was generated using the same methods noted above. The matrix of data was used to generate classifiers for all possible combinations of the six biomarkers by applying logistic regression to the data of each possible combination. A listing of all of the combinations and the biomarkers which make up each combination are noted in Table D below. The ROC curve for each resulting classifier was measured to determine the ability of each derived classifier to properly identify a test patient as having colorectal cancer. The given sensitivity (at a pre-defined specificity) and the specificity (at a pre-defined sensitivity) can be determined from the ROC curve. The resulting classifiers from this analysis is shown in Table E and the results of these classifiers are shown graphically in FIG. 5.

Table D Each combination is noted as a unique combination number ranging from 1 to 63. Presence of the number 1 in a column below a noted Gene indicates the presence of that gene within the generated classifier.

TABLE D

| Combination # | BANK1Gene01 | BCNP1Gene02 | CDAGene03 | MS4A1Gene04 | MGC20553Gene05 | CD163Gene06 |
|---|---|---|---|---|---|---|
| 1 | 1 | | | | | |
| 2 | | 1 | | | | |
| 3 | 1 | 1 | | | | |
| 4 | | | 1 | | | |
| 5 | 1 | | 1 | | | |
| 6 | | 1 | 1 | | | |
| 7 | 1 | 1 | 1 | | | |
| 8 | | | | 1 | | |
| 9 | 1 | | | 1 | | |
| 10 | | 1 | | 1 | | |
| 11 | 1 | 1 | | 1 | | |
| 12 | | | 1 | 1 | | |
| 13 | 1 | | 1 | 1 | | |
| 14 | | 1 | 1 | 1 | | |
| 15 | 1 | 1 | 1 | 1 | | |
| 16 | | | | | 1 | |
| 17 | 1 | | | | 1 | |
| 18 | | 1 | | | 1 | |
| 19 | 1 | 1 | | | 1 | |
| 20 | | | 1 | | 1 | |
| 21 | 1 | | 1 | | 1 | |
| 22 | | 1 | 1 | | 1 | |
| 23 | 1 | 1 | 1 | | 1 | |
| 24 | | | | 1 | 1 | |
| 25 | 1 | | | 1 | 1 | |
| 26 | | 1 | | 1 | 1 | |
| 27 | 1 | 1 | | 1 | 1 | |
| 28 | | | 1 | 1 | 1 | |
| 29 | 1 | | 1 | 1 | 1 | |
| 30 | | 1 | 1 | 1 | 1 | |
| 31 | 1 | 1 | 1 | 1 | 1 | |
| 32 | | | | | | 1 |
| 33 | 1 | | | | | 1 |
| 34 | | 1 | | | | 1 |
| 35 | 1 | 1 | | | | 1 |
| 36 | | | 1 | | | 1 |
| 37 | 1 | | 1 | | | 1 |
| 38 | | 1 | 1 | | | 1 |
| 39 | 1 | 1 | 1 | | | 1 |
| 40 | | | | 1 | | 1 |
| 41 | 1 | | | 1 | | 1 |
| 42 | | 1 | | 1 | | 1 |
| 43 | 1 | 1 | | 1 | | 1 |
| 44 | | | 1 | 1 | | 1 |
| 45 | 1 | | 1 | 1 | | 1 |
| 46 | | 1 | 1 | 1 | | 1 |
| 47 | 1 | 1 | 1 | 1 | | 1 |
| 48 | | | | | 1 | 1 |
| 49 | 1 | | | | 1 | 1 |
| 50 | | 1 | | | 1 | 1 |
| 51 | 1 | 1 | | | 1 | 1 |
| 52 | | | 1 | | 1 | 1 |

TABLE D-continued

| Combination # | BANK1Gene01 | BCNP1Gene02 | CDAGene03 | MS4A1Gene04 | MGC20553Gene05 | CD163Gene06 |
|---|---|---|---|---|---|---|
| 53 | 1 | | 1 | | 1 | 1 |
| 54 | | 1 | 1 | | 1 | 1 |
| 55 | 1 | 1 | 1 | | 1 | 1 |
| 56 | | | | 1 | 1 | 1 |
| 57 | 1 | | | 1 | 1 | 1 |
| 58 | | 1 | | 1 | 1 | 1 |
| 59 | 1 | 1 | | 1 | 1 | 1 |
| 60 | | | 1 | 1 | 1 | 1 |
| 61 | 1 | | 1 | 1 | 1 | 1 |
| 62 | | 1 | 1 | 1 | 1 | 1 |
| 63 | 1 | 1 | 1 | 1 | 1 | 1 |

In preferred embodiments, data representing levels of products of any combination of two of the six biomarkers in a sample isolated or derived from a test subject are input to a formula as further described herein, for the purpose of providing a probability that the test subject has one or more colorectal pathologies. In certain other embodiments, data representing levels of products of any combination of three, four, or five of the six biomarkers are input to a formula as further described herein. It is also consistent with the methods described herein that data representing levels of products of all six of the six biomarkers are input to a formula to provide a probability that a test subject has one or more colorectal pathologies.

Table E Classifiers resulting from each possible combination of the six biomarkers are noted. The Combination number corresponds to the combinations as noted in Table D. The number of genes contributing to the combination is noted, and the coefficient for that biomarker are noted within the row. Where 0 is noted as a coefficient, this biomarker does not contribute to the resulting classifier. The area under the curve (ROC area) is noted as is the sensitivity at 90% specificity and the specificity at 90% sensitivity.

TABLE E

| Comb # | # of genes | ROCarea | Sensitivity @ 90% spec | Specificity @ 90% sens | Constant | BANK1 | BCNP1 | CDA | MGC20553 | MS4A1 | CD163 |
|---|---|---|---|---|---|---|---|---|---|---|---|
| 2 | 1 | 0.8065 | 48.33 | 50.85 | −9.4336 | 0 | 1.3378 | 0 | 0 | 0 | 0 |
| 16 | 1 | 0.8062 | 33.33 | 40.68 | −5.1508 | 0 | 0 | 0 | 0 | 1.1456 | 0 |
| 1 | 1 | 0.7664 | 25.00 | 40.68 | −10.646 | 1.3395 | 0 | 0 | 0 | 0 | 0 |
| 8 | 1 | 0.6531 | 11.67 | 18.64 | 3.9001 | 0 | 0 | 0 | −0.40595 | 0 | 0 |
| 4 | 1 | 0.6421 | 26.67 | 15.25 | 3.5585 | 0 | 0 | −1.0592 | 0 | 0 | 0 |
| 32 | 1 | 0.6232 | 18.33 | 18.64 | −5.4467 | 0 | 0 | 0 | 0 | 0 | 1.0322 |
| 48 | 2 | 0.8285 | 36.67 | 61.02 | −10.284 | 0 | 0 | 0 | 0 | 1.1534 | 0.96391 |
| 34 | 2 | 0.8184 | 48.33 | 54.24 | −14.22 | 0 | 1.3294 | 0 | 0 | 0 | 0.91273 |
| 6 | 2 | 0.8155 | 33.33 | 52.54 | −6.6582 | 0 | 1.2559 | −0.65891 | 0 | 0 | 0 |
| 18 | 2 | 0.8130 | 48.33 | 50.85 | −8.6118 | 0 | 1 | 0 | 0 | 0.3475 | 0 |
| 20 | 2 | 0.8102 | 35.00 | 42.37 | −2.2241 | 0 | 0 | −0.78667 | 0 | 1.0765 | 0 |
| 3 | 2 | 0.8093 | 48.33 | 47.46 | −10.046 | 0.18289 | 1.2184 | 0 | 0 | 0 | 0 |
| 10 | 2 | 0.8068 | 51.67 | 52.54 | −11.01 | 0 | 1.3885 | 0 | 0.12681 | 0 | 0 |
| 24 | 2 | 0.8065 | 31.67 | 42.37 | −4.3207 | 0 | 0 | 0 | −7.84E−02 | 1.1282 | 0 |
| 17 | 2 | 0.8048 | 28.33 | 42.37 | −3.938 | −0.24835 | 0 | 0 | 0 | 1.3149 | 0 |
| 33 | 2 | 0.7921 | 36.67 | 49.15 | −16.106 | 1.3541 | 0 | 0 | 0 | 0 | 1.0097 |
| 5 | 2 | 0.7754 | 30.00 | 54.24 | −7.6711 | 1.2227 | 0 | −0.61344 | 0 | 0 | 0 |
| 9 | 2 | 0.7718 | 35.00 | 52.54 | −8.8519 | 1.2937 | 0 | 0 | −0.14952 | 0 | 0 |
| 36 | 2 | 0.7113 | 20.00 | 27.12 | −2.8691 | 0 | 0 | −1.391 | 0 | 0 | 1.4243 |
| 40 | 2 | 0.6983 | 15.00 | 25.42 | −1.5982 | 0 | 0 | 0 | −0.47483 | 0 | 1.1646 |
| 12 | 2 | 0.6961 | 18.33 | 18.64 | 7.3191 | 0 | 0 | −1.0488 | −0.39666 | 0 | 0 |
| 52 | 3 | 0.8319 | 26.67 | 61.02 | −8.1557 | 0 | 0 | −1.0734 | 0 | 1.0665 | 1.3105 |
| 49 | 3 | 0.8299 | 38.33 | 64.41 | −9.4457 | −0.16237 | 0 | 0 | 0 | 1.2638 | 0.95548 |
| 38 | 3 | 0.8291 | 51.67 | 52.54 | −11.787 | 0 | 1.2127 | −0.90702 | 0 | 0 | 1.1775 |
| 50 | 3 | 0.8288 | 43.33 | 55.93 | −13.395 | 0 | 0.96662 | 0 | 0 | 0.38068 | 0.91813 |
| 56 | 3 | 0.8285 | 40.00 | 59.32 | −8.8677 | 0 | 0 | 0 | −0.16768 | 1.1205 | 1.0282 |
| 35 | 3 | 0.8226 | 50.00 | 52.54 | −15.171 | 0.2494 | 1.1715 | 0 | 0 | 0 | 0.92838 |
| 22 | 3 | 0.8192 | 38.33 | 50.85 | −5.7441 | 0 | 0.90176 | −0.66762 | 0 | 0.35836 | 0 |
| 21 | 3 | 0.8192 | 25.00 | 42.37 | 1.8168 | −0.71915 | 0 | −0.9327 | 0 | 1.5568 | 0 |
| 42 | 3 | 0.8178 | 48.33 | 52.54 | −14.643 | 0 | 1.3458 | 0 | 4.17E−02 | 0 | 0.89513 |
| 14 | 3 | 0.8158 | 38.33 | 52.54 | −8.2509 | 0 | 1.3096 | −0.66151 | 0.1273 | 0 | 0 |
| 7 | 3 | 0.8155 | 33.33 | 52.54 | −6.6677 | 2.33E−03 | 1.2544 | −0.65841 | 0 | 0 | 0 |
| 19 | 3 | 0.8147 | 45.00 | 52.54 | −7.7027 | −0.18144 | 0.99459 | 0 | 0 | 0.47486 | 0 |
| 28 | 3 | 0.8124 | 38.33 | 42.37 | −1.6155 | 0 | 0 | −0.78053 | −5.87E−02 | 1.0615 | 0 |
| 26 | 3 | 0.8116 | 48.33 | 52.54 | −9.8432 | 0 | 1.0675 | 0 | 9.36E−02 | 0.31563 | 0 |
| 11 | 3 | 0.8085 | 51.67 | 47.46 | −11.398 | 0.15545 | 1.2828 | 0 | 0.11619 | 0 | 0 |
| 25 | 3 | 0.8068 | 28.33 | 47.46 | −3.1168 | −0.24726 | 0 | 0 | −7.82E−02 | 1.2971 | 0 |
| 37 | 3 | 0.8020 | 25.00 | 57.63 | −13.206 | 1.1841 | 0 | −0.93208 | 0 | 0 | 1.3051 |
| 41 | 3 | 0.8017 | 38.33 | 55.93 | −13.824 | 1.2908 | 0 | 0 | −0.23193 | 0 | 1.0935 |
| 13 | 3 | 0.7788 | 20.00 | 52.54 | −5.7872 | 1.1714 | 0 | −0.61629 | −0.15341 | 0 | 0 |
| 44 | 3 | 0.7500 | 23.33 | 49.15 | 0.93831 | 0 | 0 | −1.3775 | −0.46832 | 0 | 1.5416 |

TABLE E-continued

| Comb # | # of genes | ROCarea | Sensitivity @ 90% spec | Specificity @ 90% sens | Constant | BANK1 | BCNP1 | CDA | MGC20553 | MS4A1 | CD163 |
|---|---|---|---|---|---|---|---|---|---|---|---|
| 53 | 4 | 0.8421 | 28.33 | 62.71 | −4.0963 | −0.72824 | 0 | −1.2159 | 0 | 1.5557 | 1.3112 |
| 54 | 4 | 0.8359 | 43.33 | 54.24 | −10.864 | 0 | 0.79246 | −0.93889 | 0 | 0.43542 | 1.215 |
| 60 | 4 | 0.8345 | 26.67 | 61.02 | −6.7979 | 0 | 0 | −1.0645 | −0.16209 | 1.0289 | 1.3733 |
| 57 | 4 | 0.8322 | 41.67 | 64.41 | −8.0548 | −0.15788 | 0 | 0 | −0.16741 | 1.2282 | 1.0198 |
| 39 | 4 | 0.8294 | 51.67 | 52.54 | −11.969 | 4.28E−02 | 1.1857 | −0.89948 | 0 | 0 | 1.179 |
| 58 | 4 | 0.8288 | 43.33 | 55.93 | −13.371 | 0 | 0.96496 | 0 | −2.24E−03 | 0.38154 | 0.91909 |
| 51 | 4 | 0.8285 | 41.67 | 55.93 | −12.968 | −7.93E−02 | 0.9637 | 0 | 0 | 0.43635 | 0.91323 |
| 46 | 4 | 0.8285 | 51.67 | 50.85 | −12.048 | 0 | 1.2235 | −0.90636 | 2.49E−02 | 0 | 1.1669 |
| 23 | 4 | 0.8237 | 41.67 | 44.07 | −1.9249 | −0.65485 | 0.87804 | −0.81254 | 0 | 0.81182 | 0 |
| 43 | 4 | 0.8212 | 50.00 | 52.54 | −15.382 | 0.2432 | 1.1845 | 0 | 2.32E−02 | 0 | 0.91822 |
| 30 | 4 | 0.8195 | 43.33 | 47.46 | −6.9954 | 0 | 0.97268 | −0.669 | 9.40E−02 | 0.32588 | 0 |
| 29 | 4 | 0.8192 | 28.33 | 47.46 | 2.3538 | −0.71624 | 0 | −0.92591 | −5.37E−02 | 1.5416 | 0 |
| 15 | 4 | 0.8164 | 38.33 | 52.54 | −8.1437 | −3.34E−02 | 1.3322 | −0.66871 | 0.12965 | 0 | 0 |
| 27 | 4 | 0.8124 | 45.00 | 54.24 | −8.9424 | −0.1764 | 1.0611 | 0 | 9.25E−02 | 0.43969 | 0 |
| 45 | 4 | 0.8014 | 30.00 | 67.80 | −10.66 | 1.1055 | 0 | −0.93995 | −0.24668 | 0 | 1.3918 |
| 55 | 5 | 0.8410 | 30.00 | 57.63 | −6.9559 | −0.67682 | 0.76786 | −1.0879 | 0 | 0.9056 | 1.2208 |
| 61 | 5 | 0.8393 | 28.33 | 64.41 | −2.722 | −0.73359 | 0 | −1.2079 | −0.16199 | 1.523 | 1.3754 |
| 62 | 5 | 0.8379 | 43.33 | 55.93 | −10.555 | 0 | 0.76996 | −0.94059 | −2.76E−02 | 0.44682 | 1.228 |
| 59 | 5 | 0.8285 | 41.67 | 55.93 | −12.939 | −7.94E−02 | 0.96171 | 0 | −2.68E−03 | 0.43746 | 0.91437 |
| 47 | 5 | 0.8277 | 51.67 | 50.85 | −12.173 | 3.61E−02 | 1.1995 | −0.90005 | 2.22E−02 | 0 | 1.1693 |
| 31 | 5 | 0.8212 | 41.67 | 40.68 | −3.1633 | −0.65384 | 0.94851 | −0.81521 | 9.32E−02 | 0.77795 | 0 |
| 63 | 6 | 0.8407 | 31.67 | 61.02 | −6.5754 | −0.67929 | 0.74043 | −1.0901 | −3.29E−02 | 0.92168 | 1.2365 |

Primers and probes which were utilized for the QRT-PCR) are further described in Table 17.

Example 12

Testing a Test Subject for One or More Colorectal Pathologies Using The 6 Biomarkers (BCNP1, CD163, CDA, MS4A1, BANK1, MGC20553).

A reference population of 200 individuals is used to generate a formula which will be used to test the test subject. 100 of said individuals are confirmed to have colorectal cancer by colonoscopy. The remaining 100 individuals are screened for colorectal cancer by colonoscopy and are confirmed to be negative for colorectal cancer. Blood Samples are obtained for each of the 200 individuals and total RNA isolated from each isolated blood sample. RNA from each sample is reverse transcribed using an oligo dT primer and cDNA corresponding to the total mRNA is obtained. QRT-PCR is performed on each of the six genes in each of the samples derived from the blood sample and a ΔCt generated for each gene in reference to a Beta-actin control. A data matrix is generated of all of the data across the population. A classifier is developed using each of the following methods (a) logistic regression, (b) linear regression (c) neural networks and (d) principle component analysis. A formula consisting of each of the classifiers, wherein each classifier itself is given a weighting of equal value is generated (ie the results of each classifier when applied to a test subject will give an indication of whether the test subject has a colorectal pathology, and then the results of each classifier are tallied such that if, for example, 3 of the 4 classifiers indicate the test subject has colorectal pathology, the results of the formula indicate the test subject has colorectal pathology).

A blood sample is isolated from a test subject. Total RNA from the blood sample is isolated and cDNA derived using an oligo dT primer. QRT-PCR is performed in each of the six genes in the sample and a ΔCt generated for each gene in reference to a Beta-actin control. The data from the test subject's sample is input into the formula consisting of the four classifiers and a result of each classifier determined, along with the results of the sum of the four classifiers to provide an indication of whether said test subject has colorectal pathology, and in particular colorectal cancer.

Full Citations for References Referred to by Number in the Specification

1] Ogawa M. Differentiation and proliferation of hematopoietic stem cells. Blood 1993; 81:2844-53.

2] Liew, C C. Method for the detection of gene transcripts in blood and uses thereof. U.S. Patent Application No. 2002000268730.

3] Ma J, Liew C C. Gene profiling identifies secreted protein transcripts from peripheral blood cells in coronary artery disease. J Mol Cell Cardiol 2003; 35:993-8.

4] Tsuang M T, Nossova N, Yager T D, Tsuang M M, Guo S C, Shyu K G, et. al. Assessing the validity of blood-based gene expression profiles for the classification of schizophrenia and bipolar disorder: A preliminary report. Am J Med Genet B Neuropsychiatr Genet. 2005; 133B: 1-5.

5] K. Wayne Marshal, Hongwei Zhang, Thomas D. Yager, Nadine Nossova, Adam Dempsey, Run Zheng, Mark Han, Hongchang Tang, Samuel Chao., C. C. Liew. Blood-Based Biomarkers for Detecting Mild Osteoarthritis in the Human Knee. Osteoartlhitis and Cartilage 2005; 13: 861-871.

6] Whistler T, Unger E R, Nisenbaum R, Vernon S D. Integration of gene expression, clinical, and epidemiologic data to characterize Chronic Fatigue Syndrome. J Transl Med. 2003; 1:10.

7] Bennett L, Palucka A K, Arce E., Cantrell V, Borvak J, Banchereau J, et al. Interferon and granulopoiesis signatures in systemic lupus erythematosus blood. J Exp Med 2003; 197:711-23.

8] Zhang H Q, Lu H, Enosawa S, Takahara S, Sakamoto K, Nakajima T, et al. Microarray analysis of gene expression in peripheral blood mononuclear cells derived from long-surviving renal recipients. Transplantation Proceedings 2002; 34: 1757-9.

9] Tang Y, Nee A C, Lu A, Ran R, Sharp F R. Blood genomic expression profile for neuronal injury. J Cereb Blood Flow Metab. 2003; 23:310-9.

10] Tang Y, Gilbert D L, Glauser T A, Hershey A D, Sharp F R. Blood Gene Expression Profiling of Neurologic Diseases: A Pilot Microarray Study. Arch Neurol. 2005; 62:210-5.

11] Imperiale T F, Wagner D R, Lin C Y, Larkin G N, Rogge J D, Ransohoff D F. Results of screening colonoscopy among persons 40 to 49 years of age. N Engl J. Med. 2002 Jun. 6; 346(23): 1781-5.

12] Ransohoff D F. Colorectal cancer screening in 2005: status and challenges. Gastroenterology. 2005 May; 128 (6):1685-95

13] Ahluwalia I B, Mack K A, Murphy W, Mokdad A H, Bales V S. State-specific prevalence of selected chronic disease-related characteristics—Behavioral Risk Factor Surveillance System, 2001. MMWR Surveill Summ. 2003 Aug. 22; 52(8):1-80.

14] Whitney A R, Diehn M, Popper S J, Alizadeh A A, Boldrick J C, Relman D A, et. al.

Individuality and variation in gene expression patterns in human blood. Proc Natl Acad Sci USA. 2003; 100:1896-901.

15] Pepe M S. The Statistical Evaluation of Medical Tests for Classification and Prediction. Oxford, England: Oxford University Press; 2003.

16] Dupont W D. Statistical Modeling for Biomedical Researchers. Cambridge, England: Cambridge University Press; 2002.

17] Pampel F C. Logistic regression: A Primer. Publication # 07-132, Sage Publications: Thousand Oaks, Calif. 2000.

18] King E N, Ryan T P. A preliminary investigation of maximum likelihood logistic regression versus exact logistic regression. Am Statistician 2002; 56:163-170.

19] Metz C E. Basic principles of ROC analysis. Semin Nudl Med 1978; 8:283-98.

20] Swets J A. Measuring the accuracy of diagnostic systems. Science 1988; 240:1285-93.

21] Zweig M H, Campbell G. Receiver-operating characteristic (ROC) plots: a fundamental evaluation tool in clinical medicine. Clin Chem 1993; 39:561-77.

22] Witten I H, Frank Eibe. Data Mining: Practical Machine Learning Tools and Techniques (second edition). Morgan Kaufman 2005.

23] Deutsch J M. Evolutionary algorithms for finding optimal gene sets in microarray prediction. Bioinformatics 2003; 19:45-52.

24] Citarda F, Tomaselli G, Capocaccia R, Barcherini S, Crespi M; Italian Multicentre Study Group. Efficacy in standard clinical practice of colonoscopic polypectomy in reducing colorectal cancer incidence. Gut. 2001 June; 48(6):812-5.

25] Niels Landwehr, Mark Hall and Eibe Frank (2003) Logistic Model Trees. pp 241-252 in Machine Learning: ECML 2003: 14th European Conference on Machine Learning, Cavtat-Dubrovnik, Croatia, Sep. 22-26, 2003, Proceedings Publisher: Springer-Verlag GmbH, ISSN: 0302-9743

26] Tonkin, E. T.; Wang, T.-J.; Lisgo, S.; Bamshad, M. J.; Strachan, T. NIPBL, encoding a homolog of fungal Scc2-type sister chromatid cohesion proteins and fly Nipped-B, is mutated in Cornelia de Lange syndrome. *Nature Genet.* 36: 636-641, 2004. PubMed ID 15146185.

27] Krantz, I. D.; McCallum, J.; DeScipio, C.; Kaur, M.; Gillis, L. A.; Yaeger, D.; Jukofsky, L.; Wasserman, N.; Bottani, A.; Morris, C. A.; Nowaczyk, M. J. M.; Toriello, H.; and 9 others. Cornelia de Lange syndrome is caused by mutations in NIPBL, the human homolog of *Drosophila melanogaster* Nipped-B. *Nature Genet.* 36: 631-635, 2004. PubMed ID 15146186.

28] Nadel M R, Shapiro J A, Klabunde C N, Seeff L C, Uhler R, Smith R A, Ransohoff D F. A national survey of primary care physicians' methods for screening for fecal occult blood. Ann Intern Med. 2005 Jan. 18; 142(2):86-94.

29] Scaloni A, Jones W, Pospischil M, Sassa S, Schneewind O, Popowicz A M, Bossa F, Graziano S L, Manning J M. Deficiency of acylpeptide hydrolase in small-cell lung carcinoma cell lines. J Lab Clin Med. 1992 October; 120(4): 546-52.

30] Erlandsson R, Boldog F, Persson B, Zabarovsky E R, Allikmets R L, Sumegi J, Klein G, Jornvall H. The gene from the short arm of chromosome 3, at D3F15S2, frequently deleted in renal cell carcinoma, encodes acylpeptide hydrolase. Oncogene. 1991 July; 6(7):1293-5.

31] Brown M S, Goldstein J L. A proteolytic pathway that controls the cholesterol content of membranes, cells, and blood. Proc Natl Acad Sci USA. 1999 Sep. 28; 96(20): 11041-8.

32] Adams J C, Seed B, Lawler J. Muskelin, a novel intracellular mediator of cell adhesive and cytoskeletal responses to thrombospondin-1. EMBO J. 1998 Sep. 1; 17(17):4964-74.

33] Gillis L A, McCallum J, Kaur M, DeScipio C, Yaeger D, Mariani A, Kline A D, Li H H, Devoto M, Jackson L G, Krantz I D. NIPBL mutational analysis in 120 individuals with Cornelia de Lange syndrome and evaluation of genotype-phenotype correlations. Am J Hum Genet. 2004 October; 75(4):610-23. Epub 2004 Aug. 18.

34] Takakura S, Kohno T, Manda R, Okamoto A, Tanaka T, Yokota J. Genetic alterations and expression of the protein phosphatase 1 genes in human cancers. Int J Oncol. 2001 April; 18(4):817-24.

35] Periale T F, Ransohoff D F, Itzkowitz S H, Turnbull B A, Ross M E; Colorectal Cancer. Study Group. Fecal DNA versus fecal occult blood for colorectal-cancer screening in an average-risk population. N Engl J. Med. 2004 Dec. 23; 351(26):2704-14.

All patents, patent applications, and published references cited herein are hereby incorporated by reference in their entirety.

One skilled in the art will readily appreciate that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

While this invention has been particularly shown and described with references to preferred embodiments thereof, it will be understood by those skilled in the art that various changes in form and details may be made therein without departing from the scope of the invention encompassed by the appended claims.

TABLES

Table 1 is found in the instant specification after Table 17, and before the sequence listing and claims.

TABLE 2

| Gene Symbol | AffySpot | p-value (MW) | p-value (t-test) | Fold change | Direction | Gene Description |
|---|---|---|---|---|---|---|
| APEH | 201284_s_at | | 6.0e−03 | 0.91 | downregulated | N-acylaminoacyl-pept |
| Clorf22 | 220342_x_at | <0.001 | 3.15049390173162e−03 | 1.07 | upregulated | chromosome 1 open re |
| ESR1 | 215551_at | 0.058 | 0.03 | 0.87 | downregulated | estrogen receptor 1 |
| ETS1 | 214447_at | 0.132 | 0.15 | 0.93 | downregulated | v-ets erythroblastos |
| FLJ14624 | 225666_at | | 0.01 | 0.76 | downregulated | hypothetical protein |
| FLJ20701 | | | 0.01 | 0.76 | downregulated | hypothetical protein |
| FLJ23091 | 221958_s_at | | 0.05 | 0.83 | downregulated | putative NFkB activa |
| G2 | 234784_at | 0.182 | 0.18 | 0.78 | downregulated | G2 protein |
| ICOS | 210439_at | | 0.07 | 0.88 | downregulated | inducible T-cell co- |
| ITCH | 235057_at | <0.001 | 1.73049856446377e−06 | 1.13 | upregulated | itchy homolog E3 ubi |
| MBTPS1 | 217543_s_at | | 8.0e−03 | 1.21 | upregulated | membrane-bound trans |
| MGC40157 | 225065_x_at | 0.301 | 0.04 | 1.19 | downregulated | hypothetical protein |
| MGC45871 | 226905_at | | 0.11 | 1.35 | upregulated | hypothetical protein |
| MKLN1 | 242984_at | 0.003 | 0.04 | 1.06 | upregulated | muskelin 1, intracel |
| MMP9 | 203936_s_at | 0.006 | 7.80154116715436e−03 | 1.24 | upregulated | matrix metalloprotei |
| NIPBL | 156074_at | 0.005 | 0.01 | 1.07 | upregulated | Nipped-B homolog (Dr |
| RPS24 | 1555878_at | | 0.05 | 0.88 | downregulated | ribosomal protein S2 |
| SMARCA1 | 203874_s_at | 0.077 | 0.06 | 0.82 | downregulated | SWI/SNF related, mat |

TABLE 3

| Gene Symbol | RNA Accession No. | Protein Accession No. | Description |
|---|---|---|---|
| FLJ14624 | NM_032813 | NP_116202 | *Homo sapiens* hypothetical protein FLJ14624 (FLJ14624), mRNA |
| FLJ14624 | NM_032813 | NP_116202 | *Homo sapiens* hypothetical protein FLJ14624 (FLJ14624), mRNA |
| ETS1 | NM_005238 | NP_005229 | *Homo sapiens* v-ets erythroblastosis virus E26 oncogene homolog 1 (avian) (ETS1), mRNA |
| RPS24 | NM_033022 | NP_148982 | *Homo sapiens* ribosomal protein S24 (RPS24), transcript variant 1, mRNA |
| RPS24 | NM_001026 | NP_001017 | *Homo sapiens* ribosomal protein S24 (RPS24), transcript variant 2, mRNA |
| FLJ20701 | NM_017933 | NP_060403 | *Homo sapiens* hypothetical protein FLJ20701 (FLJ20701), mRNA |
| MKLN1 | NM_013255 | NP_037387 | *Homo sapiens* muskelin 1, intracellular mediator containing kelch motifs (MKLN1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| FLJ20701 | NM_017933 | NP_060403 | *Homo sapiens* hypothetical protein FLJ20701 (FLJ20701), mRNA |
| RPS24 | NM_033022 | NP_148982 | *Homo sapiens* ribosomal protein S24 (RPS24), transcript variant 1, mRNA |
| RPS24 | NM_001026 | NP_001017 | *Homo sapiens* ribosomal protein S24 (RPS24), transcript variant 2, mRNA |
| APEH | NM_001640 | NP_001631 | *Homo sapiens* N-acylaminoacyl-peptide hydrolase (APEH), mRNA |
| MBTPS1 | NM_003791 | NP_003782 | *Homo sapiens* membrane-bound transcription factor protease, site 1 (MBTPS1), transcrip |
| MBTPS1 | NM_201268 | NP_957720 | *Homo sapiens* membrane-bound transcription factor protease, site 1 (MBTPS1), transcrip |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| MMP9 | NM_004994 | NP_004985 | *Homo sapiens* matrix metalloproteinase 9 (gelatinase B, 92 kDa gelatinase, 92 kDa type I |
| MKLN1 | NM_013255 | NP_037387 | *Homo sapiens* muskelin 1, intracellular mediator containing kelch motifs (MKLN1), mRNA |
| ESR1 | NM_000125 | NP_000116 | *Homo sapiens* estrogen receptor 1 (ESR1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| ITCH | NM_031483 | NP_113671 | *Homo sapiens* itchy homolog E3 ubiquitin protein ligase (mouse) (ITCH), mRNA |
| ITCH | NM_031483 | NP_113671 | *Homo sapiens* itchy homolog E3 ubiquitin protein ligase (mouse) (ITCH), mRNA |
| ICOS | NM_012092 | NP_036224 | *Homo sapiens* inducible T-cell co-stimulator (ICOS), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| ETS1 mRNA | NM_005238 | NP_005229 | *Homo sapiens* v-ets erythroblastosis virus E26 oncogene homolog 1 (avian) (ETS1), |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ITCH | NM_031483 | NP_113671 | *Homo sapiens* itchy homolog E3 ubiquitin protein ligase (mouse) (ITCH), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| MBTPS1 | NM_003791 | NP_003782 | *Homo sapiens* membrane-bound transcription factor protease, site 1 (MBTPS1), transcrip |
| MBTPS1 | NM_201268 | NP_957720 | *Homo sapiens* membrane-bound transcription factor protease, site 1 (MBTPS1), transcrip |
| FLJ20701 | NM_017933 | NP_060403 | *Homo sapiens* hypothetical protein FLJ20701 (FLJ20701), mRNA |
| C1orf22 | NM_025191 | NP_079467 | *Homo sapiens* chromosome 1 open reading frame 22 (C1orf22), mRNA |

TABLE 3-continued

| Gene Symbol | RNA Accession No. | Protein Accession No. | Description |
|---|---|---|---|
| C1orf22 | NM_025191 | NP_079467 | *Homo sapiens* chromosome 1 open reading frame 22 (C1orf22), mRNA |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| C1orf22 | NM_025191 | NP_079467 | *Homo sapiens* chromosome 1 open reading frame 22 (C1orf22), mRNA |
| ETS1 mRNA | NM_005238 | NP_005229 | *Homo sapiens* v-ets erythroblastosis virus E26 oncogene homolog 1 (avian) (ETS1), |
| MGC40157 | NM_152350 | NP_689563 | *Homo sapiens* hypothetical protein MGC40157 (MGC40157), mRNA |
| MKLN1 mRNA | NM_013255 | NP_037387 | *Homo sapiens* muskelin 1, intracellular mediator containing kelch motifs (MKLN1), |
| FLJ14624 | NM_032813 | NP_116202 | *Homo sapiens* hypothetical protein FLJ14624 (FLJ14624), mRNA |
| MGC45871 | NM_182705 | NP_874364 | *Homo sapiens* hypothetical protein MGC45871 (MGC45871), mRNA |
| MGC45871 | NM_182705 | NP_874364 | *Homo sapiens* hypothetical protein MGC45871 (MGC45871), mRNA |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| MKLN1 mRNA | NM_013255 | NP_037387 | *Homo sapiens* muskelin 1, intracellular mediator containing kelch motifs (MKLN1), |
| ESR1 | NM_000125 | NP_000116 | *Homo sapiens* estrogen receptor 1 (ESR1), mRNA |
| ITCH | NM_031483 | NP_113671 | *Homo sapiens* itchy homolog E3 ubiquitin protein ligase (mouse) (ITCH), mRNA |
| MKLN1 mRNA | NM_013255 | NP_037387 | *Homo sapiens* muskelin 1, intracellular mediator containing kelch motifs (MKLN1), |
| FLJ20701 | NM_017933 | NP_060403 | *Homo sapiens* hypothetical protein FLJ20701 (FLJ20701), mRNA |
| FLJ20701 | NM_017933 | NP_060403 | *Homo sapiens* hypothetical protein FLJ20701 (FLJ20701), mRNA |
| ITCH | NM_031483 | NP_113671 | *Homo sapiens* itchy homolog E3 ubiquitin protein ligase (mouse) (ITCH), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| MKLN1 mRNA | NM_013255 | NP_037387 | *Homo sapiens* muskelin 1, intracellular mediator containing kelch motifs (MKLN1), |
| MKLN1 mRNA | NM_013255 | NP_037387 | *Homo sapiens* muskelin 1, intracellular mediator containing kelch motifs (MKLN1), |

TABLE 4

| Gene Symbol | SensePrimer | SEQ ID NO | AntisensePrimer | SEQ ID NO | TaqManProbe | SEQ ID NO |
|---|---|---|---|---|---|---|
| APEH | GCCCTGTATTATGTGGACCT | 54 | AGATGGGTACTGCAGGTAGA | 55 | CCGGCTGAGCCCAGACCAAT | 56 |
| APEH | CACTCGGAGACACACTTGTT | 57 | CTTGGTCTGGCTTCTTCAG | 58 | CATCGCTGGCACTGACGTCCA | 59 |
| APEH | ACTCGGAGACACACTTGTTG | 60 | CTTGGTCTGGCTTCTTCAG | 61 | CATCGCTGGCACTGACGTCCA | 62 |
| APEH | AGTGGTGGTAGATGTTGTGC | 63 | AGACCACTCTCTGGCTGTC | 64 | TGCAGCCTTCTGCCTTTGGGA | 65 |
| APEH | CACTTGTTGTATGTGGCAGA | 66 | GCCTGGCTATCTCATCATC | 67 | | |
| Clorf22 | TAGGGAGGAGAAACAGAAGC | 68 | GGCCTCTAACTCGACCTCTA | 69 | TGGAACATGCTTACCCTGCTGATGA | 70 |
| Clorf22 | TGTGGTGGATAAGAGCTGTC | 71 | CCCATCTTCTTCAGGATTTC | 72 | TGGCCATGAAATCTCTGGCTCTCA | 73 |
| Clorf22 | GAGGAGAGTTTCAGGAGTGG | 74 | CTCGCATCTTTGAGGTGAAT | 75 | TGGCCATGAAATCTCTGGCTCTCA | 76 |
| Clorf22 | TTGCTTGGAGATGACAGTTT | 77 | AGCATTGGTTTGTGGATATG | 78 | | |
| ESR1 | GGCACATCTTCTGTCTTCTG | 79 | CTGTGAAGAGCTACGGGAAT | 80 | TGGAATCCCTTTGGCTGTTCCC | 81 |
| ESR1 | TGGCACATCTTCTGTCTTCT | 82 | CTGTGAAGAGCTACGGGAAT | 83 | TGGAATCCGTTTGGCTGTTCCC | 84 |
| ESR1 | CCCTACTACCTGGAGAACGA | 85 | ATTGGTACTGGCCAATCTTT | 86 | CTGCCACCCTGGCGTCGATT | 87 |
| ESR1 | CACCATTCCCAAGTTAATCC | 88 | GAAATGCAGTTGGAAACAGA | 89 | TGGGACCAAAGTTCATTTGCTCCA | 90 |
| ESR1 | TGCCCTACTACCTGGAGAAC | 91 | ATTGGTACTGGCCAATCTTT | 92 | AGCCCAGCGGCTACACGGTG | 93 |
| ESR1 | GTGCCCTACTACCTGGAGAA | 94 | ATTGGTACTGGCCAATCTTT | 95 | AGCCCAGCGGCTACACGGTG | 96 |
| ESR1 | TGTGCAATGACTATGCTTCA | 97 | TTATCAATGGTGCACTGGTT | 98 | | |
| ESR1 | TGTGCAATGACTATGCTTCA | 99 | TTTATCAATGGTGCACTGGT | 100 | | |
| ETS1 | TGGGTGGTTTATACACTGGA | 101 | ATAAGGGTTTCACCCAGCTA | 102 | CCAGATTTGCCCATCCTTCCTCTG | 103 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| ETS1 | GAGCTCCTCTCCCTCAAGTA | 104 | GGTGACGACTTCTTGTTGA | 105 | CCTCGGTCATTCTCCGAGACCC | 106 |
| ETS1 | GGATGTCAGGTGAGACTGTG | 107 | GCCTTCAAGTCATTCCTCTC | 108 | CCCTGGCATCACCTGTGCCA | 109 |
| ETS1 | TCAAACAAGAAGTCGTCACC | 110 | GCGATCACAACTATCGTAGC | 111 | CCCGAGTTTACCACGACTGGTCCTC | 112 |
| ETS1 | CCGCTATACCTCGGATTACT | 113 | GCGTCTGATAGGACTCTGTG | 114 | CCCAGTGTGTTCCACCATCGGA | 115 |
| FLJ14624 | ACAGCTGCCATCAGAAACTA | 116 | GCTTCCTGTAGCTCATTCCT | 117 | CCGGGAAGCTGTAAGATTAAATCCCAA | 118 |
| FLJ14624 | TGATAAAGGCAACCAGACAG | 119 | AGCTTCGTGTAGCTCATTCC | 120 | TGCCATCAGAAACTACCGGGAAGC | 121 |
| FLJ14624 | GGATTTCTCGTTATCCCATT | 122 | TCTTGGTATGTTTGCTCAGG | 123 | AGGACACGCTCCGCGACCAC | 124 |
| FLJ14624 | CAAATACAGCCAGACTTTGC | 125 | TTTAATTGCTGTCCGGTAAC | 126 | TGCTGCTTCAAACCGTTTCAGGC | 127 |
| FLJ14624 | CAAATACAGCCAGACTTTGC | 128 | GTTTAATTGCTGTCCGGTAA | 129 | TGCTGCTTCAAACCGTTTCAGGC | 130 |
| FLJ14624 | CTTGGTGATAGGCAAATTCA | 131 | AGCAGGGTCATTCTGAAGAG | 132 | CCCGTTCCTGAGCATGCCGA | 133 |
| FLJ14624 | TTTGGCTGTGCTTTATCATC | 134 | CAGCAGACCGTAATTCTCCT | 135 | TGTTTCTTGGCCAAGTCTAGATGTCCC | 136 |
| FLJ20701 | ATTGGAGGACAAGAGCAGAT | 137 | CCATCGCTCTCTAGATTGG | 138 | TTCTTAGGTGCCGCAGTGCCC | 139 |
| FLJ20701 | CCTTCAGGAAGACTTTCCAC | 140 | CTCAAGTTCATTCAGCCATC | 141 | ACGGGCGGATCCACAGCAAC | 142 |
| FLJ20701 | TGATCAGCAAGTGAACACAC | 143 | CTCGGTGATAGCAAATCAGA | 144 | TGCATCCTTGATGGCAAGCTCA | 145 |
| FLJ20701 | GTGATCAGCAAGTGAACACA | 146 | CTCGGTGATAGCAAATCAGA | 147 | TGCATCCTTGATGGCAAGCTCA | 148 |
| FLJ20701 | TTAATGGTCCTGTCTGATGC | 149 | GGGTCTCTAGACAAGCCAAG | 150 | | |
| FLJ20701 | AGATTTGCAGACACAGAAGC | 151 | TTCTAACATCAGGTGGTTGC | 152 | | |
| FLJ23091 | TACAACTCACGAATCCCTTCT | 153 | ACAGGAAGTAGAGGCAGAGG | 154 | | |
| FLJ23091 | CAACTCACGAATCCCTTCTAC | 155 | ACAGGAAGTAGAGGCAGAGG | 156 | | |
| FLJ23091 | ACAACTCACGAATCCCTTCTA | 157 | ACAGGAAGTAGAGGCAGAGG | 158 | | |
| FLJ23091 | AACTCACGAATCCCTTCTACA | 159 | ACAGGAAGTAGAGGCAGAGG | 160 | | |
| FLJ23091 | GGGATTTCCATGACCTTTAT | 161 | ATCCAGAAGGACAGAAGCAT | 162 | TGCCCTGTCGGATGTCACCA | 163 |
| FLJ23091 | ATTGAAGAGGCAATTCCAAG | 164 | TTTAGCTTGAAGGCAATGTC | 165 | CCACATGGAGATGAGTCCTTGGTTCC | 166 |
| ICOS | CATGTGTAATGCTGGATGTG | 167 | AAACAACTCAGGGAACACCT | 168 | TGGACAACCTGACTGGCTTTGCA | 169 |
| ICOS | CAGGCCTCTGGTATTTCTTT | 170 | ATTTGTACACCTCCGTTGTG | 171 | TTGGCAGAACCATTGATTTCTCCTGTT | 172 |
| ICOS | AAACATGAAGTCAGGCCTCT | 173 | GTACACCTCCGTTGTGAAAT | 174 | TTGGCAGAACCATTGATTTCTCCTGTT | 175 |
| ICOS | GTCAGGCCTCTGGTATTTCT | 176 | ATTTGTACACCTCCGTTGTG | 177 | TTGGCAGAACCATTGATTTCTCCTGTT | 178 |
| ICOS | GAAGTCAGGCCTCTGGTATT | 179 | ATTTGTACACCTCCGTTGTG | 180 | TTGGCAGAACCATTGATTTCTCCTGTT | 181 |
| ITCH | CAGATCCAAGGATGAAACAA | 182 | ACCACCATTTGAGAGTGATG | 183 | CACCAGCTCCTGCATCTTCAGGG | 184 |
| ITCH | TCAATCCAGATCACCTGAAA | 185 | AATCCTTGAGTCCAACTGGT | 186 | CCCATGGAACAGAGCCATGGC | 187 |
| ITCH | AAGCTGTTGTTTGCCATAGA | 188 | CAGAGAAGGACAAACATTGC | 189 | TGCCCATTCATGGTGCAAGTTCTC | 190 |
| ITCH | AAGCTGTTGTTTGCCATAGA | 191 | GCAGAGAAGGACAAACATTG | 192 | TGCCCATTCATGGTGCAAGTTCTC | 193 |
| ITCH | GCTGTTGTTTGCCATAGAAG | 194 | CAGAGAAGGACAAACATTGC | 195 | TGCCCATTCATGGTGCAAGTTCTC | 196 |
| ITCH | GCTGTTGTTTGCCATAGAAG | 197 | GCAGAGAAGGACAAACATTG | 198 | TGCCCATTCATGGTGCAAGTTCTC | 199 |
| MBTPS1 | CAATGACGGACCTCTTTATG | 200 | GGTAGCTCCCAGGTAGTCAT | 201 | TGCCGCCTACTCCAATCACATCC | 202 |
| MBTPS1 | TCTGTGGGAAGAAACATCTG | 203 | TGATGAGAATTCCACCTTCA | 204 | | |
| MBTPS1 | AATCCATCCAGTGACTACCC | 205 | ACTTGAGGGAACGAAAGACT | 206 | AACATCAAACGGGTCACGCCC | 207 |
| MBTPS1 | CAGCCAAAGCTAGAAATTCA | 208 | TAGGGTAGTCACTGGATGGA | 209 | TTCACTGCTCTTCAGGGCACTTGAA | 210 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| MBTPS1 | GCAATGACGGACCTCTTTAT | 211 | GGTAGCTCCCAGGTAGTCAT | 212 | TGCCGCCTACTCCAATCACATCC | 213 |
| MGC40157 | AGAATCAGCATCATGTTTGG | 214 | ATAACCTTCTCTTGGGCTGA | 215 | CCTCATGGCAGGCTCCTGGC | 216 |
| MGC40157 | TCAGCCCAAGAGAAGGTTAT | 217 | TGAGCATGTCCTCTGATACA | 218 | TCCCAAGGACCAGTAGCTGCCA | 219 |
| MGC40157 | GACTACAGCTCACAGCACAC | 220 | AAAGCTACAACTTGGCCTGT | 221 | TGCCCAGGCTGGTCTCAGGC | 222 |
| MGC40157 | TCAGCCCAAGAGAAGGTTAT | 223 | AGGCAAGCATGTTTCTACAC | 224 | TCCCAAGGACCAGTAGCTGCCA | 225 |
| MGC40157 | ACTACAGCTCACAGCACACC | 226 | AAAGCTACAACTTGGCCTGT | 227 | TGCCCAGGCTGGTCTCAGGC | 228 |
| MGC40157 | TCAGCCCAAGAGAAGGTTAT | 229 | CATAAGGCAAGCATGTTTCT | 230 | TCCCAAGGACCAGTAGCTGCCA | 231 |
| MGC40157 | AGGCTCATGGATCACTCTTT | 232 | GGTACGCAATCCAGTTCTCT | 233 | CCGGCCTTCGCAGACTCCAG | 234 |
| MCG45871 | GACCTCTCTGATGAATGCTG | 235 | AATGACGTGAAGGGTAAGGT | 236 | ACCGGCTCTCCGGGTGTCGT | 237 |
| MCG45872 | GACCTCTCTGATGAATGCTG | 238 | GAATGACGTGAAGGGTAAGG | 239 | ACCGGCTCTCCCGCTGTCCT | 240 |
| MCG45873 | GACCTCTCTGATGAATGCTG | 241 | GAATGACGTGAAGGGTAAGGT | 242 | ACCGGCTCTCCCGCTGTCCT | 243 |
| MCG45874 | GACCTCTCTGATGAATGCTG | 244 | GGAATGACGTGAAGGGTAAG | 245 | AGCGGCTCTCCCGGTGTCCT | 246 |
| MCG45875 | CCTCTCTGATGAATGCTGAC | 247 | GAATGACGTGAAGGGTAAGG | 248 | ACCGGCTCTCCCGCTGTCCT | 249 |
| MCG45876 | ACCTCTCTGATGAATGCTGA | 250 | GAATGACGTGAAGGGTAAGG | 251 | ACCGGCTCTCCCGCTGTCCT | 252 |
| MKLN1 | CCAGTGAACCACAATTCAGT | 253 | ATGCAGTGTCCTATTCGAGA | 254 | TGGATGTCCTCAGGCCCAGCA | 255 |
| MKLN1 | GGATCACACCTATGCTCAAA | 256 | CCATTTCTGTGTCCAGTGAC | 257 | TGACAGCATGACTCCTCCTAAAGGCA | 258 |
| MKLN1 | ATTTGAGAGAGGAGGCTGAG | 259 | AATGAAATGCCTGTCAGTTG | 260 | CCACTGGACAACCACAAACCATTTCTC | 261 |
| MKLN1 | GACTTGTAATGGCAGCGTAG | 262 | CTCGAAGAAGTTTCCAGGTT | 263 | TGACAGCAGAGCCAGTGAACCACA | 264 |
| MKLN1 | ACTTGTAATGGCAGCGTAGA | 265 | CTCGAAGAAGTTTCCAGGTT | 266 | TGACAGCAGAGCCAGTGAACCACA | 267 |
| MMP9 | ACTTTGACAGCGACAAGAAGT | 268 | GCGGTACATAGGGTACATGA | 269 | CGCCGCCACGAGGAAGAAAC | 270 |
| MMP9 | AACTTTGACAGCGACAAGAA | 271 | GAAGGGGTACATAGGGTACAT | 272 | CGCCGCCACGAGGAAGAAAC | 273 |
| MMP9 | CAGTACCACGGCCAACTAC | 274 | TGGAAGATGAATGGAAACTG | 275 | CCCATCAGCATTGCCGTCCC | 276 |
| MMP9 | CCACTACTGTGCCTTTGAGT | 277 | GTACTTCCGATCCTTGAACA | 278 | TTCCCAATCTCCGCGATGGC | 279 |
| MMP9 | CCACTACTGTGCCTTTGAGT | 280 | CTTCGCATCCTTGAAGAAA | 281 | TTCCCAATCTCCGCGATGGC | 282 |
| NIPBL | CACGAATAGCAGAAGAGGTG | 283 | GTATGTCACCTTCTGGGTCA | 284 | CAGCTTGTCCATAGCCTCAACCAGG | 285 |
| NIPBL | CCCATCCTTCAAGTTACACA | 286 | ATTAGCTGAATTGCCAGACA | 287 | TCCACAGATGCAACAAGCATCGG | 288 |
| NIPBL | GGGATTGCTAGTCTCACAGA | 289 | TCTTCTGCTATTCGTGCATT | 290 | TCCTGAACCAGCTGCCTCTTCCA | 291 |
| NIPBL | CCCATCGTTCAAGTTACACA | 292 | AGACAACGGACCAGAAACTT | 293 | TCCACAGATGCAACAAGCATCGG | 294 |
| NIPBL | GCACAGGCTAAGTAGTGACG | 295 | AGGTGGTCTTGAGCCTTTAG | 296 | TTTCCCTTGAGATCTCCACAGCCA | 297 |
| NIPBL | CACCAATAGCAGAAGAGGTG | 298 | GTATGTCACCTTCTGGGTCA | 299 | CAGCTTGTCCATAGCCTCAACCAGG | 300 |
| NIPBL | CCCATCCTTCAAGTTACACA | 301 | ATTAGCTGAATTGCCAGACA | 302 | TCCACAGATGCAACAAGCATCGG | 303 |
| NIPBL | GGGATTGCTAGTCTCACAGA | 304 | TCTTCTGCTATTCGTGCATT | 305 | TCCTGAACCAGCTGCCTCTTCCA | 306 |
| NIPBL | CCCATCCTTCAAGTTACACA | 307 | AGACAACGGACCAGAAACTT | 308 | TCCACAGATGCAACAAGCATCGG | 309 |
| NIPBL | GCACAGGCTAAGTAGTGACG | 310 | AGGTGGTCTTGAGCCTTTAG | 311 | TTTCCCTTGAGATCTCCACAGCCA | 312 |
| RPS24 | CACCGTAACTATCCGCACTA | 313 | CGGTGTGGTCTTGTACATTT | 314 | AGGCACTGTCGCCTTCCCGG | 315 |
| RPS24 | AAGAAAGCAACGAAAGGAAC | 316 | TCATTGCAGCACCTTTACTC | 317 | TGCCAGCACCAACATTGGCC | 318 |
| RPS24 | AGACATGGCCTGTATGAGAA | 319 | ATCCAATCTCCAGCTCACTT | 320 | TGCCAGCACCAACATTGGCC | 321 |
| RPS24 | AAGACATGGCCTGTATGAGA | 322 | ATCCAATCTCCAGCTCACTT | 323 | TGCCAGCACCAACATTGGCC | 324 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| RPS24 | GACATGGCCTGTATGAGAAG | 325 | ATCCAATGTCCAGCTCAGTT | 326 | TGCCAGCACCAACATTGGCC | 327 |
| RPS24 | AAGGAACGCAAGAACAGAAT | 328 | ATTGCAGCACCTTTACTCCT | 329 | TGCCAGCACCAACATTGGCC | 330 |
| SMARCA1 | TACCTGGTCATTGATGAAGC | 331 | CAAAGGTGTTCCAGTTAGGA | 332 | CGTGAGTTCAAGTCGACTAACCGCTTG | 333 |
| SMARCA1 | TACCTGGTCATTGATGAAGC | 334 | TTATTCTGCAAAGGTGTTCC | 335 | TTCAAGTCGACTAACCGCTTGCTCC | 336 |
| SMARCA1 | TGGACCCAGAATATGAAGAG | 337 | ATGTTCAGTGGAGATGTTGG | 338 | TCTCTTTGCTCGGTCGGCTTTCA | 339 |
| SMARCA1 | CTTTGCTTGGTTACCTGAAA | 340 | AAACAAATGACACGGAGAGA | 341 | CCGAAATATTCCTGGACCTCACATGG | 342 |
| SMARCA1 | GGAAATGGACCCAGAATATG | 343 | GTTGGAGATTTCTGTGCTGA | 344 | TCTCTTTGCTCGGTCGGCTTTCA | 345 |
| SMARCA1 | AAGGAAATGGACCCAGAATA | 346 | CTGAAGGCTGAATGAAATGT | 347 | TCTCTTTGCTCGGTCGGCTTTCA | 348 |
| SMARCA1 | AGTGGGATGTTTGCGTTACT | 349 | CACGAACAATCTCTGAAAGC | 350 | TCATCAATGACCAGGTATCGCCAGTG | 351 |

TABLE 5

| Gene Symbol | Description | Commercially Available Antibody Reference | Scientific Reference |
|---|---|---|---|
| APEH | N-acylaminoacyl-peptide hydrolase | | |
| C1orf22 | chromosome 1 open reading frame 22 | | |
| ESR1 | estrogen receptor 1 | Ab2746 (Abcam) | Shevde N K & Pike J W Estrogen modulates the recruitment of myelopoietic cell progenitors in rat through a stromal cell-independent mechanism involving apoptosis. Blood 87: 2683-92 (1996). Yang N N et al. Identification of an estrogen response element activated by metabolites of 17beta-estradiol and raloxifene. Science 273: 1222-5 (1996). |
| ETS1 | v-ets erythroblastosis virus E26 oncogene homolog 1 (avian) | Ab10936 (Abcam) | Pande P et al. Ets-1: a plausible marker of invasive potential and lymph node metastasis in human oral squamous cell carcinomas. J Pathol 189: 40-5 (1999). Nakayama T et al. Expression of the Ets-1 proto-oncogene in human gastric carcinoma: correlation with tumor invasion. Am J Pathol 149: 1931-9 (1996). Bories J C et al. Increased T-cell apoptosis and terminal B-cell differentiation induced by inactivation of the Ets-1 proto-oncogene. Nature 377: 635-8 (1995). Wernert N et al. Stromal expression of c-Ets1 transcription factor correlates with tumor invasion. Cancer Res 54: 5683-8 (1994). |
| FLJ14624 | | | |
| FLJ20701 | putative NFkB activating protein 373 | | |
| FLJ23091 | inducible T-cell co-stimulator | | |
| G2 | G2 protein | | |
| ICOS | inducible T-cell co-stimulator | Ab3744 (Abcam) | |
| ITCH | itchy homolog E3 ubiquitin protein ligase (mouse) | | |
| MBTPS1 | membrane-bound transcription factor protease, site 1 | | |

TABLE 5-continued

| Gene Symbol | Description | Commercially Available Antibody Reference | Scientific Reference |
|---|---|---|---|
| MGC40157 | hypothetical protein MGC40157 | | |
| MGC45871 | hypothetical protein MGC45871 | | |
| MKLN1 | muskelin 1, intracellular mediator containing kelch motifs | | |
| MMP9 | matrix metalloproteinase 9 (gelatinase B, 92 kDa gelatinase, 92 kDa type IV collagenase) | Ab5707 | |
| NIPBL | Nipped-B homolog (*Drosophila*) | | |
| RPS24 | ribosomal protein S24 | | |
| SMARCA1 | SWI/SNF related, matrix associated, actin dependent regulator of chromatin, subfamily a, member 1 | Ab21924 (Abcam) | Lazzaro M A & Picketts D J Cloning and characterization of the murine Imitation Switch (ISWI) genes: differential expression patterns suggest distinct developmental roles for Snf2h and Snf2l. J Neurochem 77: 1145-56 (2001). |

TABLE 6

| | | 5'Primer | | | 3'Primer | | | Pro- |
|---|---|---|---|---|---|---|---|---|
| Symbol | Ref. ID | Primer Sequence | Posi-tion | SEQ ID NO: | Primer Sequence | Posi-tion | SEQ ID NO: | duct Length |
| APEH | NM_001640 | AAGGATGTCCAGTTTGCAGTGG | 2081 | 878 | TGGCAGGAAATGAAGCCAGCAT | 2184 | 886 | 104 |
| FLJ23091 | NM_024911 | ACAGGCATCTATGGGATGTGGA | 1694 | 879 | AGATCGCCATTGGACTGGTCTT | 1794 | 887 | 104 |
| MBTPS1 | NM_003791 | TCGGTACTCCAAGGTTCTGGA | 3220 | 880 | TGTTTCCAAAGGTTACTGGGCG | 3348 | 888 | 129 |
| MGC40157 | NM_152350 | ACCCGAGAGAACTGGATTGCGT | 359 | 881 | GCTCCAATACTCAGCTGCCAAA | 469 | 889 | 111 |
| MGC45871 | NM_182705 | CCACCAAAGGAAGTAAGGTACAC | 362 | 882 | TAGTTGCGCCACGTGCCATT | 507 | 890 | 146 |
| MKLN1 | NM_013255 | GAGGGCCGAAATTGGTGTTTGA | 1169 | 883 | ATTGTGGTTCACTGGCTCTGCT | 1297 | 891 | 129 |
| NIPBL | NM_015384 | AGTGTACGCCACTTTGCCCTAA | 6886 | 884 | ATCAGCCTTGTTCCGCATAGCA | 7017 | 892 | 132 |
| PPP1R2 | NM_006241 | AAGATGCCTGTAGTGACACCGA | 250 | 885 | ATCCGATACTTTGGCTCCAAGC | 349 | 893 | 100 |

TABLE 7

| | AJ36h | | Blind test | |
|---|---|---|---|---|
| | No Polyp | Polyp | No Polyp | Polyp |
| Sample Size | 110 | 68 | 40 | 40 |
| Gender (F/M) | 55/54* | 22/45* | 21/19 | 13/27 |
| Age mean (range) | 57 (23~83) | 57 (38~82) | 57 (40~79) | 60 (38~76) |
| Polyp Subtype | | | | |
| Tubular adenoma | | 21 (31%) | | 14 (35%) |
| Hyperplastic | | 18 (27%) | | 15 (38%) |
| High risk pathology | | 7 (10%) | | 3 (7.5%) |
| Others | | 22 (32%) | | 8 (20%) |

*one sample missing information

TABLE 8

| Equ # | # ratios | ROC area | Constant | MGC-45871-APEH | MKLN1-APEH | MGC-45871-FLJ-23091 | MKLN1-FLJ23091 | NIPBL-FLJ23091 | MGC-45871-MGC-40157 | MKLN-1-MGC-40157 | NIPBL-MGC-40157 | MGC-45871-PPP1R2 | MKLN1-PPP1R2 | Thresh |
|---|---|---|---|---|---|---|---|---|---|---|---|---|---|---|
| 26692 | 5 | 0.718 | −2.483 | 0 | 0.173 | 0 | −0.291 | 0 | 0 | 0 | −0.173 | −0.863 | −0.929 | −0.481 |
| 26690 | 5 | 0.718 | −2.483 | 0.173 | 0 | 0 | −0.291 | 0 | 0 | 0 | −0.173 | −1.036 | −0.756 | −0.481 |
| 26658 | 5 | 0.718 | −2.483 | 0.173 | 0 | −0.291 | 0 | 0 | 0 | 0 | −0.173 | −0.745 | −1.047 | −0.481 |
| 26660 | 5 | 0.718 | −2.483 | 0 | 0.173 | −0.291 | 0 | 0 | 0 | 0 | −0.173 | −0.572 | −1.220 | −0.481 |
| 25732 | 5 | 0.718 | −3.284 | 0 | 0.441 | 0 | 0 | −0.230 | 0 | −0.514 | 0 | −0.793 | −0.916 | −0.014 |
| 25218 | 5 | 0.718 | −3.285 | 0.441 | 0 | 0 | 0 | −0.230 | −0.514 | 0 | 0 | −0.720 | −0.989 | −0.014 |
| 25730 | 5 | 0.718 | −3.284 | 0.441 | 0 | 0 | 0 | −0.230 | 0 | −0.514 | 0 | −1.234 | −0.475 | −0.014 |
| 25220 | 5 | 0.718 | −3.285 | 0 | 0.441 | 0 | 0 | −0.230 | −0.514 | 0 | 0 | −0.279 | −1.430 | −0.014 |
| 17030 | 5 | 0.718 | −3.285 | −0.279 | 0.720 | 0 | 0 | −0.230 | −0.514 | 0 | 0 | 0 | −1.709 | −0.014 |
| 18052 | 5 | 0.718 | −3.284 | 0 | 0.441 | 0 | 0 | −0.230 | −0.793 | 0.279 | 0 | 0 | −1.709 | −0.014 |

TABLE 9

| Parameter | Blind |
|---|---|
| Number of Samples | 80 |
| Number of Equations | 10 |
| Sensitivity (TPF) | 43% (17/40) |
| Specificity (TNF) | 80% (32/40) |
| Overall accuracy | 61% (49/80) |

TABLE 10

| Reporter Gene | Protein Activity & Measurement |
|---|---|
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

Table 11 is found in the instant specification after Tables 17 and 1, and before the sequence listing and claims.

Lengthy table referenced here

US08249814-20120821-T00001

Please refer to the end of the specification for access instructions.

Lengthy table referenced here

US08249814-20120821-T00002

Please refer to the end of the specification for access instructions.

Lengthy table referenced here

US08249814-20120821-T00003

Please refer to the end of the specification for access instructions.

Lengthy table referenced here

US08249814-20120821-T00004

Please refer to the end of the specification for access instructions.

Lengthy table referenced here

US08249814-20120821-T00005

Please refer to the end of the specification for access instructions.

Lengthy table referenced here

US08249814-20120821-T00006

Please refer to the end of the specification for access instructions.

Lengthy table referenced here

US08249814-20120821-T00007

Please refer to the end of the specification for access instructions.

Lengthy table referenced here

US08249814-20120821-T00008

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08249814B2). An electronic copy of the table will also be available from the USPTO upon request and payment of the fee set forth in 37 CFR 1.19(b)(3).

We claim:

1. A method of determining a probability that a test subject has colorectal cancer, the method comprising:

(a) determining the gene-specific levels of mRNA transcribed from each gene of a set of genes consisting of CDA and BANK1 in blood of the test subject, thereby obtaining test levels; and (b) applying to the test levels a classifier for determining a probability that the gene-specific levels of mRNA transcribed from each gene of the set of genes in blood of a subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, thereby determining a probability that the test subject has colorectal cancer.

2. A computer implemented method of determining a probability that a test subject has colorectal cancer, the method comprising:

using a suitably programmed computer, applying a classifier to data representing the gene-specific levels of mRNA transcribed from each gene of a set of genes consisting of CDA and BANK1 in blood of a test subject, the classifier being for determining a probability that the gene-specific levels of mRNA transcribed from each gene of the set of genes in blood of a subject classify with the gene-specific levels of mRNA transcribed from the set of genes in blood of subjects having colorectal cancer as opposed to the gene-specific levels of mRNA transcribed from the set of genes in blood of subjects not having colorectal cancer, thereby determining a probability that the test subject has colorectal cancer.

3. The method of claim 1, wherein the classifier has a form:

$$Y=C+\Sigma\beta_{ij}(X_i/X_j),$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$, is a level of mRNA of an ith gene of the set of genes, $X_j$, is a level of mRNA of a jth gene of the set of genes where the ith gene is not the jth gene, wherein $\beta_{ij}$ is a logistic regression equation coefficient, wherein C is a logistic regression equation constant, and wherein $\beta_{ij}$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

4. A non-transitory computer-readable medium comprising instructions for applying a classifier to data representing the gene-specific levels of mRNA transcribed from each gene of a set of genes consisting of CDA and BANK1 in blood of a test subject, the classifier being for determining a probability that the gene-specific levels of mRNA transcribed from each gene of the set of genes in blood of a subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer.

5. The computer-readable medium of claim 4, wherein the classifier has a form:

$$Y=C+\Sigma\beta_{ij}(X_i/X_j),$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$, is a level of mRNA of an ith gene of the set of genes, $X_j$, is a level of mRNA of a jth gene of the set of genes where the ith gene is not the jth gene, wherein $\beta_{ij}$ is a logistic regression equation coefficient, wherein C is a logistic regression equation constant, and wherein $\beta_{ij}$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

6. A computer system for determining a probability that a test subject has colorectal cancer, the computer system comprising a processor; and a memory configured with instructions that cause said processor to apply a classifier to data representing the gene-specific levels of mRNA transcribed from each gene of a set of genes consisting of CDA and BANK1in blood of a test subject, the classifier being for determining a probability that the gene-specific levels of mRNA transcribed from each gene of the set of genes in blood of a subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer.

7. The system of claim 6, wherein the classifier has a form:

$$Y=C+\Sigma\beta_{ij}(X_i/X_j),$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from the set of genes in blood of subjects not having colorectal cancer, wherein $X_i$, is a level of mRNA of an ith gene of the set of genes, $X_j$, is a level of mRNA of a jth gene of the set of genes where the ith gene is not the jth gene, wherein $\beta_{ij}$ is a logistic regression equation coefficient, wherein C is a logistic regression equation constant, and wherein $\beta_{ij}$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

8. The method of claim 2, wherein the classifier has a form:

$$Y=C+\Sigma\beta_{ij}(X_i/X_j),$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$, is a level of mRNA of an ith gene of the set of genes, $X_j$, is a level of mRNA of a jth gene of the set of genes where the ith gene is not the jth gene, wherein $\beta_{ij}$ is a logistic regression equation coefficient, wherein C is a logistic regression equation constant, and wherein $\beta_{ij}$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

9. The method of claim 1, wherein the levels of mRNA are determined using amplification.

10. The method of claim 2, wherein the levels of mRNA are determined using amplification.

11. The computer-readable medium of claim 4, wherein the levels of mRNA are determined using amplification.

12. The computer system of claim 6, wherein the levels of mRNA are determined using amplification.

13. The method of claim 1, wherein the levels of mRNA are determined relative to levels of mRNA transcribed from ACTB.

14. The method of claim 2, wherein the levels of mRNA are determined relative to levels of mRNA transcribed from ACTB.

15. The computer-readable medium of claim 4, wherein the levels of mRNA are determined relative to levels of mRNA transcribed from ACTB.

16. The computer system of claim 6, wherein the levels of mRNA are determined relative to levels of mRNA transcribed from ACTB.

* * * * *